(12) United States Patent
Miyazaki et al.

(10) Patent No.: US 10,065,950 B2
(45) Date of Patent: Sep. 4, 2018

(54) SUBSTITUTED THIAZOLES AS HIV INTEGRASE INHIBITORS

(75) Inventors: Susumu Miyazaki, Osaka (JP); Yuki Bessho, Osaka (JP); Kaoru Adachi, Osaka (JP); Seiji Kawashita, Osaka (JP); Hirotaka Isoshima, Osaka (JP); Kengo Oshita, Osaka (JP); Shunichi Fukuda, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 1005 days.

(21) Appl. No.: 13/034,866

(22) Filed: Feb. 25, 2011

(65) Prior Publication Data

US 2012/0108564 A1     May 3, 2012

Related U.S. Application Data

(60) Provisional application No. 61/339,729, filed on Mar. 9, 2010.

(30) Foreign Application Priority Data

Feb. 26, 2010   (JP) .................... 2010-043567

(51) Int. Cl.
| | |
|---|---|
| *A61K 31/427* | (2006.01) |
| *C07D 277/20* | (2006.01) |
| *C07D 471/04* | (2006.01) |
| *A61K 31/4985* | (2006.01) |
| *A61K 31/5377* | (2006.01) |

(52) U.S. Cl.
CPC ........ *C07D 471/04* (2013.01); *A61K 31/4985* (2013.01); *A61K 31/5377* (2013.01)

(58) Field of Classification Search
CPC .................. A61K 31/427; C07D 277/20
USPC .......................... 514/365; 548/202
See application file for complete search history.

(56) References Cited

U.S. PATENT DOCUMENTS

| | | |
|---|---|---|
| 7,211,572 B2 | 5/2007 | Miyazaki et al. |
| 7,399,763 B2 | 7/2008 | Wai |
| 7,435,735 B2 | 10/2008 | Wai et al. |
| 7,517,532 B2 | 4/2009 | Wai et al. |
| 7,538,112 B2 | 5/2009 | Wai et al. |
| 7,820,680 B2 | 10/2010 | Williams et al. |
| 7,858,788 B2 | 12/2010 | Yoshida et al. |
| 8,129,385 B2 | 3/2012 | Johns et al. |
| 8,188,271 B2 | 5/2012 | Yoshida et al. |
| 2005/0054645 A1 | 3/2005 | Miyazaki et al. |
| 2007/0161639 A1 | 7/2007 | Jones et al. |
| 2008/0161311 A1 | 7/2008 | Miyazaki et al. |
| 2009/0099168 A1 | 4/2009 | Doughi et al. |
| 2009/0312335 A1 | 12/2009 | Wai et al. |
| 2011/0028487 A1 | 2/2011 | Deadman et al. |
| 2011/0039842 A1 | 2/2011 | Deadman et al. |
| 2011/0212102 A1 | 9/2011 | Lehmann-Lintz et al. |
| 2011/0212103 A1 | 9/2011 | Heckel et al. |
| 2011/0217311 A1 | 9/2011 | Lehmann-Lintz et al. |
| 2011/0281861 A1 | 11/2011 | Deadman et al. |
| 2012/0115875 A1 | 5/2012 | Johns et al. |
| 2013/0143941 A1 | 6/2013 | Winters et al. |

FOREIGN PATENT DOCUMENTS

| | | |
|---|---|---|
| CA | 2789457 * | 9/2011 |
| WO | WO 2004/024078 A2 | 3/2004 |
| WO | WO 2004/047725 A2 | 6/2004 |
| WO | WO 2005/016927 A1 | 2/2005 |
| WO | WO 2005/041664 A1 | 5/2005 |
| WO | WO 2005/087766 A1 | 9/2005 |
| WO | WO 2005/092099 A1 | 10/2005 |
| WO | WO 2005/110414 A2 | 11/2005 |
| WO | WO 2005/110415 A1 | 11/2005 |
| WO | WO 2006/066414 A1 | 6/2006 |
| WO | WO 2006/088173 A1 | 8/2006 |
| WO | WO 2006/116764 A1 | 11/2006 |
| WO | WO 2007/049675 A1 | 5/2007 |
| WO | WO 2007/050510 A2 | 5/2007 |
| WO | WO 2010/000030 A1 | 1/2010 |

(Continued)

OTHER PUBLICATIONS

Vippagunta, et al. Advanced Drug Delivery Reviews, 48, 2001, 18.*

(Continued)

*Primary Examiner* — Douglas M Willis
(74) *Attorney, Agent, or Firm* — Finnegan, Henderson, Farabow, Garrett & Dunner LPP

(57) ABSTRACT

[Problem] Provided is a novel 1,3,4,8-tetrahydro-2H-pyrido[1,2-a]pyrazine derivative or a pharmaceutically acceptable salt thereof, or a solvate thereof, which is useful as an anti-HIV agent.

[Solving Means] The present invention provides a compound represented by the following formula [I]

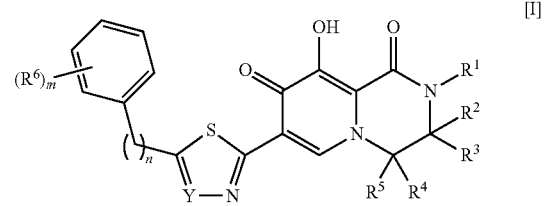

wherein each symbol is as defined in the specification, or a pharmaceutically acceptable salt thereof, or a solvate thereof.

20 Claims, No Drawings
Specification includes a Sequence Listing.

(56) References Cited

FOREIGN PATENT DOCUMENTS

| WO | WO 2010/000031 A1 | 1/2010 |
| WO | WO 2010/000032 A1 | 1/2010 |
| WO | WO 2011/129095 A1 | 10/2011 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/JP2011/054404 dated Mar. 22, 2011.
Supplementary European Search Report for EP Application No. 11747546.7 dated Jun. 28, 2013.
Chilean Search Report for Chilean Patent Application No. 2355-2012 dated Sep. 13, 2013.

* cited by examiner

```
                       SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination of
      HIV integrase

<400> SEQUENCE: 1 accctttag tcagtgtgga aaatctctag ca                                    32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination
      of HIV integrase

<400> SEQUENCE: 2
actgctagag attttccaca ctgactaaaa g                                    31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase

<400> SEQUENCE: 3
tgaccaaggg ctaattcact                                                 20

<210> SEQ ID NO 4
<211> LENGTH: 20
<212> TYPE: DNA
<213> ORGANISM: Artificial Sequence
<220> FEATURE:
```

```
<223> OTHER INFORMATION: Target minus strand for activity determination
       of HIV integrase

<400> SEQUENCE: 4
agtgaattag cccttggtca                                            20
```

SUBSTITUTED THIAZOLES AS HIV INTEGRASE INHIBITORS

This application claims the benefit of Japanese Patent Application No. 2010-043567, filed Feb. 26, 2010, and claims the benefit of U.S. Provisional Application No. 61/339,729, filed Mar. 9, 2010.

TECHNICAL FIELD

The present invention relates to a novel 1,3,4,8-tetrahydro-2H-pyrido[1,2-a]pyrazine derivative useful as an anti-HIV agent, a pharmaceutically acceptable salt thereof, and a solvate thereof. In addition, the present invention relates to a pharmaceutical composition comprising the derivative or a pharmaceutically acceptable salt thereof, or a solvate thereof, and a pharmaceutically acceptable carrier; an anti-HIV agent, an HIV integrase inhibitor and the like, comprising the derivative or a pharmaceutically acceptable salt thereof, or a solvate thereof as an active ingredient; an anti-HIV agent comprising a combination of the derivative or a pharmaceutically acceptable salt thereof, or a solvate thereof, and one or more kinds of other anti-HIV active substances; and the like.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a medicament that eradicates HIV in a living organism or suppresses its growth is effective for the prophylaxis or treatment of AIDS.

HIV possesses a bimolecular RNA gene in a shell, which is covered with an envelope protein. The RNA codes for several enzymes (protease, reverse transcriptase, integrase) characteristic of the virus and the like. Translated reverse transcriptase and integrase are present in the shell, and protease is present inside and outside the shell.

HIV contacts and invades a host cell, causes uncoating, and releases a complex of RNA and integrase and the like into the cytoplasm. From the RNA, DNA is transcribed by reverse transcriptase, and a full length double stranded DNA is produced. The DNA moves into the nucleus of the host cell and is incorporated by integrase into the DNA of the host cell. The incorporated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine and the like have been already on the market as reverse transcriptase inhibitors, and indinavir, nelfinavir and the like as protease inhibitors.

In addition, a multiple drug combination therapy using these medicaments in combination (to be also referred to as HAART (highly active antiretroviral therapy)) is also used. For example, 3 agent combination therapy using two agents from reverse transcriptase inhibitors (zidovudine and lamivudine, or tenofovir and emtricitabine), and a non-nucleic acid reverse transcriptase inhibitor (efavirenz), or a protease inhibitor (lopinavir, fosamprenavir or atazanavir) in combination with ritonavir, and the like is used in clinical practice, and such multiple drug combination therapy is becoming the mainstream of the AIDS treatment.

However, some of these medicaments are known to cause side effects such as liver function failure, central nervous disorders (e.g., vertigo), and the like. In addition, acquisition of resistance to a medicament causes a problem. Even worse, emergence of an HIV that shows multiple drug resistance in a multiple drug combination therapy has been known.

Under the circumstances, a further development of a novel medicament, particularly a development of an anti-HIV agent based on a new mechanism, has been desired, wherein a development of an anti-HIV agent having an integrase inhibitory activity is expected, because an integrase characteristic of retrovirus is an essential enzyme for the growth of HIV.

SUMMARY OF THE INVENTION

Problems to be Solved by the Invention

From the findings obtained from pharmacological studies and clinical results heretofore, an anti-HIV agent is effective for the prophylaxis or treatment of AIDS, and particularly a compound having an integrase inhibitory activity can be an effective anti-HIV agent.

Therefore, the present invention aims at provision of a compound having an anti-HIV activity, particularly a compound having an integrase inhibitory activity.

Means of Solving the Problems

The present inventors have conducted intensive studies in an attempt to find a compound having an anti-HIV action, particularly a compound having an integrase inhibitory action, and completed the present invention.

More specifically, the present invention provides the following.

[1] A compound represented by the following formula [I] or a pharmaceutically acceptable salt thereof, or a solvate thereof (sometimes to be abbreviated as "the compound of the present invention" in the present specification):

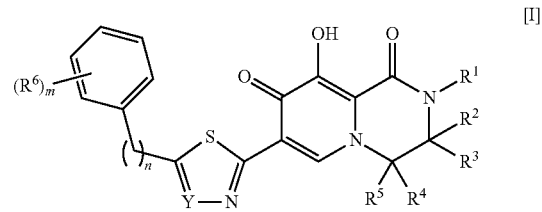

wherein
$R^1$ is
(1) a $C_{1-6}$ alkyl group optionally substituted by the same or different 1 to 5 substituents selected from
  (i) a $C_{3-8}$ cycloalkyl group, and
  (ii) a $C_{1-6}$ alkoxy group,
(2) a $C_{3-8}$ cycloalkyl group, or
(3) a saturated monocyclic heterocyclic group containing, besides carbon atom, 1 to 3 hetero atoms selected from a nitrogen atom, an oxygen atom and a sulfur atom, $R^2$, $R^3$, $R^4$ and $R^5$ are the same or different and each is
(1) a hydrogen atom,
(2) a carboxyl group,
(3) —CO—$NR^aR^b$ wherein $R^a$ and $R^b$ are the same or different and each is
  (i) a hydrogen atom,
  (ii) a $C_{1-6}$ alkyl group optionally substituted by the same or different 1 to 5 substituents selected from the following group B, or
  (iii) a $C_{3-8}$ cycloalkyl group, or
  $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the following group B,
(4) a $C_{1-8}$ alkyl group optionally substituted by the same or different 1 to 5 substituents selected from the following group A, or
(5) a cyano group,
or
$R^2$ and $R^3$, or $R^4$ and $R^5$ optionally form, together with the carbon atom bonded thereto,
i) $C_{3-8}$ cycloalkane, or
ii) a saturated monocyclic hetero ring containing, besides carbon atom, 1 to 6 hetero atoms selected from a nitrogen atom, an oxygen atom and a sulfur atom,
wherein $R^2$, $R^3$, $R^4$ and $R^5$ are not hydrogen atoms at the same time,
$R^6$ is
(1) a $C_{1-6}$ alkyl group optionally substituted by the same or different 1 to 5 halogen atoms,
(2) a $C_{1-6}$ alkoxy group,
(3) a halogen atom, or
(4) a $C_{3-8}$ cycloalkyl group,
Y is
(1) CH, or
(2) a nitrogen atom,
m is an integer of 1 to 5, and when m is an integer of 2 to 5, then each $R^6$ may be the same or different, and
n is an integer of 1 to 3,
group A:
(a) —CO—$NR^{41}R^{42}$
  wherein $R^{41}$ and $R^{42}$ are the same or different and each is
    (i) a hydrogen atom,
    (ii) a $C_{1-6}$ alkyl group optionally substituted by the same or different 1 to 5 substituents selected from the following group B, or
    (iii) a $C_{3-8}$ cycloalkyl group, or
    $R^{41}$ and $R^{42}$ optionally form, together with the nitrogen atom bonded thereto, a saturated monocyclic hetero ring optionally containing, besides carbon atom and one nitrogen atom, 1 to 3 hetero atoms selected from a nitrogen atom, an oxygen atom and a sulfur atom, and optionally substituted by the same or different 1 to 5 substituents selected from the following group B,
(b) a hydroxyl group,
(c) a $C_{1-6}$ alkoxy group,
(d) a $C_{1-6}$ alkoxy-$C_{1-6}$ alkoxy group,
(e) a cyano group,
(f) —$NR^{43}R^{44}$
  wherein $R^{43}$ and $R^{44}$ are the same or different and each is
    (i) a hydrogen atom,
    (ii) a $C_{1-6}$ alkyl group,
    (iii) a $C_{1-6}$ alkyl-carbonyl group, or
    (iv) a $C_{1-6}$ alkyl-sulfonyl group, or
    $R^{43}$ and $R^{44}$ optionally form, together with the nitrogen atom bonded thereto, a hetero ring optionally containing, besides carbon atom and one nitrogen atom, 1 to 5 hetero atoms selected from a nitrogen atom, an oxygen atom and a sulfur atom, and optionally substituted by 1 or 2 oxo groups,
(g) a carboxyl group,
(h) a $C_{1-6}$ alkyl-sulfonyl group, and
(i) a $C_{1-6}$ alkyl-carbonyl group;
group B:
(a) a hydroxyl group,
(b) a $C_{1-6}$ alkoxy group,
(c) a $C_{1-6}$ alkoxy-$C_{1-6}$ alkyl group
(d) a $C_{3-8}$ cycloalkyl group, and
(e) an oxo group.

[2] The compound of the above-mentioned [1], wherein $R^1$ is a $C_{1-6}$ alkyl group optionally substituted by the same or different 1 to 5 substituents selected from
  (i) a $C_{3-8}$ cycloalkyl group, and
  (ii) a $C_{1-8}$ alkoxy group,
or a pharmaceutically acceptable salt thereof, or a solvate thereof.

[3] The compound of the above-mentioned [2], wherein $R^1$ is a $C_{1-6}$ alkyl group, or a pharmaceutically acceptable salt thereof, or a solvate thereof.

[4] The compound of the above-mentioned [2], wherein $R^1$ is a $C_{1-6}$ alkyl group substituted by a $C_{3-8}$ cycloalkyl group, or a pharmaceutically acceptable salt thereof, or a solvate thereof.

[5] The compound of the above-mentioned [1], wherein $R^1$ is a $C_{3-8}$ cycloalkyl group, or a pharmaceutically acceptable salt thereof, or a solvate thereof.

[6] The compound of the above-mentioned [1], wherein one of $R^2$, $R^3$, $R^4$ and $R^5$ is —CO—$NR^aR^b$
  wherein $R^a$ and $R^b$ are the same or different and each is
    (i) a hydrogen atom,
    (ii) a $C_{1-8}$ alkyl group optionally substituted by the same or different 1 to 5 substituents selected from group B, or
    (iii) a $C_{3-8}$ cycloalkyl group, or
    $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B,
or a pharmaceutically acceptable salt thereof, or a solvate thereof.

[7] The compound of the above-mentioned [1], wherein one of $R^2$, $R^3$, $R^4$ and $R^5$ is a $O_{1-8}$ alkyl group optionally substituted by the same or different 1 to 5 substituents selected from group A, or a pharmaceutically acceptable salt thereof, or a solvate thereof.

[8] The compound of the above-mentioned [1], wherein $R^6$ is a halogen atom, or a pharmaceutically acceptable salt thereof, or a solvate thereof.

[9] The compound of the above-mentioned [1], wherein Y is CH, or a pharmaceutically acceptable salt thereof, or a solvate thereof.

[10] The compound of the above-mentioned [1], wherein Y is a nitrogen atom, or a pharmaceutically acceptable salt thereof, or a solvate thereof.

[11] The compound of the above-mentioned [1], wherein m is 1 or 2, or a pharmaceutically acceptable salt thereof, or a solvate thereof.

[12] The compound of the above-mentioned [1], wherein n is 1, or a pharmaceutically acceptable salt thereof, or a solvate thereof.

[13] The compound of the above-mentioned [1], which is represented by the following formula [I-1], or a pharmaceutically acceptable salt thereof, or a solvate thereof:

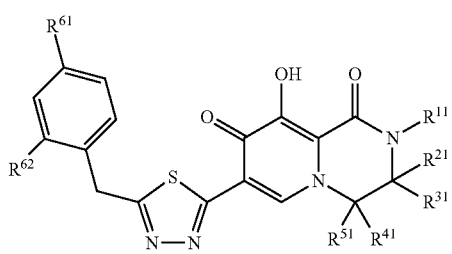

wherein
$R^{11}$ is
(1) a $C_{1-6}$ alkyl group optionally substituted by the same or different 1 to 5 substituents selected from
   (i) a $C_{3-6}$ cycloalkyl group, and
   (ii) a $C_{1-6}$ alkoxy group, or
(2) a $C_{3-6}$ cycloalkyl group,
$R^{21}$, $R^{31}$, $R^{41}$ and $R^{51}$ are the same or different and each is
(1) a hydrogen atom,
(2) —CO—NR$^a$R$^b$
   wherein R$^a$ and R$^b$ are the same or different and each is
   (i) a hydrogen atom,
   (ii) a $C_{1-6}$ alkyl group optionally substituted by the same or different 1 to 5 substituents selected from group B, or
   (iii) a $C_{3-8}$ cycloalkyl group, or
   R$^a$ and R$^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B, or
(3) a $C_{1-6}$ alkyl group optionally substituted by the same or different 1 to 5 substituents selected from group A,
wherein $R^{21}$, $R^{31}$, $R^{41}$ and $R^{51}$ are not hydrogen atoms at the same time,
$R^{61}$ is a halogen atom, and
$R^{62}$ is a hydrogen atom or a halogen atom.

[14] The compound of the above-mentioned [13], wherein $R^{21}$ is a $C_{1-6}$ alkyl group optionally substituted by the same or different 1 to 5 substituents selected from group A, and
$R^{31}$, $R^{41}$ and $R^{51}$ are each a hydrogen atom,
or a pharmaceutically acceptable salt thereof, or a solvate thereof.

[15] The compound of the above-mentioned [13], wherein $R^{21}$ is a $C_{1-6}$ alkyl group, and
$R^{31}$, $R^{41}$ and $R^{51}$ are each a hydrogen atom,
or a pharmaceutically acceptable salt thereof, or a solvate thereof.

[16] The compound of the above-mentioned [13], wherein $R^{41}$ is a $C_{1-6}$ alkyl group optionally substituted by the same or different 1 to 5 substituents selected from group A, and
$R^{21}$, $R^{31}$ and $R^{51}$ are each a hydrogen atom, or a pharmaceutically acceptable salt thereof, or a solvate thereof.

[17] The compound of the above-mentioned [13], wherein $R^{21}$ is a $C_{1-6}$ alkyl group optionally substituted by the same or different 1 to 5 substituents selected from group A,
$R^{41}$ is a $C_{1-6}$ alkyl group, and
$R^{31}$ and $R^{51}$ are each a hydrogen atom,
or a pharmaceutically acceptable salt thereof, or a solvate thereof.

[18] The compound of the above-mentioned [1], which is represented by the following formula [I-2], or a pharmaceutically acceptable salt thereof, or a solvate thereof:

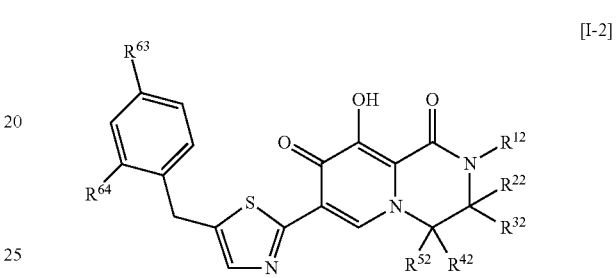

wherein
$R^{12}$ is a $C_{1-6}$ alkyl group optionally substituted by the same or different 1 to 5 substituents selected from
   (i) a $C_{3-8}$ cycloalkyl group, and
   (ii) a $C_{1-6}$ alkoxy group,
$R^{22}$, $R^{32}$, $R^{42}$ and $R^{52}$ are the same or different and each is
(1) a hydrogen atom,
(2) —CO—NR$^a$R$^b$
   wherein R$^a$ and R$^b$ are the same or different and each is
   (i) a hydrogen atom,
   (ii) a $C_{1-6}$ alkyl group optionally substituted by the same or different 1 to 5 substituents selected from group B, or
   (iii) a $C_{3-8}$ cycloalkyl group, or
   R$^a$ and R$^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B, or
(3) a $C_{1-6}$ alkyl group optionally substituted by the same or different 1 to 5 substituents selected from group A,
wherein $R^{22}$, $R^{32}$, $R^{42}$ and $R^{52}$ are not hydrogen atoms at the same time,
$R^{63}$ is a halogen atom, and
$R^{64}$ is a hydrogen atom or a halogen atom.

[19] The compound of the above-mentioned [18], wherein $R^{42}$ is —CO—NR$^a$R$^b$
   wherein R$^a$ and R$^b$ form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B,
$R^{52}$ is a $C_{1-6}$ alkyl group, and
$R^{22}$ and $R^{32}$ is a hydrogen atom,
or a pharmaceutically acceptable salt thereof, or a solvate thereof.

[20] The compound of the above-mentioned [1], which is represented by the formula, or a pharmaceutically acceptable salt thereof, or a solvate thereof:

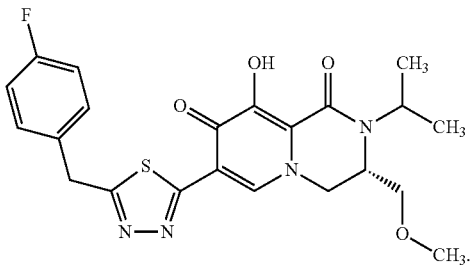 [SMILES: COC[C@@H]1Cn2cc(-c3nnc(Cc4ccc(F)cc4)s3)c(=O)c(O)c2C(=O)N1C(C)C]

[21] The compound of the above-mentioned [1], which is represented by the formula, or a pharmaceutically acceptable salt thereof, or a solvate thereof:

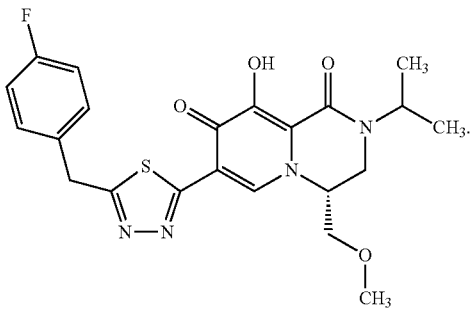 [SMILES: COC[C@H]1CN(C(C)C)C(=O)c2c(O)c(=O)c(-c3nnc(Cc4ccc(F)cc4)s3)cn21]

[22] The compound of the above-mentioned [1], which is represented by the formula, or a pharmaceutically acceptable salt thereof, or a solvate thereof:

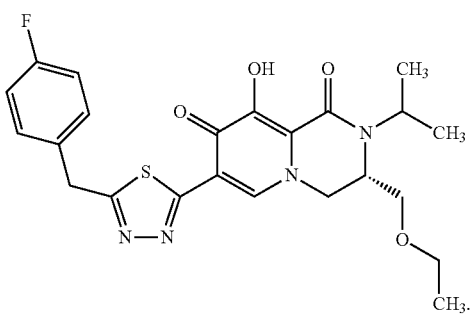 [SMILES: CCOC[C@@H]1Cn2cc(-c3nnc(Cc4ccc(F)cc4)s3)c(=O)c(O)c2C(=O)N1C(C)C]

[23] The compound of the above-mentioned [1], which is represented by the formula, or a pharmaceutically acceptable salt thereof, or a solvate thereof:

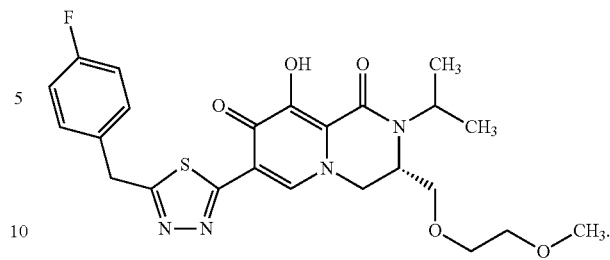

[24] The compound of the above-mentioned [1], which is represented by the formula, or a pharmaceutically acceptable salt thereof, or a solvate thereof:

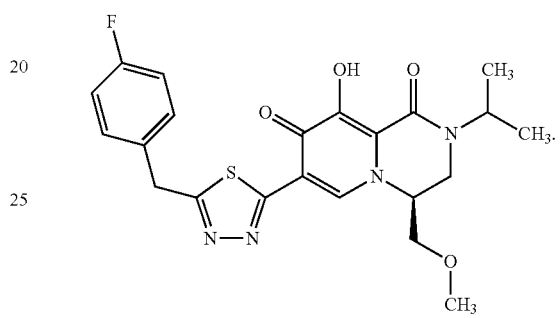

[25] The compound of the above-mentioned [1], which is represented by the formula, or a pharmaceutically acceptable salt thereof, or a solvate thereof:

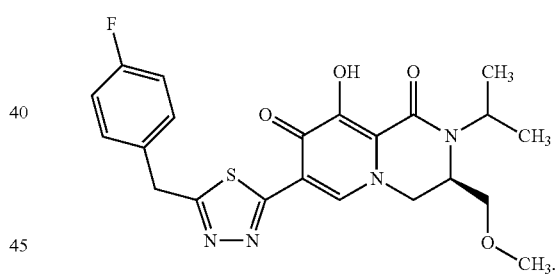

[26] The compound of the above-mentioned [1], which is represented by the formula, or a pharmaceutically acceptable salt thereof, or a solvate thereof:

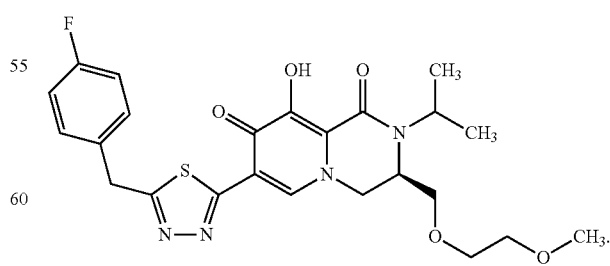

[27] The compound of the above-mentioned [1], which is represented by the formula, or a pharmaceutically acceptable salt thereof, or a solvate thereof:

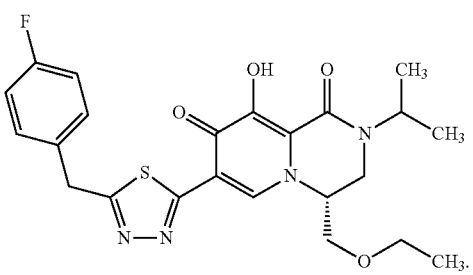 [SMILES: CCOC[C@H]1CN(C(C)C)C(=O)c2c(O)c(=O)c(-c3nnc(Cc4ccc(F)cc4)s3)cn21]

[28] The compound of the above-mentioned [1], which is to represented by the formula, or a pharmaceutically acceptable salt thereof, or a solvate thereof:

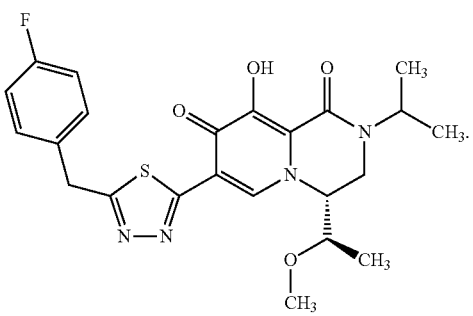 [SMILES: CO[C@H](C)[C@H]1CN(C(C)C)C(=O)c2c(O)c(=O)c(-c3nnc(Cc4ccc(F)cc4)s3)cn21]

[29] The compound of the above-mentioned [1], which is represented by the formula, or a pharmaceutically acceptable salt thereof, or a solvate thereof:

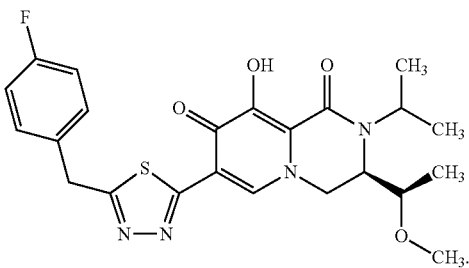 [SMILES: CO[C@H](C)[C@H]1Cn2cc(-c3nnc(Cc4ccc(F)cc4)s3)c(=O)c(O)c2C(=O)N1C(C)C]

[30] A pharmaceutical composition comprising the compound of any one of the above-mentioned [1] to [29] or a pharmaceutically acceptable salt thereof, or a solvate thereof, and a pharmaceutically acceptable carrier.
[31] An anti-HIV agent comprising the compound of any one of the above-mentioned [1] to [29] or a pharmaceutically acceptable salt thereof, or a solvate thereof, as an active to ingredient.
[32] An HIV integrase inhibitor comprising the compound of any one of the above-mentioned [1] to [29] or a pharmaceutically acceptable salt thereof, or a solvate thereof, as an active ingredient.
[33] An anti-HIV agent comprising the compound of any one of the above-mentioned [1] to [29] or a pharmaceutically acceptable salt thereof, or a solvate thereof, in combination with one or more other kinds of anti-HIV active substances.
[34] Use of the compound of any one of the above-mentioned [1] to [29] or a pharmaceutically acceptable salt thereof, or a solvate thereof, for the production of an anti-HIV agent.
[35] Use of the compound of any one of the above-mentioned [1] to [29] or a pharmaceutically acceptable salt thereof, or a solvate thereof, for the production of an HIV integrase inhibitor.
[36] A method for the prophylaxis or treatment of an HIV infectious disease in a mammal, which comprises administering an effective amount of the compound of any one of the above-mentioned [1] to [29] or a pharmaceutically acceptable salt thereof, or a solvate thereof, to said mammal.
[37] The method of the above-mentioned [36], which further comprises administering an effective amount of one or more other kinds of anti-HIV active substances to the mammal.
[38] A method for inhibiting HIV integrase in a mammal, which comprises administering an effective amount of the compound of any one of the above-mentioned [1] to [29] or a pharmaceutically acceptable salt thereof, or a solvate thereof, to said mammal.
[39] An anti-HIV composition comprising the compound of any one of the above-mentioned [1] to [29] or a pharmaceutically acceptable salt thereof, or a solvate thereof, and a pharmaceutically acceptable carrier.
[40] A pharmaceutical composition for inhibiting HIV integrase, comprising the compound of any one of the above-mentioned [1] to [29] or a pharmaceutically acceptable salt thereof, or a solvate thereof, and a pharmaceutically acceptable carrier.
[41] A commercial package comprising the pharmaceutical composition of the above-mentioned [30] and a written matter associated therewith, which states that the pharmaceutical composition can or should be used for treating HIV.
[42] A kit comprising the pharmaceutical composition of the above-mentioned [30] and a written matter associated therewith, which states that the pharmaceutical composition can or should be used for treating HIV.

Effect of the Invention

The compound of the present invention can be medicaments effective for the prophylaxis or treatment of HIV infections or AIDS, as anti-HIV agents, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be medicaments safe for human body with a fewer side effects.

DESCRIPTION OF EMBODIMENTS

The definitions of respective substituents and respective moieties used in the present specification are as follows.
The "halogen atom" is a fluorine atom, a chlorine atom, a bromine atom or an iodine atom.
The "$C_{1-6}$ alkyl group" is a straight chain or branched chain alkyl group having 1 to 6 carbon atoms, preferably a straight chain or branched chain alkyl group having 1 to 4 carbon atoms. Specific examples include a methyl group, an ethyl group, a propyl group, an isopropyl group, a butyl group, an isobutyl group, a sec-butyl group, a tert-butyl group, a pentyl group, an isopentyl group, a 1,1-dimethylpropyl group, a 1,2-dimethylpropyl group, a 2,2-dimethylpropyl group, a 1-ethylpropyl group, a hexyl group and the like.

The "$C_{1-6}$ alkoxy group" is a straight chain or branched chain alkoxy group having 1 to 6 carbon atoms, preferably a straight chain or branched chain alkoxy group having 1 to 4 carbon atoms. Specific examples include a methoxy group, an ethoxy group, a propoxy group, an isopropyloxy group, a butoxy group, an isobutyloxy group, a tert-butyloxy group, a pentyloxy group, a hexyloxy group and the like.

The "$C_{1-6}$ alkoxy-$C_{1-6}$ alkyl group" is that wherein the alkoxy moiety is the "$C_{1-6}$ alkoxy group" defined above, and the alkyl moiety is the "$C_{1-6}$ alkyl group" defined above. Preferred is a $C_{1-6}$ alkoxy-$C_{1-6}$ alkyl group wherein the alkoxy moiety is a straight chain or branched chain alkoxy group having 1 to 4 carbon atoms, and the alkyl moiety is a straight chain or branched chain alkyl group having 1 to 4 carbon atoms. Examples of the $C_{1-6}$ alkoxy-$C_{1-6}$ alkyl group include a methoxymethyl group, a methoxyethyl group, a methoxypropyl group, a methoxybutyl group, a methoxypentyl group, a methoxyhexyl group, an ethoxymethyl group, an ethoxyethyl group, an ethoxypropyl group, an ethoxybutyl group, an ethoxypentyl group, an ethoxyhexyl group, a propoxymethyl group, a propoxyethyl group, a propoxypropyl group, a propoxybutyl group, a propoxypentyl group, a propoxyhexyl group, a butoxymethyl group, a butoxyethyl group, a butoxypropyl group, a butoxybutyl group, a butoxypentyl group, a butoxyhexyl group, a pentyloxymethyl group, a pentyloxyethyl group, a pentyloxypropyl group, a pentyloxybutyl group, a pentyloxypentyl group, a pentyloxyhexyl group, a hexyloxymethyl group, a hexyloxyethyl group, a hexyloxypropyl group, a hexyloxybutyl group, a hexyloxypentyl group, a hexyloxyhexyl group and the like.

The "$C_{1-6}$ alkoxy-$C_{1-6}$ alkoxy group" is that wherein the $C_{1-6}$ alkoxy moiety is the "$C_{1-6}$ alkoxy group" defined above, preferably a straight chain or branched chain alkoxy group having 1 to 4 carbon atoms. Examples thereof include a methoxymethoxy group, a methoxyethoxy group, a methoxypropoxy group, a methoxybutoxy group, a methoxypentyloxy group, a methoxyhexyloxy group, an ethoxymethoxy group, an ethoxyethoxy group, an ethoxypropoxy group, an ethoxybutoxy group, an ethoxypentyloxy group, an ethoxyhexyloxy group, a propoxymethoxy group, a propoxyethoxy group, a propoxypropoxy group, a propoxybutoxy group, a propoxypentyloxy group, a propoxyhexyloxy group, a butoxymethoxy group, a butoxyethoxy group, a butoxypropoxy group, a butoxybutoxy group, a butoxypentyloxy group, a butoxyhexyloxy group, a pentyloxymethoxy group, a pentyloxyethoxy group, a pentyloxypropoxy group, a pentyloxybutoxy group, a pentyloxypentyloxy group, a pentyloxyhexyloxy group, a hexyloxymethoxy group, a hexyloxyethoxy group, a hexyloxypropoxy group, a hexyloxybutoxy group, a hexyloxypentyloxy group, a hexyloxyhexyloxy group and the like.

The "$C_{1-6}$ alkyl-carbonyl group" is an alkyl-carbonyl group wherein the $C_{1-6}$ alkyl moiety is the "$C_{1-6}$ alkyl group" defined above, preferably a straight chain or branched chain alkyl group having 1 to 4 carbon atoms. Examples thereof include a methylcarbonyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, an isopentylcarbonyl group, a 1,1-dimethylpropylcarbonyl group, hexylcarbonyl group and the like.

The "$C_{1-6}$ alkyl-sulfonyl group" is an alkyl-sulfonyl group wherein the $C_{1-6}$ alkyl moiety is the "$C_{1-6}$ alkyl group" defined above, preferably a straight chain or branched chain alkyl group having 1 to 4 carbon atoms. Examples thereof include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, an isopentylsulfonyl group, a 1,1-dimethylpropylsulfonyl group, a hexylsulfonyl group and the like.

The "$C_{3-8}$ cycloalkyl group" is a saturated cycloalkyl group having 3 to 8 carbon atoms, preferably 3 to 5 carbon atoms, and examples thereof include a cyclopropyl group, a cyclobutyl group, a cyclopentyl group, a cyclohexyl group, a cycloheptyl group, a cyclooctyl group and the like.

The "$C_{3-8}$ cycloalkane" is saturated cycloalkane having 3 to 8 carbon atoms, preferably 3 to 5 carbon atoms, and examples thereof include cyclopropane, cyclobutane, cyclopentane, cyclohexane, cycloheptane, cyclooctane and the like.

The "hetero ring" means a saturated or unsaturated (including partially unsaturated and completely unsaturated) monocyclic hetero ring containing, besides carbon atom, 1 to 6 hetero atoms selected from a nitrogen atom, an oxygen atom and a sulfur atom, or a fused ring of the hetero rings, or a fused ring of a carbon ring selected from benzene, cyclopentane and cyclohexane, and the hetero ring.

Examples of the above-mentioned "saturated monocyclic hetero ring containing, besides carbon atom, 1 to 6 hetero atoms selected from a nitrogen atom, an oxygen atom and a sulfur atom" include a 4- to 7-membered saturated monocyclic hetero ring containing, besides carbon atom, 1 to 6 hetero atoms selected from a nitrogen atom, an oxygen atom and a sulfur atom, and the like. Specific examples thereof include azetidine, pyrrolidine, tetrahydrofuran, tetrahydrothiophene, imidazolidine, pyrazolidine, 1,3-dioxolane, 1,3-oxathioran, oxazolidine, thiazolidine, piperidine, piperazine, tetrahydropyran, tetrahydrothiopyran, dioxane, morpholine, thiomorpholine and the like.

Examples of the above-mentioned "unsaturated (including partially unsaturated and completely unsaturated) monocyclic hetero ring containing, besides carbon atom, 1 to 6 hetero atoms selected from a nitrogen atom, an oxygen atom and a sulfur atom" include a 4- to 7-membered unsaturated (including partially unsaturated and completely unsaturated) monocyclic hetero ring containing, besides carbon atom, 1 to 6 hetero atoms selected from a nitrogen atom, an oxygen atom and a sulfur atom, and the like. Specific examples thereof include pyrroline, furan, thiophene, imidazole, imidazoline, pyrazole, oxazole, isoxazole, thiazole, isothiazole, 1,2,4-triazole, 1,2,3-triazole, tetrazole, 1,3,4-oxadiazole, 1,2,4-oxadiazole, 1,3,4-thiadiazole, 1,2,4-thiadiazole, furazan, pyridine, pyrimidine, 3,4-dihydropyrimidine, pyridazine, pyrazine, 1,3,5-triazine, pyrazoline, oxazoline, isooxazoline, thiazoline, isothiazoline, pyran and the like.

Examples of the above-mentioned "fused ring of the hetero rings, or fused ring of a carbon ring selected from benzene, cyclopentane and cyclohexane, and the hetero ring" include indole, isoindole, benzimidazole, indazole, benzothiazole, benzofuran, isobenzofuran, indolizine, quinoline, isoquinoline, 1,2-dihydroquinoline, quinazoline, quinoxaline, cinnoline, phthalazine, quinolizidine, purine, pteridine, indoline, isoindoline, 5,6,7,8-tetrahydroquinoline, 1,2,3,4-tetrahydroquinoline, 1,3-benzodioxolane, 3,4-methylenedioxypyridine, 4,5-ethylenedioxypyrimidine, chromene, chromane, isochromane, 1,2,4-benzotriazine and the like.

The "saturated monocyclic hetero ring" formed by $R^a$ and $R^b$ together with the nitrogen atom bonded thereto means a saturated monocyclic hetero ring optionally containing, besides carbon atom and one nitrogen atom, 1 to 5 hetero atoms selected from a nitrogen atom, an oxygen atom and a sulfur atom, and examples thereof include a 4- to 7-membered (e.g., 4- to 6-membered) saturated monocyclic hetero ring optionally containing, besides carbon atom and one nitrogen atom, 1 to 5 (e.g., 1 to 3, preferably 1) hetero atoms selected from nitrogen atom, oxygen atom and sulfur atom, and the like. Specific examples of the saturated monocyclic hetero ring include those exemplified as the above-mentioned "saturated monocyclic hetero ring containing, beside carbon atom, 1 to 6 hetero atoms selected from a nitrogen atom, an oxygen atom and a sulfur atom", which contain, beside carbon atom and one nitrogen atom, 1 to 5 hetero atoms selected from a nitrogen atom, an oxygen atom and a sulfur atom.

The saturated monocyclic hetero ring is optionally substituted by the same or different 1 to 5 (e.g., 1 to 3, preferably 1) substituents selected from the following group B.

The "saturated monocyclic hetero ring" formed by $R^2$ and $R^3$ or $R^4$ and $R^5$, together with the carbon atom bonded thereto means a saturated monocyclic hetero ring containing, besides carbon atom, 1 to 6 hetero atoms selected from a nitrogen atom, an oxygen atom and a sulfur atom, and examples thereof include a 5- to 7-membered (e.g., 6-membered) saturated monocyclic hetero ring containing, besides carbon atom, 1 to 6 (e.g., 1 to 3, preferably 1) hetero atoms selected from a nitrogen atom, an oxygen atom and a sulfur atom, and the like. Specific examples of the saturated monocyclic hetero ring include those similar to the saturated monocyclic hetero rings exemplified as the above-mentioned "saturated monocyclic hetero ring containing, besides carbon atom, 1 to 6 hetero atoms selected from a nitrogen atom, an oxygen atom and a sulfur atom".

The "saturated monocyclic hetero ring" formed by $R^{A1}$ and $R^{A2}$ together with the nitrogen atom bonded thereto means a saturated monocyclic hetero ring optionally containing, besides carbon atom and one nitrogen atom, 1 to 3 hetero atoms selected from a nitrogen atom, an oxygen atom and a sulfur atom, and examples thereof include a 4- to 6-membered saturated monocyclic hetero ring optionally containing, besides carbon atom and one nitrogen atom, 1 to 3 (e.g., 1) hetero atoms selected from a nitrogen atom, an oxygen atom and a sulfur atom and the like. Specific examples of the saturated monocyclic hetero ring include those exemplified as the above-mentioned "saturated monocyclic hetero ring containing, besides carbon atom, 1 to 6 hetero atoms selected from a nitrogen atom, an oxygen atom and a sulfur atom", which optionally contain, besides carbon atom and one nitrogen atom, 1 to 3 hetero atoms selected from a nitrogen atom, an oxygen atom and a sulfur atom.

The saturated monocyclic hetero ring is optionally substituted by the same or different 1 to 5 substituents selected from the following group B.

The "hetero ring" formed by $R^{A3}$ and $R^{A4}$ together with the nitrogen atom bonded thereto means a hetero ring optionally containing, besides carbon atom and one nitrogen atom, 1 to 5 hetero atoms selected from a nitrogen atom, an oxygen atom and a sulfur atom, and examples thereof include a 4- to 6-membered (e.g., 5-membered) monocyclic hetero ring, a 8- to 10-membered (e.g., 9-membered) fused cyclic hetero ring and the like, optionally containing, besides carbon atom and one nitrogen atom, 1 to 5 hetero atoms selected from a nitrogen atom, an oxygen atom and a sulfur atom. Specific examples of the hetero ring include those exemplified as the above-mentioned "hetero ring", which optionally contain, besides carbon atom and one nitrogen atom, 1 to 5 hetero atoms selected from a nitrogen atom, an oxygen atom and a sulfur atom.

The hetero ring is optionally substituted by 1 or 2 oxo groups.

The "saturated monocyclic heterocyclic group" for $R^1$ means a saturated monocyclic heterocyclic group containing, besides carbon atom, 1 to 3 hetero atoms selected from a nitrogen atom, an oxygen atom and a sulfur atom, and examples thereof include a 5- or 6-membered saturated monocyclic heterocyclic group containing, besides carbon atom, 1 to 3 (e.g., 1) hetero atoms selected from a nitrogen atom, an oxygen atom and a sulfur atom, and the like. Specific examples of the saturated monocyclic heterocyclic group include groups derived from those exemplified as the above-mentioned "saturated monocyclic hetero ring containing, besides carbon atom, 1 to 6 hetero atoms selected from a nitrogen atom, an oxygen atom and a sulfur atom", which optionally contain, besides carbon atom, 1 to 3 hetero atoms selected from a nitrogen atom, an oxygen atom and a sulfur atom and the like. Examples thereof include a pyrrolidinyl group, a tetrahydrofuryl (e.g., 3-tetrahydrofuryl) group, a tetrahydrothienyl group, an imidazolidinyl group, a pyrazolidinyl group, a 1,3-dioxolanyl group, a 1,3-oxathioranyl group, an oxazolidinyl group, a thiazolidinyl group, a piperidinyl group, a piperazinyl group, a tetrahydropyranyl group, a tetrahydrothiopyranyl group, a dioxanyl group, a morpholinyl group, a thiomorpholinyl group and the like.

The "group A" includes the following substituents (a) to (i).
(a) —CO—NR$^{A1}$R$^{A2}$
  wherein $R^{A1}$ and $R^{A2}$ are the same or different and each is
    (i) a hydrogen atom,
    (ii) a $C_{1-6}$ alkyl group optionally substituted by the same or different 1 to 5 substituents selected from the following group B, or
    (iii) a $C_{3-43}$ cycloalkyl group, or
    $R^{A1}$ and $R^{A2}$ optionally form, together with the nitrogen atom bonded thereto, a saturated monocyclic hetero ring optionally containing, besides carbon atom and one nitrogen atom, 1 to 3 hetero atoms selected from a nitrogen atom, an oxygen atom and a sulfur atom, and optionally substituted by the same or different 1 to 5 substituents selected from the following group B,
(b) a hydroxyl group,
(c) a $C_{1-6}$ alkoxy group,
(d) a $C_{1-6}$ alkoxy-$C_{1-6}$ alkoxy group,
(e) a cyano group,
(f) —NR$^{A3}$R$^{A4}$
  wherein $R^{A3}$ and $R^{A4}$ are the same or different and each is
    (i) a hydrogen atom,
    (ii) a $C_{1-6}$ alkyl group,
    (iii) a $C_{1-6}$ alkyl-carbonyl group, or
    (iv) a $C_{1-6}$ alkyl-sulfonyl group, or
    $R^{A3}$ and $R^{A4}$ optionally form, together with the nitrogen atom bonded thereto, a hetero ring optionally containing, besides carbon atom and one nitrogen atom, 1 to 5 hetero atoms selected from a nitrogen atom, an oxygen atom and a sulfur atom, and optionally substituted by 1 or 2 oxo groups,
(g) a carboxyl group,
(h) a $C_{1-6}$ alkyl-sulfonyl group, and
(i) a $C_{1-6}$ alkyl-carbonyl group.

The "$C_{1-6}$ alkyl group optionally substituted by the same or different 1 to 5 substituents selected from group A" is that wherein the "$C_{1-6}$ alkyl group" defined above is optionally substituted by the same or different 1 to 5 (e.g., 1 to 3, preferably 1) substituents selected from "group A" defined above, and includes an unsubstituted $C_{1-6}$ alkyl group.

The "group B" includes the following substituents (a) to (e).
(a) a hydroxyl group,
(b) a $C_{1-6}$ alkoxy group,
(c) a $C_{1-6}$ alkoxy-$C_{1-6}$ alkyl group,
(d) a $C_{3-8}$ cycloalkyl group, and
(e) an oxo group.

The "$C_{1-6}$ alkyl group optionally substituted by the same or different 1 to 5 substituents selected from group B" is that wherein the "$C_{1-6}$ alkyl group" defined above is optionally substituted by the same or different 1 to 5 (e.g., 1 to 3, preferably 1) substituents selected from the "group B" defined above, and includes an unsubstituted $C_{1-6}$ alkyl group.

The "saturated monocyclic hetero ring is optionally substituted by the same or different 1 to 5 substituents selected from group B" for $R^a$ and $R^b$, or $R^{A1}$ and $R^{A2}$ means that the "saturated monocyclic hetero ring" defined above which is formed by $R^a$ and $R^b$, or $R^{A1}$ and $R^{A2}$ together with the nitrogen atom bonded thereto is optionally substituted by the same or different 1 to 5 (e.g., 1 to 3, preferably 1) substituents selected from the "group B" defined above, and includes an unsubstituted saturated monocyclic hetero ring.

In the above-mentioned formula [I], preferable groups are as described below.

$R^1$ is
(1) a $C_{1-6}$ alkyl group optionally substituted by the same or different 1 to 5 substituents selected from
    (i) a $C_{3-8}$ cycloalkyl group, and
    (ii) a $C_{1-6}$ alkoxy group,
(2) a $C_{3-8}$ cycloalkyl group, or
(3) a saturated monocyclic heterocyclic group containing, besides carbon atom, 1 to 3 hetero atoms selected from a nitrogen atom, an oxygen atom and a sulfur atom.

Preferable embodiment of $R^1$ is a $C_{1-6}$ alkyl group optionally substituted by the same or different 1 to 5 substituents selected from
    (i) a $C_{3-8}$ cycloalkyl group, and
    (ii) a $C_{1-6}$ alkoxy group.

More preferable embodiment of $R^1$ is a $C_{1-6}$ alkyl group.

A different, more preferable embodiment of $R^1$ is a $C_{1-6}$ alkyl group substituted by a $C_{3-8}$ cycloalkyl group.

A different, preferable embodiment of $R^1$ is a $C_{3-8}$ cycloalkyl group.

Further different preferable embodiments of $R^1$ are
(1) a $C_{1-6}$ alkyl group optionally substituted by the same or different 1 to 3 $C_{3-8}$ cycloalkyl groups,
(2) a $C_{3-8}$ cycloalkyl group,
(3) a 5- or 6-membered saturated monocyclic heterocyclic group containing, besides carbon atom, 1 to 3 (e.g., 1) hetero atoms selected from a nitrogen atom, an oxygen atom and a sulfur atom, and the like.

Of these, preferred are a methyl group, a cyclopropylmethyl group, an ethyl group, a 1-cyclopropylethyl group, a propyl group, an isopropyl group, a butyl group, an isobutyl group, a sec-butyl group, a tert-butyl group, a 1,2-dimethylpropyl group, a 2,2-dimethylpropyl group, a 1-ethylpropyl group, a cyclopropyl group, a cyclobutyl group, a cyclopentyl group, a tetrahydrofuryl (e.g., 3-tetrahydrofuryl) group and the like.

$R^2$, $R^3$, $R^4$ and $R^5$ are the same or different and each is
(1) a hydrogen atom,
(2) a carboxyl group,
(3) —CO—$NR^aR^b$
    wherein $R^a$ and $R^b$ are the same or different and each is
    (i) a hydrogen atom,
    (ii) a $C_{1-6}$ alkyl group optionally substituted by the same or different 1 to 5 substituents selected from the above-mentioned group B, or
    (iii) a $C_{3-8}$ cycloalkyl group, or
    $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the above-mentioned group B,
(4) a $C_{1-6}$ alkyl group optionally substituted by the same or different 1 to 5 substituents selected from the above-mentioned group A, or
(5) a cyano group.

In a preferable embodiment of $R^2$, $R^3$, $R^4$ and $R^5$, one of $R^2$, $R^3$, $R^4$ and $R^5$ is —CO—$NR^aR^b$
    wherein $R^a$ and $R^b$ are the same or different and each is
    (i) a hydrogen atom,
    (ii) a $C_{1-6}$ alkyl group optionally substituted by the same or different 1 to 5 substituents selected from the above-mentioned group B, or
    (iii) a $C_{3-8}$ cycloalkyl group, or
    $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the above-mentioned group B.

In another preferable embodiment of $R^2$, $R^3$, $R^4$ and $R^5$, one of $R^2$, $R^3$, $R^4$ and $R^5$ is a $C_{1-6}$ alkyl group optionally substituted by the same or different 1 to 5 substituents selected from the above-mentioned group A.

Further preferable embodiments of $R^2$, $R^3$, $R^4$ and $R^5$ are respectively shown below.

As $R^2$, preferred are
(1) a hydrogen atom,
(2) a carboxyl group,
(3) —CO—$NR^aR^b$
    wherein $R^a$ and $R^b$ are the same or different and each is
    (i) a hydrogen atom, and
    (ii) a $C_{1-6}$ alkyl group, or
    $R^a$ and $R^b$ optionally form, together with the nitrogen atom bonded thereto, a 4- to 7-membered (e.g., 4- to 6-membered) saturated monocyclic hetero ring optionally containing, besides carbon atom and one nitrogen atom, 1 to 5 (e.g., 1 to 3, preferably 1) hetero atoms selected from a nitrogen atom, an oxygen atom and a sulfur atom,
(4) a $C_{1-6}$ alkyl group optionally substituted by the same or different 1 to 3 (e.g., 1) substituents selected from
    (a) —CO—$NR^{A1}R^{A2}$
        wherein $R^{A1}$ and $R^{A2}$ are the same or different and each is
        (i) a hydrogen atom, or
        (ii) a $C_{1-6}$ alkyl group,
    (b) a hydroxyl group,
    (c) a $C_{1-6}$ alkoxy group,
    (d) a $C_{1-6}$ alkoxy-$C_{1-6}$ alkoxy group, (e) a cyano group,
(f) —NR$^{A3}$R$^{A4}$
  wherein R$^{A3}$ and R$^{A4}$ are the same or different and each is
  (i) a hydrogen atom,
  (ii) a $C_{1-6}$ alkyl group,
  (iii) a $C_{1-6}$ alkyl-carbonyl group, or
  (iv) a $C_{1-6}$ alkyl-sulfonyl group, and
(g) a carboxyl group, and
(5) a cyano group.

As R$^2$, more preferred are
(1) a hydrogen atom,
(2) a carboxyl group,
(3) —CO—NR$^a$R$^b$
  wherein R$^a$ and R$^b$ are the same or different and each is
  (i) a hydrogen atom,
  (ii) a methyl group,
  (ii') an ethyl group,
  (ii'') an isopropyl group, or
  (ii''') a tert-butyl group, or
  R$^a$ and R$^b$ optionally form, together with the nitrogen atom bonded thereto, a saturated monocyclic hetero ring selected from azetidine, pyrrolidine and morpholine,
(4) a methyl group, an ethyl group, a propyl goroup, or an isopropyl group, which is optionally substituted by the same or different 1 to 3 (e.g., 1) substituents selected from
  (a) —CO—NR$^{A1}$R$^{A2}$
    wherein R$^{A1}$ and R$^{A2}$ are the same or different and each is
    (i) a hydrogen atom, or
    (ii) a methyl group,
  (b) a hydroxyl group,
  (c) a methoxy group,
  (c') an ethoxy group,
  (c'') an isopropoxy group,
  (d) a methoxyethoxy group,
  (e) a cyano group,
  (f) —NR$^{A3}$R$^{A4}$
    wherein R$^{A3}$ and R$^{A4}$ are the same or different and each is a hydrogen atom, a methyl group, a methylcarbonyl group, an isopropylcarbonyl group, a tert-butylcarbonyl group, a 1,1-dimethylpropylcarbonyl group or a methylsulfonyl group, and
  (g) a carboxyl group, and
(5) a cyano group.

As R$^3$, preferred are
(1) a hydrogen atom, and
(2) a $C_{1-6}$ alkyl group optionally substituted by a $C_{1-6}$ alkoxy group.

As R$^3$, more preferred are a hydrogen atom, a methyl group and a methoxymethyl group.

As R$^4$, preferred are
(1) a hydrogen atom,
(2) a carboxyl group,
(3) —CO—NR$^a$R$^b$
  wherein R$^a$ and R$^b$ are the same or different and each is
  (i) a hydrogen atom,
  (ii) a $C_{1-6}$ alkyl group optionally substituted by the same or different 1 to 5 (e.g., 1 to 3, preferably 1) substituents selected from a $C_{1-6}$ alkoxy group and a $C_{3-8}$ cycloalkyl group, or
  (iii) a $C_{3-8}$ cycloalkyl group, or
  R$^a$ and R$^b$ optionally form, together with the nitrogen atom bonded thereto, a saturated monocyclic hetero ring which is a 4- to 7-membered (e.g., 4- to 6-membered) saturated monocyclic hetero ring which is optionally containing, besides carbon atom and one nitrogen atom, 1 to 5 (e.g., 1 to 3, preferably 1) hetero atoms selected from a nitrogen atom, an oxygen atom and a sulfur atom, and optionally substituted by the same or different 1 to 5 (e.g., 1 to 3, preferably 1) substituents selected from (a) a hydroxyl group, (b) a $C_{1-6}$ alkoxy group, (c) a $C_{1-6}$ alkoxy-$C_{1-6}$ alkyl group and (d) an oxo group,
(4) a $C_{1-6}$ alkyl group optionally substituted by the same or different 1 to 5 (e.g., 1 to 3, preferably 1) substituents
  (a) —CO—NR$^{A1}$R$^{A2}$
    wherein R$^{A1}$ and R$^{A2}$ are the same or different and each is selected from
    (i) a hydrogen atom,
    (ii) a $C_{1-6}$ alkyl group optionally substituted by the same or different 1 to 5 (e.g., 1 to 3, preferably 1) $C_{1-6}$ alkoxy groups, or
    (iii) a $C_{3-8}$ cycloalkyl group, or
    R$^{A1}$ and R$^{A2}$ optionally form, together with the nitrogen atom bonded thereto, a saturated monocyclic hetero ring which is a 4- to 6-membered saturated monocyclic hetero ring optionally containing, besides carbon atom and one nitrogen atom, 1 to 3 (e.g., 1) hetero atoms selected from a nitrogen atom, an oxygen atom and a sulfur atom, and optionally substituted by a $C_{1-6}$ alkoxy group,
  (b) a hydroxyl group,
  (c) a $C_{1-6}$ alkoxy group,
  (d) a $C_{1-6}$ alkoxy-$C_{1-6}$ alkoxy group,
  (e) a cyano group,
  (f) —NR$^{A3}$R$^{A4}$
    wherein R$^{A3}$ and R$^{A4}$ are the same or different and each is
    (i) a hydrogen atom,
    (ii) a $C_{1-6}$ alkyl group,
    (iii) a $C_{1-6}$ alkyl-carbonyl group, or
    (iv) a $C_{1-6}$ alkyl-sulfonyl group, or
    R$^{A3}$ and R$^{A4}$ optionally form, together with the nitrogen atom bonded thereto, a hetero ring which is a 4- to 7-membered (e.g., 6-membered) monocyclic hetero ring, or a 8- to 10-membered (e.g., 9-membered) fused cyclic hetero ring optionally containing, besides carbon atom and one nitrogen atom, 1 to 5 hetero atoms selected from a nitrogen atom, an oxygen atom and a sulfur atom, and optionally substituted by 1 or 2 oxo groups,
  (g) a carboxyl group,
  (h) a $C_{1-6}$ alkyl-sulfonyl group, and
  (i) a $C_{1-6}$ alkyl-carbonyl group, and
(5) a cyano group.

As R$^4$, more preferred are
(1) a hydrogen atom,
(2) a carboxyl group,
(3) —CO—NR$^a$R$^b$
  wherein R$^a$ and R$^b$ are the same or different and each is
  (i) a hydrogen atom,
  (ii) a methyl group, an ethyl group, an isopropyl group or an isobutyl group, which is optionally substituted by the same or different one substituent selected from a methoxy group and a cyclopropyl group, or
  (iii) a cyclopropyl group, or
  R$^a$ and R$^b$ optionally form, together with the nitrogen atom bonded thereto, a saturated monocyclic hetero ring selected from azetidine, pyrrolidine, piperidine and morpholine, which is optionally substituted by one substituent selected from a hydroxyl group, a methoxy group, a methoxymethyl group and an oxo group,
(4) a methyl group, an ethyl group, a propyl group, an isopropyl group or a tert-butyl group, which is optionally substituted by one or two substituents selected from
(a) —CO—NR$^{41}$R$^{42}$
wherein R$^{41}$ and R$^{42}$ are the same or different and each is
(i) a hydrogen atom,
(ii) a methyl group, an ethyl group, an isopropyl group or an isobutyl group, which is optionally substituted by a methoxy group, or
(iii) a cyclopropyl group, or
R$^{41}$ and R$^{42}$ optionally form, together with the nitrogen atom bonded thereto, a saturated monocyclic hetero ring selected from azetidine, piperidine and morpholine, and optionally substituted by a methoxy group,
(b) a hydroxyl group,
(c) a methoxy group,
(c') an ethoxy group,
(c") a propoxy group,
(c''') an isopropoxy group,
(c"") a butoxy group,
(d) a methoxyethoxy group,
(d') an ethoxyethoxy group,
(d") a methoxypropoxy group,
(d''') a methoxyisopropoxy group,
(d"") an isopropoxyethoxy group,
(e) a cyano group,
(f) —NR$^{43}$R$^{44}$
wherein R$^{43}$ and R$^{44}$ are the same or different and each is a hydrogen atom, a methyl group, an ethyl group, an isopropyl group, a methylcarbonyl group, an ethylcarbonyl group, an isopropylcarbonyl group, a methylsulfonyl group or a tert-butylsulfonyl group, or
R$^{43}$ and R$^{44}$ optionally form, together with the nitrogen atom bonded thereto, pyrazole, triazole (e.g., 1,2,4-triazole), tetrazole, oxazolidine or isoindoline, which is optionally substituted by 1 or 2 oxo groups,
(g) a carboxyl group,
(h) a methylsulfonyl group, and
(i) a methylcarbonyl group, and
(5) a cyano group.

As R$^5$, preferred are a hydrogen atom and a C$_{1-6}$ alkyl group optionally substituted by one substituent selected from a C$_{1-6}$ alkoxy group and a C$_{1-6}$ alkoxy-C$_{1-6}$ alkoxy group.

As R$^5$, more preferred are a hydrogen atom and a methyl group or an ethyl group, which is optionally substituted by one substituent selected from a methoxy group and a methoxyethoxy group.

R$^2$ and R$^3$, or R$^4$ and R$^5$ optionally form, together with the carbon atom bonded thereto, i) C$_{3-8}$ cycloalkane or ii) a saturated monocyclic hetero ring containing, besides carbon atom, 1 to 6 hetero atoms selected from a nitrogen atom, an oxygen atom and a sulfur atom.

As the ring formed by R$^2$ and R$^3$, or R$^4$ and R$^5$ together with the carbon atom bonded thereto, preferred are
i) C$_{3-8}$ cycloalkane, and
ii) a 5- to 7-membered (e.g., 6-membered) saturated monocyclic hetero ring containing, besides carbon atom, 1 to 6 (e.g., 1 to 3, preferably 1) hetero atoms selected from a nitrogen atom, an oxygen atom and a sulfur atom.

As the ring formed by R$^2$ and R$^3$, or R$^4$ and R$^5$ together with the carbon atom bonded thereto, more preferred are cyclopropane and tetrahydropyran.

Here, R$^2$, R$^3$, R$^4$ and R$^5$ are not hydrogen atoms at the same time.

R$^6$ is
(1) a C$_{1-6}$ alkyl group optionally substituted by the same or different 1 to 5 (e.g., 1 to 3) halogen atoms,
(2) a C$_{1-6}$ alkoxy group,
(3) a halogen atom, or
(4) a C$_{3-8}$ cycloalkyl group.

As R$^6$, preferred is a halogen atom.

Other preferable embodiments of R$^6$ are a methyl group, a trifluoromethyl group, a methoxy group, an ethoxy group, a fluorine atom, a chlorine atom, a bromine atom and a cyclopropyl group.

Y is
(1) CH, or
(2) a nitrogen atom.

As Y, preferred is CH.

Other preferable embodiment of Y is a nitrogen atom.

m is an integer of 1 to 5, and when m is an integer of 2 to 5, the above-mentioned R$^6$ may be the same or different.

As m, preferred is 1 to 3.

As m, more preferred is 1 or 2.

n is an integer of 1 to 3.

As n, preferred is 1.

In the above-mentioned formula [I-1], preferable groups are as described below.

R$^{11}$ is
(1) a C$_{1-6}$ alkyl group optionally substituted by the same or different 1 to 5 substituents selected from
(i) a C$_{3-8}$ cycloalkyl group, and
(ii) a C$_{1-6}$ alkoxy group, or
(2) a C$_{3-8}$ cycloalkyl group.

As R$^{11}$, those exemplified as the preferable embodiments of R$^1$ in the above-mentioned formula (I), which are within the scope of R$^{11}$, are preferable.

R$^{21}$, R$^{31}$, R$^{41}$ and R$^{51}$ are the same or different and each is
(1) a hydrogen atom,
(2) —CO—NR$^a$R$^b$
wherein R$^a$ and R$^b$ are the same or different and each is
(i) a hydrogen atom,
(ii) a C$_{1-6}$ alkyl group optionally substituted by the same or different 1 to 5 substituents selected from the above-mentioned group B, and
(iii) a C$_{3-8}$ cycloalkyl group, or
R$^a$ and R$^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the above-mentioned group B, or
(3) a C$_{1-6}$ alkyl group optionally substituted by the same or different 1 to 5 substituents selected from the above-mentioned group A.

As R$^{21}$, preferred is a hydrogen atom.

Other preferable embodiment of R$^{21}$ is a C$_{1-6}$ alkyl group optionally substituted by the same or different 1 to 5 substituents selected from the above-mentioned group A. More preferred is a C$_{1-6}$ alkyl group.

Examples of yet other preferable embodiment of $R^{21}$ include those exemplified as the preferable embodiments of $R^2$ in the above-mentioned formula (I), which are within the scope of $R^{21}$.

As $R^{31}$, preferred is a hydrogen atom.

Examples of other preferable embodiment of $R^{31}$ include those exemplified as the preferable embodiments of $R^3$ in the above-mentioned formula (I), which are within the scope of $R^{31}$.

As $R^{41}$, preferred is a hydrogen atom.

Other preferable embodiment of $R^{41}$ is a $C_{1-6}$ alkyl group optionally substituted by the same or different 1 to 5 substituents selected from the above-mentioned group A. More preferred is a $C_{1-6}$ alkyl group.

Examples of yet other preferable embodiment of $R^{41}$ include those exemplified as the preferable embodiments of $R^4$ in the above-mentioned formula (I), those contained within the scope of $R^{41}$.

As $R^{51}$, preferred is a hydrogen atom.

Other preferable embodiments of $R^{51}$ are those exemplified as the preferable embodiments of $R^5$ in the above-mentioned formula (I), which are within the scope of $R^{51}$.

Here, $R^{21}$, $R^{31}$, $R^{41}$ and $R^{51}$ are not hydrogen atoms at the same time.

$R^{61}$ is a halogen atom.

As $R^{61}$, preferred are a fluorine atom and a chlorine atom.

$R^{62}$ is a hydrogen atom or a halogen atom.

As $R^{62}$, preferred are a hydrogen atom, a fluorine atom and a bromine atom.

In the above-mentioned formula [I-2], preferable groups are as described below.

$R^{12}$ is a $C_{1-6}$ alkyl group optionally substituted by the same or different 1 to 5 substituents selected from (i) a $C_{3-8}$ cycloalkyl group, and (ii) a $C_{1-6}$ alkoxy group.

As $R^{12}$, those exemplified as the preferable embodiments of $R^1$ in the above-mentioned formula (I), which are within the scope of $R^{12}$, are preferable.

$R^{22}$, $R^{32}$, $R^{42}$ and $R^{52}$ are the same or different and each is (1) a hydrogen atom, (2) —CO—$NR^aR^b$ wherein $R^a$ and $R^b$ are the same or different and each is (i) a hydrogen atom, (ii) a $C_{1-6}$ alkyl group optionally substituted by the same or different 1 to 5 substituents selected from the above-mentioned group B, or (iii) a $C_{3-8}$ cycloalkyl group, or $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the above-mentioned group B, or (3) a $C_{1-6}$ alkyl group optionally substituted by the same or different 1 to 5 substituents selected from the above-mentioned group A.

As $R^{22}$, preferred is a hydrogen atom.

Other preferable embodiments of $R^{22}$ are those exemplified as the preferable embodiments of $R^2$ in the above-mentioned formula (I), which are within the scope of $R^{22}$.

As $R^{32}$, preferred is a hydrogen atom.

Other preferable embodiments of $R^{32}$ are those exemplified as the preferable embodiments of $R^3$ in the above-mentioned formula (I), which are within the scope of $R^{32}$.

As $R^{42}$, preferred is —CO—$NR^aR^b$ wherein $R^a$ and $R^b$ form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the above-mentioned group B.

Other preferable embodiments of $R^{42}$ are those exemplified as the preferable embodiments of $R^4$ in the above-mentioned formula (I), which are within the scope of $R^{42}$.

As $R^{52}$, preferred is a $C_{1-6}$ alkyl group.

Other preferable embodiments of $R^{52}$ are those exemplified as the preferable embodiments of $R^5$ in the above-mentioned formula (I), which are within the scope of $R^{52}$.

Here, $R^{22}$, $R^{32}$, $R^{42}$ and $R^{52}$ are not hydrogen atoms at the same time.

$R^{63}$ is a halogen atom.

As $R^{63}$, preferred is a fluorine atom.

$R^{64}$ is a hydrogen atom or a halogen atom.

As $R^{64}$, preferred are a hydrogen atom and a fluorine atom.

As the compound of the present invention, compounds represented by the above-mentioned formula [I], the formula [I-1] and the formula [I-2], and compounds described in the following Examples are preferable.

A pharmaceutically acceptable salt of the "compounds represented by the above-mentioned formula [I], the formula [I-1] and the formula [I-2]" (hereinafter to be also referred to as the compound of the present invention) may be any salt as long as it forms an atoxic salt with the compound of the present invention. Examples thereof include a salt with an inorganic acid, a salt with an organic acid, a salt with an inorganic base, a salt with an organic base, a salt with an amino acid and the like.

Examples of the salt with an inorganic acid include salts with hydrochloric acid, nitric acid, sulfuric acid, phosphoric acid, hydrobromic acid and the like.

Examples of the salt with an organic acid include salts with oxalic acid, malonic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with an inorganic base include sodium salt, potassium salt, calcium salt, magnesium salt, ammonium salt and the like.

Examples of the salt with an organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with an amino acid include salts with lysine, arginine, aspartic acid, glutamic acid and the like.

Each salt can be obtained by reacting a compound represented by the formula [I], the formula [I-1] and the formula [I-2] with an inorganic base, an organic base, an inorganic acid, an organic acid or an amino acid according to a method known per se.

In the present invention, as the pharmaceutically acceptable salt of the compounds represented by the formula [I], the formula [I-1] and the formula [I-2], preferred are salts with hydrochloric acid (e.g., 1 hydrochloride, 2 hydrochloride), salts with hydrobromic acid (e.g., 1 hydrobromide, 2 hydrobromide), and sodium salt.

The "solvate" is a compound represented by the formula [I], the formula [I-1] and the formula [I-2] or a pharmaceutically acceptable salt thereof, with which a molecule of a solvent is coordinated, and also encompasses hydrates (also referred to as water-containing compound). The solvate is preferably a pharmaceutically acceptable solvate, such as a 1 hydrate, a ½ hydrate, a 2 hydrate, a 1 hydrate of sodium salt, a 1 methanolate, a 1 ethanolate, a 1 acetonitrilate, a ⅔ ethanolate of 2 hydrochloride of the compound represented by the formula [I], the formula [I-1] and the formula [I-2] and the like.

A solvate of a compound represented by the formula [I], the formula [I-1] and the formula [I-2] or a pharmaceutically acceptable salt thereof can be obtained according to a method known per se.

In addition, there can be various isomers of compounds represented by the above-mentioned formulas [I], [I-1] and [I-2]. For example, when E form and Z form are present as geometric isomers, and when an asymmetric carbon atom is present, enantiomers and diastereomers are present as stereo isomers based on them. In addition, when axial chirality is present, stereo isomers based thereon are present. Where necessary, tautomers can be present. Accordingly, all of such isomers and mixtures thereof are encompassed in the scope of the present invention. As the compound of the present invention, one isolated and purified from various isomers, by-products, metabolites or prodrugs is preferable, and one having a purity of not less than 90% is preferable and one having a purity of not less than 95% is more preferable.

In addition, the compounds represented by the formula [I], the formula [I-1] and the formula [I-2] may be crystal or amorphous.

In addition, a compound represented by the formula [I], the formula [I-1] and the formula [I-2] may be labeled with an isotope (e.g., $^3H$, $^{14}C$, $^{35}S$ etc.).

As the compounds represented by the formula [I], the formula [I-1] and the formula [I-2] or a pharmaceutically acceptable salt thereof, or a solvate thereof, compounds represented by the formula [I], the formula [I-1] and the formula [I-2] or a pharmaceutically acceptable salt thereof, or a solvate thereof, which is substantially purified, is preferable. More preferred is compounds represented by the formula [I], the formula [I-1] and the formula [I-2] or a pharmaceutically acceptable salt thereof, or a solvate thereof, which has been purified to a purity of not less than 80%.

In the present invention, a prodrug of a compound represented by the formula [I], the formula [I-1] and the formula [I-2] can also be a useful medicament.

A "prodrug" is a derivative of the compound of the present invention, which has a chemically or metabolically decomposable group and which restores to the original compound to show its inherent efficacy after administration to the body by, for example, hydrolysis, solvolysis or decomposition under physiological conditions. It includes a complex and a salt, not involving a covalent bond.

The prodrug is utilized, for example, for improving absorption by oral administration or targeting of a target site.

Examples of the site to be modified include highly reactive functional groups in the compound of the present invention, such as hydroxyl group, carboxyl group, amino group and the like.

Examples of the hydroxyl-modifying group include acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumaryl group and the like. In addition, a sodium salt of 3-carboxybenzoyl group, 2-carboxyethylcarbonyl group and the like can also be used.

Examples of the carboxyl-modifying group include methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethoxycarbonyloxy) ethyl group, 1-(isopropyloxycarbonyloxy)ethyl group, 1-(cyclohexyloxycarbonyloxy)ethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like.

Examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like.

Examples of the "pharmaceutical composition" include oral preparations such as tablet, capsule, granule, powder, troche, syrup, emulsion, suspension and the like, and parenteral agents such as external preparation, suppository, injection, eye drop, transnasal agent, pulmonary preparation and the like.

The pharmaceutical composition of the present invention (e.g., an anti-HIV composition, a pharmaceutical composition for HIV integrase inhibitory etc.) is produced by appropriately admixing a suitable amount of a compound represented by the formula [I], the formula [I-1] or the formula [I-2] of the present invention or a salt thereof, or a solvate thereof with at least one kind of a pharmaceutically acceptable carrier according to a method known per se in the technical field of pharmaceutical preparations. The content of the compound represented by the formula [I], the formula [I-1] or the formula [I-2] of the present invention or a salt thereof, or a solvate thereof in the pharmaceutical composition varies depending on the dosage form, the dose and the like, and the like. It is, for example, 0.1 to 100 wt % of the whole composition.

Examples of the "pharmaceutically acceptable carrier" include various organic or inorganic carrier substances conventionally used as preparation materials such as excipient, disintegrant, binder, fluidizer, lubricant and the like for solid dosage forms, and solvent, solubilizing agent, suspending agent, isotonicity agent, buffering agent, soothing agent and the like for liquid preparations. Where necessary, additives such as preservative, antioxidant, colorant, sweetening agent and the like are used.

Examples of the "excipient" include lactose, sucrose, D-mannitol, D-solbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "fluidizer" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agent" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonicity agent" include glucose, D-sorbitol, sodium chloride, D-mannitol and the like.

Examples of the "buffering agent" include sodium hydrogen phosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color yellow 4 or 5 etc.), 13-carotene and the like.

Examples of the "sweetening agent" include saccharin sodium, dipotassium glycyrrhizinate, aspartame and the like.

The pharmaceutical composition of the present invention can be administered not only to human but also to mammals other than human (e.g., mouse, rat, hamster, guinea pig, rabbit, cat, dog, swine, bovine, horse, sheep, monkey etc.) orally or parenterally (e.g., topical, rectal, intravenous administration etc.). While the dose varies depending on the subject of administration, disease, symptom, dosage form, administration route and the like, for example, the dose for oral administration to an adult patient (body weight: about 60 kg) is generally within the scope of about 1 mg to 1 g per day, based on the compound of the present invention as an active ingredient. The amount can be administered in one to several portions.

The compounds represented by the above-mentioned formula [I], the formula [I-1] and the formula [I-2] or a pharmaceutically acceptable salt thereof, or a solvate thereof inhibits HIV integrase, and can be used as an active ingredient of a therapeutic agent or prophylactic agent for HIV infection.

To "inhibit HIV integrase" means to specifically inhibit the function as HIV integrase to eliminate or attenuate the activity thereof. For example, it means to specifically inhibit the function of HIV integrase under the conditions of the below-mentioned Experimental Example 1. As the "inhibition of HIV integrase", preferred is "inhibition of human HIV integrase". As the "HIV integrase inhibitor", preferred is a "human HIV integrase inhibitor".

The compounds represented by the above-mentioned formula [I], the formula [I-1] and the formula [I-2] or a pharmaceutically acceptable salt thereof, or a solvate thereof can be used in combination (hereinafter to be referred to as combination use) with other single or plural medicaments (hereinafter to be also referred to as a concomitant drug) by a conventional method generally employed in the medicament field.

The administration frequency of the compounds represented by the above-mentioned formula [I], the formula [I-1] and the formula [I-2], or a pharmaceutically acceptable salt thereof, or a solvate thereof, and a concomitant drug is not limited, and they may be administered as a combined agent to the subject of administration, or the two may be administered simultaneously or at certain time intervals. In addition, they may be used as a medicament in the form of a kit containing the pharmaceutical composition of the present invention and a concomitant drug. The dose of the concomitant drug may be determined according to the dosage used clinically, and can be appropriately determined depending on the subject of administration, disease, symptom, dosage form, administration route, administration time, combination and the like. The administration form of the concomitant drug is not particularly limited, and the compound of the present invention or a salt thereof, or a solvate thereof and the concomitant drug need only be combined.

An anti-HIV agent is generally required to sustain its effect for a long time, so that can be effective not only for temporal suppression of viral growth but also prohibition of viral re-growth. This means that a prolonged administration is necessary and that a high single dose may be frequently inevitable to sustain effect for a longer period through the night. Such prolonged and high dose administration increases the risk of causing side effects.

In view of this, one of the preferable embodiments of the compound of the present invention is such compound permitting high absorption by oral administration, and such compound capable of maintaining blood concentration of the administered compound for an extended period of time.

In addition to the above-mentioned, preferable embodiments of the compound of the present invention are a compound having fine pharmacological activity (e.g., a compound having strong HIV integrase inhibitory activity, a compound having high anti-HIV activity), a compound having fine bioavailability (e.g., a compound having high cellular membrane permeability, a compound stable to metabolic enzyme, a compound with low binding ability to protein and the like), a compound having an anti-HIV activity against HIV having G140S/Q148H mutation, and the like.

Of the compounds of the present invention, a compound having high pharmacological activity (concretely, $IC_{50}$ of HIV integrase inhibitory activity is less than 0.1 µM, preferably less than 0.01 µM) and high oral absorption, whose blood concentration is maintained for a long time after administration, is more preferable.

Using the above-mentioned compound, dose and/or frequency of administration of the compound of the present invention to human are/is expected to be decreased. Preferable administration frequency is not more than twice a day, more preferably, not more than once a day (e.g., once a day, once in two days, etc.).

The compound of the present invention can be used for the improvement of viremia due to HIV and/or maintenance of improved condition thereof, prophylaxis and treatment of virus infections, particularly, an HIV infection and/or maintenance of improved condition thereof.

As an index of the "treatment", "improvement" or "effect", a decrease in the virus level or HIV RNA level in the body, particularly in blood, can be used.

The "prophylaxis of HIV infection" includes administration of a medicament to a person with suspected or possible HIV infection (infection due to transfusion, infection from mother to child), and the like.

By the "prophylaxis of AIDS" is meant, for example, administration of a medicament to an individual who tested HIV positive but has not yet developed the disease state of AIDS; administration of a medicament to an individual who shows an improved disease state of AIDS after treatment but who carries HIV still to be eradicated and whose relapse of AIDS is worried; administration of a medicament before infection with HIV out of a fear of possible infection; and the like.

Examples of the "other anti-HIV agents" and "other anti-HIV active substances" to be used for a multiple drug combination therapy include an anti-HIV antibody or other antibody, an HIV vaccine or other vaccine, immunostimulants such as interferon, interferon agonist and the like, a ribozyme against HIV, an HIV antisense drug, an HIV reverse transcriptase inhibitor, an HIV protease inhibitor, an HIV integrase inhibitor, an inhibitor of attachment between a receptor (CD4, CXCR4, CCR5 and the like) of a host cell recognized by virus and the virus (CCR5 antagonist and the like), a DNA polymerase inhibitor or DNA synthesis inhibitor, a medicament acting on HIVp24, an HIV fusion inhibitor, an IL-2 agonist or antagonist, a TNF-α antagonist, an α-glucosidase inhibitor, a purine nucleoside phosphorylase inhibitor, an apoptosis agonist or inhibitor, a cholinesterase inhibitor, an immunomodulator and the like.

Specific examples of the HIV reverse transcriptase inhibitor include Retrovir(R) (zidovudine), Epivir(R) (lamivudine), Zerit(R) (sanilvudine), Videx(R) (didanosine), Hivid(R) (zalcitabine), Ziagen(R) (abacavir sulfate), Viramune(R) (nevirapine), Stocrin(R) (efavirenz), Rescriptor(R) (delavirdine mesylate), Combivir(R) (zidovudine+lamivudine), Trizivir(R) (abacavir sulfate+lamivudine+zidovudine), Coactinon(R) (emivirine), Phosphonovir(R), Coviracil(R), alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis(isopropoxycarbonyloxymethyl)ester fumarate), DPC-083 ((4S)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2(1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, BCH-10618, DPC-083, Etravirine, BCH-13520, MIV-210, Abacavir sulfate/lamivudine, GS-7340, GW-5634, GW-695634, TMC-278 and the like, wherein (R) means a registered trademark (hereinafter the same) and the names of other medicaments are general names.

Specific examples of the HIV protease inhibitor include Crixivan(R) (indinavir sulfate ethanolate), saquinavir, Invirase(R) (saquinavir mesylate), Norvir(R) (ritonavir), Viracept(R) (nelfinavir mesylate), lopinavir, Prozei(R) (amprenavir), Kaletra(R) (ritonavir+lopinavir), mozenavir dimesylate ([4R-(4α,5α,6β)]-1,3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)—N-tert-butyl-3-[(2S,3S)-2-hydroxy-3-N-1(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy)phenylcarbonylamino]-1-oxabutyl]-4-[(2-methylphenyl)methylamino]carbonyl-4(R)-5,5-dimethyl-1,3-thiazole), BMS-232632 (dimethyl (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedicarboxylate), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649, AG-1859 and the like.

The HIV integrase inhibitor is exemplified by S-1360, L-870810 and the like, the DNA polymerase inhibitor or DNA synthesis inhibitor is exemplified by Foscavir(R), ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β,12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubitecan and the like, the HIV antisense drug is exemplified by HGTV-43, GEM-92 and the like, the anti-HIV antibody or other antibody is exemplified by NM-01, PRO-367, KD-247, Cytolin(R), TNX-355 (CD4 antibody), AGT-1, PRO-140 (CCR5 antibody), Anti-CTLA-4MAb and the like, the HIV vaccine or other vaccine is exemplified by ALVAC(R), AIDSVAX(R), Remune(R), HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, Anti-Tat, MVA-F6 Nef vaccine, HIV rev vaccine, C4-V3 peptide, p2249f, VIR-201, HGP-30W, TBC-3B, PARTICLE-3B, Antiferon (interferon-α vaccine) and the like, the interferon or interferon agonist is exemplified by Sumiferon(R), MultiFeron(R), interferon-τ, Reticulose, human leukocyte interferon α and the like, the CCR5 antagonist is exemplified by SCH-351125 and the like, the medicament acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl]naphthyl-2,5-dimethoxyphenyl-1,4-dihydrazone), T-1249, Synthetic Polymeric Construction No3, pentafuside, FP-21399, PRO-542, Enfuvirtide and the like, the IL-2 agonist or antagonist is exemplified by interleukin-2, Imunace(R), Proleukin(R), Multikine(R), Ontak(R) and the like, the TNF-α antagonist is exemplified by Thalomid(R) (thalidomide), Remicade(R) (infliximab), curdlan sulfate and the like, the α-glucosidase inhibitor is exemplified by Bucast(R) and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z(R), Panavir(R), Coenzyme Q10 (2-deca(3-methyl-2-butenylene)-5,6-dimethoxy-3-methyl-p-benzoquinone) and the like, the cholinesterase inhibitor is exemplified by Cognex(R) and the like, and the immunomodulator is exemplified by Immunox(R), Prokine(R), Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602, TK-303 (Elvitegravir) and the like.

In addition, Neurotropin(R), Lidakol(R), Ancer 20(R), Ampligen(R), Anticort(R), Inactivin(R), PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)-FTC, Ushercell, D2S, BufferGel(R), VivaGel(R), Glyminox vaginal gel, sodium lauryl sulfate, 2F5, 2F5/2G12, VRX-496, Ad5gag2, BG-777, IGIV-C, BILR-255 and the like are exemplified.

The compound of the present invention can be combined with one or more (e.g., 1 or 2) kinds of other anti-HIV active substances (to be also referred to as other anti-HIV agents), and used as an anti-HIV agent and the like for the prophylaxis or treatment of HIV infection. As the "other anti-HIV agents" and "other anti-HIV active substances" to be used for a multiple drug combination therapy with the compound of the present invention, preferred are an HIV reverse transcriptase inhibitor and an HIV protease inhibitor. Two or three, or even a greater number of medicaments can be used in combination, wherein a combination of medicaments having different action mechanisms is one of the preferable embodiments. In addition, selection of medicaments free of side effect duplication is preferable.

Specific examples of the combination of medicaments include a combination of a group consisting of efavirenz, tenofovir, emtricitabine, indinavir, nelfinavir, atazanavir, ritonavir+indinavir, ritonavir+lopinavir, ritonavir+saquinavir, didanosine+lamivudine, zidovudine+didanosine, stavudine+didanosine, zidovudine+lamivudine, stavudine+lamivudine and tenofovir+emtricitabine, and the compound of the present invention (Guidelines for the Use of Antiretroviral Agents in HIV-Infected Adults and Adolescents. Aug. 13, 2001). Particularly preferred is a combined use of two agents with efavirenz, indinavir, nelfinavir, tenofovir, emtricitabine, zidovudine or lamivudine, and a combined use of three agents with zidovudine+lamivudine, tenofovir+lamivudine, tenofovir+zidovudine, tenofovir+efavirenz, tenofovir+nelfinavir, tenofovir+indinavir, tenofovir+emtricitabine, emtricitabine+lamivudine, emtricitabine+zidovudine, emtricitabine+efavirenz, emtricitabine+nelfinavir, emtricitabine+indinavir, nelfinavir+lamivudine, nelfinavir+zidovudine, nelfinavir+efavirenz, nelfinavir+indinavir, efavirenz+lamivudine, efavirenz+zidovudine or efavirenz+indinavir.

In the case of combined administration, the compound of the present invention can be administered simultaneously with a medicament to be used in combination (hereinafter concomitant drug) or administered at certain time intervals. In the case of combined administration, a pharmaceutical composition comprising the compound of the present invention and a concomitant drug can be administered. Alternatively, a pharmaceutical composition comprising the compound of the present invention and a pharmaceutical composition comprising a concomitant drug may be administered separately. The administration route of the compound of the present invention and that of the concomitant drug may be the same or different.

In the case of a combined administration, the compound of the present invention can be administered once a day or several times a day in a single dose of 0.01 mg to 1 g, or may be administered at a smaller dose. The concomitant drug can be administered at a dose generally used for the prevention or treatment of an HIV infection, for example, at a single dose of 0.01 mg to 0.3 g. Alternatively, it may be administered in a smaller dose.

Now, production methods of the compound of the present invention are specifically explained. However, the present invention is not limited to these production methods. For production of the compound of the present invention, the order of reactions can be appropriately changed. The reactions may be performed from a reasonable step or a reasonable substitution moiety. In addition, an appropriate substituent conversion (conversion or further modification of substituent) step may be inserted between respective steps. When a reactive functional group is present, protection and deprotection may be appropriately performed. Furthermore, to promote the progress of reactions, reagents other than those exemplified below may be used as appropriate. The starting compounds whose production methods are not described are commercially available or can be easily prepared by a combination of known synthesis reactions. The compound obtained in each step can be purified by conventional methods such as distillation, recrystallization, column chromatography and the like. In some cases, the next step may be performed without isolation and purification.

In the following production methods, the "room temperature" means 1 to 40° C.

Production Method I

Production Method I-1

Of compounds [I-3-1] in the below-mentioned production method I-3, compound [I-1-6] which is compound [I-3-1] wherein Y is CH can be synthesized by the following method.

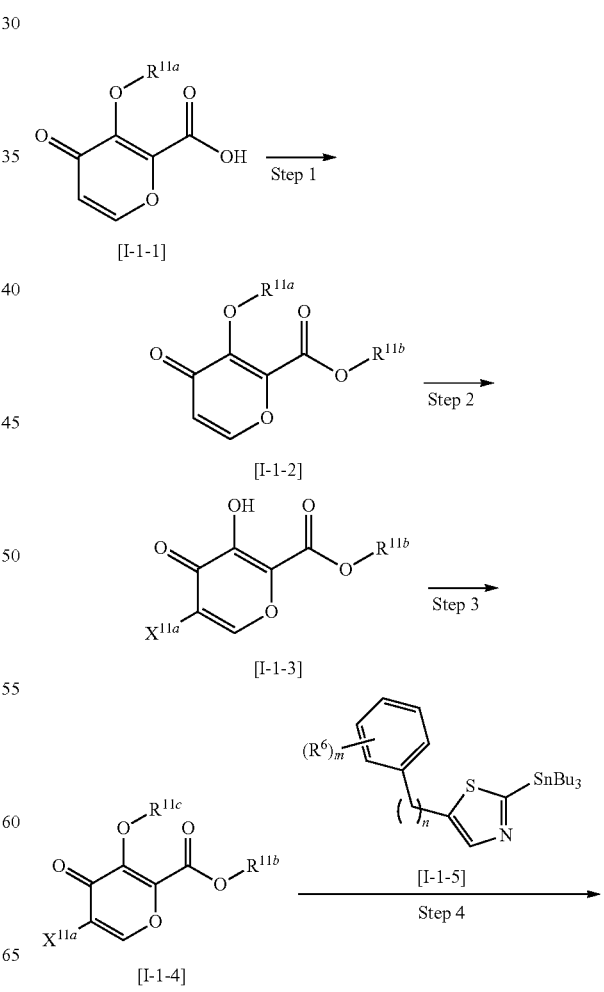

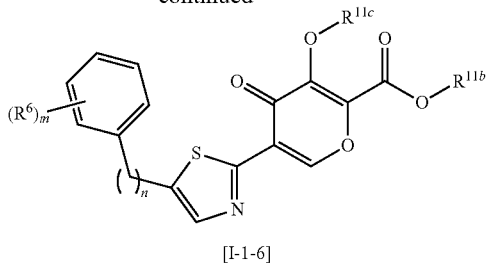

[I-1-6]

wherein $R^{11a}$ and $R^{11c}$ are the same or different and each is a hydroxyl-protecting group such as an acetyl group, a benzyl group, a methyl group, an ethyl group, an isopropyl group, a trimethylsilyl group, a triethylsilyl group, a tert-butyldimethylsilyl group, a triisopropylsilyl group, a tert-butyldiphenylsilyl group and the like, $R^{11b}$ is a carboxyl-protecting group such as a methyl group, an ethyl group, a benzyl group, a tert-butyl group and the like, $X^{11a}$ is a halogen atom such as a chlorine atom, a bromine atom and the like, and other symbols are each as described above.

Step 1

Compound [I-1-2] can be obtained by introducing a protecting group into the carboxyl group of compound [I-1-1] according to a known method.

For example, when $R^{11b}$ is a methyl group, compound [I-1-2] can be obtained by reacting compound [I-1-1] with trimethylsilyldiazomethane at a low temperature to room temperature in a single or mixed solvent such as tetrahydrofuran (THF), toluene, methanol, ethanol and the like.

Step 2

Compound [I-1-3] can be obtained by introducing a halogen atom $X^{11a}$ into compound [I-1-2] according to a known method.

For example, when $X^{11a}$ is a bromine atom, compound [I-1-3] can be obtained by reacting compound [I-1-2] with a bromination reagent (e.g., bromine, trimethylphenylammonium tribromide etc.) at room temperature to under heating in a solvent such as chloroform, methylene chloride, acetic acid and the like.

Step 3

Compound [I-1-4] can be obtained by introducing a protecting group into a hydroxyl group of compound [I-1-3] according to a known method.

For example, when $R^{11c}$ is a benzyl group, compound [I-1-4] can be obtained by reacting compound [I-1-3] with benzyl halide (e.g., benzyl chloride, benzyl bromide etc.) at room temperature to under heating in the presence of a base such as potassium acetate, potassium carbonate, potassium hydrogen carbonate, sodium hydrogen carbonate, potassium phosphate, triethylamine, sodium hydrogen phosphate, cesium carbonate, sodium hydride, potassium t-butoxide, lithiumdiisopropylamide (LDA) and the like in a solvent such as N,N-dimethylformamide (DMF), dimethylacetamide (DMA), acetonitrile, 1,2-dimethoxyethane, THF, toluene and the like.

Step 4

Compound [I-1-6] can be obtained by subjecting compound [I-1-4] to a coupling reaction with compound [I-1-5] in the presence of a palladium catalyst (e.g., tris(dibenzylideneacetone)dipalladium(0), tetrakis(triphenylphosphine)palladium(0) and bis(triphenylphosphine)palladium (II) dichloride etc.) at room temperature to under heating in a solvent such as DMF, DMA, acetonitrile, toluene, 1,4-dioxane and the like. For preferable progress of the reaction, a ligand (e.g., tri(2-furyl)phosphine, tributylphosphine etc.) may be further added.

For example, compound [I-1-5] wherein n is 1 can be obtained in the same manner as in step 1R-2 and step 1R-3 of the below-mentioned Reference Example 1.

Production Method 1-2

Of compounds [I-3-1] in the below-mentioned production method I-3, compound [I-2-9] which is compound [I-3-1] wherein Y is a nitrogen atom and $R^{13b}$ is an ethyl group can be synthesized by the following method.

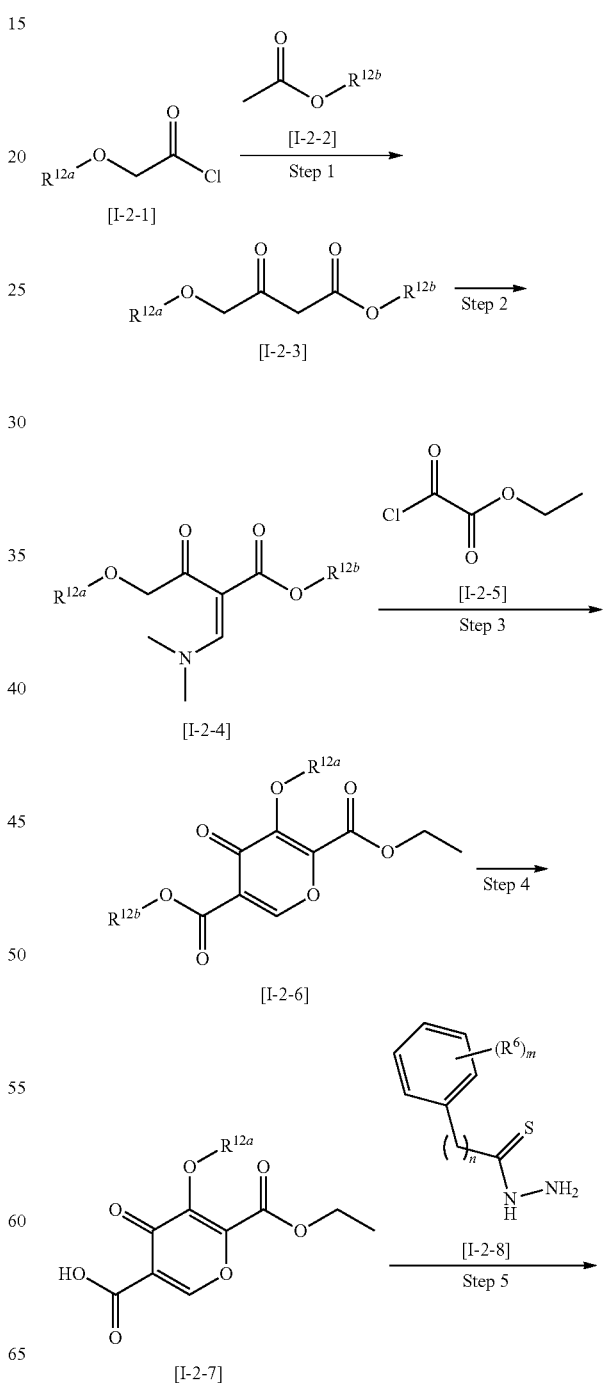

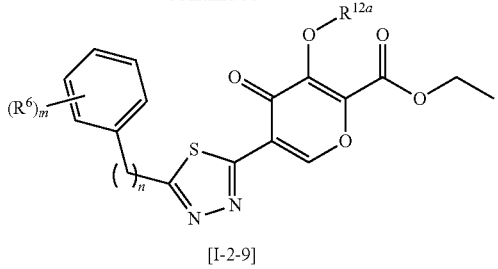

[I-2-9]

wherein $R^{12a}$ is a hydroxyl-protecting group such as acetyl group, benzyl group, methyl group, ethyl group, isopropyl group, trimethylsilyl group, triethylsilyl group, tert-butyldimethylsilyl group, triisopropylsilyl group, tert-butyldiphenylsilyl group and the like, $R^{12b}$ is a carboxyl-protecting group such as methyl group, ethyl group, benzyl group, tert-butyl group and the like, and other symbols are each as described above.

Step 1

Compound [I-2-3] can be obtained by reacting compound [I-2-1] with compound [I-2-2] at −78° C. to room temperature conditions in a solvent such as DMF, DMA, dimethyl sulfoxide (DMSO), THF, toluene and the like, in the presence of a base such as sodium hydride, lithiumdiisopropylamide (LDA), lithium hexamethyldisilazide (LHMDS) and the like.

Step 2

Compound [I-2-4] can be obtained by reacting Compound [I-2-3] with N,N-dimethylformamidedimethylacetal at room temperature to under heating in a solvent such as DMF, acetonitrile, THF, chloroform, ethyl acetate, methylene chloride, toluene and the like.

Step 3

Compound [I-2-6] can be obtained by adding a base such as sodium hydride, LDA, LHMDS and the like to a solution of Compound [I-2-4] dissolved in a solvent such as DMF, DMA, DMSO, THF, toluene and the like at −78° C. to room temperature, reacting the compound with compound [I-2-5] and treating same with triethylamine, diisopropylethylamine or the like.

Step 4

Compound [I-2-7] can be obtained by removing the carboxyl-protecting group $R^{12b}$ of compound [I-2-6] by a known method. For example, when the protecting group is a tert-butyl group, compound [I-2-7] can be obtained by stirring compound [I-2-6] at a low temperature to under heating in a single or mixed solvent of hexane, chloroform, methylene chloride, ethyl acetate, toluene, 1,2-dimethoxyethane, 1,4-dioxane, THF, methanol, ethanol, 2-propanol, DMSO, DMF, DMA, acetonitrile, water and the like in the presence of acid such as p-toluenesulfonic acid, methanesulfonic acid, boron trifluoride, boron trichloride, boron tribromide, aluminum trichloride, hydrochloric acid, hydrogen bromide, phosphoric acid, sulfuric acid, acetic acid, trifluoroacetic acid and the like.

Step 5

Compound [I-2-9] can be obtained by converting compound [I-2-7] to acid chloride by a known method, and further reacting the compound with compound [I-2-8]. Specifically, compound [I-2-9] can be obtained by converting compound [I-2-7] to acid chloride with a chlorinating agent such as oxalyl chloride, thionyl chloride, phosphorus trichloride and the like at a low temperature to room temperature in a single or mixed solvent of hexane, chloroform, methylene chloride, ethyl acetate, toluene, 1,2-dimethoxyethane, 1,4-dioxane, THF and the like in the presence of a catalytic amount of DMF where necessary, and reacting the compound with compound [I-2-8].

Production Method I-3

A compound represented by the above-mentioned formula [I] can be synthesized by the following method.

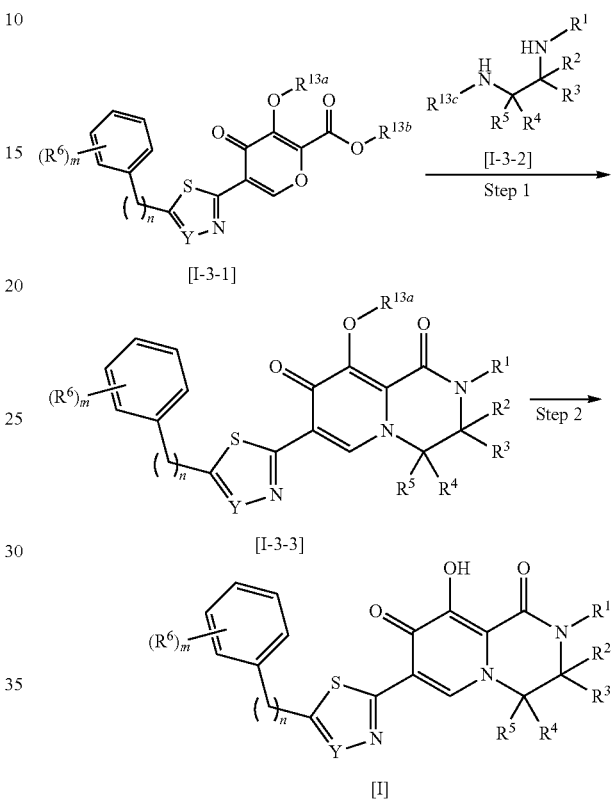

wherein $R^{13a}$ is a hydroxyl-protecting group such as acetyl group, benzyl group, methyl group, ethyl group, isopropyl group, trimethylsilyl group, triethylsilyl group, tert-butyldimethylsilyl group, triisopropylsilyl group, tert-butyldiphenylsilyl group and the like, $R^{13b}$ is a carboxyl-protecting group such as methyl group, ethyl group, benzyl group, tert-butyl group and the like, $R^{13c}$ is an amino-protecting group such as benzyloxycarbonyl group, tert-butoxycarbonyl group, benzyl group and the like, and other symbols are each as described above.

Step 1

Compound [I-3-3] can be obtained by reacting compound [I-3-1] with compound [I-3-2], wherein amino-protecting group $R^{13c}$ is removed in advance according to a known method at room temperature to under heating in a single or mixed solvent of chloroform, dichloromethane, DMF, DMA, DMSO, acetonitrile, 1,2-dimethoxyethane, THF, toluene, water and the like, and cyclizing the compound in the presence of a base such as triethylamine, diisopropylamine, diisopropylethylamine, diazabicycloundecene, sodium carbonate, potassium carbonate, sodium hydrogen carbonate and the like. The cyclization reaction can also be performed in the presence of acid such as acetic acid, p-toluenesulfonic acid, methanesulfonic acid, boron trifluoride, boron trichloride, boron tribromide, hydrochloric acid, hydrogen bromide, phosphoric acid, sulfuric acid and the like.

Step 2

Compound [I] can be obtained by removing the hydroxyl-protecting group $R^{13a}$ of compound [I-3-3] by a known method. For example, when the protecting group is a benzyl group, compound [I] can be obtained by stirring compound [I-3-3] at a low temperature to room temperature in a single or mixed solvent of hexane, chloroform, methylene chloride, ethyl acetate, toluene, methanol, ethanol, 2-propanol, THF, 1,4-dioxane, acetonitrile, water and the like, in the presence of acid such as hydrochloric acid, sulfuric acid, hydrogen bromide, phosphoric acid, acetic acid, trifluoroacetic acid and the like. The acid may be used as a solvent.

Production Method 1-4

Compound [I-3-2] in the above-mentioned production method I-3 (corresponding to the following compound [I-4-3]) can be synthesized by the following method.

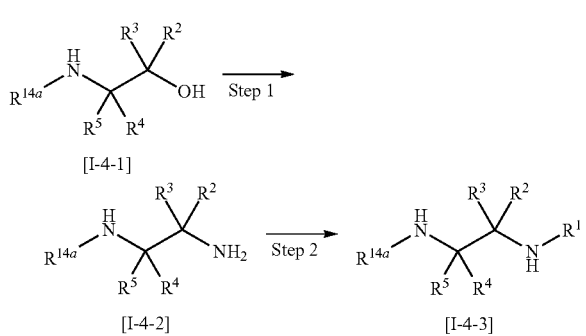

wherein $R^{14a}$ is an amino-protecting group such as benzyloxycarbonyl group, tert-butoxycarbonyl group, benzyl group and the like, and other symbols are each as described above.

Step 1

Compound [I-4-1] obtainable from a commercially available compound by a known method is reacted with phthalimide at a low temperature to under heating in a single or mixed solvent of THF, methylene chloride, chloroform, DMF, ethyl acetate, toluene and the like in the presence of a phosphorus reagent such as triphenylphosphine, diphenyl (2-pyridyl)phosphine, tributylphosphine, tri-tert-butylphosphine and the like and an azo compound such as diisopropylazodicarboxylate, diethylazodicarboxylate, N,N,N',N'-tetramethylazodicarboxamide, 1,1'-(azodicarbonyl)dipiperidine and the like, and the obtained compound is further treated with hydrazine to remove a phthaloyl group to give amine compound [I-4-2].

Step 2

Compound [I-4-2] is reacted with a ketone compound or aldehyde compound at a low temperature to room temperature in a solvent such as DMF, acetonitrile, THF, chloroform, ethyl acetate, methylene chloride, toluene and the like, and the mixture is stirred in the presence of a reducing agent such as sodium borohydride, sodium triacetoxyborohydride and the like to introduce substituent $R^1$ into the amino group of compound [I-4-2], whereby compound [I-4-3] can be obtained.

Production Method I-5

Of compounds [I-3-2] in the above production method I-3, a compound, which is compound [I-3-2] wherein particularly $R^2$ and $R^3$ are each a hydrogen atom, one of $R^4$ and $R^5$ is a carboxyl group or —CO—$NR^aR^b$ wherein $R^a$ and $R^b$ are as described above, and the other is a $C_{1-6}$ alkyl group optionally substituted by the same or different 1 to 5 substituents selected from the aforementioned group A, can be synthesized by the following method.

wherein $R^{15a}$ is an amino-protecting group such as benzyloxycarbonyl group, tert-butoxycarbonyl group, benzyl group and the like, $R^{15b}$ is a carboxyl-protecting group such as methyl group, ethyl group, benzyl group, tert-butyl group and the like, $R^{15c}$ is a $C_{1-6}$ alkyl group optionally substituted by the same or different 1 to 5 substituents selected from the aforementioned group A, and other symbols are each as to described above.

Step 1

Compound [I-5-2] can be obtained by oxidizing the hydroxyl group of compound [I-5-1] obtainable from a commercially available compound by a known method, to a aldehyde group by a chromium oxide-pyridine complex (e.g., pyridinium chlorochromate, pyridinium dichromate and the like), a metal oxidant (e.g., chromium oxide, silver carbonate, manganese dioxide and the like), by DMSO oxidization using various DMSO activators such as oxalyl chloride, trifluoroacetic anhydride, acetic anhydride, dicyclohexylcarbodiimide (DCC), sulfur trioxide-pyridine complex and the like, Dess-Martin oxidization and the like according to a known method.

Step 2

Compound [I-5-3] can be obtained by subjecting the aldehyde group of compound [I-5-2] to a reductive amination under similar conditions as in production method I-4, step 2. The obtained compound [I-5-3] is cyclized by the above-mentioned method, and the carboxyl-protecting group $R^{15b}$ is removed by a known method and, where necessary, the resulting compound is reacted with an amine compound by a known method to give the object compound.

Production Method II

Production Method II-1

Of the compounds represented by the above-mentioned formula [I], compound [II-1-6], which is compound [I] wherein Y is CH can be synthesized by the following method.

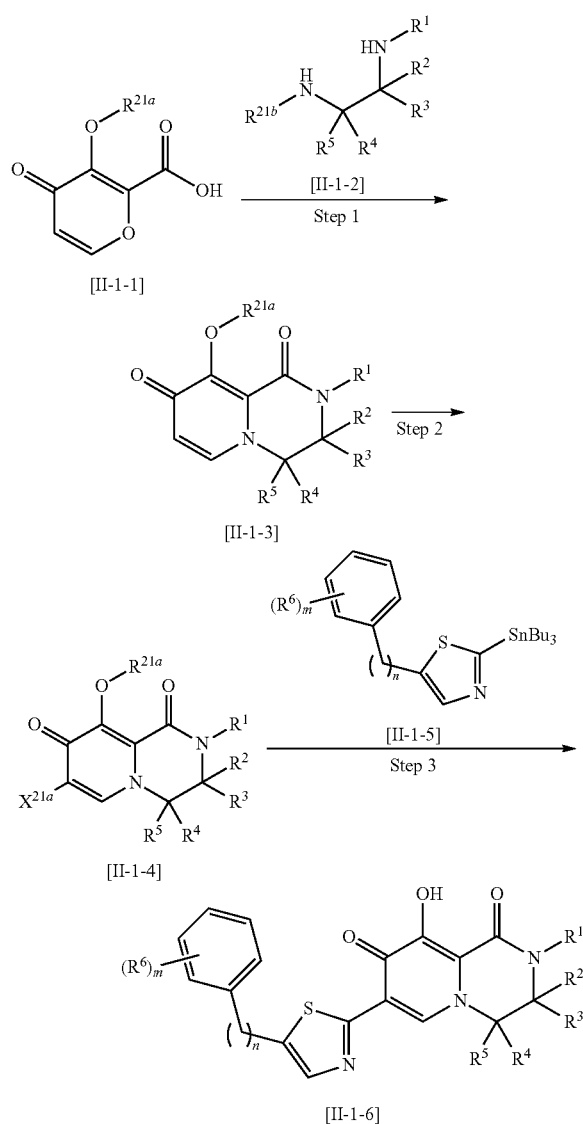

Compound [II-1-2] can be obtained by a method similar to that of Production method 1-4.

Step 2

Compound [II-1-4] can be obtained by introducing leaving group $X^{21a}$ into compound [II-1-3] by a known method. For example, when the leaving group $X^{21a}$ is a bromine atom, the bromine atom is introduced into compound [II-1-3] by a method similar to that in production method I-1, step 2 to give compound [II-1-4].

Step 3

Compound [II-1-4] is reacted with compound [II-1-5] by a method similar to that of production method I-1, step 4, and the hydroxyl-protecting group $R^{21a}$ is removed by a method similar to that of production method I-3, step 2, whereby compound [II-1-6] can be obtained.

Production Method II-2

Of the compounds represented by the above-mentioned formula [I], a compound, which is compound [I] wherein particularly $R^2$ and $R^3$ are each a hydrogen atom, and one of $R^4$ and $R^5$ is a methyl group substituted by —$NR^{43}R^{44}$ wherein $R^{43}$ and $^{44}$ are as described above, and the other is a $C_{1-6}$ alkyl group optionally substituted by the same or different 1 to 5 substituents selected from the aforementioned group A, can be synthesized by the following method.

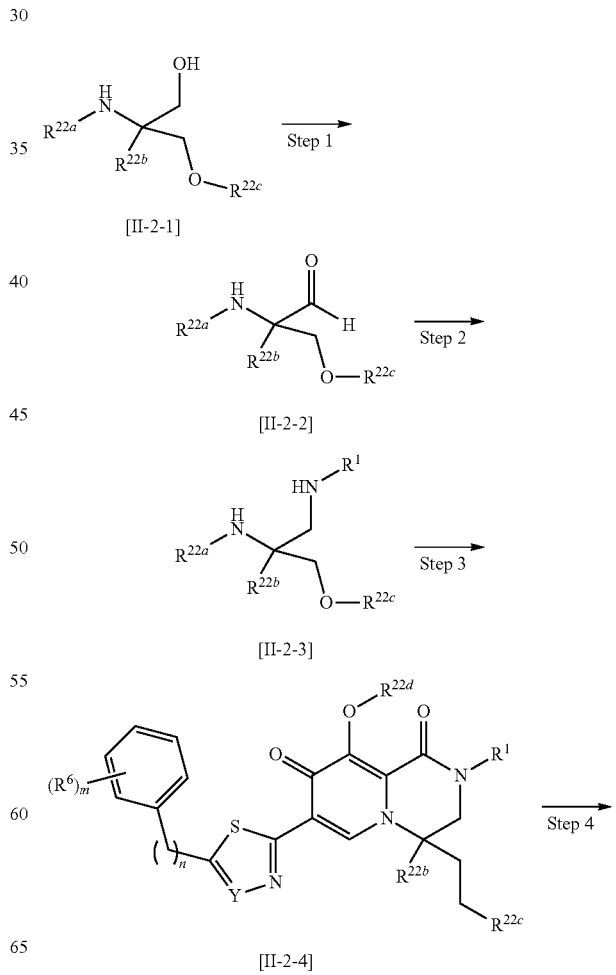

wherein $R^{21a}$ is a hydroxyl-protecting group such as acetyl group, benzyl group, methyl group, ethyl group, isopropyl group, trimethylsilyl group, triethylsilyl group, tert-butyldimethylsilyl group, triisopropylsilyl group, tert-butyldiphenylsilyl group and the like, $R^{21b}$ is an amino-protecting group such as benzyloxycarbonyl group, tert-butoxycarbonyl group, benzyl group and the like, $X^{21a}$ is a leaving group such as a halogen atom (e.g., fluorine atom, chlorine atom, bromine atom, iodine atom and the like), p-toluenesulfonyloxy group (OTs), methanesulfonyloxy group (OMs), trifluoromethanesulfonyloxy group (OTf) and the like, and other symbols are each as described above.

Step 1

Compound [II-1-3] can be obtained by converting compound [II-1-1] to acid chloride by a known method at a low temperature to under heating, reacting the acid chloride with compound [II-1-2], removing the amino-protecting group $R^{21b}$, and stirring the mixture in the presence of a base such as potassium acetate, potassium carbonate, potassium hydrogen carbonate, sodium hydrogen carbonate, potassium phosphate, triethylamine, diisopropylethylamine, sodium hydrogen phosphate, cesium carbonate and the like.

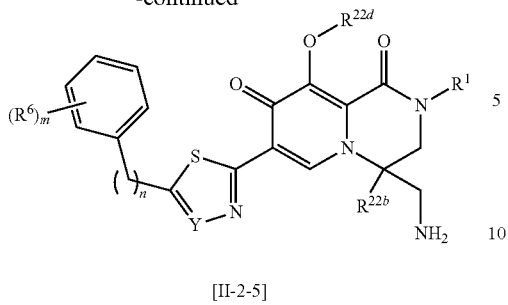

[II-2-5]

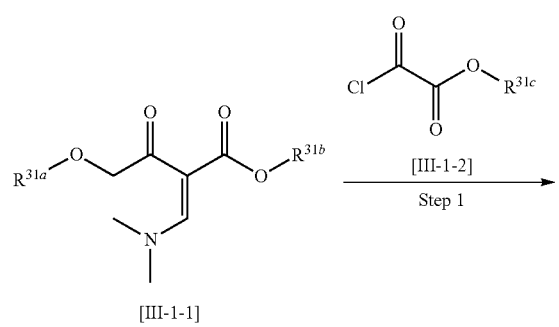

[III-1-1]  [III-1-2]

Step 1

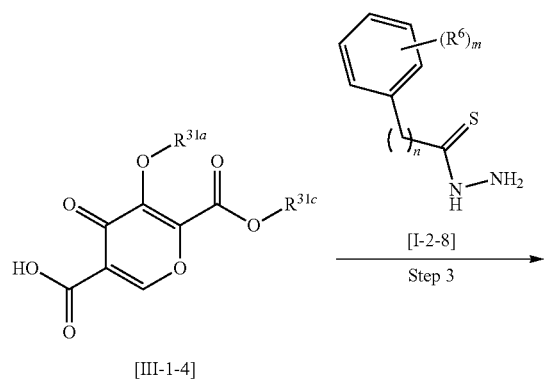

[III-1-3]

Step 2 wherein $R^{22a}$ is an amino-protecting group such as benzyloxycarbonyl group, tert-butoxycarbonyl group, benzyl group and the like, $R^{22b}$ is a $C_{1-6}$ alkyl group optionally substituted by the same or different 1 to 5 substituents selected from the aforementioned group A, $R^{22a}$ and $R^{22d}$ are the same or different, and each is a hydroxyl-protecting group such as acetyl group, benzyl group, methyl group, ethyl group, isopropyl group, trimethylsilyl group, triethylsilyl group, tert-butyldimethylsilyl group, triisopropylsilyl group, tert-butyldiphenylsilyl group and the like, and other symbols are each as described above.

Step 1

The hydroxyl group of compound [II-2-1] is oxidized, by a known method to give aldehyde group, whereby compound [II-2-2] can be obtained. The known method is the same as the one indicated for, for example, the production method I-5, step 1.

Step 2

Compound [II-2-3] can be obtained by subjecting compound [II-2-2] to reductive amination by the same method as in the production method I-5, step 2.

Step 3

Compound [II-2-4] can be obtained from compound [II-2-3] by the same method as in production method II-1, step 1 to step 3.

Step 4

The hydroxyl-protecting group $R^{22c}$ of compound [II-2-4] is removed by a known method, and the hydroxyl group is appropriately subjected to substituent conversion to a leaving group (OTs, OMs, OTf etc.). After reaction with potassium phthalimide, and the phthaloyl group is removed by a method similar to production method I-4, step 1 to give compound [II-2-5]. The obtained compound [II-2-5] is subjected to an appropriately combination of removal of hydroxyl-protecting group $R^{22d}$ by a method similar to production method I-3, step 2, and modification of amino group of compound [II-2-5] by a known method to give the object compound.

Production Method III

Of compounds represented by the above-mentioned formula [I], compound [III-1-9], which is compound [I] wherein Y is a nitrogen atom can be synthesized by the following method.

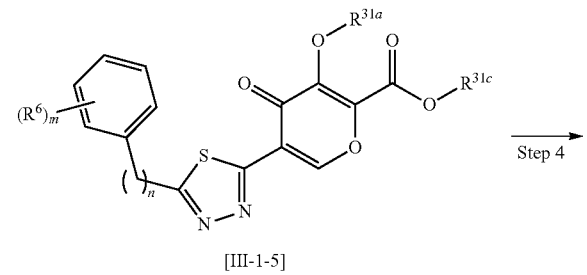

[III-1-4]  [I-2-8]

Step 3

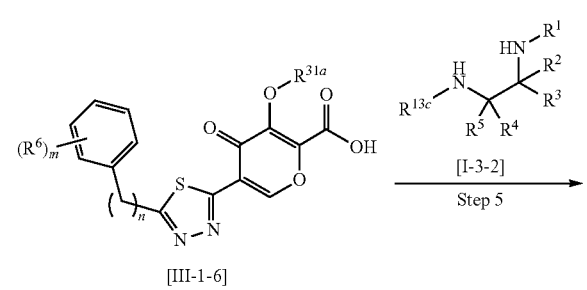

[III-1-5]

Step 4

[III-1-6]  [I-3-2]

Step 5

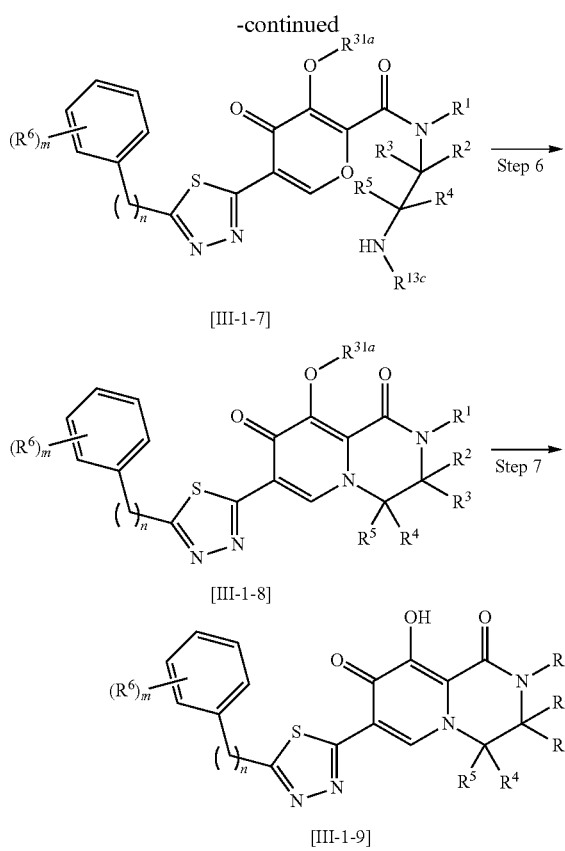

[III-1-7]

[III-1-8]

[III-1-9]

wherein $R^{31a}$ is a hydroxyl-protecting group such as acetyl group, benzyl group, methyl group, ethyl group, isopropyl group, trimethylsilyl group, triethylsilyl group, tert-butyldimethylsilyl group, triisopropylsilyl group, tert-butyldiphenylsilyl group and the like, $R^{31b}$ and $R^{31c}$ are the same or different and each is a carboxyl-protecting group such as methyl group, ethyl group, benzyl group, tert-butyl group and the like, and other symbols are each as described above.

Step 1

Compound [III-1-3] can be obtained by reacting compound [III-1-1] with compound [III-1-2] by a method similar to production method I-2, step 3.

Step 2

Compound [III-1-4] can be obtained by removing the carboxyl-protecting group $R^{31b}$ of compound [III-1-3] by a method similar to production method I-2, step 4.

Step 3

Compound [III-1-5] can be obtained by reacting compound [III-1-4] with compound [I-2-8] by a method similar to production method I-2, step 5.

Step 4

Compound [III-1-6] can be obtained by removing the carboxyl-protecting group $R^{31c}$ of compound [III-1-5] by a known method.

Step 5

Compound [III-1-7] can be obtained by converting compound [III-1-6] to acid chloride by a method similar to production method I-2, step 5, and reacting the acid chloride with compound [I-3-2] in a solvent such as hexane, chloroform, methylene chloride, ethyl acetate, toluene, 1,2-dimethoxyethane, 1,4-dioxane, THF and the like in the presence of a base such as potassium acetate, potassium carbonate, potassium hydrogen carbonate, sodium hydrogen carbonate, potassium phosphate, triethylamine, diisopropylethylamine, sodium hydrogen phosphate, cesium carbonate and the like.

Step 6

Compound [III-1-8] can be obtained by removing the amino-protecting group $R^{13c}$ of compound [III-1-7] by a known method, and performing cyclization by a method similar to a cyclization reaction of production method II-1, step 1 in the presence of a base.

Step 7

Compound [III-1-9] can be obtained by removing the hydroxyl-protecting group $R^{31a}$ of compound [III-1-8] by a known method. For example, when the protecting group is a benzyl group, a method similar to production method I-3, step 2 can be used.

EXAMPLES

Now, the production methods of the compound of the present invention are specifically explained by referring to Examples, which are not to be construed as limitative.

The abbreviations used in the Examples mean the following.

Bn: benzyl group
Boc: tert-butoxycarbonyl group
Et: ethyl group
Me: methyl group
Ms: methanesulfonyl group
TBS: tert-butyldimethylsilyl group
TFA: trifluoroacetic acid
THP: tetrahydropyranyl group
Z: benzyloxycarbonyl group In addition, the following $^1$H-NMR values were measured by resolution 400 MHz.

Reference Example 1

Step 1R-1

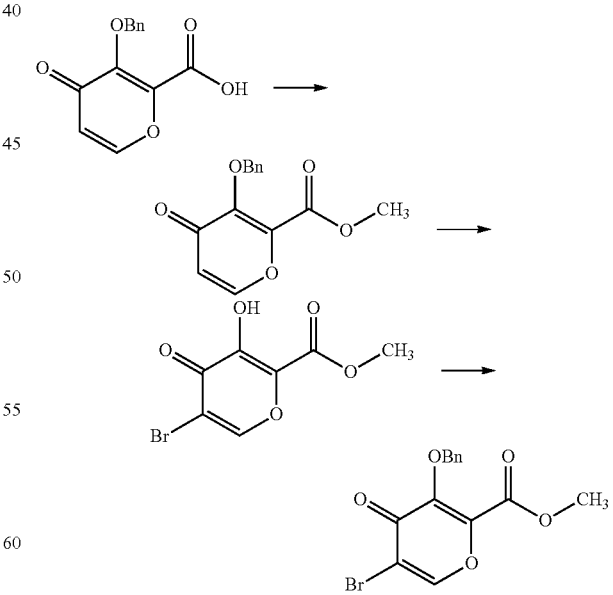

3-benzyloxy-4-oxo-4H-pyran-2-carboxylic acid (11.43 g) was suspended in methanol (20 mL)-tetrahydrofuran (80 mL), 2M (trimethylsilyl)diazomethane/hexane solution (46.4 mL) was added dropwise under ice-cooling, and the mixture was stirred at room temperature for 1.5 hr. The solvent was evaporated under reduced pressure and the obtained residue was dissolved in chloroform (80 mL). Thereto was added bromine (23 mL) and the mixture was stirred for 2 days at 75° C. The mixture was allowed to cool to room temperature, hexane was added and the precipitated solid was collected by filtration. The obtained is solid was dissolved in dimethylformamide (54 mL), potassium carbonate (7.1 g) and benzyl bromide (5.6 ml) were added, and the mixture was stirred at 80° C. for 40 min. The mixture was allowed to cool to room temperature and filtered. The filtrate was concentrated and 1N aqueous hydrochloric acid solution was added to the obtained residue. The mixture was extracted twice with ethyl acetate. The combined ethyl acetate layer was washed with saturated brine, dried, and concentrated. The concentrate was purified by silica gel column chromatography (ethyl acetate:hexane=1:20-1:4), the eluate was concentrated, and the precipitated crystals were collected by filtration to give the object compound (7.65 g) described in the above-mentioned scheme.

$^1$H-NMR (CDCl$_3$) δ: 8.11 (s, 1H), 7.49-7.44 (m, 2H), 7.40-7.32 (m, 3H), 5.32 (s, 2H), 3.89 (s, 3H).

Step 1R-2

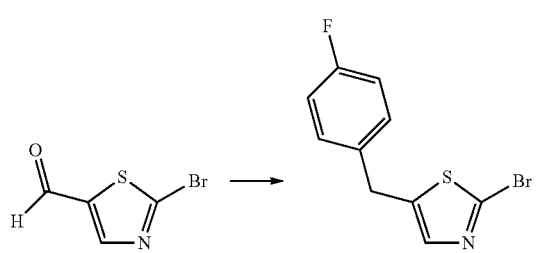 [SMILES: O=Cc1cnc(Br)s1 ; Fc1ccc(Cc2cnc(Br)s2)cc1]

To a solution of 2-bromothiazole-5-carbaldehyde (14 g) in THF (300 mL) was added dropwise 1M (4-fluorophenyl)magnesium bromide/THF solution (80 mL) at −78° C., and the mixture was stirred for 1 hr. Saturated aqueous ammonium chloride solution was added, and the mixture was allowed to cool to room temperature, and extracted with ethyl acetate. The organic layer was washed with saturated brine, dried, and concentrated. Trifluoroacetic acid (100 mL) and triethylsilane (58 mL) were added to the obtained residue, and the mixture was stirred for 100 min at 75° C. The mixture was allowed to cool to room temperature and concentrated, and the residue was purified by silica gel column chromatography (ethyl acetate:hexane=1:50-1:9) to give the object compound (16.8 g) described in the above-mentioned scheme.

$^1$H-NMR (CDCl$_3$) δ: 7.31-7.29 (m, 1H), 7.21-7.14 (m, 2H), 7.05-6.98 (m, 2H), 4.07 (s, 2H).

Step 1R-3

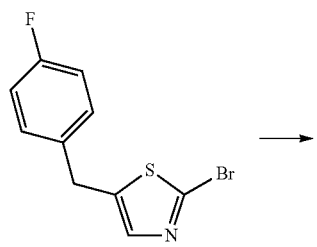

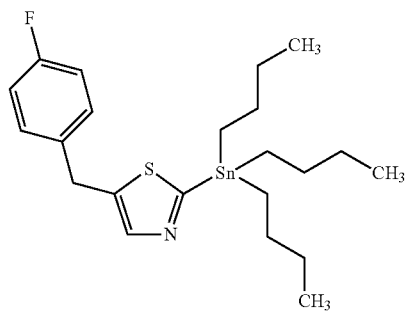

To a solution of the compound (3.2 g) obtained in step 1R-2 in THF (50 mL) was added dropwise 1.6M n-butyllithium/hexane solution (8.1 mL) at −78° C. and the mixture was stirred for 10 min. Tributyltin chloride (3.5 mL) was added, and the mixture was stirred at −78° C. for 30 min and at room temperature for 30 min. Ice-cold water was added and the mixture was extracted with ethyl acetate. The organic layer was washed with saturated brine, dried, and concentrated to give the object compound (6.2 g) described in the above-mentioned scheme as a crude product.

$^1$H-NMR (THF) δ: 7.76-7.74 (m, 1H), 7.25-7.21 (m, 2H), 7.03-6.97 (m, 2H), 4.19 (s, 2H), 1.65-1.56 (m, 6H), 1.40-1.28 (m, 6H), 1.20-1.13 (m, 6H), 0.91-0.85 (m, 9H).

Step 1R-4

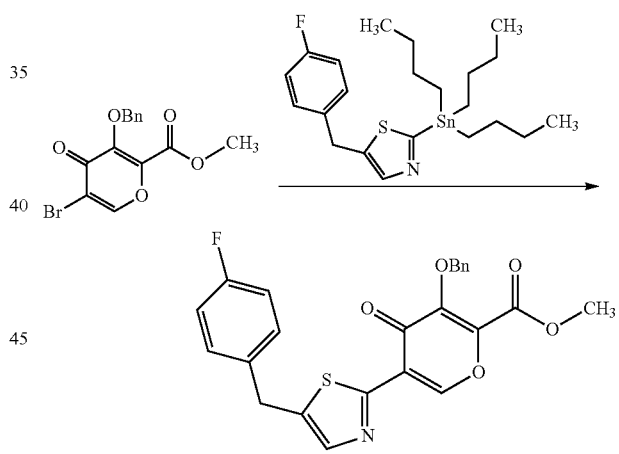

Under an argon stream, tris(dibenzylideneacetone)dipalladium(0) (84 mg) and tri(2-furyl)phosphine (85 mg) were suspended in toluene (1.5 mL), and the suspension was stirred at room temperature for 15 min. The compound (890 mg) obtained in step 1R-3 and the compound (310 mg) obtained in step 1R-1 were added, and the mixture was stirred at 80° C. for 1 hr. The obtained reaction mixture was filtered through celite, and concentrated, and the concentrate was purified by silica gel column chromatography (ethyl acetate:hexane=1:20-1:4) to give the object compound (190 mg) described in the above-mentioned scheme.

$^1$H-NMR (CDCl$_3$) δ: 8.91 (s, 1H), 7.62-7.61 (m, 1H), 7.51-7.45 (m, 2H), 7.40-7.32 (m, 3H), 7.25-7.19 (m, 2H), 7.04-6.97 (m, 2H), 5.37 (s, 2H), 4.19 (s, 2H), 3.91 (s, 3H).

Reference Example 2

Step 2R-1

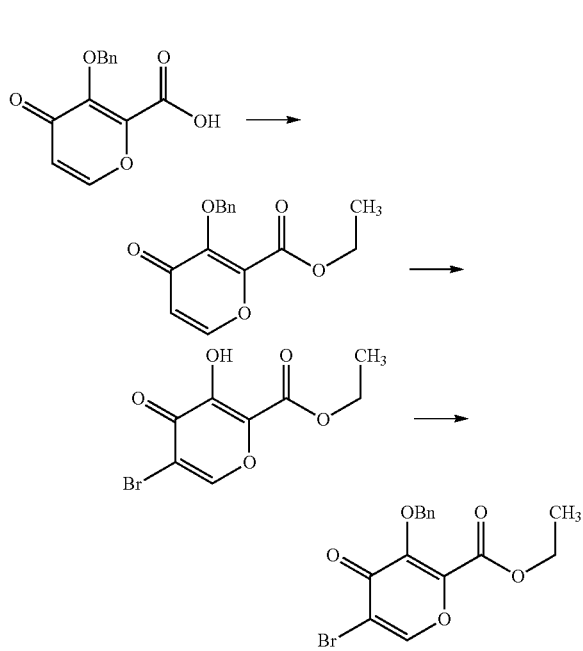

In the same manner as in step 1R-1 except that 3-benzyloxy-4-oxo-4H-pyran-2-carboxylic acid (15.0 g) was ethylated with iodoethane, the object compound (10.97 g) described in the above-mentioned scheme was obtained.

$^1$H-NMR (CDCl$_3$) δ: 8.11 (s, 1H), 7.50-7.46 (m, 2H), 7.40-7.32 (m, 3H), 5.31 (s, 2H), 4.36 (q, 2H, J=7.2 Hz), 1.33 (t, 3H, J=7.2 Hz).

Step 2R-2

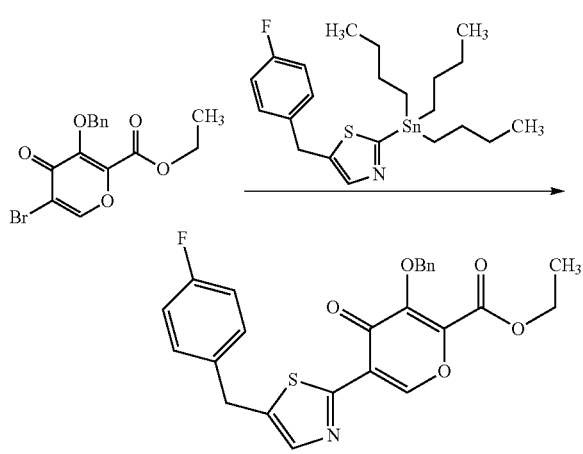

In the same manner as in step 1R-4, the object compound (1.0 g) described in the above-mentioned scheme was obtained from the compound (1.2 g) obtained in step 2R-1.

$^1$H-NMR (CDCl$_3$) δ: 8.91 (s, 1H), 7.62-7.61 (m, 1H), 7.51-7.47 (m, 2H), 7.39-7.31 (m, 3H), 7.25-7.20 (m, 2H), 7.04-6.97 (m, 2H), 5.37 (s, 2H), 4.38 (q, 2H, J=7.2 Hz), 4.19 (s, 2H), 1.34 (t, 3H, J=7.2 Hz).

Reference Example 3

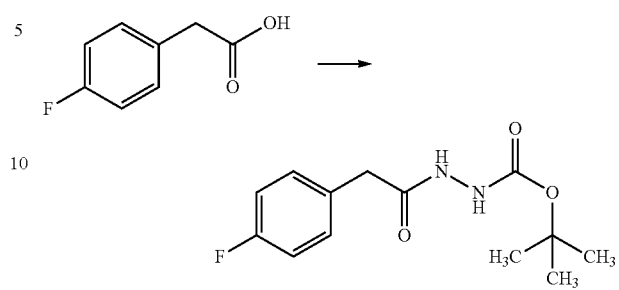

Step 3R-1

To a solution of 4-fluorophenylacetic acid (25 g) and tert-butyl carbazate (22.5 g) in DMF (200 ml) were added 1-hydroxybenzotriazole hydrate (HOBT.H$_2$O (27.3 g)) and 1-ethyl-3-(3-dimethylaminopropyl)carbodiimide hydrochloride (WSC.HCl (34.1 g)), and the mixture was stirred at room temperature overnight. Saturated aqueous sodium hydrogen carbonate solution was added, and the mixture was stirred for a while and extracted with ethyl acetate. The organic layer was washed with saturated aqueous sodium hydrogen carbonate solution and saturated brine, dried over magnesium sulfate, and is concentrated to give the object compound (32.3 g) described in the above-mentioned scheme as a crude product.

Step 3R-2

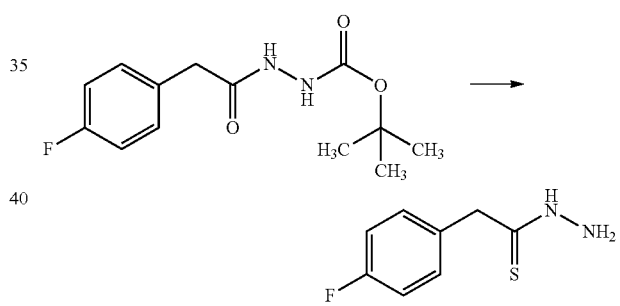

To a solution of the compound (32.3 g) obtained in step 3R-1 in THF (300 mL) was added a Lawesson reagent (48.7 g), and the mixture was stirred at 50° C. overnight and allowed to cool. The reaction mixture was poured into a stirred saturated aqueous sodium hydrogen carbonate solution by small portions, and the mixture was stirred at room temperature for 30 min. The mixture was extracted twice with ethyl acetate, and the organic layer was washed with saturated aqueous sodium hydrogen carbonate solution and saturated brine, dried over magnesium sulfate, and concentrated. To the residue was added 4N hydrochloric acid/dioxane solution (300 mL), and the mixture was stirred at room temperature for 1 hr. The precipitated salt was collected by filtration, and dissolved in water (200 mL), and the solution was neutralized with sodium hydrogen carbonate and extracted twice with ethyl acetate. The organic layer was washed with saturated brine, dried over sodium sulfate, and concentrated. To the residue was added ethyl acetate/hexane (1:4) solution and the mixture was slurry washed. The residue was collected by filtration, and dried to give the object compound (15.78 g) described in the above-mentioned scheme.

$^1$H-NMR (CDCl$_3$) δ: 8.27-8.03 (br m, 1H), 7.26-7.20 (m, 2H), 7.10-7.03 (m, 2H), 4.88-4.75 (br m, 2H), 4.08 (s, 2H).

Example 1

Step 1-1

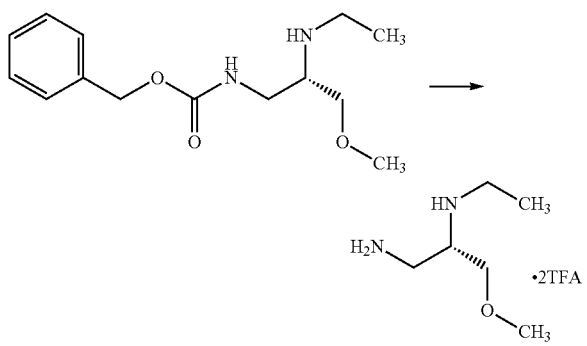

To a solution of (S)-2-ethylamino-3-methoxypropylcarbamic acid benzyl ester (76 mg) in methanol (10 mL) was added a 7.5% palladium-carbon catalyst (100 mg), and the reaction mixture was stirred under a moderate-pressure (0.4 MPa) in a hydrogen atmosphere at room temperature for 3 hr. The reaction mixture was filtered through celite, trifluoroacetic acid (1 mL) was added and the mixture was concentrated to give the object compound (133 mg) described in the above-mentioned scheme as a crude product.

Step 1-2

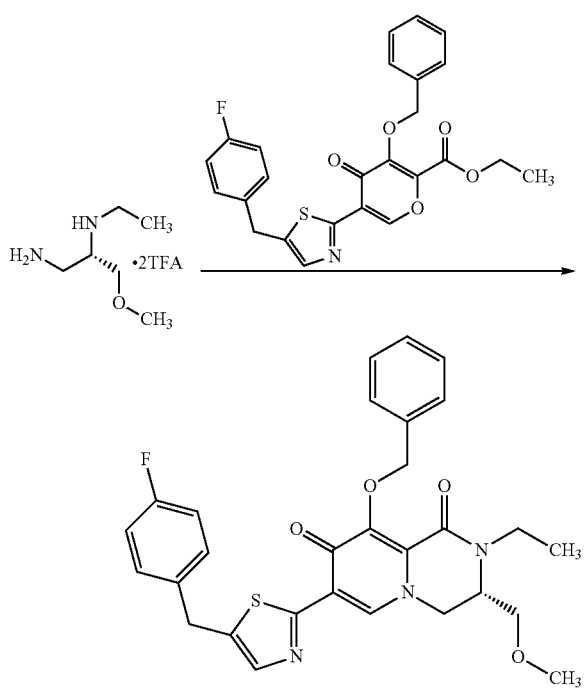

To a solution of the compound (55 mg) obtained in step 1-1 in tetrahydrofuran (1.5 mL) was added diisopropylethylamine (160 μL), and the mixture was stirred for 10 min. A solution of the compound (46 mg) obtained in Reference Example 2 in tetrahydrofuran (1 mL) was added, and the mixture was stirred at room temperature for 30 min. The reaction mixture was concentrated, toluene (4 mL) and 1,8-diazabicyclo[5.4.0]undec-7-ene (200 μL) were added, and the mixture was stirred at 110° C. for 15 min. Acetic acid (500 μL) was added, and the mixture was stirred at 110° C. for 1 hr. The reaction mixture was allowed to cool to room temperature, and diluted with ethyl acetate. The mixture was washed with 5% aqueous potassium hydrogen sulfate solution, dried and concentrated, and the concentrate was purified by silica gel thin layer chromatography (ethyl acetate: methanol=20:1) to give the object compound (56 mg) described in the above-mentioned scheme.

Step 1-3

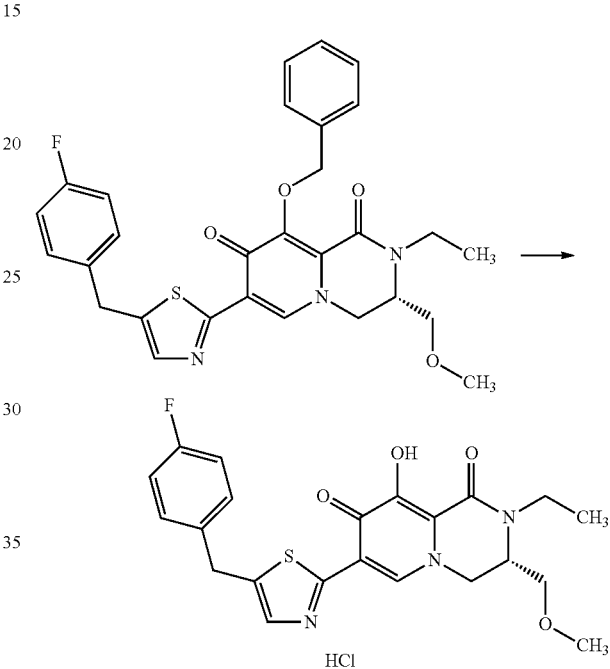

Compound (56 mg) obtained in step 1-2 was dissolved in trifluoroacetic acid (1.0 mL), and the mixture was stood at room temperature for 1 hr. The reaction solution was concentrated, ethyl acetate was added and the mixture was concentrated. Ethyl acetate, 4N hydrochloric acid/ethyl acetate solution, and hexane were added to allow crystallization to give the object compound (28 mg) described in the above-mentioned scheme.

$^1$H-NMR (DMSO-d$_6$) δ: 12.30 (br s, 1H), 8.64 (s, 1H), 7.66 (s, 1H), 7.34-7.30 (m, 2H), 7.16-7.11 (m, 2H), 4.57 (d, 1H, J=13.5 Hz), 4.39 (dd, 1H, J=13.5, 3.9 Hz), 4.19 (s, 2H), 4.12-4.10 (m 1H), 3.87-3.80 (m, 1H), 3.53-3.44 (m, 2H), 3.27-3.22 (m, 1H), 3.20 (s, 3H), 1.18 (t, 3H, J=7.1 Hz).

Example 2

Step 2-1

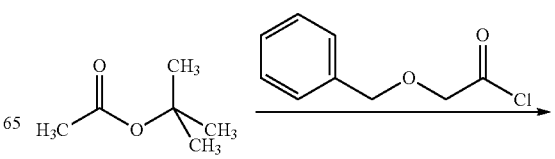

-continued

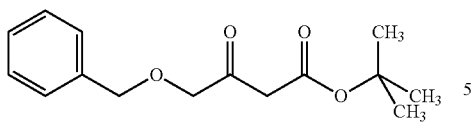

Under nitrogen, a solution of 1M lithium bis(trimethylsilyl)amide-THF/ethylbenzene (100 mL) in THF (100 mL) was cooled to −70° C., and tert-butyl acetate (13.5 mL) was added dropwise under stirring. After stirring for 15 min, benzyloxyacetyl chloride (7.52 mL) was added dropwise. After stirring for 1 hr, 2N aqueous hydrochloric acid solution was added to the reaction mixture until its pH reached 3 and the mixture was allowed to warm to room temperature. The mixture was extracted with ethyl acetate, and the organic layer was washed with 2N aqueous hydrochloric acid solution and saturated brine, dried over sodium sulfate and concentrated. The above operation was repeated, and the both were combined to give the object compound (40.3 g) described in the above-mentioned scheme as a crude product.

Step 2-2

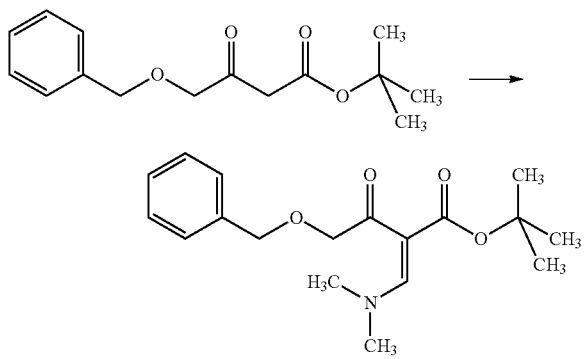

To a solution of the compound (38 g) obtained in step 2-1 in toluene (80 mL) was added dimethylformamidedimethylacetal (38 mL), and the mixture was stirred at 100° C. for 1 hr. The mixture was allowed to cool, and concentrated, and the concentrate was purified by silica gel column chromatography (ethyl acetate:hexane=1:2-ethyl acetate) to give the object compound (11.3 g) described in the above-mentioned scheme.

$^1$H-NMR (CDCl$_3$) δ: 7.66 (s, 1H), 7.40-7.13 (m, 5H), 4.60 (s, 2H), 4.42 (s, 2H), 3.40-2.65 (m, 6H), 1.45 (s, 9H).

Step 2-3

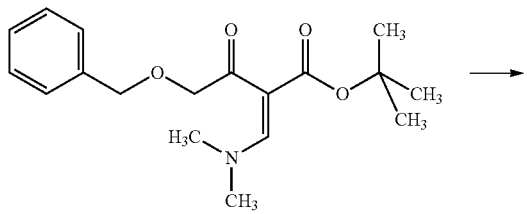

-continued

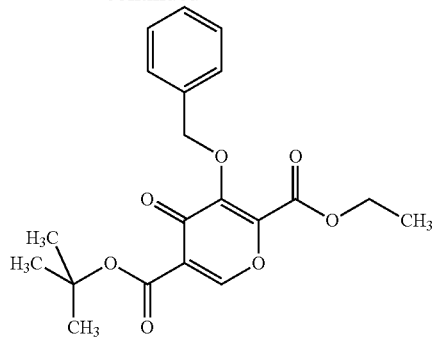

Under nitrogen, a solution of 1M lithium bis(trimethylsilyl)amide-THF/ethylbenzene (42.5 mL) in THF (150 mL) was cooled to −70° C., and a solution of the compound (11.3 g) obtained in step 2-2 in THF (50 mL) was added dropwise over 3 min under stirring. After stirring for 20 min, ethyl chloroglyoxylate (4.75 mL) was added at once. After stirring for 25 min, saturated aqueous potassium hydrogen sulfate solution and ethyl acetate were added and the mixture was allowed to warm to room temperature. The organic layer was separated, washed with saturated brine, dried over sodium sulfate, and concentrated. Toluene was added to the residue, and the mixture was concentrated once. Toluene (100 mL) and triethylamine (10 mL) were added and the mixture was stirred at room temperature. One hour later, the mixture was concentrated, and the concentrate was purified by silica gel column chromatography (ethyl acetate:hexane=1:6-1:3) to give the object compound (6.03 g) described in the above-mentioned scheme.

$^1$H-NMR (CDCl$_3$) δ: 8.39 (s, 1H), 7.51-7.47 (m, 2H), 7.39-7.30 (m, 3H), 5.32 (s, 2H), 4.34 (q, 2H, J=7.2 Hz), 1.57 (s, 9H), 1.31 (t, 3H, J=7.2 Hz).

Step 2-4

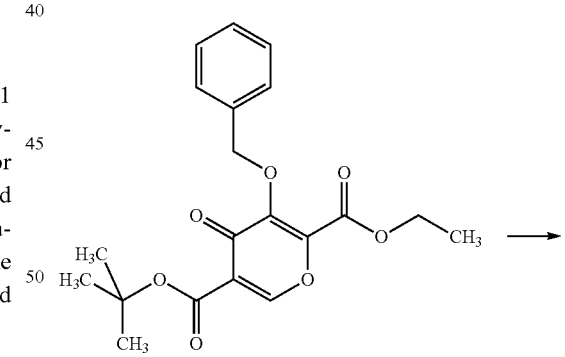

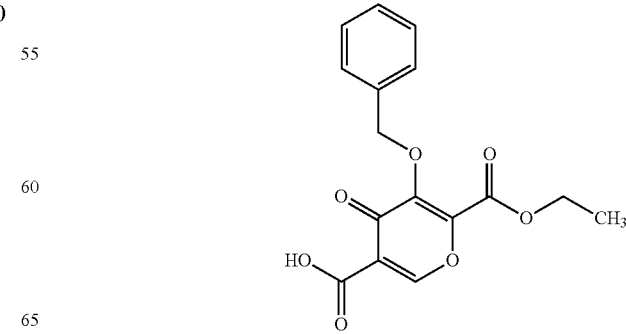

To a solution of the compound (18.7 g) obtained in step 2-3 in ethyl acetate (20 mL) was added 4N hydrochloric acid/ethyl acetate (200 mL) under stirring, and the mixture was stirred at room temperature for 1 hr. To the reaction mixture was added hexane (1 L), the mixture was stirred for a while, and the crystals were collected by filtration, and dried to give the object compound (11.1 g) described in the above-mentioned scheme.

$^1$H-NMR (CDCl$_3$) δ: 13.03 (s, 1H), 8.80 (s, 1H), 7.47-7.43 (m, 2H), 7.41-7.35 (m, 3H), 5.38 (s, 2H), 4.40 (q, 2H, J=7.2 Hz), 1.35 (t, 3H, J=7.2 Hz).

Step 2-5

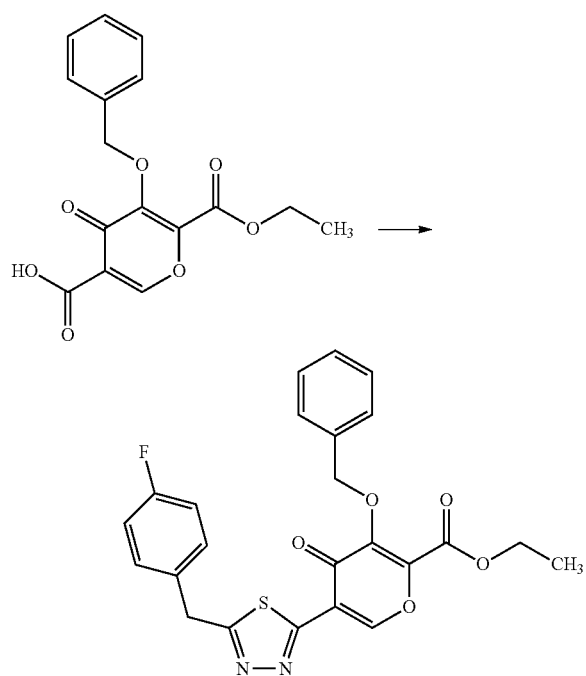

To a solution of the compound (6 g) obtained in step 2-4 in toluene (80 mL) were added oxalyl chloride (3.27 mL) and dimethylformamide (0.04 mL) under stirring, and the mixture was stirred at room temperature for 2 hr. The reaction mixture was concentrated, chloroform (100 ml) and the compound (5.22 g) obtained in Reference Example 3 were added, and the mixture was stirred at room temperature overnight. 5% Aqueous potassium hydrogen sulfate solution was added, and the mixture was extracted twice with chloroform. The organic layer was washed with 5% aqueous potassium hydrogen sulfate solution and saturated brine, dried over magnesium sulfate, and concentrated. The concentrate was purified by silica gel column chromatography (ethyl acetate:hexane=1:4-1:3), ethyl acetate/hexane (1:3) solution was added, and the mixture was slurry washed. The residue was collected by filtration, and dried to give the object compound (6.348 g) described in the above-mentioned scheme.

$^1$H-NMR (CDCl$_3$) δ: 9.07 (s, 1H), 7.49-7.44 (m, 2H), 7.39-7.28 (m, 5H), 7.07-7.00 (m, 2H), 5.35 (s, 2H), 4.46 (s, 2H), 4.39 (q, 2H, J=7.1 Hz), 1.34 (t, 3H, J=7.1 Hz).

Step 2-6

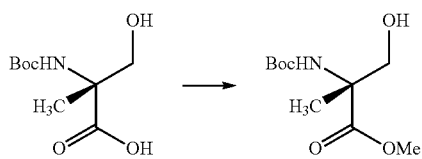 [SMILES: CC(C)(C)OC(=O)N[C@](C)(CO)C(=O)O ; COC(=O)[C@@](C)(CO)NC(=O)OC(C)(C)C]

To a solution of (R)-2-tert-butoxycarbonylamino-3-hydroxy-2-methylpropionic acid (5.00 g) in dimethylformamide (50 mL) were added potassium carbonate (6.31 g) and iodomethane (2.84 mL), and the mixture was stirred at room temperature for 3 hr. Water (100 mL) was added, and the mixture was extracted with ethyl acetate (150 mL). The organic layer was washed with saturated aqueous sodium hydrogen carbonate solution (100 mL), dried and concentrated to give the object compound (5.06 g) described in the above-mentioned scheme.

$^1$H-NMR (CDCl$_3$) δ: 5.29 (br s, 1H), 3.99 (dd, 1H, J=11.6, 6.0 Hz), 3.83-3.73 (m, 1H), 3.78 (s, 3H), 3.23 (br s, 1H), 1.48 (s, 3H), 1.45 (s, 9H).

Step 2-7

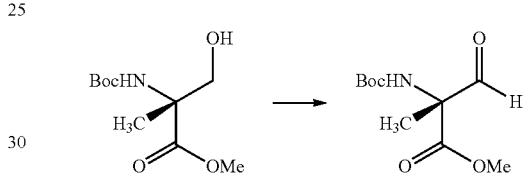

To a solution of the compound (2.50 g) obtained in step 2-6 in dimethyl sulfoxide (25 mL) were added triethylamine (2.25 mL) and a pyridine-sulfur trioxide complex (2.62 g), and the mixture was stirred at room temperature for 1 hr. 1N Aqueous hydrochloric acid solution (100 mL) was added, and the mixture was extracted with ethyl acetate (200 mL). The organic layer was washed successively with 1N aqueous hydrochloric acid solution (100 mL) and saturated aqueous sodium hydrogen carbonate solution (100 mL), dried and concentrated to give the object compound (1.22 g) described in the above-mentioned scheme.

$^1$H-NMR (CDCl$_3$) δ: 9.57 (s, 1H), 5.63 (br s, 1H), 3.81 (s, 3H), 1.57 (s, 3H), 1.45 (s, 9H).

Step 2-8

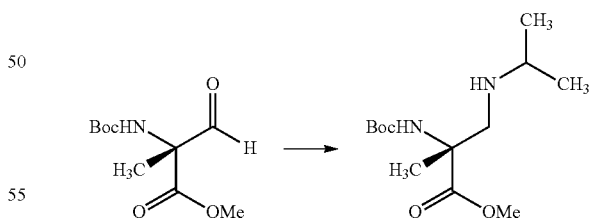

To a solution of the compound (660 mg) obtained in step 2-7 in chloroform (7.0 mL) were added isopropylamine (368 μL), acetic acid (245 μL) and sodium triacetoxyborohydride (955 mg), and the mixture was stirred at room temperature for 18 hr. Saturated aqueous sodium hydrogen carbonate solution (30 mL) and chloroform (50 mL) were added and the mixture was partitioned. The organic layer was washed with saturated aqueous sodium hydrogen carbonate solution (30 mL), dried and concentrated. The concentrate was purified by silica gel column chromatography (chloroform:

methanol=10:1) to give the object compound (764 mg) described in the above-mentioned scheme.

$^1$H-NMR (CDCl$_3$) δ: 5.74 (br s, 1H), 3.74 (s, 3H), 2.89 (br s, 2H), 2.73 (sep, 1H, J=6.2 Hz), 1.52 (s, 3H), 1.44 (s, 9H), 1.02 (d, 3H, J=6.2 Hz), 1.02 (d, 3H, J=6.2 Hz).

Step 2-9

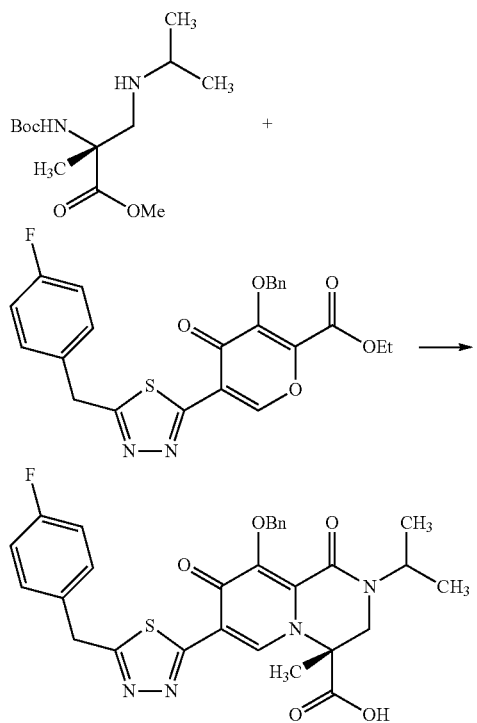

The compound (155 mg) obtained in step 2-8 was dissolved in trifluoroacetic acid solution (1.0 mL), and the mixture was stirred at room temperature for 30 min. The mixture was concentrated, chloroform was added, and the mixture was concentrated. This operation was performed twice. Toluene (5 mL), diisopropylethylamine (395 μL) and the compound (200 mg) obtained in step 2-5 were added, and the mixture was stirred at room temperature for 30 min. Toluene (5 mL) and 1,8-diazabicyclo[5.4.0]undec-7-ene (100 μL) were added, and the mixture was stirred at 120° C. for 1 hr. The reaction mixture was allowed to cool to room temperature, acetic acid (1.0 mL) was added, and the mixture was further stirred at 110° C. for 1 hr. 2N Aqueous hydrochloric acid solution (30 mL) was added, and the mixture was extracted with ethyl acetate (60 mL). The organic layer was dried and concentrated, toluene was added, and this operation was repeated twice to give the object compound (263 mg) described in the above-mentioned scheme.

$^1$H-NMR (CDCl$_3$) δ: 8.87 (s, 1H), 7.59 (d, 2H, J=7.0 Hz), 7.41-7.13 (m, 4H), 7.08-6.98 (m, 3H), 5.46 (d, 1H, J=10.0 Hz), 5.23 (d, 1H, J=10.0 Hz), 4.86 (sep, 1H, J=6.3 Hz), 4.44 (s, 2H), 3.85 (d, 1H, J=13.5 Hz), 3.44 (d, 1H, J=13.5 Hz), 1.96 (s, 3H), 1.14 (d, 3H, J=6.3 Hz), 1.12 (d, 3H, J=6.3 Hz).

Step 2-10

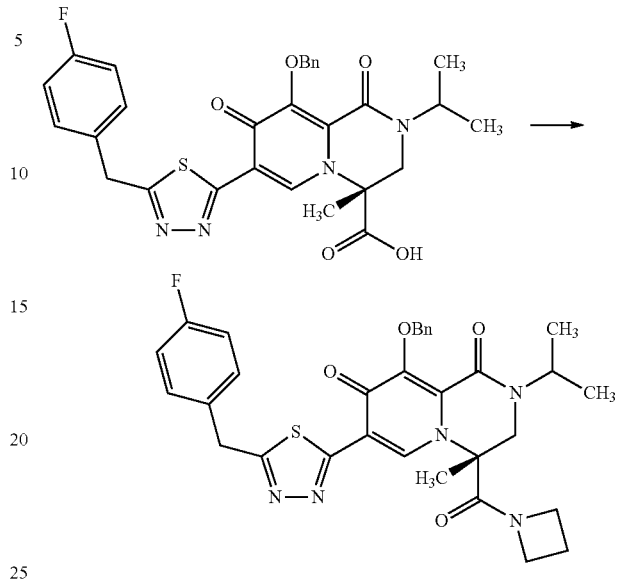

To a solution of the compound (40.0 mg) obtained in step 2-9,1-ethyl-3-(3-dimethylaminopropyl)carbodiimide hydrochloride (28.0 mg) and 1-hydroxybenzotriazole hydrate (22.0 mg) in dimethylformamide (400 μL) was added azetidine (20 μL), and the mixture was stirred at room temperature for 18 hr. Saturated aqueous sodium hydrogen carbonate solution (10 mL) was added, and the mixture was extracted with ethyl acetate (25 mL). The organic layer was washed successively with 1N aqueous hydrochloric acid solution (10 mL) and saturated aqueous sodium hydrogen carbonate solution (10 mL), dried and concentrated. The concentrate was purified by silica gel thin layer chromatography (chloroform:methanol=15:1) to give the object compound (26.7 mg) described in the above-mentioned scheme.

$^1$H-NMR (CDCl$_3$) δ: 8.99 (s, 1H), 7.64-7.58 (m, 2H), 7.36-7.27 (m, 5H), 7.07-6.99 (m, 2H), 5.53 (d, 1H, J=10.0 Hz), 5.39 (d, 1H, J=10.0 Hz), 4.82 (sep, 1H, J=6.7 Hz), 4.46 (s, 2H), 4.10-3.92 (m, 2H), 3.97 (d, 1H, J=13.4 Hz), 3.75-3.66 (m, 1H), 3.61-3.51 (m, 1H), 3.27 (d, 1H, J=13.4 Hz), 2.19-2.05 (m, 2H), 1.97 (s, 3H), 1.15 (d, 6H, J=6.7 Hz).

Step 2-11

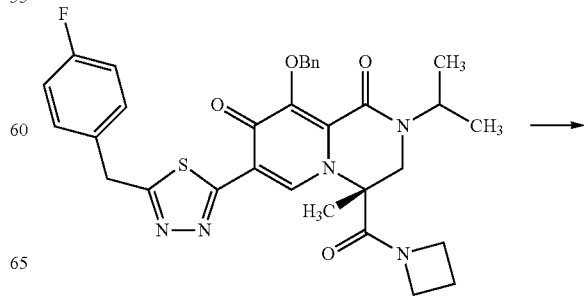

-continued

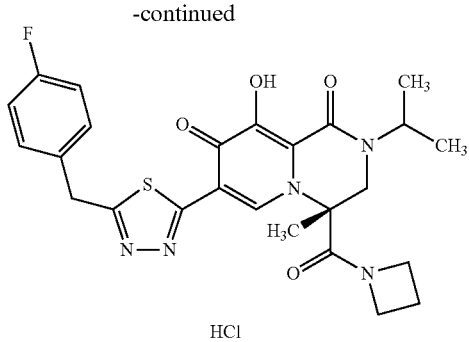

HCl

The compound (25.0 mg) obtained in step 2-10 was dissolved in trifluoroacetic acid (1.0 mL), and the mixture was stirred at room temperature for 30 min. The reaction solution was concentrated, chloroform was added, and the mixture was concentrated. 4N Hydrochloric acid/ethyl acetate solution was added, and the mixture was concentrated. Crystallization from ethyl acetate-hexane gave the object compound (17.2 mg) described in the above-mentioned scheme.

$^1$H-NMR (DMSO-$d_6$) δ: 12.91 (br s, 1H), 8.71 (s, 1H), 7.46-7.38 (m, 2H), 7.23-7.15 (m, 2H), 4.70 (sep, 1H, J=6.7 Hz), 4.48 (s, 2H), 4.29-4.18 (br m, 1H), 4.02 (d, 1H, J=13.9 Hz), 3.90-3.81 (br m, 2H), 3.80-3.72 (br m, 1H), 3.71 (d, 1H, J=13.9 Hz), 2.16-2.04 (br m, 2H), 1.99 (s, 3H), 1.16 (d, 3H, J=6.7 Hz), 1.14 (d, 3H, J=6.7 Hz).

Example 3

Step 3-1

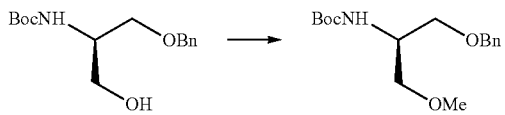 [SMILES: CC(C)(C)OC(=O)N[C@H](CO)COCc1ccccc1 ; COC[C@H](COCc1ccccc1)NC(=O)OC(C)(C)C]

To a solution of (R)-1-benzyloxymethyl-2-hydroxyethyl-carbamic acid tert-butyl ester (5.0 g) and 2,6-di-tert-butylpyridine (8.0 mL) in chloroform (50 mL) were added iodomethane (1.33 mL) and silver(I) trifluoromethanesulfonate (6.85 g) under ice-cooling, and the mixture was stirred for 30 min, and further stirred at room temperature for 1 hr. The reaction suspension was filtered through celite, and concentrated, and the concentrate was purified by silica gel column chromatography (ethyl acetate:hexane=1:20-1:4) to give the object compound (2.8 g) described in the above-mentioned scheme.

$^1$H-NMR (CDCl$_3$) δ: 7.38-7.27 (m, 5H), 4.97-4.85 (m, 1H), 4.53 (s, 2H), 4.00-3.81 (m, 1H), 3.59 (dd, 1H, J=9.4, 4.2 Hz), 3.51 (dd, 1H, J=9.4, 5.8 Hz), 3.51 (dd, 1H, J=9.4, 4.4 Hz), 3.44 (dd, 1H, J=9.4, 6.0 Hz), 3.34 (s, 3H), 1.44 (s, 9H).

Step 3-2

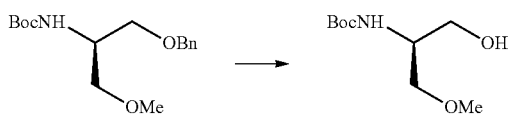 [SMILES: COC[C@H](COCc1ccccc1)NC(=O)OC(C)(C)C ; COC[C@H](CO)NC(=O)OC(C)(C)C]

To a solution of the compound (2.8 g) obtained in step 3-1 in methanol (100 mL) was added a 7.5% palladium-carbon catalyst (1.4 g), and the mixture was stirred at room temperature for 17 hr under a hydrogen atmosphere and moderate pressure (0.4 MPa). The reaction mixture was filtered through celite and concentrated to give the object compound (2.05 g) described in the above-mentioned scheme.

$^1$H-NMR (CDCl$_3$) δ: 5.22-5.10 (m, 1H), 3.84-3.64 (m, 3H), 3.60-3.49 (m, 2H), 3.37 (s, 3H), 2.73-2.55 (m, 1H), 1.45 (s, 9H).

Step 3-3

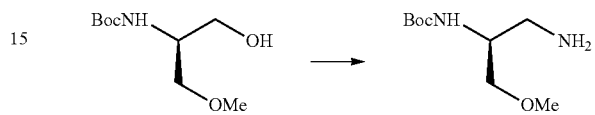

To a solution of the compound (1.6 g) obtained in step 3-2, phthalimide (1.38 g) and triphenylphosphine (2.47 g) in tetrahydrofuran (20 mL) was added dropwise 2.2M diethyl azodicarboxylate/toluene solution (4.3 mL) under ice-cooling, and the mixture was stirred at room temperature for 20 min. The reaction mixture was concentrated, and the concentrate was purified by silica gel column chromatography (ethyl acetate:hexane=1:10-1:2). The obtained solid was dissolved in ethanol (30 mL)-toluene (30 mL), hydrazine monohydrate (1.6 mL) was added, and the mixture was stirred at 80° C. for 40 min. The mixture was allowed to cool to room temperature, the solid was filtered off, and the filtrate was concentrated. Toluene was added to the residue, and the precipitated solid was filtered off. The filtrate was concentrated to give the object compound (1.3 g) described in the above-mentioned scheme.

$^1$H-NMR (CDCl$_3$) δ: 5.08-4.89 (m, 1H), 3.71-3.63 (m, 1H), 3.50 (dd, 1H, J=9.5, 3.7 Hz), 3.40 (dd, 1H, J=9.5, 5.1 Hz), 3.35 (s, 3H), 2.84 (dd, 1H, J=13.0, 6.0 Hz), 2.80 (dd, 1H, J=13.0, 6.0 Hz), 1.45 (s, 9H).

Step 3-4

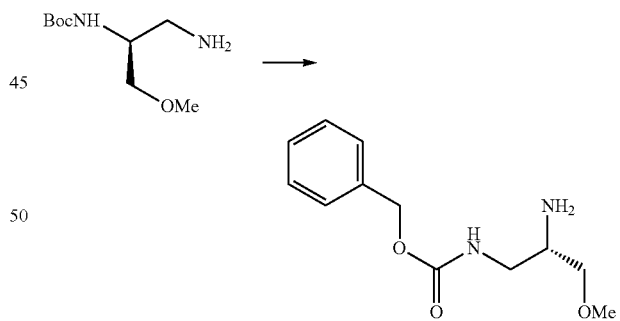

To a solution of the compound (0.8 g) obtained in step 3-3 in dioxane (8 mL) was added saturated aqueous sodium hydrogen carbonate solution (2 mL), benzyl chloroformate (0.84 mL) was added dropwise under ice-cooling, and the mixture was stirred for 40 min, and at room temperature for 10 min. Water (15 mL) was added, and the mixture was extracted with ethyl acetate. The extract was dried, and concentrated, and the concentrate was purified by silica gel column chromatography (ethyl acetate:hexane=1:10-1:2). To the obtained solid was added 4N hydrochloric acid/dioxane solution (5 ml), and the mixture was stirred at room temperature for 30 min. The reaction mixture was concentrated, and the residue was dissolved in chloroform. Saturated aqueous sodium hydrogen carbonate solution (2 mL) was added, and the mixture was stirred. The mixture was extracted with chloroform, and the organic layer was dried and concentrated to give the object compound (639 mg) described in the above-mentioned scheme.

$^1$H-NMR (CDCl$_3$) δ: 7.39-7.28 (m, 5H), 5.27-5.20 (m, 1H), 5.10 (s, 2H), 3.41-3.24 (m, 3H), 3.35 (s, 3H), 3.18-3.01 (m, 2H), 1.39 (br s, 2H).

Step 3-5

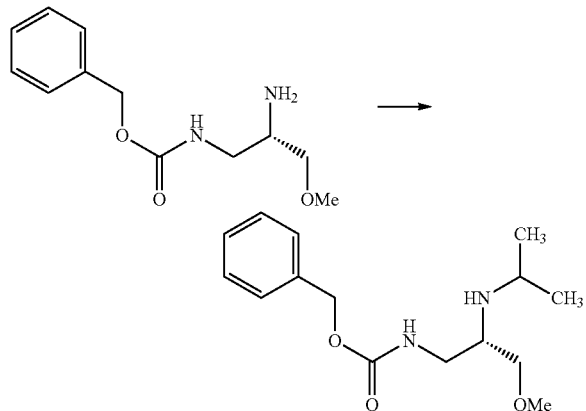

To a solution of the compound (150 mg) obtained in step 3-4 in chloroform (4 mL) were added acetone (70 μL), acetic acid (54 μL) and sodium triacetoxyborohydride (200 mg) under ice-cooling, and the mixture was stirred at room temperature overnight. The reaction mixture was diluted with chloroform, saturated aqueous sodium hydrogen carbonate solution was added, and the mixture was stirred. The chloroform layer was washed with saturated brine, dried, and concentrated to give the object compound (156 mg) described in the above-mentioned scheme.

$^1$H-NMR (CDCl$_3$) δ: 7.39-7.28 (m, 5H), 5.39-5.29 (m, 1H), 5.10 (s, 2H), 3.42-3.28 (m, 3H), 3.33 (s, 3H), 3.22-3.14 (m, 1H), 2.96-2.82 (m, 2H), 1.04 (d, 3H, J=6.8 Hz), 1.02 (d, 3H, J=6.8 Hz).

Step 3-6

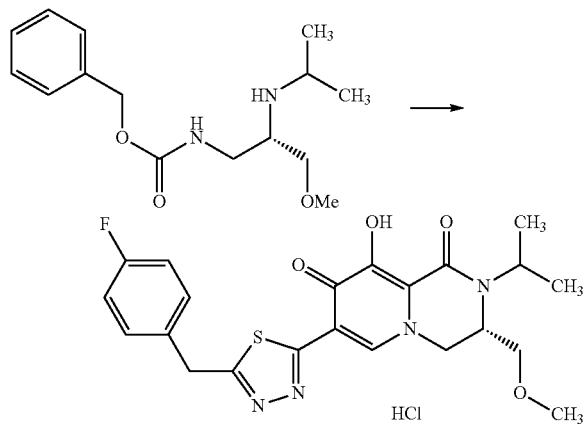

In the same manner as in step 2-9 and step 2-11, the object compound (17.0 mg) described in the above-mentioned scheme was obtained from the compound (156 mg) obtained in step 3-5. For removal of the amino-protecting group (benzyloxycarbonyl group) of the compound obtained in step 3-5, a known method was used according to the protecting group.

$^1$H-NMR (DMSO-d$_6$) δ: 8.84 (s, 1H), 7.43-7.38 (m, 2H), 7.21-7.14 (m, 2H), 4.66 (d, 1H, J=13.2 Hz), 4.47 (sep, 1H, J=6.7 Hz), 4.47 (s, 2H), 4.34 (dd, 1H, J=13.5, 3.7 Hz), 4.22-4.17 (m, 1H), 3.49 (dd, 1H, J=10.6, 4.3 Hz), 3.39 (dd, 1H, J=10.6, 7.5 Hz), 3.21 (s, 3H), 1.30 (d, 3H, J=6.7 Hz), 1.28 (d, 3H, J=6.7 Hz).

Example 4

Step 4-1

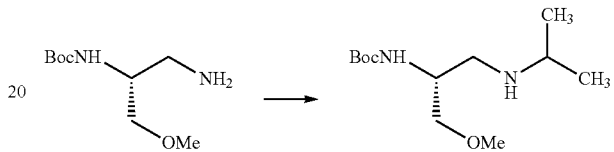

To a solution of (R)-1-aminomethyl-2-methoxyethylcarbamic acid tert-butyl ester (1.0 g) produced from (S)-1-benzyloxymethyl-2-hydroxyethylcarbamic acid tert-butyl ester in the same manner as in Example 3, step 3-1 to step 3-3 in chloroform (15 mL) were added acetone (432 μl) and acetic acid (337 μL) under ice-cooling, sodium triacetoxyborohydride (1.25 g) was added at room temperature, and the mixture was stirred at room temperature for 14 hr. To the reaction mixture was added saturated aqueous sodium hydrogen carbonate solution, and the mixture was extracted 3 times with chloroform. The combined chloroform layer was dried, and concentrated, and the concentrate was purified by silica gel column chromatography (chloroform:methanol=50:1-7:1) to give the object compound (1.12 g) described in the above-mentioned scheme.

$^1$H-NMR (CDCl$_3$) δ: 5.09-4.90 (m, 1H), 3.81-3.69 (m, 1H), 3.49 (dd, 1H, J=9.5, 4.0 Hz), 3.43-3.37 (m, 1H), 3.34 (s, 3H), 2.82-2.68 (m, 3H), 1.45 (s, 9H), 1.04 (d, 3H, J=6.4 Hz), 1.03 (d, 3H, J=6.4 Hz).

Step 4-2

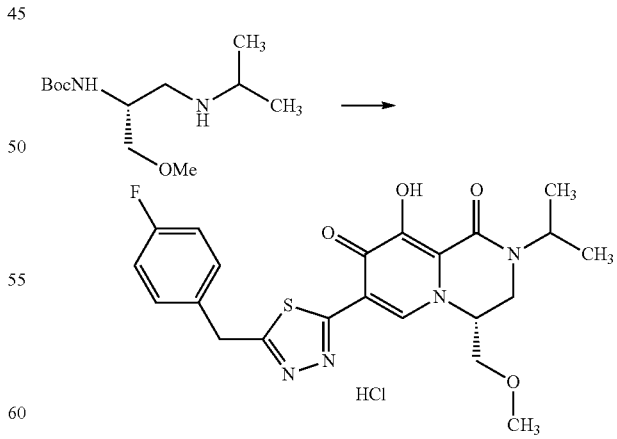

In the same manner as in step 2-9 and step 2-11 (known deprotection and condensation reactions may be omitted as necessary), the object compound (10.8 mg) described in the above-mentioned scheme was obtained from the compound (19.0 mg) obtained in step 4-1.

$^1$H-NMR (DMSO-d$_6$) δ: 12.82 (br s, 1H), 8.80 (s, 1H), 7.45-7.38 (m, 2H), 7.23-7.15 (m, 2H), 5.01-4.93 (m, 1H), 4.77 (sep, 1H, J=6.7 Hz), 4.47 (s, 2H), 3.84 (dd, 1H, J=13.8, 4.1 Hz), 3.75 (dd, 1H, J=13.8, 1.3 Hz), 3.65-3.54 (m, 2H), 3.25 (s, 3H), 1.16 (d, 3H, J=6.7 Hz), 1.16 (d, 3H, J=6.7 Hz).

Example 5

Step 5-1

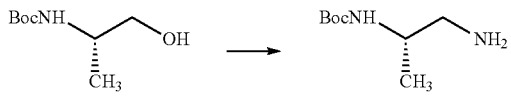

In the same manner as in step 3-3, the object compound (1.0 g) described in the above-mentioned scheme was obtained from (S)-2-hydroxy-1-methylethylcarbamic acid tert-butyl ester (1.4 g).

$^1$H-NMR (CDCl$_3$) δ: 4.68-4.49 (m, 1H), 3.71-3.58 (m, 1H), 2.74 (dd, 1H, J=13.0, 4.9 Hz), 2.62 (dd, 1H, J=13.0, 6.5 Hz), 1.45 (s, 9H), 1.12 (d, 3H, J=6.7 Hz).

Step 5-2

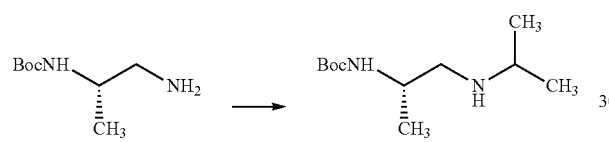

In the same manner as in step 4-1, the object compound (180 mg) described in the above-mentioned scheme was obtained from the compound (190 mg) obtained in step 5-1.

$^1$H-NMR (CDCl$_3$) δ: 4.91-4.66 (m, 1H), 3.81-3.66 (m, 1H), 2.81 (sep, 1H, J=6.4 Hz), 2.66 (dd, 1H, J=12.0, 4.9 Hz), 2.60 (dd, 1H, J=12.0, 6.7 Hz), 1.45 (s, 9H), 1.14 (d, 3H, J=6.6 Hz), 1.06 (d, 6H, J=6.4 Hz).

Step 5-3

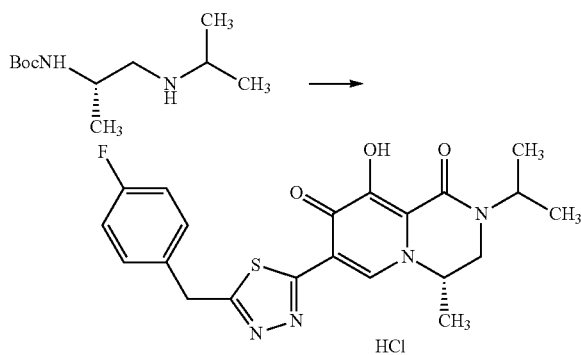

In the same manner as in step 2-9 and step 2-11, the object compound (27.5 mg) described in the above-mentioned scheme was obtained from the compound (30.0 mg) obtained in step 5-2.

$^1$H-NMR (DMSO-d$_6$) δ: 12.81 (br s, 1H), 8.91 (s, 1H), 7.45-7.38 (m, 2H), 7.22-7.15 (m, 2H), 4.92 (ddd, 1H, J=6.8, 3.5, 2.2 Hz), 4.80 (t, 1H, J=6.8 Hz), 4.47 (s, 2H), 3.81 (dd, 1H, J=13.5, 3.5 Hz), 3.63 (dd, 1H, J=13.5, 2.2 Hz), 1.39 (d, 3H, J=6.8 Hz), 1.19 (d, 3H, J=6.8 Hz), 1.16 (d, 3H, J=6.8 Hz).

Example 6

Step 6-1

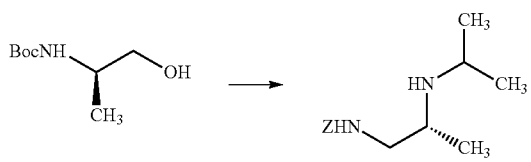

In the same manner as in step 3-3 to step 3-5, the object compound (105 mg) described in the above-mentioned scheme was obtained from (R)-2-hydroxy-1-methylethylcarbamic acid tert-butyl ester (2.0 g).

$^1$H-NMR (CDCl$_3$) δ: 7.40-7.28 (m, 5H), 5.28 (br s, 1H), 5.10 (s, 2H), 3.29-3.17 (m, 1H), 3.02-2.92 (m, 1H), 2.92-2.80 (m, 2H), 1.04 (d, 6H, J=6.3 Hz), 0.99 (d, 3H, J=6.0 Hz).

Step 6-2

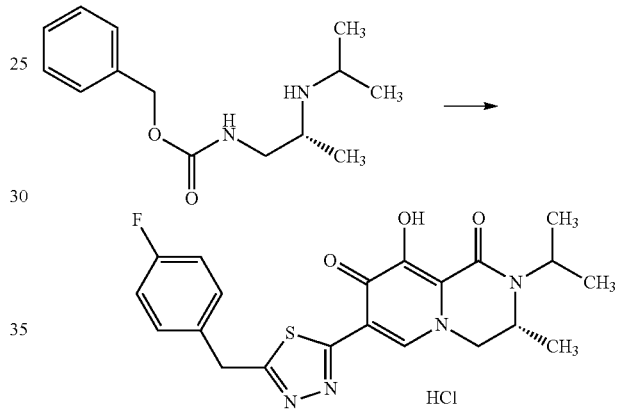

In the same manner as in step 2-9 and step 2-11 (known deprotection and condensation reactions may be omitted as necessary), the object compound (16.6 mg) described in the above-mentioned scheme was obtained from the compound (105 mg) obtained in step 6-1. For removal of the amino-protecting group (benzyloxycarbonyl group) of the compound obtained in step 6-1, a known method was used according to the protecting group.

$^1$H-NMR (DMSO-d$_6$) δ: 12.54 (br s, 1H), 8.85 (s, 1H), 7.44-7.38 (m, 2H), 7.22-7.15 (m, 2H), 4.62-4.53 (m, 1H), 4.51-4.44 (m, 3H), 4.32 (dd, 1H, J=13.1, 3.4 Hz), 4.26-4.18 (m, 1H), 1.27 (d, 3H, J=6.7 Hz), 1.26 (d, 3H, J=6.7 Hz), 1.21 (d, 3H, J=6.5 Hz).

Example 7

Step 7-1

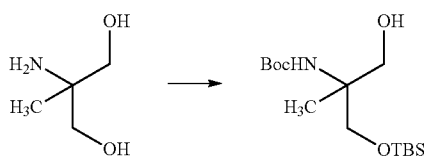

2-Amino-2-methyl-1,3-propanediol (20.0 g) was suspended in tetrahydrofuran (400 mL), and di-tert-butyl dicarbonate (41.6 g) was added. The mixture was stirred at room temperature for 3 hr and concentrated. Dimethylformamide (200 mL) was added to dissolve the concentrate again, imidazole (13.0 g) and tert-butylchlorodimethylsilane (29.3 g) were added, and the mixture was stirred at room temperature for 15 hr. Water (500 mL) was added, and the mixture was extracted with ethyl acetate (800 mL). The organic layer was washed with water (400 mL), dried, and concentrated. The concentrate was purified by silica gel column chromatography (ethyl acetate:hexane=1:10) to give the object compound (35.9 g) described in the above-mentioned scheme.

$^1$H-NMR (CDCl$_3$) δ: 5.13 (br s, 1H), 4.00 (br s, 1H), 3.77 (d, 1H, J=9.7 Hz), 3.70 (dd, 1H, J=11.4, 4.2 Hz), 3.61 (d, 1H, J=9.7 Hz), 3.55 (dd, 1H, J=11.4, 8.4 Hz), 1.44 (s, 9H), 1.19 (s, 3H), 0.90 (s, 9H), 0.07 (s, 6H).

Step 7-2

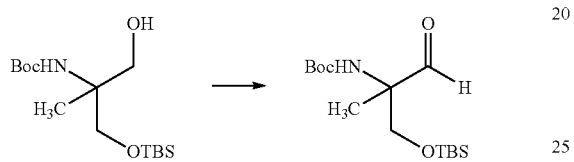

To a solution of the compound (15.5 g) obtained in step 7-1 in dimethyl sulfoxide (120 mL) were added triethylamine (8.12 mL) and a sulfur trioxide-pyridine complex (11.9 g), and the mixture was stirred at room temperature for 3 hr. 1N Aqueous hydrochloric acid solution (300 mL) was added, and the mixture was extracted with ethyl acetate (700 mL). The organic layer was washed successively with 1N aqueous hydrochloric acid solution (150 mL) and saturated aqueous sodium hydrogen carbonate solution (200 mL), dried, and concentrated. The concentrate was purified by silica gel column chromatography (ethyl acetate:hexane=1:20) to give the object compound (11.0 g) described in the above-mentioned scheme.

$^1$H-NMR (CDCl$_3$) δ: 9.49 (s, 1H), 5.29 (br s, 1H), 3.86-3.71 (br m, 2H), 1.45 (s, 9H), 1.34 (s, 3H), 0.88 (s, 9H), 0.05 (s, 6H).

Step 7-3

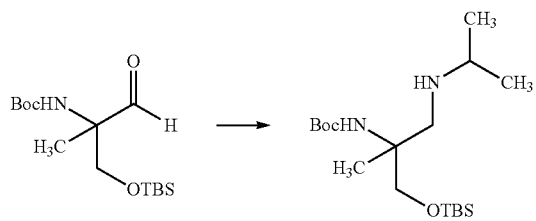 [SMILES: CC(C=O)(CO[Si](C)(C)C(C)(C)C)NC(=O)OC(C)(C)C ; CC(C)NCC(C)(CO[Si](C)(C)C(C)(C)C)NC(=O)OC(C)(C)C]

To a solution of the compound (11.0 g) obtained in step 7-2 in chloroform (110 mL) were added isopropylamine (4.46 mL), acetic acid (2.97 mL) and sodium triacetoxyborohydride (11.6 g), and the mixture was stirred at room temperature for 15 hr. The mixture was partitioned between saturated aqueous sodium hydrogen carbonate solution (150 mL) and chloroform (200 mL). The organic layer was washed twice with saturated aqueous sodium hydrogen carbonate solution (100 mL), dried, and concentrated. The concentrate was purified by silica gel column chromatography (chloroform:methanol=10:1) to give the object compound (14.1 g) described in the above-mentioned scheme.

$^1$H-NMR (CDCl$_3$) δ: 5.43 (br s, 1H), 3.73 (d, 1H, J=9.6 Hz), 3.58 (d, 1H, J=9.6 Hz), 2.80-2.66 (m, 2H), 2.55 (d, 1H, J=11.6 Hz), 1.43 (s, 9H), 1.24 (s, 3H), 1.05 (br s, 6H), 0.89 (s, 9H), 0.05 (s, 6H).

Step 7-4

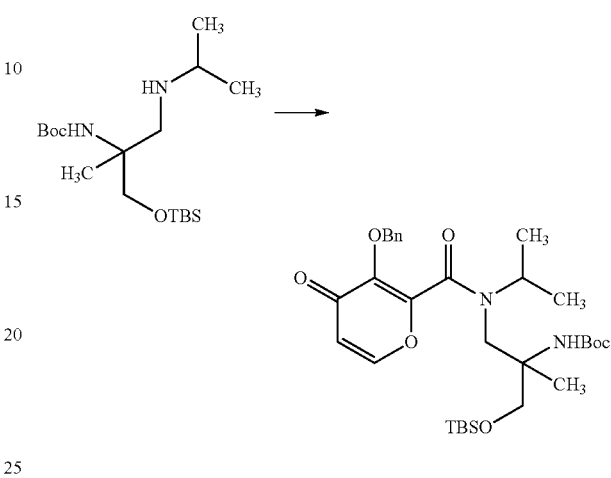

To a solution of 3-benzyloxy-4-oxo-4H-pyran-2-carboxylic acid (5.00 g) in toluene (100 mL) were added triethylamine (3.40 mL) and thionyl chloride (1.78 mL) at 0° C., and the mixture was stirred at 0° C. for 30 min. The precipitated salt was filtered off, the filtrate was concentrated, and the concentrate was dissolved in tetrahydrofuran (40 mL). This tetrahydrofuran solution was added dropwise to a solution of the compound (10.3 g) obtained in step 7-3 and pyridine (30 mL) in tetrahydrofuran (60 mL) at 0° C., and the mixture was stirred at room temperature for 30 min. The reaction mixture was concentrated, toluene was added and the mixture was concentrated. This operation was performed twice. 1N Aqueous hydrochloric acid solution (150 mL) was added, and the mixture was extracted with ethyl acetate (250 mL). The organic layer was washed with saturated aqueous sodium hydrogen carbonate solution (100 mL), dried, and concentrated. The concentrate was purified by silica gel column chromatography (chloroform:methanol=50:1) to give the object compound (9.65% g) described in the above-mentioned scheme.

$^1$H-NMR (CDCl$_3$) δ: 7.74-7.66 (m, 1H), 7.46-7.28 (m, 5H), 6.50-6.42 (m, 1H), 5.96 (br s, 1H), 5.28-5.14 (m, 2H), 4.02-3.33 (m, 5H), 1.47-1.37 (m, 9H), 1.29-1.00 (m, 9H), 0.95-0.83 (m, 9H), 0.13-0.03 (m, 6H).

Step 7-5

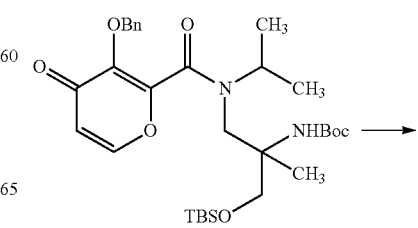

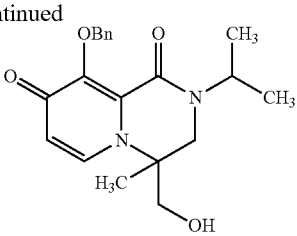

To the compound (9.65 g) obtained in step 7-4 was added 4N hydrochloric acid/ethyl acetate solution (100 mL), and the mixture was stirred at room temperature for 30 min. This was concentrated, ethanol (400 mL) and saturated aqueous sodium hydrogen carbonate solution (100 mL) were added, and the mixture was stirred at room temperature for 18 hr. The insoluble material was filtered off, and the filtrate was concentrated. Water (100 mL) was added, and the mixture was extracted twice with chloroform (200 mL, 100 mL). The organic layer was dried, and concentrated, and the concentrate was purified by silica gel column chromatography (chloroform:methanol=30:1-20:1-10:1) to give the object compound (2.20 g) described in the above-mentioned scheme.

$^1$H-NMR (CDCl$_3$) δ: 7.52 (d, 2H, J=7.9 Hz), 7.48 (d, 1H, J=7.9 Hz), 7.37-7.22 (m, 3H), 6.25 (d, 1H, J=7.9 Hz), 5.79 (br s, 1H), 5.20 (d, 1H, J=10.0 Hz), 5.17 (d, 1H, J=10.0 Hz), 4.85 (sep, 1H, J=6.5 Hz), 3.80 (d, 1H, J=12.1 Hz), 3.61 (d, 1H, J=12.1 Hz), 3.35 (d, 1H, J=14.2 Hz), 3.14 (d, 1H, J=14.2 Hz), 1.47 (s, 3H), 1.12 (d, 3H, J=6.5 Hz), 1.11 (d, 3H, J=6.5 Hz).

Step 7-6

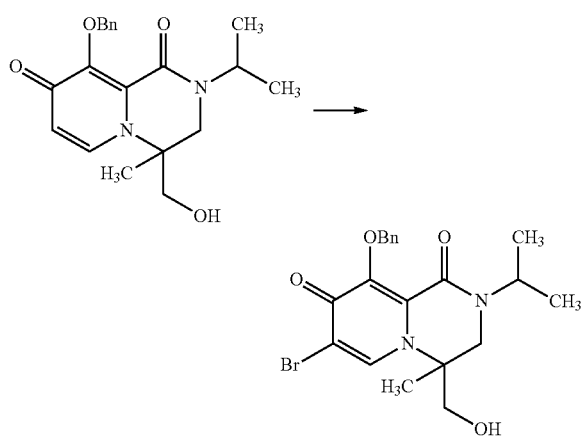

The compound (2.20 g) obtained in step 7-5, trimethylphenylammonium tribromide (3.48 g) and sodium hydrogen carbonate (1.04 g) were dissolved in 2:1 chloroform-methanol (60 mL), and the mixture was stirred at room temperature for 30 min. Saturated aqueous sodium hydrogen carbonate solution (100 mL) was added, and the mixture was extracted with chloroform (200 ml). The organic layer was washed successively with 1N aqueous hydrochloric acid solution (100 mL) and saturated aqueous sodium hydrogen carbonate solution (100 mL), dried, and concentrated to give the object compound (2.23 g) described in the above-mentioned scheme.

$^1$H-NMR (DMSO-d$_6$) δ: 8.22 (s, 1H), 7.53 (d, 2H, J=7.0 Hz), 7.41-7.27 (m, 3H), 5.48 (br s, 1H), 5.10 (d, 1H, J=10.2 Hz), 5.03 (d, 1H, J=10.2 Hz), 4.67 (sep, 1H, J=6.7 Hz), 3.66 (d, 1H, J=11.6 Hz), 3.59 (d, 1H, J=11.6 Hz), 3.56 (d, 1H, J=14.2 Hz), 3.45 (d, 1H, J=14.2 Hz), 1.48 (s, 3H), 1.11 (d, 6H, J=6.7 Hz).

Step 7-7

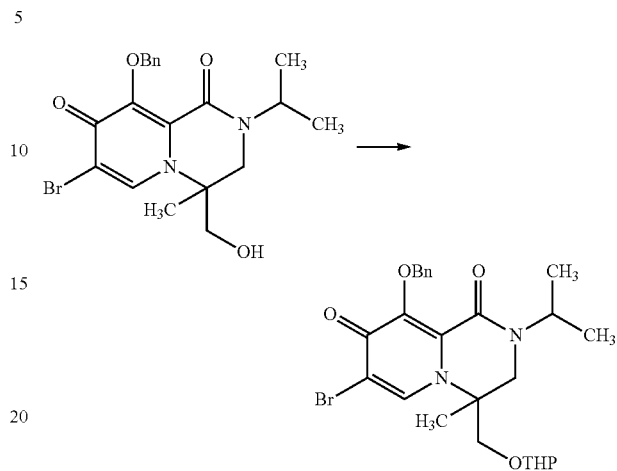

To a solution of the compound (2.12 g) obtained in step 7-6 in chloroform (45 mL) were added 3,4-dihydro-2H-pyran (882 µL) and camphorsulfonic acid (56 mg), and the mixture was stirred at room temperature for 2 hr. The reaction mixture was concentrated, and the concentrate was purified by silica gel column chromatography (chloroform:methanol=30:1) to give the object compound (2.23 g) described in the above-mentioned scheme.

$^1$H-NMR (CDCl$_3$) δ: 7.91-7.89 (m, 1H), 7.72-7.66 (m, 2H), 7.37-7.27 (m, 3H), 5.41-5.36 (m, 1H), 5.27-5.17 (m, 1H), 5.02-4.92 (m, 1H), 4.61-4.48 (m, 1H), 3.92-3.81 (m, 1H), 3.79-3.27 (m, 5H), 1.78-1.48 (m, 9H), 1.20-1.14 (m, 6H).

Step 7-8

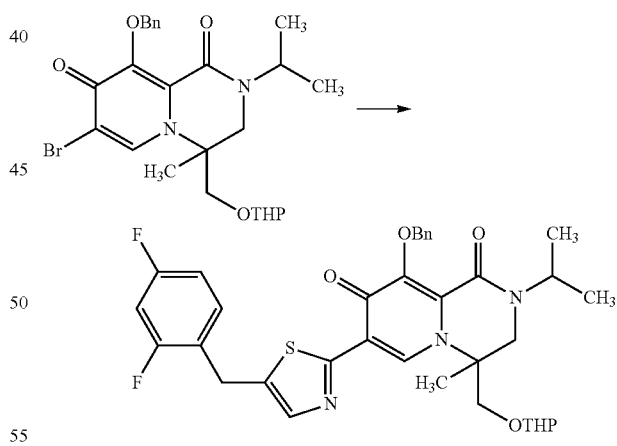

The compound (250 mg) obtained in step 7-7, tris(dibenzylideneacetone)dipalladium (44 mg), tri(2-furyl)phosphine (45 mg) and 5-(2,4-difluorobenzyl)-2-tributylstanylthiazole (835 mg) were dissolved in dioxane (5.0 mL), and the mixture was heated in a microwave apparatus at 110° C. for 40 min. This operation was performed twice using the same amounts, and the reaction mixtures were combined and concentrated. The concentrate was purified by silica gel column chromatography (chloroform:methanol=30:1) to give the object compound (682 mg) described in the above-mentioned scheme.

¹H-NMR (CDCl₃) δ: 8.78-8.74 (m, 1H), 7.72-7.67 (m, 2H), 7.60-7.56 (m, 1H), 7.37-7.17 (m, 4H), 6.86-6.71 (m, 2H), 5.52-5.46 (m, 1H), 5.34-5.25 (m, 1H), 5.03-4.93 (m, 1H), 4.62-4.53 (m, 1H), 4.20-4.14 (m, 2H), 4.02-3.87 (m, 1H), 3.77-3.43 (m, 5H), 3.36-3.26 (m, 1H), 1.78-1.42 (m, 8H), 1.21-1.13 (m, 6H).

Step 7-9

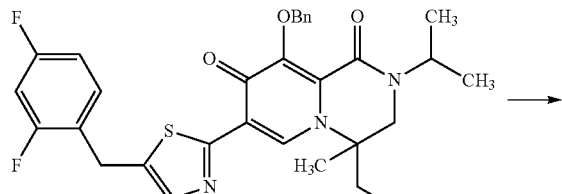

The compound (682 mg) obtained in step 7-8 was dissolved in tetrahydrofuran-methanol-water (4:1:1, 6.0 mL). Acetic acid (2.0 mL) was added, and the mixture was stirred at 80° C. for 30 hr. The reaction mixture was concentrated, toluene was added, and the mixture was concentrated. This operation was performed twice, and the concentrate was purified by silica gel column chromatography (chloroform:methanol=40:1) to give the object compound (390 mg) described in the above-mentioned scheme.

¹H-NMR (CDCl₃) δ: 8.66 (s, 1H), 7.67-7.62 (m, 2H), 7.51 (s, 1H), 7.36-7.25 (m, 3H), 7.24-7.15 (m, 1H), 6.84-6.75 (m, 2H), 5.40 (d, 1H, J=9.7 Hz), 5.29 (d, 1H, J=9.7 Hz), 4.93 (sep, 1H, J=6.7 Hz), 4.14 (s, 2H), 3.86 (s, 2H), 3.51 (d, 1H, J=13.9 Hz), 3.25 (d, 1H, J=13.9 Hz), 1.65 (s, 3H), 1.16 (d, 3H, J=6.7 Hz), 1.15 (d, 3H, J=6.7 Hz).

Step 7-10

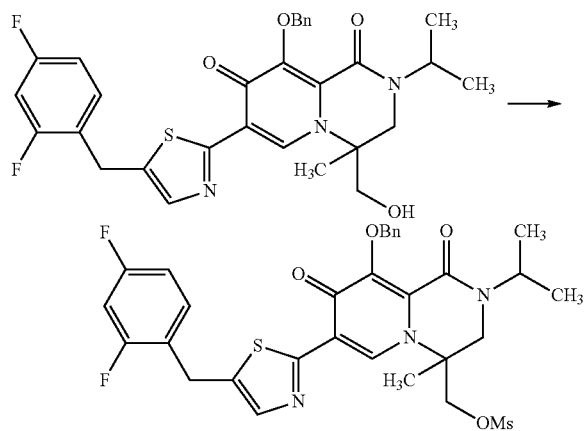

To a solution of the compound (250 mg) obtained in step 7-9 in chloroform (5.0 mL) were added triethylamine (93 μL) and methanesulfonyl chloride (41 μL) at 0° C., and the mixture was stirred at 0° C. for 1 hr. Triethylamine (93 μL) and methanesulfonyl chloride (41 μL) were added, and the mixture was further stirred at 0° C. for 1 hr. Saturated aqueous sodium hydrogen carbonate solution (20 mL) was added, and the mixture was extracted with chloroform (40 mL). The organic layer was washed with 1N aqueous hydrochloric acid solution (20 mL), dried, and concentrated to give the object compound (295 mg) described in the above-mentioned scheme.

¹H-NMR (CDCl₃) δ: 7.68-7.61 (m, 4H), 7.40-7.20 (m, 4H), 6.92-6.82 (m, 2H), 5.45 (d, 1H, J=9.8 Hz), 5.32 (d, 1H, J=9.8 Hz), 4.98 (sep, 1H, J=6.8 Hz), 4.80 (br s, 1H), 4.50 (d, 1H, J=10.1 Hz), 4.19 (s, 2H), 3.58 (d, 1H, J=14.1 Hz), 3.37 (d, 1H, J=14.1 Hz), 3.20 (br s, 3H), 1.85 (s, 3H), 1.22 (d, 3H, J=6.8 Hz), 1.19 (d, 3H, J=6.8 Hz).

Step 7-11

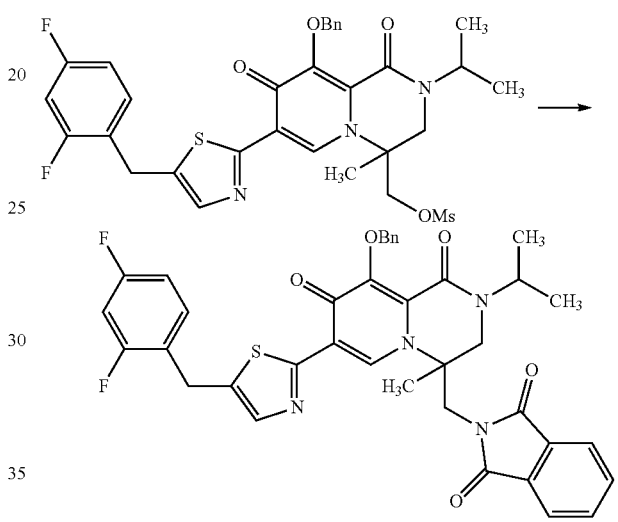

The compound (30 mg) obtained in step 7-10 and potassium phthalimide (26 mg) were dissolved in dimethylformamide (1.0 mL), and the mixture was heated in a microwave apparatus at 150° C. for 2 hr. This operation was performed two more times using the compound (115 mg) obtained in step 7-10, potassium phthalimide (100 mg) and dimethylformamide (4.0 mL), and all the reaction mixtures were combined. Water (30 mL) was added, and the mixture was extracted with ethyl acetate (60 mL). The organic layer was washed successively with 1N aqueous hydrochloric acid solution (30 mL) and saturated aqueous sodium hydrogen carbonate solution (30 mL), dried and concentrated. The concentrate was purified by silica gel column chromatography (chloroform:methanol=30:1) to give the object compound (277 mg) described in the above-mentioned scheme.

¹H-NMR (CDCl₃) δ: 8.45 (s, 1H), 7.91-7.58 (m, 7H), 7.40-7.14 (m, 4H), 6.85-6.76 (m, 2H), 5.60 (d, 1H, J=9.7 Hz), 5.31 (d, 1H, J=9.7 Hz), 5.07 (sep, 1H, J=6.7 Hz), 4.21 (d, 1H, J=14.4 Hz), 4.12 (s, 2H), 3.88 (d, 1H, J=14.4 Hz), 3.58 (d, 1H, J=13.9 Hz), 3.47 (d, 1H, J=13.9 Hz), 1.78 (s, 3H), 1.29 (d, 3H, J=6.7 Hz), 1.21 (d, 3H, J=6.7 Hz).

Step 7-12

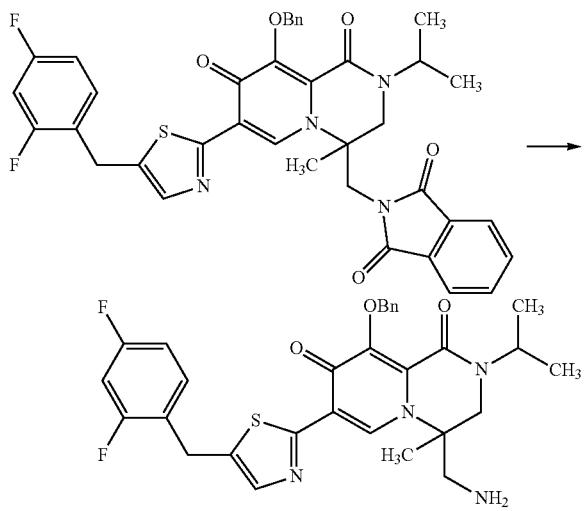

To a solution of the compound (277 mg) obtained in step 7-11 in 1:1 ethanol-toluene (6.0 mL) was added hydrazine monohydrate (60 μL), and the mixture was stirred at 80° C. for 3 hr. Furthermore, hydrazine monohydrate (60 μL) was added, and the mixture was stirred at 80° C. for 2 hr. The precipitate was filtered off, and the filtrate was concentrated, and the concentrate was purified by silica gel column chromatography (chloroform:methanol=30:1-20:1) to give the object compound (104 mg) described in the above-mentioned scheme.

$^1$H-NMR (CDCl$_3$) δ: 8.71 (s, 1H), 7.71-7.63 (m, 2H), 7.59 (s, 1H), 7.38-7.27 (m, 3H), 7.25-7.16 (m, 1H), 6.85-6.76 (m, 2H), 5.53 (d, 1H, J=9.7 Hz), 5.26 (d, 1H, J=9.7 Hz), 4.97 (sep, 1H, J=6.7 Hz), 4.18 (s, 2H), 3.51 (d, 1H, J=13.9 Hz), 3.32 (d, 1H, J=13.9 Hz), 3.05 (d, 1H, J=13.7 Hz), 2.98 (d, 1H, J=13.7 Hz), 1.67 (s, 3H), 1.20 (d, 3H, J=6.7 Hz), 1.18 (d, 3H, J=6.7 Hz).

Step 7-13

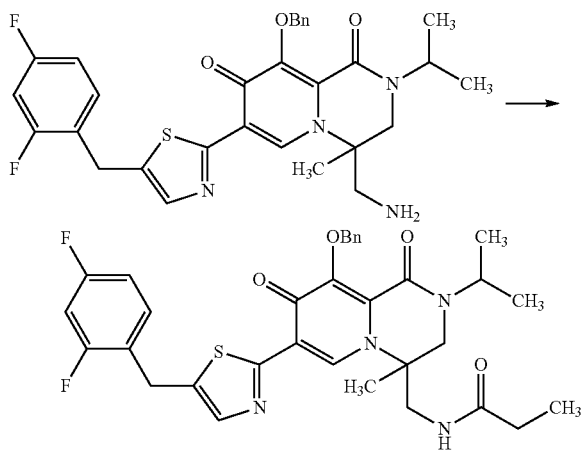

To a solution of the compound (20.0 mg) obtained in step 7-12 in chloroform (400 μL) were added triethylamine (9.9 μL) and propionyl chloride (4.8 μL), and the mixture was stirred at room temperature for 1 hr. The obtained reaction mixture was directly purified by silica gel thin layer chromatography (chloroform:methanol=10:1) to give the object compound (14.2 mg) described in the above-mentioned scheme.

$^1$H-NMR (CDCl$_3$) δ: 8.58 (s, 1H), 7.64-7.59 (m, 2H), 7.52 (s, 1H), 7.36-7.27 (m, 3H), 7.25-7.17 (m, 1H), 6.86-6.78 (m, 2H), 6.21 (br s, 1H), 5.40 (d, 1H, J=9.7 Hz), 5.28 (d, 1H, J=9.7 Hz), 4.96 (sep, 1H, J=6.7 Hz), 4.15 (s, 2H), 3.76 (dd, 1H, J=14.7, 7.1 Hz), 3.55 (dd, 1H, J=14.7, 6.4 Hz), 3.39 (d, 1H, J=13.7 Hz), 3.35 (d, 1H, J=13.7 Hz), 2.28 (dt, 2H, J=14.5, 6.6 Hz), 1.61 (s, 3H), 1.17 (d, 3H, J=6.7 Hz), 1.16 (d, 3H, J=6.7 Hz), 1.14 (t, 3H, J=7.7 Hz).

Step 7-14

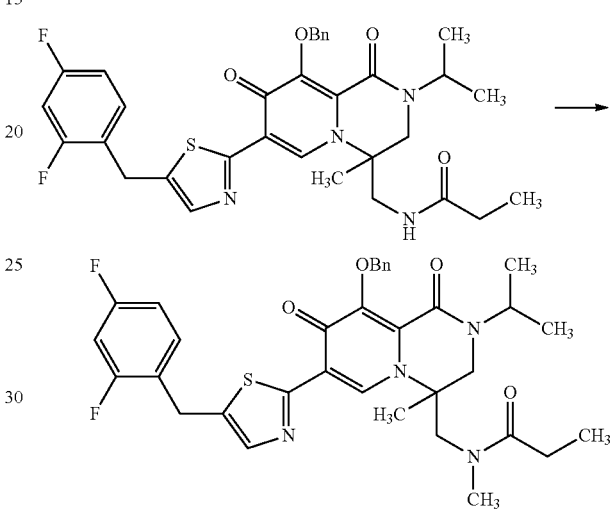

To a solution of the compound (14.0 mg) obtained in step 7-13 in tetrahydrofuran (1.0 ml) were added excess amounts of iodomethane and potassium tert-butoxide at 0° C. (until disappearance of starting materials). The obtained reaction mixture was directly purified by silica gel thin layer chromatography (chloroform:methanol=15:1) to give the object compound (5.6 mg) described in the above-mentioned scheme.

$^1$H-NMR (CDCl$_3$) δ: 8.60 (s, 1H), 7.68-7.63 (m, 2H), 7.58 (s, 1H), 7.36-7.27 (m, 3H), 7.25-7.19 (m, 1H), 6.86-6.77 (m, 2H), 5.58 (d, 1H, J=10.0 Hz), 5.32 (d, 1H, J=10.0 Hz), 4.98 (sep, 1H, J=6.7 Hz), 4.28 (d, 1H, J=14.4 Hz), 4.19 (s, 2H), 3.47 (d, 1H, J=14.2 Hz), 3.32 (d, 1H, J=14.2 Hz), 3.12 (d, 1H, J=14.4 Hz), 2.54 (s, 3H), 2.37 (dq, 1H, J=15.5, 7.0 Hz), 2.30 (dq, 1H, J=15.5, 7.0 Hz), 1.69 (s, 3H), 1.21 (d, 3H, J=6.7 Hz), 1.17 (d, 3H, J=6.7 Hz), 1.15 (t, 3H, J=7.0 Hz).

Step 7-15

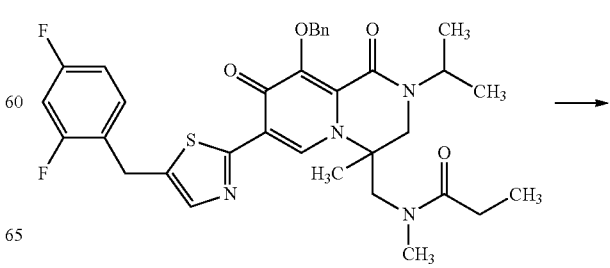

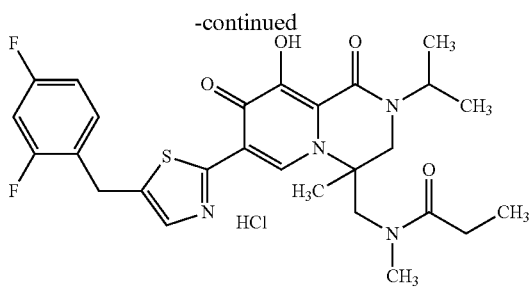

The compound (5.6 mg) obtained in step 7-14 was dissolved in trifluoroacetic acid (1.0 mL), and the mixture was stirred at room temperature for 1 hr. The reaction solution was concentrated, chloroform was added, and the mixture was concentrated. 4N Hydrochloric acid/ethyl acetate solution was added, and the mixture was concentrated. Crystallization from ethyl acetate-hexane gave the object compound (3.2 mg) described in the above-mentioned scheme.

$^1$H-NMR (DMSO-$d_6$) δ: 13.18 (br s, 1H), 8.41 (s, 1H), 7.65 (s, 1H), 7.44 (td, 1H, J=8.8, 6.7 Hz), 7.25 (ddd, 1H, J=10.2, 9.3, 2.6 Hz), 7.07 (tdd, 1H, J=8.8, 2.6, 0.9 Hz), 4.80 (sep, 1H, J=6.7 Hz), 4.21 (s, 2H), 3.83 (d, 1H, J=14.1 Hz), 3.78 (d, 1H, J=13.7 Hz), 3.68 (d, 1H, J=13.7 Hz), 3.51 (d, 1H, J=14.1 Hz), 2.77 (s, 3H), 2.16-2.03 (m, 2H), 1.67 (s, 3H), 1.22 (d, 3H, J=6.7 Hz), 1.17 (d, 3H, J=6.7 Hz), 0.69 (t, 3H, J=7.3 Hz).

Example 8

Step 8-1

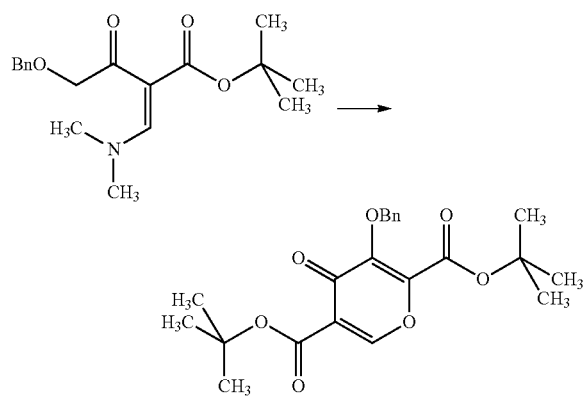

Under nitrogen, a solution of 1.6M lithium hexamethyldisilazide-THF (11.73 mL) in THF (100 mL) was cooled to −78° C., and a solution of the compound (5 g) obtained in step 2-2 in THF (15 mL) was added dropwise over 2 min under stirring. After stirring for 13 min, tert-butyl chloroglyoxylate (3.58 mL) was added at once. After stirring for 25 min, saturated aqueous potassium hydrogen sulfate solution and ethyl acetate were added, and the mixture was allowed to warm to room temperature. The organic layer was separated, washed with saturated aqueous potassium hydrogen sulfate solution and saturated brine, dried over sodium sulfate, and concentrated. Toluene was added to the residue, and the mixture was concentrated once. Toluene (100 mL) and triethylamine (10 mL) were added and the mixture was stirred at room temperature, and concentrated 30 min later. The above-mentioned operation was repeated once more, and the both were combined and purified by silica gel column chromatography (ethyl acetate:hexane=1:9-1:6) to give the object compound (4.496 g) described in the above-mentioned scheme.

$^1$H-NMR (CDCl$_3$) δ: 8.37 (s, 1H), 7.52-7.49 (m, 2H), 7.39-7.29 (m, 3H), 5.27 (s, 2H), 1.57 (s, 9H), 1.51 (s, 9H).

Step 8-2

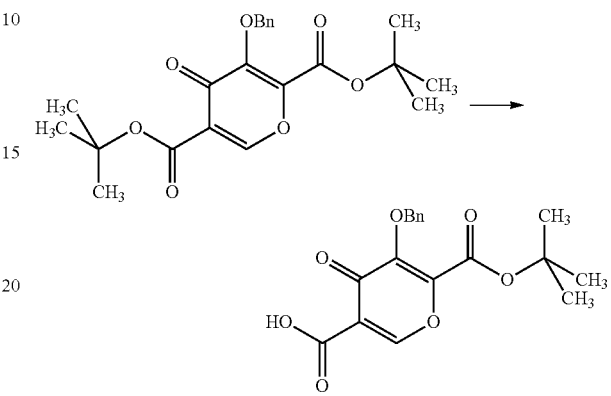

To a solution of the compound (4.49 g) obtained in step 8-1 in dioxane (5 mL) was added 4N hydrochloric acid/dioxane solution (20 mL) with stirring, and the mixture was stirred at room temperature for 20 min. The reaction mixture was concentrated, ethyl acetate/hexane (1:4) solution was added and the mixture was slurry washed. The residue was collected by filtration, and dried to give the object compound (3.30 g) described in the above-mentioned scheme.

$^1$H-NMR (CDCl$_3$) δ: 8.78 (s, 1H), 7.48-7.44 (m, 2H), 7.41-7.34 (m, 3H), 5.34 (s, 2H), 1.54 (s, 9H).

Step 8-3

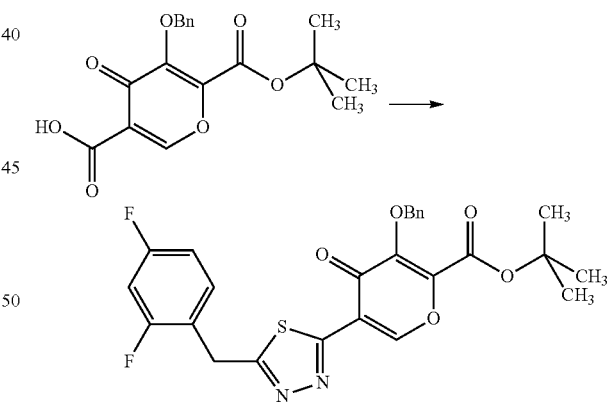

To a solution of the compound (1 g) obtained in step 8-2 in toluene (20 mL)/chloroform (5 mL) were added oxalyl chloride (0.326 mL) and dimethylformamide (0.01 mL) under stirring, and the mixture was stirred at room temperature for 30 min. The reaction mixture was concentrated, THF (20 mL) was added, and the mixture was cooled to −78° C. under nitrogen. Triethylamine (1.21 mL) and (2,4-difluorophenyl)thioacetic acid hydrazide (555 mg) were added, and the temperature of the mixture was raised slowly. After 25 min, ethyl acetate and water were added, and the mixture was warmed to room temperature. The mixture was extracted twice with ethyl acetate, and the organic layer was washed with saturated brine, dried over sodium sulfate, and concentrated. To the residue was added acetic acid (20 mL), and the mixture was stirred at 100° C. for 2 hr. The mixture was allowed to cool to room temperature, and concentrated. The concentrate was purified by silica gel column chromatography (ethyl acetate:hexane=1:9-1:4) to give the object compound (112 mg) described in the above-mentioned scheme.

¹H-NMR (CDCl₃) δ: 9.05 (s, 1H), 7.50-7.46 (m, 1H), 7.39-7.18 (m, 5H), 6.91-6.80 (m, 2H), 5.32 (s, 2H), 4.49 (s, 2H), 1.53 (s, 9H).

Step 8-4

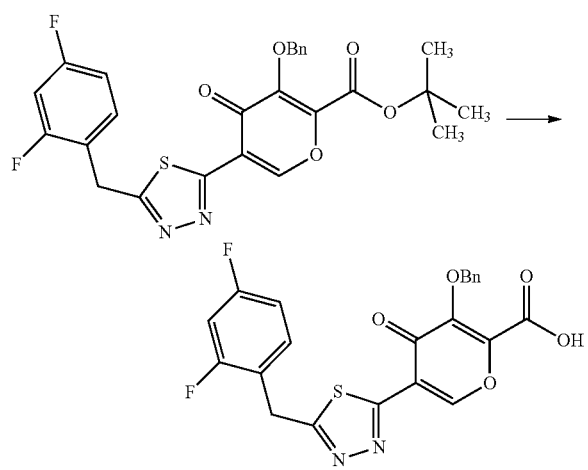

A solution of the compound (1.01 g) obtained in step 8-3 in formic acid (20 mL) was stirred at room temperature for 2 hr. The reaction mixture was concentrated, ethyl acetate/hexane (1:4) solution was added and the mixture was slurry washed. The crystals were collected by filtration. The mother liquor was concentrated, formic acid (20 mL) was added, and the mixture was stirred at room temperature for 3 hr. The reaction mixture was concentrated, ethyl acetate/hexane (1:4) solution was added and the mixture was slurry washed. The crystals were collected by filtration. The both crystals were combined and dried to give the object compound (238 mg) described in the above-mentioned scheme.

¹H-NMR (CDCl₃) δ: 9.13 (s, 1H), 7.43-7.18 (m, 6H), 6.93-6.79 (m, 2H), 5.67 (s, 2H), 4.51 (s, 2H).

Step 8-5

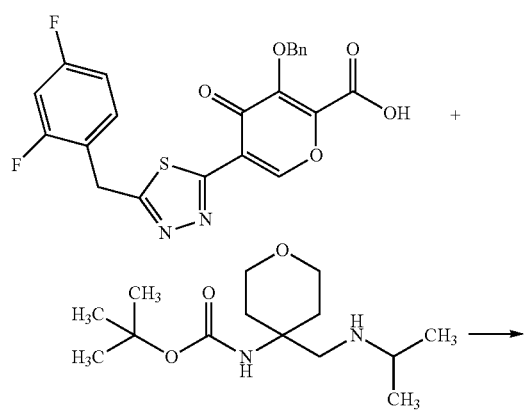

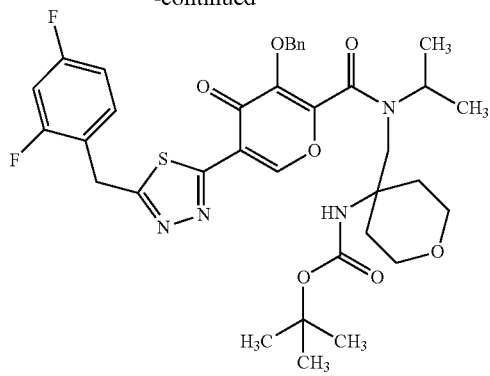

To a solution of the compound (69 mg) obtained in step 8-4 in N,N-dimethylformamide (1.5 mL) were added O-(7-azabenzotriazol-1-yl)-N,N,N',N'-tetramethyluronium hexafluorophosphate (HATU) (86 mg), 1-hydroxy-7-azabenzotriazole (HOAt) (31 mg), triethylamine (1.1 mL) and [4-(isopropylaminomethyl)tetrahydropyran-4-yl]carbamic acid tert-butyl ester (49 mg) under ice-cooling, and the mixture was stirred at room temperature overnight. To the reaction mixture was added 5% aqueous potassium hydrogen sulfate solution, and the mixture was extracted with ethyl acetate. The organic layer was washed with saturated aqueous sodium hydrogen carbonate solution, dried, and concentrated. The concentrate was purified by silica gel thin layer chromatography (chloroform:methanol=10:1) to give the object compound (18 mg) described in the above-mentioned scheme.

Step 8-6

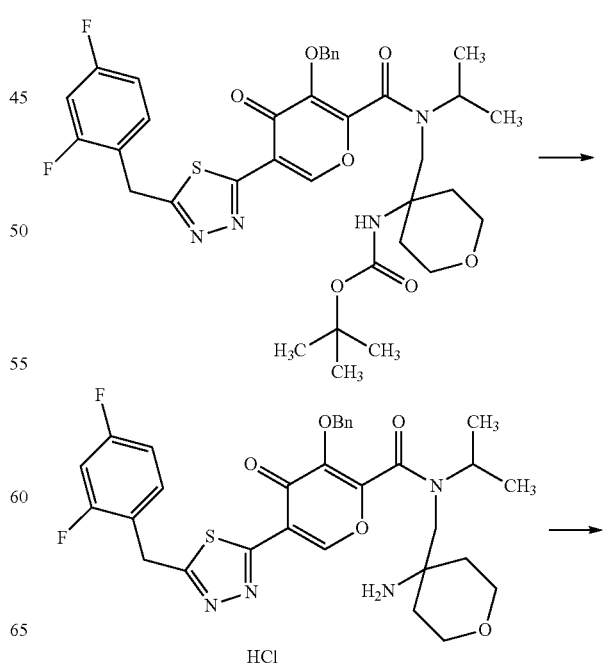

-continued

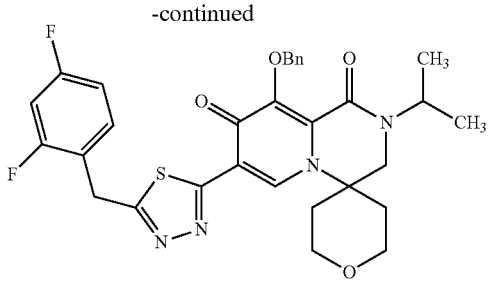

To the compound (18 mg) obtained in step 8-5 was added 4N hydrochloric acid/dioxane solution (1 mL), and the mixture was left standing at room temperature for 1.5 hr. The reaction mixture was concentrated, 2-propanol (6 mL), water (0.6 mL) and saturated aqueous sodium hydrogen carbonate solution (0.6 mL) were added, and the mixture was stirred with heating at 100° C. for 4 hr. The mixture was allowed to cool to room temperature once, left standing overnight, and stirred again with heating at 100° C. for 8 hr. To the reaction mixture was added saturated brine, and the mixture was extracted with ethyl acetate, dried and concentrated. The concentrate was purified by silica gel thin layer chromatography (chloroform:methanol=10:1) to give the object compound (10 mg) described in the above-mentioned scheme.

$^1$H-NMR (CDCl$_3$) δ: 9.05 (s, 1H), 7.66-7.62 (m, 2H), 7.38-7.28 (m, 4H), 6.88-6.81 (m, 2H), 5.38 (s, 2H), 4.97 (sep, 1H, J=7.0 Hz), 4.47 (s, 2H), 4.11-4.04 (m, 2H), 3.74-3.65 (m, 2H), 3.55 (s, 2H), 2.45-2.36 (m, 2H), 2.01-1.94 (m, 2H), 1.22 (d, 6H, J=7.0 Hz).

Step 8-7

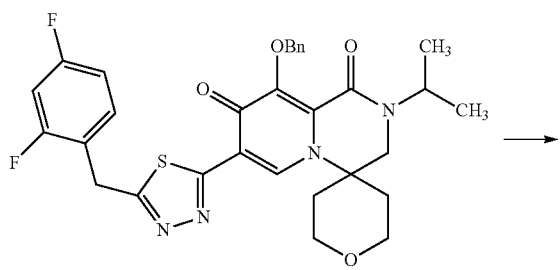

The compound (10 mg) obtained in step 8-6 was dissolved in trifluoroacetic acid (1.0 mL), and the mixture was stood at room temperature for 50 min. Trifluoroacetic acid solution was concentrated, 4N hydrochloric acid/dioxane solution was added and the mixture was concentrated. Toluene was added and the mixture was concentrated. The obtained residue was crystallized from ethyl acetate (0.5 mL)-hexane (2 mL) to give the object compound (4.7 mg) described in the above-mentioned scheme.

$^1$H-NMR (DMSO-d$_6$) δ: 13.25 (br s, 1H), 8.88 (s, 1H), 7.58-7.50 (m, 1H), 7.32-7.25 (m, 1H), 7.15-7.09 (m, 1H), 4.83 (sep, 1H, J=6.9 Hz), 4.50 (s, 2H), 3.89-3.82 (m, 2H), 3.88 (br s, 2H), 3.80-3.73 (m, 2H), 2.31-2.22 (m, 2H), 2.01-1.94 (m, 2H), 1.23 (d, 6H, J=6.9 Hz).

Example 9

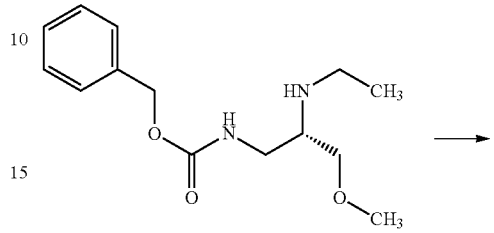

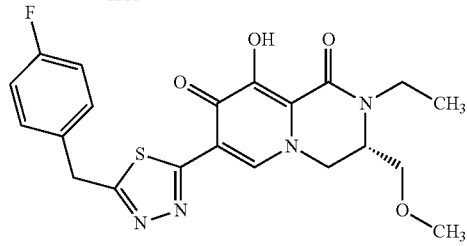

In the same manner as in step 2-9 (amino-protecting group was removed by a known method according to the protecting group) and step 2-11, the object compound (18.0 mg) described in the above-mentioned scheme was obtained from ((S)-2-ethylamino-3-methoxypropyl)carbamic acid benzyl ester (80 mg) obtainable from a commercially available compound by a known method.

$^1$H-NMR (DMSO-d$_6$) δ: 12.64-12.34 (m, 1H), 8.83 (s, 1H), 7.44-7.37 (m, 2H), 7.22-7.14 (m, 2H), 4.64 (dd, 1H, J=13.4, 1.5 Hz), 4.47 (s, 2H), 4.42 (dd, 1H, J=13.4, 4.4 Hz), 4.17-4.11 (m, 1H), 3.86 (dq, 1H, J=14.0, 7.0 Hz), 3.54 (dd, 1H, J=10.4, 4.9 Hz), 3.50 (dd, 1H, J=10.4, 6.3 Hz), 3.27 (dq, 1H, J=14.0, 7.0 Hz), 3.22 (s, 3H), 1.20 (t, 3H, J=7.0 Hz).

Example 10

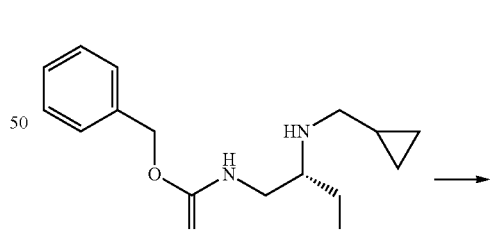

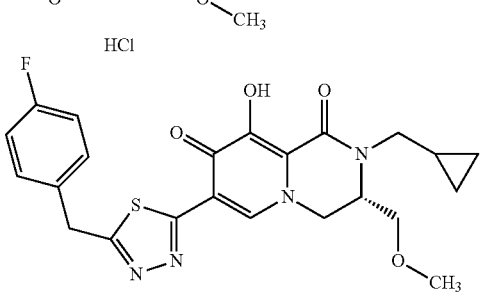

In the same manner as in step 2-9 (amino-protecting group was removed by a known method according to the protecting group) and step 2-11, the object compound (10.7 mg) described in the above-mentioned scheme was obtained from ((S)-2-cyclopropylmethylamino-3-methoxypropyl) carbamic acid benzyl ester (36 mg) obtainable from a commercially available compound by a known method.

$^1$H-NMR (DMSO-d$_6$) δ: 12.46 (br s, 1H), 8.85 (s, 1H), 7.44-7.38 (m, 2H), 7.22-7.15 (m, 2H), 4.67 (dd, 1H, J=13.7, 1.6 Hz), 4.47 (s, 2H), 4.45 (dd, 1H, J=13.7, 3.9 Hz), 4.27-4.20 (m, 1H), 3.69 (dd, 1H, J=14.0, 7.0 Hz), 3.58 (dd, 1H, J=10.3, 4.8 Hz), 3.51 (dd, 1H, J=10.3, 6.5 Hz), 3.21 (dd, 1H, J=14.0, 7.0 Hz), 3.21 (s, 3H), 1.21-1.10 (m, 1H), 0.59-0.47 (m, 2H), 0.44-0.36 (m, 1H), 0.36-0.27 (m, 1H).

Example 11

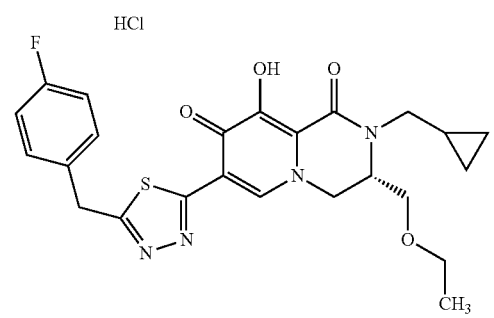

In the same manner as in step 2-9 (amino-protecting group was removed by a known method according to the protecting group) and step 2-11, the object compound (32.0 mg) described in the above-mentioned scheme was obtained from ((S)-2-cyclopropylmethylamino-3-ethoxypropyl)carbamic acid benzyl ester (295 mg) obtainable from a commercially available compound by a known method.

$^1$H-NMR (DMSO-d$_6$) δ: 12.50 (br s, 1H), 8.84 (s, 1H), 7.43-7.38 (m, 2H), 7.21-7.15 (m, 2H), 4.67 (d, 1H, J=12.3 Hz), 4.46 (s, 2H), 4.46-4.42 (m, 1H), 4.22-4.19 (m, 2H), 3.67 (dd, 1H, J=14.2, 7.2 Hz), 3.61 (dd, 1H, J=10.4, 4.4 Hz), 3.55 (dd, 1H, J=10.4, 6.2 Hz), 3.40-3.32 (m, 2H), 3.21 (dd, 1H, J=14.2, 7.0 Hz), 0.94 (t, 3H, J=7.0 Hz), 0.54-0.46 (m, 2H), 0.41-0.37 (m, 1H), 0.33-0.27 (m, 1H).

Example 12

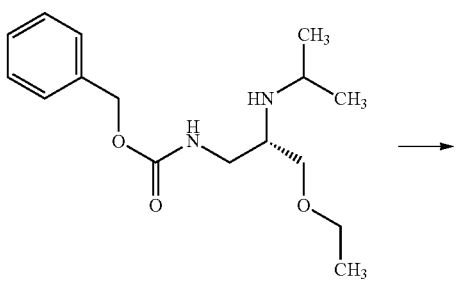

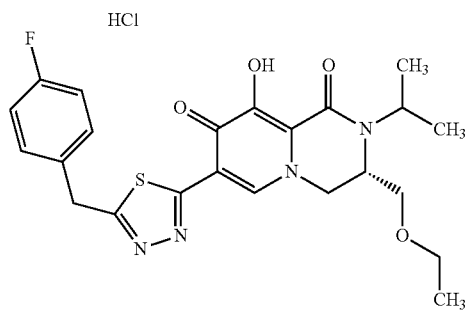

In the same manner as in step 2-9 (amino-protecting group was removed by a known method according to the protecting group) and step 2-11, the object compound (35.0 mg) described in the above-mentioned scheme was obtained from ((S)-3-ethoxy-2-isopropylaminopropyl)carbamic acid benzyl ester (230 mg) obtainable from a commercially available compound by a known method.

$^1$H-NMR (DMSO-d$_6$) δ: 12.40 (br s, 1H), 8.85 (s, 1H), 7.43-7.40 (m, 2H), 7.22-7.16 (m, 2H), 4.67, (d, 1H, J=11.9 Hz), 4.51-4.47 (m, 1H), 4.47 (s, 2H), 4.35 (dd, 1H, J=13.3, 3.9 Hz), 4.20-4.16 (m, 1H), 3.54 (dd, 1H, J=10.5, 4.1 Hz), 3.45-3.32 (m, 3H), 1.30 (d, 3H, J=4.6 Hz), 1.28 (d, 3H, J=4.6 Hz), 0.96 (t, 3H, J=7.0 Hz).

Example 13

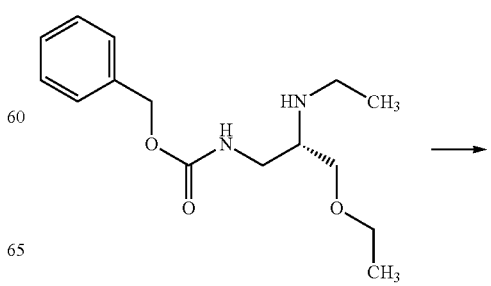

-continued

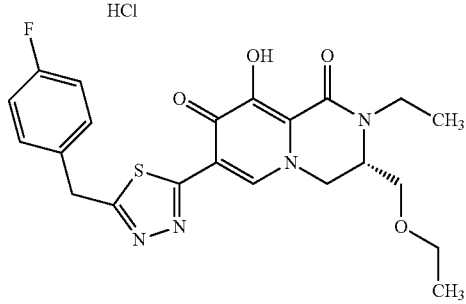

In the same manner as in step 2-9 (amino-protecting group was removed by a known method according to the protecting group) and step 2-11, the object compound (37.0 mg) described in the above-mentioned scheme was obtained from ((S)-3-ethoxy-2-ethylaminopropyl)carbamic acid benzyl ester (250 mg) obtainable from a commercially available compound by a known method.

$^1$H-NMR (DMSO-d$_6$) δ: 12.50 (br s, 1H), 8.84 (s, 1H), 7.43-7.40 (m, 2H), 7.22-7.16 (m, 2H), 4.67, (dd, 1H, J=13.5, 1.5 Hz), 4.47 (s, 2H), 4.35 (dd, 1H, J=13.5, 4.2 Hz), 4.14-4.11 (m, 1H), 3.91-3.82 (m, 1H), 3.60-3.53 (m, 2H), 3.41-3.34 (m, 2H), 3.31-3.23 (m, 1H), 1.20 (t, 3H, J=7.2 Hz), 0.96 (t, 3H, J=7.0 Hz).

Example 14

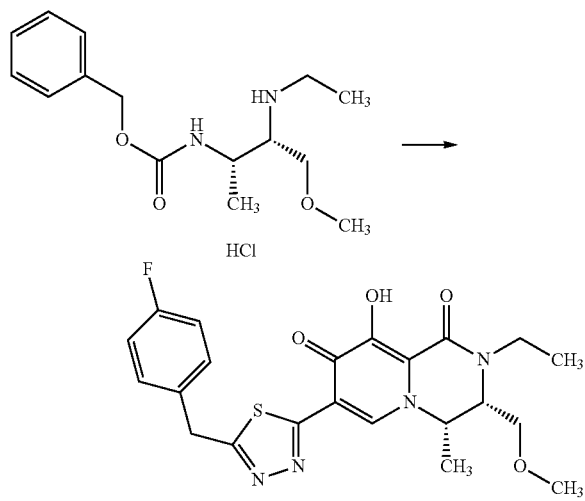

In the same manner as in step 2-9 (amino-protecting group was removed by a known method according to the protecting group) and step 2-11, the object compound (32.9 mg) described in the above-mentioned scheme was obtained from ((1S,2S)-2-ethylamino-3-methoxy-1-methylpropyl)carbamic acid benzyl ester (51 mg) obtainable from a commercially available compound by a known method.

$^1$H-NMR (DMSO-d$_6$) δ: 12.77 (br s, 1H), 8.62 (s, 1H), 7.42-7.38 (m, 2H), 7.20-7.16 (m, 2H), 4.77-4.71 (m, 1H), 4.47 (s, 2H), 4.14 (q, 1H, J=4.0 Hz), 3.92-3.84 (m, 1H), 3.59 (d, 2H, J=4.4 Hz), 3.33-3.26 (m, 1H), 3.18 (s, 3H), 1.64 (d, 3H, J=6.5 Hz), 1.21 (t, 3H, J=7.1 Hz).

Example 15

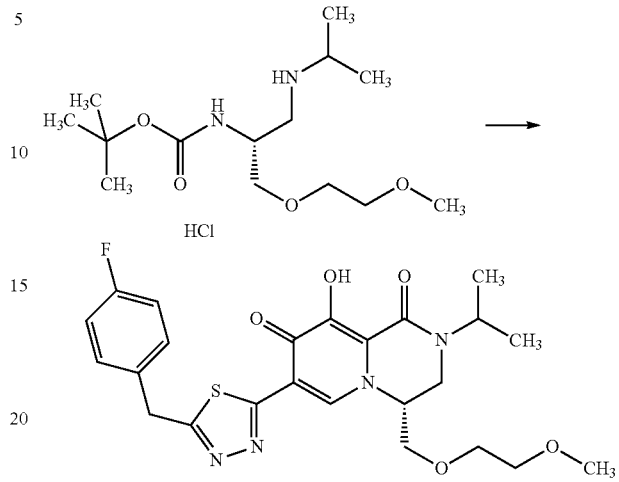

In the same manner as in step 2-9 and step 2-11, the object compound (6.2 mg) described in the above-mentioned scheme was obtained from [(R)-2-isopropylamino-1-((2-methoxyethoxy)methyl)ethyl]carbamic acid tert-butyl ester (19.3 mg) obtainable from a commercially available compound by a known method.

$^1$H-NMR (DMSO-d$_6$) δ: 12.83 (br s, 1H), 8.82 (s, 1H), 7.45-7.38 (m, 2H), 7.23-7.15 (m, 2H), 4.99-4.91 (m, 1H), 4.77 (sep, 1H, J=6.7 Hz), 4.47 (s, 2H), 3.84 (dd, 1H, J=13.8, 4.1 Hz), 3.78-3.68 (m, 2H), 3.64 (dd, 1H, J=10.4, 7.7 Hz), 3.58-3.45 (m, 2H), 3.34 (t, 2H, J=4.5 Hz), 3.11 (s, 3H), 1.17 (d, 3H, J=6.7 Hz), 1.16 (d, 3H, J=6.7 Hz).

Example 16

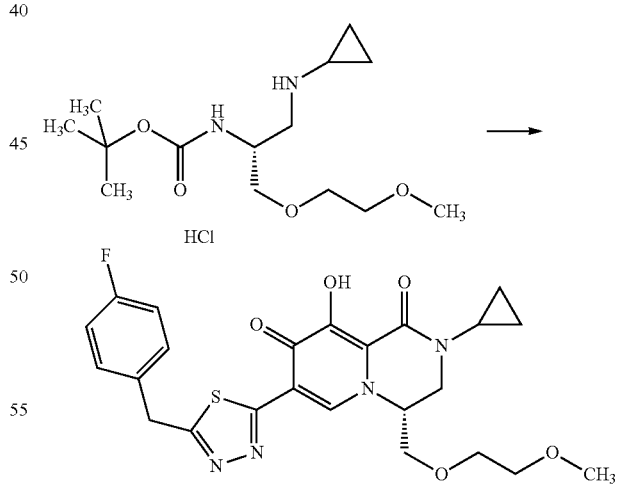

In the same manner as in step 2-9 and step 2-11, the object compound (10.7 mg) described in the above-mentioned scheme was obtained from [(R)-2-cyclopropylamino-1-((2-methoxyethoxy)methyl)ethyl]carbamic acid tert-butyl ester (16 mg) obtainable from a commercially available compound by a known method.

$^1$H-NMR (DMSO-d$_6$) δ: 8.81 (s, 1H), 7.45-7.37 (m, 2H), 7.22-7.14 (m, 2H), 4.92-4.84 (br m, 1H), 4.47 (s, 2H), 4.09-3.99 (m, 1H), 3.74-3.57 (m, 3H), 3.56-3.44 (m, 2H), 3.34 (t, 2H, J=4.6 Hz), 3.13 (s, 3H), 2.94-2.84 (m, 1H), 0.97-0.67 (m, 4H).

Example 17

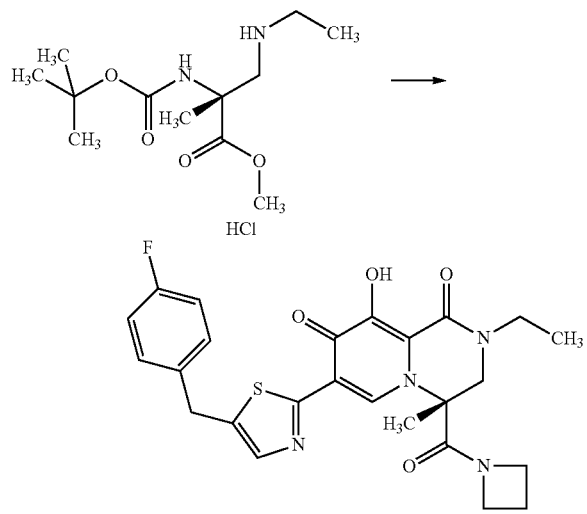

In the same manner as in step 2-9 to step 2-11, the object compound (39 mg) described in the above-mentioned scheme was obtained from (R)-2-tert-butoxycarbonylamino-3-ethylamino-2-methylpropionic acid methyl ester (60 mg) obtainable from a commercially available compound by a known method.

$^1$H-NMR (DMSO-$d_6$) δ: 12.69 (m, 1H), 8.60 (s, 1H), 7.69 (s, 1H), 7.34-7.30 (m, 2H), 7.16-7.12 (m, 2H), 4.20 (s, 2H), 4.18-4.13 (m, 1H), 4.01 (d, 1H, J=13.5 Hz), 3.89 (d, 1H, J=13.5 Hz), 3.87-3.80 (m, 2H), 3.67-3.61 (m, 1H), 3.54-3.44 (m, 2H), 2.12-2.04 (m, 2H), 1.91 (s, 3H), 1.10 (t, 3H, J=7.2 Hz).

Example 340

Step 340-1

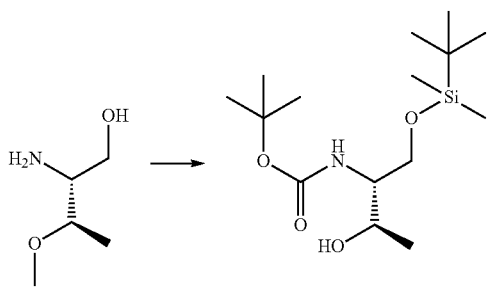

To a solution of L-threoninol (2.05 g) in chloroform (14 mL) were added di-tert-butyl dicarbonate (4.26 g) and saturated aqueous sodium hydrogen carbonate solution (10 mL) and the mixture was stirred at room temperature for 3 hr and left standing for 3 days. To the reaction mixture was added saturated brine, and the mixture was extracted with chloroform. The organic layer was dried, and concentrated. The obtained residue was dissolved in dimethylformamide (40 mL) and, under ice-cooling, imidazole (2.97 g) and tert-butylchlorodimethylsilane (1.49 g) were added, and the mixture was stirred at room temperature for 45 min. Water was added, and the mixture was extracted with ethyl acetate. The organic layer was washed with saturated brine, dried, and concentrated. The concentrate was purified by silica gel column chromatography (ethyl acetate:hexane=1:10-1:3) to give the object compound (2.39 g) described in the above-mentioned scheme.

$^1$H-NMR (CDCl$_3$) δ: 5.18 (d, 1H, J=8.2 Hz), 4.18-4.14 (m, 1H), 3.89 (dd, 1H, J=10.4, 3.3 Hz), 3.82 (dd, 1H, J=10.4, 2.6 Hz), 3.48-3.45 (m, 1H), 3.29 (s, 1H), 1.46 (s, 9H), 1.18 (d, 3H, J=6.2 Hz), 0.90 (s, 9H), 0.08 (s, 6H).

Step 340-2

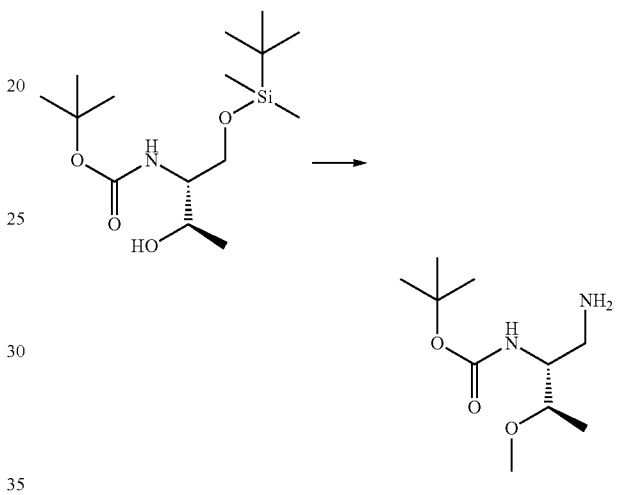

To a solution of the compound (2.39 g) obtained in step 340-1 in toluene (12 mL) were added tetrabutylammonium hydrogen sulfate (76 mg), 50% aqueous sodium hydroxide solution (8 mL) and methyl sulfate (922 μL) under ice-cooling, and the mixture was stirred at room temperature for 90 min. Ice water was added, and the mixture was extracted with toluene. The organic layer was washed with saturated brine, dried, and concentrated. The obtained residue was dissolved in to tetrahydrofuran (20 mL), 1.0M tetrabutylammonium fluoride/tetrahydrofuran solution (8.16 mL) was added and the mixture was stirred at room temperature for 100 min. Water was added, and the mixture was extracted with ethyl acetate. The organic layer was washed with saturated brine, dried and concentrated. Toluene was added and the mixture was concentrated again. To a solution of the obtained residue in tetrahydrofuran (40 mL) were added phthalimide (1.85 g) and triphenylphosphine (3.30 g), 2.2M diethyl azodicarboxylate/toluene solution (5.05 mL) was added dropwise under ice-cooling, and the mixture was stirred at room temperature for 90 min. The reaction mixture was concentrated, and the concentrate was purified by silica gel column chromatography (ethyl acetate:hexane=1:10-1:2). The obtained solid was dissolved in ethanol (60 mL)-toluene (60 mL), hydrazine monohydrate (2.05 mL) was added, and the mixture was stirred at 80° C. for 4 hr. The mixture was allowed to cool to room temperature, the solid was filtered off, and the filtrate was concentrated. Toluene was added to the residue, and the precipitated solid was filtered off. The filtrate was concentrated to give the object compound (1.54 g) described in the above-mentioned scheme.

¹H-NMR (CDCl₃) δ: 4.82 (br s, 1H), 3.52-3.45 (m, 2H), 3.31 (s, 3H), 2.81 (dd, 2H, J=13.0, 6.0 Hz), 2.76 (dd, 2H, J=13.0, 7.1 Hz), 1.51 (br s, 2H), 1.15 (d, 3H, J=6.2 Hz).

Step 340-3

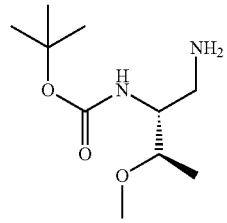

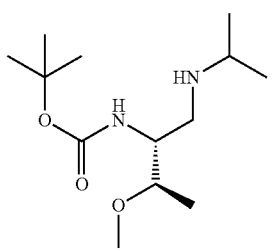

To a solution of the compound (187 mg) obtained in step 340-2 in chloroform (3 mL) were added acetone (76 μL), acetic acid (59 μL) and sodium triacetoxyborohydride (218 mg) under ice-cooling, and the mixture was stirred at room temperature for 5 hr. The reaction mixture was diluted with chloroform, saturated aqueous sodium hydrogen carbonate solution was added and the mixture was stirred. The chloroform layer was dried and concentrated to give the object compound (190 mg) described in the above-mentioned scheme.

¹H-NMR (CDCl₃) δ: 4.84 (br s, 1H), 3.59-3.50 (m, 2H), 3.32 (s, 3H), 2.83-2.66 (m, 3H), 1.51 (br s, 1H), 1.14 (d, 3H, J=6.4 Hz), 1.04 (d, 3H, J=6.4 Hz), 1.04 (d, 3H, J=6.4 Hz).

Step 340-4

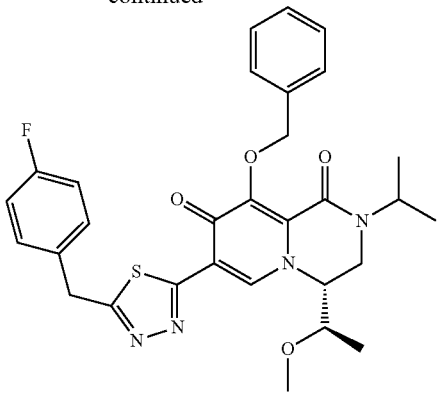

The compound (190 mg) obtained in step 340-3 was dissolved in trifluoroacetic acid (2.0 mL), and the mixture was stood at room temperature for 20 min. Trifluoroacetic acid solution was concentrated, tetrahydrofuran (1.58 mL) and diisopropylethylamine (636 μL) were added to give a solution.

To a solution of the compound (75 mg) obtained in step 2-5 in tetrahydrofuran (500 μL) was added the above-mentioned solution (634 μL), and the mixture was stirred at room temperature for 15 min. Toluene (6 mL) and 1,8-diazabicyclo[5.4.0]undec-7-ene (250 μL) were added and the mixture was stirred at 100° C. for 20 min. Acetic acid (750 μL) was added and the mixture was stirred at 100° C. for 1 hr. The reaction mixture was allowed to cool to room temperature, 5% aqueous potassium hydrogen sulfate solution was added, and the mixture was extracted with ethyl acetate. The organic layer was washed with saturated aqueous sodium hydrogen carbonate solution and saturated brine, dried, and concentrated. The concentrate was purified by silica gel thin layer chromatography (ethyl acetate:methanol=15:1) to give the object compound (73 mg) described in the above-mentioned scheme.

¹H-NMR (CDCl₃) δ: 8.65 (s, 1H), 7.65-7.62 (m, 2H), 7.35-7.25 (m, 5H), 7.04-6.98 (m, 2H), 5.51 (d, 1H, J=9.9 Hz), 5.24 (d, 1H, J=9.9 Hz), 4.94 (sep, 1H, J=6.8 Hz), 4.43 (s, 2H), 3.93-3.89 (m, 1H), 3.67 (dd, 1H, J=14.2, 3.9 Hz), 3.47 (dq, 1H, J=8.8, 6.0 Hz), 3.42 (dd, 1H, J=14.2, 1.5 Hz), 3.15 (s, 3H), 1.29 (d, 3H, J=6.0 Hz), 1.19 (d, 3H, J=6.8 Hz), 1.14 (d, 3H, J=6.8 Hz).

Step 340-5

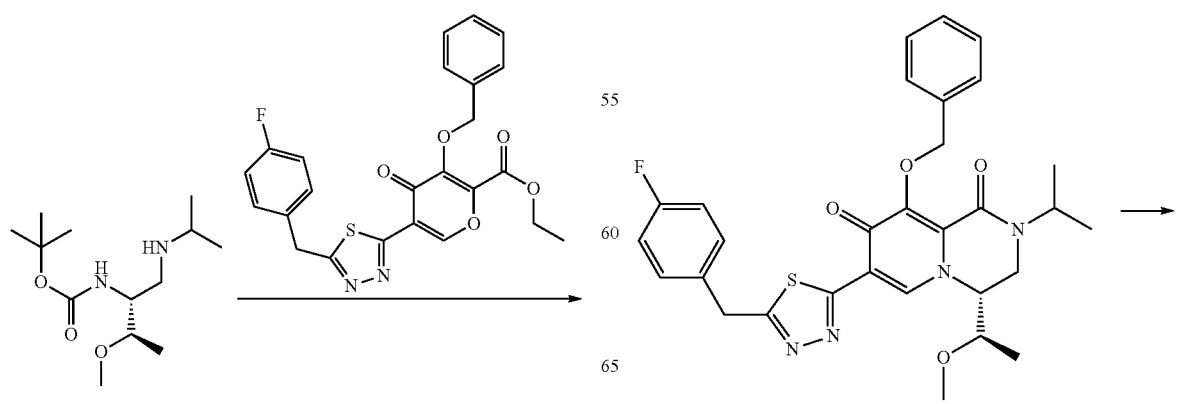

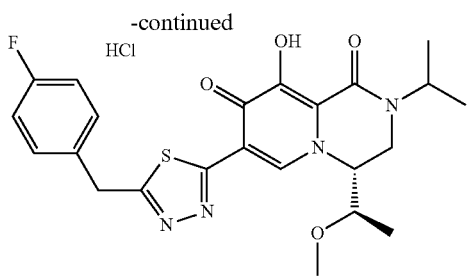

The compound (72 mg) obtained in step 340-4 was dissolved in trifluoroacetic acid (1.0 mL), and the mixture was stood at room temperature for 4 hr. Trifluoroacetic acid solution was concentrated, toluene was added and the mixture was concentrated. Ethyl acetate, 4N hydrochloric acid/ethyl acetate solution, and hexane were added to allow crystallization to give the object compound (65 mg) described in the above-mentioned scheme.

$^1$H-NMR (DMSO-D$_6$) δ: 12.82 (br s, 1H), 8.72 (s, 1H), 7.44-7.41 (m, 2H), 7.21-7.17 (m, 2H), 4.77 (sep, 1H, J=6.6 Hz), 4.65 (ddd, 1H, J=8.2, 4.1, 0.9 Hz), 4.47 (s, 2H), 3.88 (dd, 1H, J=14.0, 4.1 Hz), 3.76 (dd, 1H, J=14.0, 0.9 Hz), 3.52 (dq, 1H, J=8.2, 6.2 Hz), 3.03 (s, 3H), 1.21 (d, 3H, J=6.2 Hz), 1.20 (d, 3H, J=6.6 Hz), 1.17 (d, 3H, J=6.6 Hz).

The compounds of Examples 18 to 465 shown in the following Tables were produced in the same manner as in the above-mentioned Examples 1 to 17 and 340, or by using other conventional methods where necessary. The structural formulas and property data of the compounds of Examples 18 to 465 are shown in the following Tables.

TABLE 1-1

| No. | structural formula | salt | $^1$H-NMR |
|---|---|---|---|
| 18 | (structure) | — | $^1$H-NMR (DMSO-d$_6$) δ: 12.82 (s, 1H), 8.80 (s, 1H), 7.54 (td, 1H, J = 8.8, 6.7 Hz), 7.29 (ddd, 1H, J = 10.2, 9.3, 2.6 Hz), 7.12 (tdd, 1H, J = 8.8, 2.6 0.9 Hz), 5.01-4.93 (br m, 1H), 4.77 (sep, 1H, J = 6.7 Hz), 4.49 (s, 2H), 3.84 (dd, 1H, J = 13.9, 3.9 Hz), 3.75 (dd, 1H, J = 13.9, 1.4 Hz), 3.62 (dd, 1H, J = 10.2, 5.8 Hz), 3.57 (dd, 1H, J = 10.2, 7.7 Hz), 3.25 (s, 3H), 1.16 (d, 3H, J = 6.7 Hz), 1.16 (d, 3H, J = 6.7 Hz). |
| 19 | (structure) | — | $^1$H-NMR (DMSO-d$_6$) δ: 12.69 (br s, 1H), 8.58 (s, 1H), 7.64 (s, 1H), 7.45 (td, 1H, J = 8.8, 6.8 Hz), 7.24 (ddd, 1H, J = 10.6, 9.7, 2.9 Hz), 7.07 (tdd, 1H, J = 8.8, 2.9, 1.0 Hz), 4.75 (sep, 1H, J = 6.6 Hz), 4.69-4.59 (br m, 1H), 4.21 (s, 2H), 3.81 (dd, 1H, J = 13.5, 3.7 Hz), 3.72 (dd, 1H, J = 13.5, 1.5 Hz), 3.67 (dd, 1H, J = 11.7, 5.3 Hz), 3.53 (dd, 1H, J = 11.7, 8.6 Hz), 1.16 (d, 3H, J = 6.6 Hz), 1.15 (d, 3H, J = 6.6 Hz). |
| 20 | (structure) | — | $^1$H-NMR (DMSO-d$_6$) δ: 13.11 (br s, 1H), 8.60 (s, 1H), 7.66 (s, 1H), 7.44 (td, 1H, J = 8.7, 6.7 Hz), 7.24 (ddd, 1H, J = 10.4, 9.3, 2.8 Hz), 7.07 (tdd, 1H, J = 8.7, 2.8, 0.9 Hz), 4.79 (sep, 1H, J = 6.7 Hz), 4.21 (s, 2 H), 3.89 (d, 1H, J = 14.1 Hz), 3.79 (d, 1H, J = 14.1 Hz), 3.72 (d, 1H, J = 13.7 Hz), 3.63 (d, 1H, J = 13.7 Hz), 1.58 (s, 3H), 1.17 (d, 3H, J = 6.7 Hz), 1.17 (d, 3H, J = 6.7 Hz). |

TABLE 1-2

| No. | structural formula | salt | ¹H-NMR |
|---|---|---|---|
| 21 | | HCl | ¹H-NMR (DMSO-d₆) δ: 12.67 (s, 1H), 8.71 (s, 1H), 7.65 (s, 1H), 7.49-7.41 (m, 1H), 7.33-7.20 (m, 1H), 7.11-7.02 (m, 1H), 5.11-5.02 (m, 1H), 4.84-4.73 (m, 1H), 4.21 (s, 2H), 3.87-3.73 (m, 2H), 2.89-2.82 (m, 2H), 2.86 (s, 3H), 2.79 (s, 3H), 1.13 (d, 3H, J = 7.0 Hz), 1.13 (d, 3H, J = 6.7 Hz). |
| 22 | | — | ¹H-NMR (DMSO-d₆) δ: 12.37 (s, 1H), 8.66 (s, 1H), 8.25 (q, 1H, J = 4.4 Hz), 7.64 (s, 1H), 7.45 (td, 1H, J = 8.6, 6.5 Hz), 7.25 (ddd, 1H, J = 10.4, 9.5, 2.8 Hz), 7.07 (tdd, 1H, J = 8.6, 2.8, 0.9 Hz), 5.52-5.46 (br m, 1H), 4.69 (sep, 1H, J = 6.7 Hz), 4.22 (s, 2H), 4.02 (dd, 1H, J = 13.9, 2.1 Hz), 3.94 (dd, 1H, J = 13.9, 3.5 Hz), 2.61 (d, 3H, J = 4.4 Hz), 1.12 (d, 3H, J = 6.7 Hz), 1.03 (d, 3H, J = 6.7 Hz). |
| 23 | | — | ¹H-NMR (DMSO-d₆) δ: 12.42 (br s, 1H), 8.75 (s, 1H), 7.65 (s, 1H), 7.46 (td, 1H, J = 8.8, 7.1 Hz), 7.24 (ddd, 1H, J = 10.6, 9.7, 2.4 Hz), 7.07 (tdd, 1H, J = 8.8, 2.4, 0.9 Hz), 5.71-5.66 (br m, 1H), 4.73 (sep, 1H, J = 6.7 Hz), 4.22 (s, 2H), 4.03 (dd, 1H, J = 13.5, 2.6 Hz), 3.95 (dd, 1H, J = 13.5, 4.0 Hz), 1.16 (d, 3H, J = 6.7 Hz), 1.11 (d, 3H, J = 6.7 Hz). |

TABLE 1-3

| No. | structural formula | salt | ¹H-NMR |
|---|---|---|---|
| 24 | | — | ¹H-NMR (DMSO-d₆) δ: 12.90 (br s, 1H), 8.59 (s, 1H), 7.66 (s, 1H), 7.44 (td, 1H, J = 9.0, 7.3 Hz), 7.24 (ddd, 1H, J = 10.8, 9.3, 2.4 Hz), 7.07 (tdd, 1H, J = 9.0, 2.4, 1.0 Hz), 4.72 (sep, 1H, J = 6.7 Hz), 4.22 (s, 2H), 4.05 (d, 2H, J = 13.2 Hz), 3.74 (d, 1H, J = 13.2 Hz), 1.92 (s, 3H), 1.16 (d, 3H, J = 6.7 Hz), 1.14 (d, 3H, J = 6.7 Hz). |
| 25 | | — | ¹H-NMR (DMSO-d₆) δ: 12.39 (s, 1H), 8.66 (s, 1H), 8.36 (t, 1H, J = 5.4 Hz), 7.64 (s, 1H), 7.45 (td, 1H, J = 8.7, 6.6 Hz), 7.25 (ddd, 1H, J = 10.4, 9.3, 2.6 Hz), 7.07 (tdd, 1H, J = 8.7, 2.6, 0.9 Hz), 5.50-5.43 (br m, 1H), 4.70 (sep, 1H, J = 6.7 Hz), 4.22 (s, 2H), 4.03 (dd, 1H, J = 13.9, 1.6 Hz), 3.95 (dd, 1H, J = 13.9, 3.7 Hz), 3.09 (qd, 2H, J = 7.4, 5.4 Hz), 1.13 (d, 3H, J = 6.7 Hz), 1.05 (d, 3H, J = 6.7 Hz), 1.02 (t, 3H, J = 7.4 Hz). |

TABLE 1-3-continued

| No. | structural formula | salt | ¹H-NMR |
|---|---|---|---|
| 26 | | — | ¹H-NMR (DMSO-$d_6$) δ: 12.32 (br s, 1H), 8.71 (s, 1H), 7.63 (s, 1H), 7.46 (td, 1H, J = 8.7, 6.6 Hz), 7.25 (ddd, 1H, J = 10.4, 9.5, 2.6 Hz), 7.07 (tdd, 1H, J = 8.7, 2.6, 1.2 Hz), 6.05-6.00 (br m, 1H), 4.71 (sep, 1H, J = 6.7 Hz), 4.21 (s, 2H), 3.98 (dd, 1H, J = 14.4, 3.9 Hz), 3.80 (dd, 1H, J = 14.4, 1.4 Hz), 3.17 (s, 3H), 2.82 (s, 3H), 1.14 (d, 3H, J = 6.7 Hz), 0.98 (d, 3H, J = 6.7 Hz). |

TABLE 1-4

| No. | structural formula | salt | ¹H-NMR |
|---|---|---|---|
| 27 | | — | ¹H-NMR (DMSO-$d_6$) δ: 12.80 (s, 1H), 8.50 (s, 1H), 8.13 (t, 1H, J = 5.4 Hz), 7.66 (s, 1H), 7.44 (td, 1H, J = 8.7, 6.7 Hz), 7.24 (ddd, 1H, J = 10.4, 9.3, 2.7 Hz), 7.07 (tdd, 1H, J = 8.7, 2.7, 0.9 Hz), 4.71 (sep, 1H, J = 6.7 Hz), 4.22 (s, 2H), 4.08 (d, 1H, J = 13.8 Hz), 3.78 (d, 1H, J = 13.8 Hz), 3.17-2.98 (m, 2H), 1.92 (s, 3H), 1.15 (d, 3H, J = 6.7 Hz), 1.11 (d, 3H, J = 6.7 Hz), 1.00 (t, 3H, J = 7.2 Hz). |
| 28 | | — | ¹H-NMR (DMSO-$d_6$) δ: 12.85 (s, 1H), 8.42 (s, 1H), 7.66 (s, 1H), 7.45 (td, 1H, J = 8.7, 6.7 Hz), 7.24 (ddd, 1H, J = 10.4, 9.7, 2.8 Hz), 7.07 (tdd, 1H, J = 8.7, 2.8, 0.9 Hz), 4.73 (sep, 1H, J = 6.7 Hz), 4.22 (s, 2H), 4.12 (d, 1H, J = 14.1 Hz), 3.79 (d, 1H, J = 14.1 Hz), 2.93 (br s, 6H), 1.97 (s, 3H), 1.17 (d, 3H, J = 6.7 Hz), 1.11 (d, 3H, J = 6.7 Hz). |
| 29 | | — | ¹H-NMR (DMSO-$d_6$) δ: 12.78 (s, 1H), 8.51 (s, 1H), 8.05 (q, 1H, J = 4.2 Hz), 7.66 (s, 1H), 7.44 (td, 1H, J = 8.7, 6.6 Hz), 7.24 (ddd, 1H, J = 10.4, 9.5, 2.6 Hz), 7.07 (tdd, 1H, J = 8.7, 2.6, 0.9 Hz), 4.70 (sep, 1H, J = 6.7 Hz), 4.22 (s, 2H), 4.05 (d, 1H, J = 13.7 Hz), 3.78 (d, 1H, J = 13.7 Hz), 2.59 (d, 3H, J = 4.2 Hz), 1.92 (s, 3H), 1.14 (d, 3H, J = 6.7 Hz), 1.08 (d, 3H, J = 6.7 Hz). |

TABLE 1-5

| No. | structural formula | salt | ¹H-NMR |
|---|---|---|---|
| 30 | | HCl | ¹H-NMR (DMSO-d$_6$) δ: 13.17 (br s, 1H), 8.87 (s, 1H), 7.54 (td, 1H, J = 8.5, 6.9 Hz), 7.29 (ddd, 1H, J = 10.5, 9.3, 2.4 Hz), 7.11 (tdd, 1H, J = 8.5, 2.4, 1.2 Hz), 4.49 (s, 2H), 3.90 (s, 2H), 3.88-3.81 (m, 2H), 3.74-3.66 (m, 2H), 2.98 (ddt, 1H, J = 7.3, 6.9, 4.0 Hz), 2.28-2.19 (m, 2H), 1.98-1.91 (m, 2H), 0.93-0.80 (m, 4H). |
| 31 | | HCl | ¹H-NMR (DMSO-d$_6$) δ: 12.42 (br s, 1H), 8.65 (s, 1H), 8.30 (d, 1H, J = 7.4 Hz), 7.64 (s, 1H), 7.45 (td, 1H, J = 8.6, 6.5 Hz), 7.25 (ddd, 1H, J = 10.4, 9.5, 2.6 Hz), 7.07 (tdd, 1H, J = 8.6, 2.6, 0.9 Hz), 5.46-5.41 (br m, 1H), 4.71 (sep, 1H, J = 6.7 Hz), 4.22 (s, 2H), 4.03 (dd, 1H, J = 14.0, 1.9 Hz), 3.95 (dd, 1H, J = 14.0, 3.6 Hz), 3.85-3.74 (m, 1H), 1.13 (d, 3H, J = 6.7 Hz), 1.09 (d, 3H, J = 6.7 Hz), 1.07 (d, 3H, J = 7.0 Hz), 1.05 (d, 3H, J = 7.0 Hz). |
| 32 | | HCl | ¹H-NMR (DMSO-d$_6$) δ: 12.40 (br s, 1H), 8.68 (s, 1H), 8.31 (dd, 1H, J = 6.2, 5.7 Hz), 7.64 (s, 1H), 7.45 (td, 1H, J = 8.7, 6.6 Hz), 7.24 (ddd, 1H, J = 10.4, 9.3, 2.8 Hz), 7.07 (tdd, 1H, J = 8.7, 2.8, 1.2 Hz), 5.51-5.46 (br m, 1H), 4.68 (sep, 1H, J = 6.7 Hz), 4.21 (s, 2H), 4.04 (dd, 1H, J = 14.1, 2.1 Hz), 3.94 (dd, 1H, J = 14.1, 3.6 Hz), 2.97 (ddd, 1H, J = 12.8, 6.6, 6.2 Hz), 2.78 (ddd, 1H, J = 12.8, 6.6, 5.7 Hz), 1.67 (sep, 1H, J = 6.5 Hz), 1.12 (d, 3H, J = 6.7 Hz), 1.04 (d, 3H, J = 6.7 Hz), 0.83 (d, 3H, J = 6.5 Hz), 0.82 (d, 3H, J = 6.5 Hz). |

TABLE 1-6

| No. | structural formula | salt | ¹H-NMR |
|---|---|---|---|
| 33 | | — | ¹H-NMR (DMSO-d$_6$) δ: 8.69 (s, 1H), 7.65 (s, 1H), 7.50-7.40 (m, 1H), 7.33-7.20 (m, 1H), 7.11-7.03 (m, 1H), 5.16-5.04 (m, 1H), 4.84-4.71 (m, 1H), 4.21 (s, 2H), 3.89-3.68 (m, 2H), 2.92-2.64 (m, 2H), 1.15 (t, 6H, J = 6.3 Hz). |
| 34 | | HCl | ¹H-NMR (DMSO-d$_6$) δ: 12.64 (br s, 1H), 8.54 (s, 1H), 7.95-7.87 (m, 1H), 7.64 (s, 1H), 7.50-7.41 (m, 1H), 7.33-7.20 (m, 1H), 7.12-7.03 (m, 1H), 5.08-4.99 (m, 1H), 4.84-4.74 (m, 1H), 4.21 (s, 2H), 3.88-3.65 (m, 2H), 2.70-2.54 (m, 2H), 2.45 (d, 3H, J = 4.4 Hz), 1.17 (d, 3H, J = 6.5 Hz), 1.14 (d, 3H, J = 7.2 Hz). |

TABLE 1-6-continued

| No. | structural formula | salt | ¹H-NMR |
|---|---|---|---|
| 35 | (structure) | HCl | ¹H-NMR (DMSO-d$_6$) δ: 8.58 (s, 1H), 7.65 (s, 1H), 7.49-7.38 (m, 2H), 7.28-7.19 (m, 1H), 7.11-7.03 (m, 1H), 7.00 (br s, 1H), 5.07-4.97 (m, 1H), 4.85-4.73 (m, 1H), 4.21 (s, 2H), 3.91-3.65 (m, 2H), 2.71-2.51 (m, 2H), 1.18 (d, 3H, J = 7.0 Hz), 1.15 (d, 3H, J = 7.2 Hz). |
| 36 | (structure) | HCl | ¹H-NMR (DMSO-d$_6$) δ: 12.68 (br s, 1H), 8.46 (s, 1H), 7.85 (d, 1H, J = 7.7 Hz), 7.63 (s, 1H), 7.48-7.39 (m, 1H), 7.29-7.19 (m, 1H), 7.12-7.03 (m, 1H), 5.05-4.94 (m, 1H), 4.86-4.74 (m, 1H), 4.20 (s, 2H), 3.88-3.60 (m, 3H), 2.70-2.46 (m, 2H), 1.18 (d, 3H, J = 7.0 Hz), 1.15 (d, 3H, J = 7.2 Hz), 0.92 (d, 3H, J = 6.7 Hz), 0.69 (d, 3H, J = 6.7 Hz). |

TABLE 1-7

| No. | structural formula | salt | ¹H-NMR |
|---|---|---|---|
| 37 | (structure) | HCl | ¹H-NMR (DMSO-d$_6$) δ: 8.80 (s, 1H), 7.57-7.49 (m, 1H), 7.32-7.25 (m, 1H), 7.15-7.08 (m, 1H), 4.67 (dd, 1H, J = 13.2, 1.4 Hz), 4.51 (sep, 1H, J = 6.7 Hz), 4.48 (s, 2H), 4.34 (dd, 1H, J = 13.2, 3.5 Hz), 4.00-3.93 (m, 1H), 3.57 (dd, 1H, J = 11.5, 3.5 Hz), 3.36 (dd, 1H, J = 11.5, 8.1 Hz), 1.29 (d, 3H, J = 6.7 Hz), 1.28 (d, 3H, J = 6.7 Hz). |
| 38 | (structure) | — | ¹H-NMR (DMSO-d$_6$) δ: 12.97 (br s, 1H), 8.38 (s, 1H), 7.67 (s, 1H), 7.45 (td, 1H, J = 8.8, 6.6 Hz), 7.25 (ddd, 1H, J = 10.2, 9.3, 2.6 Hz), 7.07 (tdd, 1H, J = 8.8, 2.6, 0.9 Hz), 4.75 (sep, 1H, J = 6.7 Hz), 4.22 (s, 2H), 4.03 (d, 1H, J = 13.9 Hz), 3.80 (d, 1H, J = 13.9 Hz), 3.56-3.35 (br m, 4H), 1.90 (s, 3H), 1.59-1.50 (br m, 2H), 1.49-1.40 (br m, 4H), 1.18 (d, 3H, J = 6.7 Hz), 1.14 (d, 3H, J = 6.7 Hz). |
| 39 | (structure) | — | ¹H-NMR (DMSO-d$_6$) δ: 12.79 (br s, 1H), 8.52 (s, 1H), 7.66 (s, 1H), 7.45 (td, 1H, J = 8.8, 6.6 Hz), 7.24 (ddd, 1H, J = 10.4, 9.5, 2.6 Hz), 7.07 (tdd, 1H, J = 8.8, 2.6, 0.9 Hz), 4.70 (sep, 1H, J = 6.7 Hz), 4.21 (s, 2H), 4.11 (d, 1H, J = 13.9 Hz), 3.74 (d, 1H, J = 13.9 Hz), 3.64-3.54 (br m, 1H), 3.42-3.32 (br m, 1H), 3.32-3.22 (br m, 1H), 3.15-3.05 (br m, 1H), 2.00 (s, 3H), 1.94-1.82 (br m, 1H), 1.79-1.57 (br m, 3H), 1.16 (d, 3H, J = 6.7 Hz), 1.07 (d, 3H, J = 6.7 Hz). |

TABLE 1-8

| No. | structural formula | salt | ¹H-NMR |
|---|---|---|---|
| 40 | (structure) | HCl | ¹H-NMR (DMSO-$d_6$) δ: 12.92-12.53 (m, 1H), 8.44 (s, 1H), 7.97 (t, 1H, J = 6.3 Hz), 7.64 (s, 1H), 7.49-7.40 (m, 1H), 7.29-7.19 (m, 1H), 7.12-7.02 (m, 1H), 5.10-4.98 (m, 1H), 4.86-4.75 (m, 1H), 4.21 (s, 2H), 3.90-3.81 (m, 1H), 3.75-3.67 (m, 1H), 2.92-2.82 (m, 1H), 2.77-2.66 (m, 1H), 2.61-2.48 (m, 2H), 1.44-1.30 (m, 1H), 1.18 (d, 3H, J = 7.2 Hz), 1.15 (d, 3H, J = 7.2 Hz), 0.54 (d, 3H, J = 6.7 Hz), 0.50 (d, 3H, J = 7.2 Hz). |
| 41 | (structure) | HCl | ¹H-NMR (DMSO-$d_6$) δ: 12.88-12.50 (m, 1H), 8.68 (s, 1H), 7.65 (s, 1H), 7.49-7.40 (m, 1H), 7.28-7.20 (m, 1H), 7.11-7.03 (m, 1H), 5.11-5.03 (m, 1H), 4.84-4.73 (m, 1H), 4.21 (s, 2H), 3.88-3.73 (m, 2H), 3.54-3.19 (m, 4H), 2.87 (d, 2H, J = 7.0 Hz), 1.59-1.43 (m, 2H), 1.42-1.29 (m, 4H), 1.13 (d, 3H, J = 6.7 Hz), 1.13 (d, 3H, J = 6.5 Hz). |
| 42 | (structure) | HCl | ¹H-NMR (DMSO-$d_6$) δ: 12.45 (br s, 1H), 8.84 (s, 1H), 7.58-7.50 (m, 1H), 7.33-7.25 (m, 1H), 7.15-7.07 (m, 1H), 4.66 (dd, 1H, J = 13.4, 1.6 Hz), 4.49 (s, 2H), 4.47 (sep, 1H, J = 6.8 Hz), 4.35 (dd, 1H, J = 13.4, 3.7 Hz), 4.23-4.17 (m, 1H), 3.49 (dd, 1H, J = 10.2, 4.2 Hz), 3.39 (dd, 1H, J = 10.2, 7.4 Hz), 3.21 (s, 3H), 1.30 (d, 3H, J = 6.8 Hz), 1.28 (d, 3H, J = 6.8 Hz). |

TABLE 1-9

| No. | structural formula | salt | ¹H-NMR |
|---|---|---|---|
| 43 | (structure) | HCl | ¹H-NMR (DMSO-$d_6$) δ: 12.54 (br s, 1H), 8.83 (s, 1H), 7.57-7.49 (m, 1H), 7.32-7.25 (m, 1H), 7.14-7.07 (m, 1H), 4.65 (dd, 1H, J = 13.4, 1.4 Hz), 4.48 (s, 2H), 4.47 (dd, 1H, J = 13.4, 4.3 Hz), 4.10-4.04 (m, 1H), 3.80 (dd, 1H, J = 13.3, 8.0 Hz), 3.53 (dd, 1H, J = 10.4, 5.1 Hz), 3.49 (dd, 1H, J = 10.4, 6.3 Hz), 3.20 (s, 3H), 2.94 (dd, 1H, J = 13.3, 7.1 Hz), 2.08 (ddsep, 1H, J = 8.0, 7.1, 6.7 Hz), 0.95 (d, 3H, J = 6.7 Hz), 0.89 (d, 3H, J = 6.7 Hz). |
| 44 | (structure) | HCl | ¹H-NMR (DMSO-$d_6$) δ: 12.84 (br s, 1H), 8.81 (s, 1H), 7.59-7.49 (m, 1H), 7.33-7.23 (m, 1H), 7.16-7.07 (m, 1H), 4.99-4.90 (m, 1H), 4.77 (sep, 1H, J = 6.7 Hz), 4.48 (s, 2H), 3.93-3.60 (m, 4H), 3.58-3.44 (m, 2H), 3.33 (t, 2H, J = 4.6 Hz), 3.11 (s, 3H), 1.17 (d, 3H, J = 6.7 Hz), 1.16 (d, 3H, J = 6.7 Hz). |

TABLE 1-9-continued

| No. | structural formula | salt | ¹H-NMR |
|---|---|---|---|
| 45 | | HCl | ¹H-NMR (DMSO-d₆) δ: 12.80 (br s, 1H), 8.80 (s, 1H), 7.59-7.50 (m, 1H), 7.35-7.24 (m, 1H), 7.16-7.07 (m, 1H), 4.97-4.86 (m, 1H), 4.49 (s, 2H), 4.06 (dd, 1H, J = 13.7, 4.2 Hz), 3.80-3.66 (m, 3H), 3.59-3.46 (m, 3H), 3.36-3.31 (m, 2H), 3.22 (dd, 1H, J = 7.1, 12.6 Hz), 3.11 (s, 3H), 2.00 (sept, 1H, J = 6.6 Hz), 0.91 (d, 6H, J = 6.6 Hz). |

TABLE 1-10

| No. | structural formula | salt | ¹H-NMR |
|---|---|---|---|
| 46 | | HCl | ¹H-NMR (DMSO-d₆) δ: 12.84 (br s, 1H), 8.81 (s, 1H), 7.59-7.49 (m, 1H), 7.33-7.23 (m, 1H), 7.16-7.07 (m, 1H), 4.99-4.90 (m, 1H), 4.77 (sep, 1H, J = 6.7 Hz), 4.48 (s, 2H), 3.93-3.60 (m, 4H), 3.58-3.44 (m, 2H), 3.33 (t, 2H, J = 4.6 Hz), 3.11 (s, 3H), 1.17 (d, 3H, J = 6.7 Hz), 1.16 (d, 3H, J = 6.7 Hz). |
| 47 | | HCl | ¹H-NMR (DMSO-d₆) δ: 12.80 (br s, 1H), 8.80 (s, 1H), 7.59-7.50 (m, 1H), 7.35-7.24 (m, 1H), 7.16-7.07 (m, 1H), 4.97-4.86 (m, 1H), 4.49 (s, 2H), 4.06 (dd, 1H, J = 13.7, 4.2 Hz), 3.80-3.66 (m, 3H), 3.59-3.46 (m, 3H), 3.36-3.31 (m, 2H), 3.22 (dd, 1H, J = 7.1, 12.6 Hz), 3.11 (s, 3H), 2.00 (sept, 1H, J = 6.6 Hz), 0.91 (d, 6H, J = 6.6 Hz). |
| 48 | | HCl | ¹H-NMR (DMSO-d₆) δ: 12.55 (br s, 1H), 8.81 (s, 1H), 7.59-7.49 (m, 1H), 7.35-7.24 (m, 1H), 7.16-7.07 (m, 1H), 4.65 (d, 1H, J = 13.2 Hz), 4.53-4.45 (m, 1H), 4.48 (s, 2H), 4.09-4.01 (m, 1H), 3.80 (dd, 1H, J = 13.4, 7.9 Hz), 3.67-3.57 (m, 2H), 3.50-3.39 (m, 2H), 3.30-3.24 (m, 2H), 3.08 (s, 3H), 2.95 (dd, 1H, J = 13.4, 7.0 Hz), 2.14-2.01 (m, 1H), 0.95 (d, 3H, J = 6.5 Hz), 0.90 (d, 3H, J = 6.7 Hz). |
| 49 | | HCl | ¹H-NMR (DMSO-d₆) δ: 12.73 (br s, 1H), 8.80 (s, 1H), 7.67 (s, 1H), 7.51-7.42 (m, 1H), 7.29-7.20 (m, 1H), 7.12-7.03 (m, 1H), 5.27-5.17 (m, 1H), 4.85-4.72 (m, 1H), 4.22 (s, 2H), 3.96-3.65 (m, 2H), 3.34-3.20 (m, 2H), 1.20 (d, 3H, J = 7.2 Hz), 1.14 (d, 3H, J = 7.0 Hz). |

TABLE 1-11

| No. | structural formula | salt | ¹H-NMR |
|---|---|---|---|
| 50 | (structure) | HCl | ¹H-NMR (DMSO-d$_6$) δ: 12.38 (s, 1H), 8.95 (s, 1H), 7.57-7.50 (m, 1H), 7.32-7.25 (m, 1H), 7.14-7.08 (m, 1H), 5.00-4.91 (m, 2H), 4.73 (sep, 1H, J = 6.6 Hz), 4.52 (dd, 1H, J = 13.6, 3.9 Hz), 4.48 (s, 2H), 1.24 (d, 3H, J = 6.6 Hz), 1.13 (d, 3H, J = 6.6 Hz). |
| 51 | (structure) | HCl | ¹H-NMR (DMSO-d$_6$) δ: 12.48 (s, 1H), 8.80 (s, 1H), 8.31 (q, 1H, J = 4.6 Hz), 7.57-7.49 (m, 1H), 7.33-7.24 (m, 1H), 7.14-7.07 (m, 1H), 4.76 (d, 1H, J = 14.2 Hz), 4.73 (sep, 1H, J = 6.8 Hz), 4.60 (d, 1H, J = 4.0 Hz), 4.54 (dd, 1H, J = 14.2, 4.0 Hz), 4.48 (s, 2H), 2.60 (d, 3H, J = 4.6 Hz), 1.21 (d, 3H, J = 6.8 Hz), 1.04 (d, 3H, J = 6.8 Hz). |
| 52 | (structure) | HCl | ¹H-NMR (DMSO-d$_6$) δ: 12.95 (br s, 1H), 8.39 (s, 1H), 7.68 (s, 1H), 7.45 (td, 1H, J = 8.6, 6.7 Hz), 7.25 (ddd, 1H, J = 10.2, 9.3, 2.6 Hz), 7.07 (tdd, 1H, J = 8.6, 2.6, 0.9 Hz), 4.75 (sep, 1H, J = 6.7 Hz), 4.22 (s, 2H), 4.02 (d, 1H, J = 14.4 Hz), 3.81 (d, 1H, J = 14.4 Hz), 3.60-3.41 (br m, 8H), 1.91 (s, 3H), 1.18 (d, 3H, J = 6.7 Hz), 1.16 (d, 3H, J = 6.7 Hz). |
| 53 | (structure) | HCl | ¹H-NMR (DMSO-d$_6$) δ: 12.57 (s, 1H), 8.81 (s, 1H), 7.57-7.49 (m, 1H), 7.32-7.25 (m, 1H), 7.14-7.07 (m, 1H), 5.17 (d, 1H, J = 3.0 Hz), 4.80 (d, 1H, J = 13.7 Hz), 4.70 (sep, 1H, J = 6.7 Hz), 4.52-4.46 (m, 1H), 4.48 (s, 2H), 3.20 (s, 3H), 2.81 (s, 3H), 1.24 (d, 3H, J = 6.7 Hz), 1.00 (d, 3H, J = 6.7 Hz). |

TABLE 1-12

| No. | structural formula | salt | ¹H-NMR |
|---|---|---|---|
| 54 | (structure) | HCl | ¹H-NMR (DMSO-d$_6$) δ: 12.44 (br s, 1H), 8.81 (s, 1H), 7.59-7.48 (m, 1H), 7.34-7.23 (m, 1H), 7.16-7.06 (m, 1H), 4.69-4.61 (m, 1H), 4.53-4.43 (m, 1H), 4.48 (s, 2H), 4.36 (dd, 1H, J = 7.2, 13.4 Hz), 4.23-4.14 (m, 1H), 3.51-3.40 (m, 4H), 3.33-3.25 (m, 2H), 3.08 (s, 3H), 1.28 (d, 3H, J = 6.7 Hz), 1.29 (d, 3H, J = 6.5 Hz). |
| 55 | (structure) | HCl | ¹H-NMR (DMSO-d$_6$) δ: 12.55 (br s, 1H), 8.81 (s, 1H), 7.59-7.49 (m, 1H), 7.35-7.24 (m, 1H), 7.16-7.07 (m, 1H), 4.65 (d, 1H, J = 13.2 Hz), 4.53-4.45 (m, 1H), 4.48 (s, 2H), 4.09-4.01 (m, 1H), 3.80 (dd, 1H, J = 13.4, 7.9 Hz), 3.67-3.57 (m, 2H), 3.50-3.39 (m, 2H), 3.30-3.24 (m, 2H), 3.08 (s, 3H), 2.95 (dd, 1H, J = 13.4, 7.0 Hz), 2.14-2.01 (m, 1H), 0.95 (d, 3H, J = 6.5 Hz), 0.90 (d, 3H, J = 6.7 Hz). |

TABLE 1-12-continued

| No. | structural formula | salt | ¹H-NMR |
|---|---|---|---|
| 56 | (structure) | HCl | ¹H-NMR (DMSO-$d_6$) δ: 12.70 (br s, 1H), 8.65 (s, 1H), 7.65 (s, 1H), 7.49-7.42 (m, 1H), 7.28-7.21 (m, 1H), 7.10-7.04 (m, 1H), 4.93-4.87 (m, 1H), 4.77 (sep, 1H, J = 6.9 Hz), 4.21 (s, 2H), 3.82 (dd, 1H, J = 13.7, 4.0 Hz), 3.76-3.67 (m, 2H), 3.62 (dd, 1H, J = 10.5, 7.7 Hz), 3.56-3.45 (m, 2H), 3.35-3.32 (m, 2H), 3.12 (s, 3H), 1.16 (d, 3H, J = 6.9 Hz), 1.15 (d, 3H, J = 6.9 Hz). |

TABLE 1-13

| No. | structural formula | salt | ¹H-NMR |
|---|---|---|---|
| 57 | (structure) | HCl | ¹H-NMR (DMSO-$d_6$) δ: 12.66 (br s, 1H), 8.64 (s, 1H), 7.65 (s, 1H), 7.49-7.42 (m, 1H), 7.28-7.21 (m, 1H), 7.10-7.04 (m, 1H), 4.90-4.82 (m, 1H), 4.21 (s, 2H), 4.04 (dd, 1H, J = 13.7, 4.4 Hz), 3.78-3.64 (m, 3H), 3.56-3.45 (m, 2H), 3.45-3.28 (m, 3H), 3.21 (dd, 1H, J = 13.3, 6.9 Hz), 3.11 (s, 3H), 2.05-1.94 (m, 1H), 0.91 (d, 6H, J = 6.4 Hz). |
| 58 | (structure) | HCl | ¹H-NMR (DMSO-$d_6$) δ: 12.40 (br s, 1H), 8.63 (s, 1H), 7.64 (s, 1H), 7.49-7.41 (m, 1H), 7.28-7.20 (m, 1H), 7.11-7.04 (m, 1H), 4.62-4.55 (m, 1H), 4.46 (dd, 1H, J = 13.8, 4.4 Hz), 4.21 (s, 2H), 4.06-4.00 (m, 1H), 3.80 (dd, 1H, J = 13.4, 7.7 Hz), 3.64-3.54 (m, 2H), 3.50-3.40 (m, 2H), 3.33-3.24 (m, 2H), 3.10 (s, 3H), 2.94 (dd, 1H, J = 13.4, 7.1 Hz), 2.12-2.03 (m, 1H), 0.95 (d, 3H, J = 6.7 Hz), 0.89 (d, 3H, J = 6.7 Hz). |
| 59 | (structure) | HCl | ¹H-NMR (DMSO-$d_6$) δ: 12.30 (br s, 1H), 8.62 (s, 1H), 7.64 (s, 1H), 7.50-7.40 (m, 1H), 7.29-7.20 (m, 1H), 7.12-7.03 (m, 1H), 4.62-4.55 (m, 1H), 4.48 (sep, 1H, J = 6.7 Hz), 4.36-4.31 (m, 1H), 4.21 (s, 2H), 4.19-4.14 (m, 1H), 3.58 (dd, 1H, J = 10.3, 4.1 Hz), 3.52-3.39 (m, 3H), 3.33-3.27 (m, 2H), 3.10 (s, 3H), 1.29 (d, 3H, J = 6.7 Hz), 1.28 (d, 3H, J = 6.7 Hz). |

TABLE 1-14

| No. | structural formula | salt | ¹H-NMR |
|---|---|---|---|
| 60 | (structure) | HCl | ¹H-NMR (DMSO-$d_6$) δ: 12.44 (br s, 1H), 8.81 (s, 1H), 7.59-7.48 (m, 1H), 7.34-7.23 (m, 1H), 7.16-7.06 (m, 1H), 4.69-4.61 (m, 1H), 4.53-4.43 (m, 1H), 4.48 (s, 2H), 4.36 (dd, 1H, J = 7.2, 13.4 Hz), 4.23-4.14 (m, 1H), 3.51-3.40 (m, 4H), 3.33-3.25 (m, 2H), 3.08 (s, 3H), 1.28 (d, 3H, J = 6.7 Hz), 1.29 (d, 3H, J = 6.5 Hz). |

TABLE 1-14-continued

| No. | structural formula | salt | ¹H-NMR |
|---|---|---|---|
| 61 | | HCl | ¹H-NMR (DMSO-$d_6$) δ: 8.66 (s, 1H), 7.49-7.41 (m, 1H), 7.29-7.21 (m, 1H), 7.11-7.03 (m, 1H), 4.60 (dd, 1H, J = 13.4, 1.4 Hz), 4.47 (sep, 1H, J = 6.8 Hz), 4.33 (dd, 1H, J = 13.4, 3.7 Hz), 4.22 (s, 2H), 4.14-4.10 (m, 1H), 3.48 (dd, 1H, J = 10.3, 4.3 Hz), 3.36 (dd, 1H, J = 10.3, 7.7 Hz), 3.21 (s, 3H), 1.29 (d, 3H, J = 6.8 Hz), 1.28 (d, 3H, J = 6.8 Hz). |
| 62 | | HCl | ¹H-NMR (DMSO-$d_6$) δ: 12.42 (br s, 1H), 8.65 (s, 1H), 7.65 (s, 1H), 7.50-7.41 (m, 1H), 7.30-7.21 (m, 1H), 7.11-7.03 (m, 1H), 4.59 (dd, 1H, J = 13.7, 1.2 Hz), 4.46 (dd, 1H, J = 13.7, 4.2 Hz), 4.21 (s, 2H), 4.08-4.01 (m, 1H), 3.80 (dd, 1H, J = 13.2, 7.9 Hz), 3.52 (dd, 1H, J = 10.4, 5.4 Hz), 3.48 (dd, 1H, J = 10.4, 6.4 Hz), 3.20 (s, 3H), 2.93 (dd, 1H, J = 13.2, 7.2 Hz), 2.08 (tt, 1H, J = 6.7, 6.7 Hz), 0.95 (d, 3H, J = 6.7 Hz), 0.89 (d, 3H, J = 6.7 Hz). |

TABLE 1-15

| No | structural formula | salt | ¹H-NMR |
|---|---|---|---|
| 63 | | HCl | ¹H-NMR (CDCl$_3$) δ: 12.78 (br s, 1H), 9.36 (s, 1H), 7.38-7.30 (m, 1H), 6.92-6.84 (m, 2H), 4.58-4.51 (m, 1H), 4.48 (s, 2H), 4.05-3.98 (m, 1H), 3.76-3.63 (m, 3H), 3.51 (dd, 1H, J = 13.4. 7.9 Hz), 3.39 (s, 3H), 3.29 (dd, 1H, J = 13.4, 7.0 Hz). 2.09-1.99 (m, 1H), 1.00 (d, 3H, J = 6.7 Hz), 0.99 (d, 3H, J = 6.7 Hz). |
| 64 | | HCl | ¹H-NMR (DMSO-$d_6$) δ: 9.03 (s, 1H), 7.59-7.51 (m, 1H), 7.33-725 (m, 1H), 7.16-7.08 (m, 1H), 5.66 (dd, 1H, J = 3.0, 1.9 Hz), 5.07 (dd, 1H, J = 13.8, 1.9 Hz), 4.78 (sep, 1H, J = 6.8 Hz), 4.61 (dd, 1H, J = 13.8, 3.0 Hz), 4.51 (s, 2H), 1.31 (d, 3H, J = 6.8 Hz), 1.24 (d, 3H, J = 6.8 Hz). |
| 65 | | HCl | ¹H-NMR (DMSO-$d_6$) δ: 8.31 (s, 1H), 7.78-7.73 (m, 2H), 7.72-7.67 (m, 2H), 7.38 (td, 1H, J = 8.8, 6.8 Hz), 7.36 (s, 1H), 725 (ddd, 1H, J = 10.4, 9.0, 2.6 Hz), 7.08 (tdd, 1H, J = 8.8, 2.6, 0.9 Hz), 4.99-4.91 (br m, 1H), 4.80 (sep, 1H, J = 6.7 Hz), 4.13 (s, 2H), 4.04 (dd, 1H, J = 14.3, 4.6 Hz), 3.96 (dd, 1H, J = 13.9, 2.0 Hz), 3.89 (dd, 1H, J = 13.9, 4.0 Hz), 3.82 (dd, 1H, J = 14.3, 9.3 Hz), 12.1 (d, 3H, J = 6.7 Hz), 1.19 (d, 3H, J = 6.7 Hz). |

TABLE 1-16

| No. | structural formula | salt | ¹H-NMR |
|---|---|---|---|
| 66 | | 2HCl | ¹H-NMR (DMSO-$d_6$) δ: 12.56 (br s, 1H), 8.70 (s, 1H), 8.25-8.13 (br m, 2H), 7.66 (s, 1H), 7.45 (td, 1H, J = 8.7, 6.7 Hz), 7.25 (ddd, 1H, J = 10.4, 9.5, 2.6 Hz), 7.08 (tdd, 1H, J = 8.7, 2.6, 0.9 Hz), 4.95-4.86 (br m, 1H), 4.76 (sep, 1H, J = 6.7 Hz), 4.22 (s, 2H), 3.90 (dd, 1H, J = 13.8. 3.6 Hz), 3.84 (dd, 1H, J = 13.8, 1.9 Hz), 3.35-3.24 (br m, 1H), 3.22-3.09 (br m, 1H), 1.19 (d, 3H, J = 6.7 Hz), 1.15 (d, 3H, J = 6.7 Hz). |
| 67 | | HCl | ¹H-NMR (DMSO-$d_6$) δ: 12.68 (br s, 1H), 8.39 (s, 1H), 8.05 (t, 1H, J = 6.0 Hz), 7.64 (s, 1H), 7.46 (td, 1H, J = 8.8, 7.0 Hz), 7.25 (ddd, 1H, J = 10.4, 9.5, 2.6 Hz), 7.08 (tdd, 1H, J = 8.8, 2.6, 0.9 Hz), 4.77 (sep, 1H, J = 6.7 Hz), 4.67-4.59 (br m, 1H), 4.21 (s, 2H), 3.84 (dd, 1H, J = 13.8, 3.8 Hz), 3.74 (dd, 1H, J = 13.8, 0.9 Hz), 3.41-3.27 (m, 2H), 1.66 (s, 3H), 1.19 (d, 3H, J = 6.7 Hz), 1.16 (d, 3H, J = 6.7 Hz). |
| 68 | | HCl | ¹H-NMR (DMSO-$d_6$) δ: 12.68 (br s, 1H), 8.36 (s, 1H), 7.97 (t, 1H, J = 6.0 Hz), 7.62 (s, 1H), 7.45 (td, 1H, J = 8.7, 6.7 Hz), 7.25 (ddd, 1H, J = 10.4, 9.5, 2.6 Hz), 7.08 (tdd, 1H, J = 8.7, 2.6, 0.9 Hz), 4.77 (sep, 1H, J = 6.7 Hz), 4.68-4.60 (br m, 1H), 4.21 (s, 2H), 3.84 (dd, 1H, J = 13.7, 3.9 Hz), 3.75 (dd, 1H, J = 13.7, 1.4 Hz), 3.40-3-29 (m, 2H), 1.96-1.86 (m, 2H), 1.19 (d, 3H, J = 6.7 Hz), 1.16 (d, 3H, J = 6.7 Hz), 0.78 (t, 3H, J = 7.5 Hz). |

TABLE 1-17

| No. | structural formula | salt | ¹H-NMR |
|---|---|---|---|
| 69 | | HCl | ¹H-NMR (DMSO-$d_6$) δ: 12.66 (s, 1H), 8.33 (s, 1H), 7.93 (t, 1H, J = 6.0 Hz), 7.61 (s, 1H), 7.43 (td, 1H, J = 8.7, 6.6 Hz), 7.25 (ddd, 1H, J = 10.4. 9.5, 2.6 Hz), 7.07 (tdd, 1H, J = 8.7, 2.6, 0.9 Hz), 4.78 (sep, 1H, J = 6.7 Hz), 4.69-4.61 (br m, 1H), 4.20 (s, 2H), 3.84 (dd, 1H, J = 13.7, 3.9 Hz). 3.74 (dd, 1H, J = 13.7, 1.4 Hz), 3.38-3.32 (m, 2H), 2.15 (sep, 1H, J = 6.7 Hz), 1.19 (d, 3H, J = 6.7 Hz), 1.16 (d, 3H, J = 6.7 Hz), 0.85 (d, 3H, J = 6.7 Hz), 0.73 (d, 3H, J = 6.7 Hz). |
| 70 | | HCl | ¹H-NMR (DMSO-$d_6$) δ: 12.55 (br s, 1H), 8.75 (s, 1H), 7.58-7.50 (m, 1H), 7.34-7.24 (m, 1H), 7.16-7.07 (m, 1H), 4.49 (s, 2H), 4.43-4.30 (m, 3H), 4.03 (q, 1H, J = 7.8 Hz), 3.92-3.48 (m, 3H), 2.36-2.26 (m, 1H), 2.12-2.00 (m, 1H), 1.39 (s, 3H), 1.36 (s, 3H). |

TABLE 1-17-continued

| No. | structural formula | salt | ¹H-NMR |
|---|---|---|---|
| 71 | | HCl | ¹H-NMR (DMSO-d₆) δ: 12.64 (br s, 1H), 8.49 (s, 1H), 8.04 (d, 1H, J = 3.9 Hz), 7.65 (s, 1H), 7.50-7.40 (m, 1H), 7.29-7.20 (m, 1H), 7.11-7.03 (m, 1H), 5.07-4.96 (m, 1H), 4.84-4.72 (m, 1H), 4.21 (s, 2H), 3.87-3.59 (m, 2H), 2.71-2.30 (m, 3H), 1.15 (t, 6H, J = 7.4 Hz), 0.55-0.35 (m, 2H), 0.24-0.06 (m, 2H). |

TABLE 1-18

| No. | structural formula | salt | ¹H-NMR |
|---|---|---|---|
| 72 | | HCl | ¹H-NMR (DMSO-d₆) δ: 12.69 (br s, 1H), 8.70 (s, 1H), 7.65 (s, 1H), 7.49-7.39 (m, 1H), 7.29-7.19 (m, 1H), 7.11-7.00 (m, 1H), 5.14-5.01 (m, 1H), 4.86-4.71 (m, 1H), 4.21 (s, 2H), 3.91-3.67 (m, 2H), 3.51-3.22 (m, 8H), 2.91 (d, 2H, J = 6.5 Hz), 1.14 (d, 3H, J = 6.7 Hz), 1.13 (d, 3H, J = 6.7 Hz). |
| 73 | | HCl | ¹H-NMR (DMSO-d₆) δ: 8.69 (s, 1.0H), 7.65 (s, 1.0H), 7.49-7.40 (m, 1.0H), 7.29-7.19 (m, 1.0H), 7.11-7.02 (m, 1.0H), 5.13-5.03 (m, 1.0H), 4.84-4.72 (m, 1.0H), 4.21 (s, 2.0H), 3.88-3.55 (m, 2.0H), 3.55-3.25 (m, 4.0H), 3.15 (s, 1.5H), 3.12 (s, 1.5H), 3.02-2.82 (m, 2.0H), 2.88 (s, 1.5H), 2.79 (s, 1.5H), 1.13 (d, 6.0H, J = 6.5 Hz). |
| 74 | | HCl | ¹H-NMR (DMSO-d₆) δ: 8.85 (s, 1H), 7.57-7.50 (m, 1H), 7.32-7.25 (m, 1H), 7.15-7.08 (m, 1H), 4.62-4.56 (m, 1H), 4.53-4.30 (m, 3H), 4.49 (s, 2H), 2.69-2.45 (m, 2H), 1.30 (d, 3H, J = 7.2 Hz), 1.28 (d, 3H, J = 7.2 Hz). |
| 75 | | HCl | ¹H-NMR (DMSO-d₆) δ: 12.50 (s, 1H), 8.80 (s, 1H), 7.57-7.49 (m, 1H), 7.33-7.25 (m, 1H), 7.15-7.08 (m, 1H), 4.57-4.46 (m, 2H), 4.48 (s, 2H), 4.45-4.34 (m, 2H), 2.84 (s, 3H), 2.83 (s, 3H), 2.81-2.54 (m, 2H), 1.28 (d, 3H, J = 6.8 Hz), 1.25 (d, 3H, J = 6.8 Hz). |

TABLE 1-19

| No. | structural formula | salt | ¹H-NMR |
|---|---|---|---|
| 76 | | HCl | ¹H-NMR (DMSO-$d_6$) δ: 12.81-12.55 (m, 1H), 8.70 (d, 1H, J = 3.7 Hz). 7.65 (s, 1H), 7.50-7.40 (m, 1H), 7.29-7.19 (m, 1H), 7.11-7.03 (m, 1H), 5.13-5.02 (m, 1H), 4.86-4.72 (m, 1H), 4.21 (s, 2H), 3.88-3.73 (m, 2H), 3.42-3.10 (m, 3H), 2.90-2.80 (m, 1H), 2.83 (s, 1.8H), 2.76 (s, 1.2H), 1.13 (d, 3H, J = 7.0 Hz), 1.12 (d, 3H. J = 6.7 Hz), 0.99 (t, 1.2H, J = 7.2 Hz), 0.93 (t, 1.8H, J = 7.4 Hz). |
| 77 | | HCl | ¹H-NMR (DMSO-$d_6$) δ: 12.67 (br s, 1H), 8.68 (s, 1H), 7.65 (s, 1H), 7.50-7.40 (m, 1H). 7.29-7.19 (m, 1H), 7.12-7.03 (m, 1H), 5.14-5.04 (m, 1H), 4.85-4.73 (m, 1H), 4.21 (s, 2H), 3.90-3.76 (m, 2H), 3.35-3.10 (m, 4H), 2.84 (d, 2H, J = 6.7 Hz), 1.13 (t, 6H, J = 6.7 Hz), 0.98 (t, 3H, J = 7.4 Hz), 0.94 (t, 3H, J = 7.4 Hz). |
| 78 | | HCl | ¹H-NMR (DMSO-$d_6$) δ: 12.66 (br s, 1H), 8.57 (s, 1H), 7.65 (s, 1H), 7.45 (td, 1H, J = 8.7, 6.6 Hz), 7.36 (dd, 1H, J = 6.7, 6.1 Hz), 7.24 (ddd, 1H, J = 10.4, 9.5, 2.8 Hz), 7.07 (tdd, 1H, J = 8.7, 2.8, 0.9 Hz), 4.75 (sep, 1H, J = 6.7 Hz), 4.71-4.63 (br m, 1H), 4.21 (s, 2H), 3.85 (dd, 1H, J = 13.8, 4.1 Hz), 3.75 (dd, 1H, J = 13.8, 1.2 Hz), 3.38 (ddd, 1H, J = 14.1, 6.1, 5.6 Hz), 3.16 (ddd, 1H, J = 14.1, 9.0, 6.7 Hz), 2.89 (s, 3H), 1.21 (d, 3H, J = 6.7 Hz), 1.16 (d, 3H, J = 6.7 Hz). |

TABLE 1-20

| No. | structural formula | salt | ¹H-NMR |
|---|---|---|---|
| 79 | | HCl | ¹H-NMR (DMSO-$d_6$) δ: 8.94 (s, 1H), 7.70 (s, 1H), 7.47 (td, 1H, J = 8.6, 6.8 Hz), 7.25 (ddd, 1H, J = 10.1, 9.5, 2.6 Hz), 7.08 (tdd, 1H, J = 8.6, 2.6, 1.1 Hz), 6.30-6.25 (br m, 1H), 4.80 (sep, 1H, J = 6.8 Hz), 4.24 (dd, 1H, J = 14.1, 2.0 Hz), 4.23 (s, 2H), 4.02 (dd, 1H, J = 14.1, 3.5 Hz), 1.23 (d, 3H, J = 6.8 Hz), 1.16 (d, 3H, J = 6.8 Hz). |
| 80 | | HCl | ¹H-NMR (DMSO-$d_6$) δ: 8.35 (s, 1H), 7.64 (s, 1H), 7.46 (td, 1H, J = 8.8, 7.1 Hz), 7.25 (ddd, 1H, J = 10.6, 9.5, 2.6 Hz), 7.08 (tdd, 1H, J = 8.8, 2.6, 1.3 Hz), 4.92-4.84 (br m, 1H), 4.78 (sep, 1H, J = 6.7 Hz), 4.21 (s, 2H), 3.87 (dd, 1H, J = 14.1, 4.4 Hz), 3.83 (dd, 1H, J = 14.1, 10.8 Hz), 3.71 (dd, 1H, J = 13.9, 1.1 Hz), 3.39 (dd, 1H, J = 13.9, 4.0 Hz), 2.90 (s, 3H), 1.77 (s, 3H), 1.19 (d, 3H, J = 6.7 Hz), 1.16 (d, 3H, J = 6.7 Hz). |

TABLE 1-20-continued

| No. | structural formula | salt | ¹H-NMR |
|---|---|---|---|
| 81 | | HCl | ¹H-NMR (DMSO-d$_6$) δ: 12.42 (s, 1H), 8.80 (s, 1H), 7.92 (q, 1H, J = 4.4 Hz), 7.57-7.50 (m, 1H), 7.33-7.26 (m, 1H), 7.15-7.08 (m, 1H), 4.53-4.30 (m, 4H), 4.49 (s, 2H), 2.56 (d, 3H, J = 4.4 Hz), 2.44-2.37 (m, 2H), 1.29 (d, 3H, J = 6.8 Hz), 1.27 (d, 3H, J = 6.8 Hz). |

TABLE 1-21

| No. | structural formula | salt | ¹H-NMR |
|---|---|---|---|
| 82 | | HCl | ¹H-NMR (DMSO-d$_6$) δ: 8.88 (s, 1H), 7.58-7.50 (m, 1H), 7.32-7.25 (m, 1H), 7.15-7.08 (m, 1H), 4.64 (d, 1H, J = 13.2 Hz), 4.54-4.41 (m, 3H), 4.49 (s, 2H), 3.12 (dd, 1H, J = 17.5, 7.0 Hz), 3.01 (dd, 1H, J = 17.5, 4.2 Hz), 1.31 (d, 3H, J = 6.8 Hz), 1.31 (d, 3H, J = 6.8 Hz). |
| 83 | | HCl | ¹H-NMR (DMSO-d$_6$) δ: 12.42 (br s, 1H), 8.82 (s, 1H), 7.44-7.37 (m, 2H), 7.22-7.14 (m, 2H), 4.68-4.62 (m, 1H), 4.55-4.42 (m, 1H), 4.47 (s, 2H), 4.36 (dd, 1H, J = 13.1, 3.6 Hz), 4.23-4.13 (m, 1H), 3.52-3.39 (m, 4H), 3.32-3.25 (m, 2H), 3.09 (s, 3H), 1.29 (d, 3H, J = 6.7 Hz), 1.28 (d, 3H, J = 6.7 Hz). |
| 84 | | HCl | ¹H-NMR (DMSO-d$_6$) δ: 12.48 (br s, 1H), 8.82 (s, 1H), 7.44-7.36 (m, 2H), 7.22-7.15 (m, 2H), 4.70-4.64 (m, 1H), 4.61-4.50 (m, 1H), 4.47 (s, 2H), 4.45-4.37 (m, 1H), 4.31-4.23 (m, 1H), 3.58-3.39 (m, 4H), 3.31-3.25 (m, 2H), 3.09 (s, 3H), 2.37-2.12 (m, 4H), 1.75-1.62 (m, 2H). |
| 85 | | HCl | ¹H-NMR (DMSO-d$_6$) δ: 12.82 (s, 1H), 8.80 (s, 1H), 7.54 (td, 1H, J = 8.8, 6.7 Hz), 7.29 (ddd, 1H, J = 10.2, 9.3, 2.6 Hz), 7.12 (tdd, 1H, J = 8.8, 2.6 0.9 Hz), 5.01-4.93 (br m, 1H), 4.77 (sep, 1H, J = 6.7 Hz), 4.49 (s, 2H), 3.84 (dd, 1H, J = 13.9, 3.9 Hz), 3.75 (dd, 1H, J = 13.9, 1.4 Hz), 3.62 (dd, 1H, J = 10.2, 5.8 Hz), 3.57 (dd, 1H, J = 10.2, 7.7 Hz), 3.25 (s, 3H), 1.16 (d, 3H, J = 6.7 Hz), 1.16 (d, 3H, J = 6.7 Hz). |

TABLE 1-22

| No. | structural formula | salt | ¹H-NMR |
|---|---|---|---|
| 86 | | HCl | ¹H-NMR (DMSO-d$_6$) δ: 12.73 (br s, 1H), 8.82 (s, 1H), 7.58-7.50 (m, 1H), 7.33-7.25 (m, 1H), 7.15-7.08 (m, 1H), 5.00-4.84 (m, 2H), 4.49 (s, 2H), 3.98-3.87 (m, 2H), 3.74 (dd, 1H, J = 10.4, 6.0 Hz), 3.64 (dd, 1H, J = 10.4, 7.4 Hz), 3.58-3.46 (m, 2H), 3.34 (t, 2H, J = 4.6 Hz), 3.12 (s, 3H), 2.34-2.03 (m, 4H), 1.76-1.65 (m, 2H). |
| 87 | | HCl | ¹H-NMR (DMSO-d$_6$) δ: 12.83 (br s, 1H), 8.80 (s, 1H), 7.59-7.49 (m, 1H), 7.35-7.24 (m, 1H), 7.16-7.07 (m, 1H), 5.01-4.93 (m, 1H), 4.77 (t, 1H, J = 6.7 Hz), 4.49 (s, 2H), 3.84 (dd, 1H, J = 13.7, 3.9 Hz), 3.75 (dd, 1H, J = 13.7, 2.5 Hz), 3.62 (dd, 1H, J = 10.2, 5.8 Hz), 3.57 (dd, 1H, J = 10.2, 7.7 Hz), 3.25 (s, 3H), 1.16 (d, 3H, J = 6.7 Hz), 1.16 (d, 3H, J = 6.7 Hz). |
| 88 | | HCl | ¹H-NMR (DMSO-d$_6$) δ: 12.82 (br s, 1H), 8.80 (s, 1H), 7.45-7.39 (m, 2H), 7.22-7.15 (m, 2H), 5.01-4.94 (m, 1H), 4.77 (sep, 1H, J = 6.7 Hz), 4.47 (s, 2H), 3.84 (dd, 1H, J = 13.7, 3.9 Hz), 3.75 (dd, 1H, J = 13.7. 1.6 Hz), 3.62 (dd, 1H, J = 10.4, 5.8 Hz), 3.57 (dd, 1H, J = 10.4, 7.7 Hz), 3.25 (s, 3H), 1.16 (d, 3H, J = 6.7 Hz), 1.16 (d, 3H, J = 6.7 Hz). |
| 89 | | HCl | ¹H-NMR (DMSO-d$_6$) δ: 12.76 (br s, 1H), 8.78 (s, 1H), 7.58-7.50 (m, 1H), 7.32-7.26 (m, 1H), 7.14-7.08 (m, 1H), 4.99-4.89 (m, 1H), 4.49 (s, 2H), 4.07 (dd, 1H, J = 13.7, 4.4 Hz), 3.74-3.56 (m, 4H), 3.44-3.33 (m, 1H), 3.25 (s, 3H), 1.14 (t, 3H, J = 7.2 Hz). |

TABLE 1-23

| No. | structural formula | salt | ¹H-NMR |
|---|---|---|---|
| 90 | | HCl | ¹H-NMR (DMSO-d$_6$) δ: 12.47 (s, 1H), 8.87 (s, 1H), 7.57-7.49 (m, 1H), 7.32-724 (m, 1H), 7.15-7.07 (m, 1H), 4.66 (dd, 1H, J = 13.5, 1.7 Hz), 4.53 (sep, 1H, J = 6.8 Hz), 4.49 (s, 2H), 4.35-4.28 (m, 1H), 4.14-4.07 (m, 1H), 3.62-3.47 (m, 2H), 1.81-1.51 (m, 2H), 1.29 (d, 6H, J = 6.8 Hz). |

TABLE 1-23-continued

| No. | structural formula | salt | ¹H-NMR |
|---|---|---|---|
| 91 | | HCl | ¹H-NMR (DMSO-d₆) δ: 12.76-12.55 (br m, 1H), 8.61 (s, 1H), 7.61 (s, 1H), 7.25 (dd, 1H, J = 8.5, 6.9 Hz), 6.92 (dd, 1H, J = 11.3, 2.4 Hz), 6.73 (td, 1H, J = 8.5, 2.4 Hz), 4.94-4.86 (br m, 1H), 4.77 (sep, 1H, J = 6.9 Hz), 4.09 (s, 2H), 3.84-3.79 (m, 1H), 3.83 (s, 3H), 3.76-3.69 (m, 1H), 3.60 (dd, 1H, J = 10.5, 5.6 Hz), 3.54 (dd, 1H, J = 10.5, 7.7 Hz), 3.23 (s, 3H), 1.16 (d, 3H, J = 6.9 Hz), 1.15 (d, 3H, J = 6.9 Hz). |
| 92 | | HCl | ¹H-NMR (DMSO-d₆) δ: 12.70 (br s, 1H), 8.81 (s, 1H), 7.45-7.38 (m, 2H), 7.22-7.15 (m, 2H), 5.02-4.85 (m, 2H), 4.47 (s, 2H), 3.98-3.87 (m, 2H), 3.65 (dd, 1H, J = 10.3, 5.8 Hz), 3.57 (dd, 1H, J = 10.3, 7.5 Hz), 3.25 (s, 3H), 2.31-2.04 (m, 4H), 1.77-1.65 (m, 2H). |

TABLE 1-24

| No. | structural formula | salt | ¹H-NMR |
|---|---|---|---|
| 93 | | HCl | ¹H-NMR (DMSO-d₆) δ: 8.84 (s, 1H), 7.57-7.49 (m, 1H), 7.32-725 (m, 1H), 7.15-7.07 (m, 1H), 4.68 (d, 1H, J = 13.2 Hz), 4.60-4.49 (m, 1H), 4.48 (s, 2H), 4.41 (dd, 1H, J = 13.2, 3.7 Hz), 4.32-4.25 (m, 1H), 3.43 (dd, 1H, J = 10.4, 4.6 Hz), 3.39 (dd, 1H, J = 10.4, 6.8 Hz), 3.21 (s, 3H), 2.39-2.11 (m, 4H), 1.77-1.63 (m, 2H). |
| 94 | | HCl | ¹H-NMR (DMSO-d₆) δ: 12.79 (br s, 1H), 8.60 (s, 1H), 7.67 (s, 1H), 7.45 (td, 1H, J = 8.2, 6.0 Hz), 7.24 (ddd, 1H, J = 10.4, 9.5, 2.6 Hz), 7.07 (tdd, 1H, J = 8.2, 2.6, 0.9 Hz), 4.70 (sep, 1H, J = 6.7 Hz), 4.22 (s, 2H), 4.19-4.14 (br m, 1H), 4.09 (d, 1H, J = 14.1 Hz), 4.00 (d, 1H, J = 14.1 Hz), 3.88-3.81 (br m, 2H), 3.74-3.69 (br m, 1H), 2.14-2.04 (br m, 2H), 1.94 (s, 3H), 1.16 (d, 3H, J = 6.7 Hz), 1.13 (d, 3H, J = 6.7 Hz). |
| 95 | | HCl | ¹H-NMR (DMSO-d₆) δ: 8.84 (s, 1H), 7.43-7.38 (m, 2H), 7.21-7.14 (m, 2H), 4.66 (d, 1H, J = 13.2 Hz), 4.47 (sep, 1H, J = 6.7 Hz), 4.47 (s, 2H), 4.34 (dd, 1H, J = 13.5, 3.7 Hz), 422-4.17 (m, 1H), 3.49 (dd, 1H, J = 10.6, 4.3 Hz), 3.39 (dd, 1H, J = 10.6, 7.5 Hz), 3.21 (s, 3H), 1.30 (d, 3H, J = 6.7 Hz), 1.28 (d, 3H, J = 6.7 Hz). |

TABLE 1-25

| No | structural formula | salt | ¹H-NMR |
|---|---|---|---|
| 96 | | HCl | ¹H-NMR (DMSO-d$_6$) δ: 12.45 (br s, 1H), 8.84 (s, 1H), 7.58-7.50 (m, 1H), 7.33-7.25 (m, 1H), 7.15-7.07 (m, 1H), 4.66 (dd, 1H, J = 13.4, 1.6 Hz), 4.49 (s, 2H), 4.47 (sep, 1H, J = 6.8 Hz), 4.35 (dd, 1H, J = 13.4, 3.7 Hz), 4.23-4.17 (m, 1H), 3.49 (dd, 1H, J = 10.2, 4.2 Hz), 3.39 (dd, 1H, J = 10.2, 7.4 Hz), 3.21 (s, 3H), 1.30 (d, 3H, J = 6.8 Hz), 1.28 (d, 3H, J = 6.8 Hz). |
| 97 | | HCl | ¹H-NMR (DMSO-d$_6$) δ: 12.76 (br s, 1H), 8.78 (s, 1H), 7.58-7.50 (m, 1H), 7.32-7.26 (m, 1H), 7.14-7.08 (m, 1H), 4.99-4.89 (m, 1H), 4.49 (s, 2H), 4.07 (dd, 1H, J = 13.7, 4.4 Hz), 3.74-3.56 (m, 4H), 3.44-3.33 (m, 1H), 3.25 (s, 3H), 1.14 (t, 3H, J = 12 Hz). |
| 98 | | HCl | ¹H-NMR (DMSO-d$_6$) δ: 12.51 (br s, 1H), 8.84 (s, 1H), 7.58-7.49 (m, 1H), 7.33-7.25 (m, 1H), 7.15-7.08 (m, 1H), 4.71-4.64 (m, 1H), 4.60-4.46 (m, 3H), 4.41 (dd, 1H, J = 13.7, 3.9 Hz), 4.31-4.25 (m, 1H), 3.46-3.36 (m, 2H), 3.21 (s, 3H), 2.37-2.12 (m, 4H), 1.77-1.64 (m, 2H). |

TABLE 1-26

| No. | structural formula | salt | ¹H-NMR |
|---|---|---|---|
| 99 | | HCl | ¹H-NMR (DMSO-d$_6$) δ: 12.46 (br s, 1H), 8.84 (s, 1H), 7.57-7.50 (m, 1H), 7.32-7.25 (m, 1H), 7.15-7.08 (m, 1H), 4.66 (dd, 1H, J = 13.2, 1.6 Hz), 4.52-4.42 (m, 1H), 4.49 (s, 2H), 4.35 (dd, 1H, J = 13.2, 4.0 Hz), 4.23-4.17 (m, 1H), 3.49 (dd, 1H, J = 10.4, 4.3 Hz), 3.39 (dd, 1H, J = 10.4, 7.5 Hz), 3.21 (s, 3H), 1.30 (d, 3H, J = 6.8 Hz), 1.28 (d, 3H, J = 6.8 Hz). |
| 100 | | HCl | ¹H-NMR (DMSO-d$_6$) δ: 12.56 (br s, 1H), 9.02 (s, 1H), 7.53 (td, 1H, J = 8.5, 6.4 Hz), 7.29 (ddd, 1H, J = 10.5, 9.7, 2.4 Hz), 7.12 (tdd, 1H, J = 8.5, 2.4, 1.2 Hz), 4.72 (s, 2H), 4.49 (s, 2H), 4.16-4.02 (br m, 1H), 3.82-3.78 (m, 2H), 3.74-3.66 (m, 2H), 2.21-2.13 (m, 2H), 1.64-1.58 (m, 2H), 1.43 (d, 6H, J = 6.4 Hz). |

TABLE 1-26-continued

| No. | structural formula | salt | ¹H-NMR |
|---|---|---|---|
| 101 | | HCl | ¹H-NMR (DMSO-$d_6$) δ: 12.66 (br s, 1H), 8.66 (s, 1H), 7.66 (s, 1H), 7.51-7.40 (m, 1H), 7.29-7.20 (m, 1H), 7.11-7.03 (m, 1H), 5.45-5.34 (m, 1H), 4.83-4.70 (m, 1H), 4.21 (s, 2H), 3.95-3.85 (m, 2H), 3.81-3.59 (m, 2H), 3.05 (s, 3H), 1.20 (d, 3H, J = 6.7 Hz), 1.14 (d, 3H, J = 6.7 Hz). |

TABLE 1-27

| No. | structural formula | salt | ¹H-NMR |
|---|---|---|---|
| 102 | | HCl | ¹H-NMR (DMSO-$d_6$) δ: 12.50 (br s, 1H), 8.83 (s, 1H), 7.57-7.50 (m, 1H), 7.33-7.25 (m, 1H), 7.15-7.08 (m, 1H), 4.64 (dd, 1H, J = 13.7, 1.6 Hz), 4.49 (s, 2H), 4.43 (dd, 1H, J = 13.7, 4.1 Hz), 4.17-4.12 (m, 1H), 3.86 (dq, 1H, J = 13.4, 7.0 Hz), 3.54 (dd, 1H, J = 10.2, 5.1 Hz), 3.50 (dd, 1H, J = 10.2, 6.3 Hz), 3.27 (dq, 1H, J = 13.4, 7.0 Hz), 3.21 (s, 3H), 1.18 (t, 3H, J = 7.0 Hz). |
| 103 | | HCl | ¹H-NMR (DMSO-$d_6$) δ: 8.61 (s, 1H), 7.70 (s, 1H), 7.36-7.29 (m, 2H), 7.18-7.11 (m, 2H), 4.80 (sep, 1H, J = 6.7 Hz), 4.20 (s, 2H), 3.74 (d, 1H, J = 13.7 Hz), 3.64 (d, 1H, J = 10.4 Hz), 3.64 (d, 1H, J = 13.7 Hz), 3.58 (d, 1H, J = 10.4 Hz), 3.24 (s, 3H), 1.63 (s, 3H), 1.18 (d, 3H, J = 6.7 Hz), 1.17 (d, 3H, J = 6.7 Hz). |
| 104 | | HCl | ¹H-NMR (DMSO-$d_6$) δ: 12.79 (br s, 1H), 8.53 (s, 1H), 8.14 (q, 1H, J = 4.4 Hz), 7.69 (s, 1H), 7.36-7.30 (m, 2H), 7.18-7.11 (m, 2H), 4.70 (sep, 1H, J = 6.7 Hz), 4.21 (s, 2H), 4.09 (d, 1H, J = 13.9 Hz), 3.77 (d, 1H, J = 13.9 Hz), 2.60 (d, 3H, J = 4.4 Hz), 1.93 (s, 3H), 1.14 (d, 3H, J = 6.7 Hz), 1.09 (d, 3H, J = 6.7 Hz). |

TABLE 1-28

| No. | structural formula | salt | ¹H-NMR |
|---|---|---|---|
| 105 | | HCl | ¹H-NMR (DMSO-d$_6$) δ: 12.80 (br s, 1H), 8.52 (s, 1H), 8.18 (t, 1H, J = 5.2 Hz), 7.68 (s, 1H), 7.36-7.30 (m, 2H), 7.18-7.11 (m, 2H), 4.71 (sep, 1H, J = 6.7 Hz), 4.21 (s, 2H), 4.11 (d, 1H, J = 13.9 Hz), 3.78 (d, 1H, J = 13.9 Hz), 3.18-2.98 (m, 2H), 1.92 (s, 3H), 1.15 (d, 3H, J = 6.7 Hz), 1.11 (d, 3H, J = 6.7 Hz), 1.00 (t, 3H, J = 7.2 Hz). |
| 106 | | HCl | ¹H-NMR (DMSO-d$_6$) δ: 12.84 (br s, 1H), 8.50 (s, 1H), 8.07 (d, 1H, J = 7.4 Hz), 7.68 (s, 1H), 7.36-7.30 (m, 2H), 7.18-7.11 (m, 2H), 4.72 (sep, 1H, J = 6.7 Hz), 4.21 (s, 2H), 4.16 (d, 1H, J = 14.1 Hz), 3.81 (sep, 1H, J = 6.7 Hz), 3.79 (d, 1H, J = 14.1 Hz), 1.93 (s, 3H), 1.16 (d, 3H, J = 6.7 Hz), 1.15 (d, 3H, J = 6.7 Hz), 1.07 (d, 3H, J = 6.7 Hz), 1.06 (d. 3H, J = 6.7 Hz). |
| 107 | | HCl | ¹H-NMR (DMSO-d$_6$) δ: 12.85 (s, 1H), 8.43 (s, 1H), 7.69 (s, 1H), 7.37-7.29 (m, 2H), 7.19-7.11 (m, 2H), 4.73 (sep, 1H, J = 6.7 Hz), 4.21 (s, 2H), 4.12 (d, 1H, J = 14.1 Hz), 3.79 (d, 1H, J = 14.1 Hz), 2.93 (s, 6H), 1.98 (s, 3H), 1.17 (d, 3H, J = 6.7 Hz), 1.11 (d, 3H, J = 6.7 Hz). |

TABLE 1-29

| No. | structural formula | salt | ¹H-NMR |
|---|---|---|---|
| 108 | | HCl | ¹H-NMR (DMSO-d$_6$) δ: 12.96 (br s, 1H), 8.39 (s, 1H), 7.69 (s, 1H), 7.37-7.30 (m, 2H), 7.19-7.11 (m, 2H), 4.75 (sep, 1H, J = 6.7 Hz), 4.21 (s, 2H), 4.03 (d, 1H, J = 14.4 Hz), 3.80 (d, 1H, J = 14.4 Hz), 3.56-3.37 (br m, 4H), 1.90 (s, 3H), 1.59-1.50 (br m, 2H), 1.50-1.41 (br m, 4H), 1.18 (d, 3H, J = 6.7 Hz), 1.14 (d, 3H, J = 6.7 Hz). |

TABLE 1-29-continued

| No. | structural formula | salt | ¹H-NMR |
|---|---|---|---|
| 109 | (structure) | HCl | ¹H-NMR (DMSO-d₆) δ: 12.79 (br s, 1H), 8.54 (s, 1H), 7.69 (s, 1H), 7.37-7.30 (m, 2H), 7.19-7.11 (m, 2H), 4.70 (sep, 1H, J = 6.7 Hz), 4.21 (s, 2H), 4.12 (d, 1H, J = 14.1 Hz), 3.75 (d, 1H, J = 14.1 Hz), 3.65-3.53 (br m, 1H), 3.43-3.33 (br m, 1H), 3.33-3.23 (br m, 1H), 3.16-3.05 (br m, 1H), 2.01 (s, 3H), 1.94-1.84 (br m, 1H), 1.81-1.56 (br m, 3H), 1.16 (d, 3H, J = 6.7 Hz), 1.08 (d, 3H, J = 6.7 Hz). |
| 110 | (structure) | HCl | ¹H-NMR (DMSO-d₆) δ: 13.12 (s, 1H), 8.63 (s, 1H), 7.69 (s, 1H), 7.36-7.30 (m, 2H), 7.18-7.11 (m, 2H), 4.79 (sep, 1H, J = 6.7 Hz), 4.20 (s, 2H), 3.74 (d, 1H, J = 10.2 Hz), 3.73 (d, 1H, J = 13.9 Hz), 3.66 (d, 1H, J = 10.2 Hz), 3.65 (d, 1H, J = 13.9 Hz), 3.54-3.42 (m, 2H), 3.38-3.30 (m, 2H), 3.11 (s, 3H), 1.63 (s, 3H), 1.18 (d, 3H, J = 6.7 Hz), 1.17 (d, 3H, J = 6.7 Hz). |

TABLE 1-30

| No. | structural formula | salt | ¹H-NMR |
|---|---|---|---|
| 111 | (structure) | HCl | ¹H-NMR (DMSO-d₆) δ: 13.14 (s, 1H), 8.63 (s, 1H), 7.69 (s, 1H), 7.36-7.30 (m, 2H), 7.18-7.11 (m, 2H), 4.79 (sep, 1H, J = 6.7 Hz), 4.21 (s, 2H), 3.72 (d, 1H, J = 13.7 Hz), 3.64 (d, 1H, J = 13.7 Hz), 3.61 (s, 2H), 1.59 (s, 3H), 1.17 (d, 3H, J = 6.7 Hz), 1.17 (d, 3H, J = 6.7 Hz). |
| 112 | (structure) | HCl | ¹H-NMR (DMSO-d₆) δ: 12.87 (br s, 1H), 8.61 (s, 1H), 7.70 (s, 1H), 7.37-7.30 (m, 2H), 7.18-7.11 (m, 2H), 4.73 (sep, 1H, J = 6.7 Hz), 4.21 (s, 2H), 4.06 (d, 1H, J = 13.7 Hz), 3.80 (d, 1H, J = 13.7 Hz), 1.98 (s, 3H), 1.16 (d, 3H, J = 6.7 Hz), 1.14 (d, 3H, J = 6.7 Hz). |
| 113 | (structure) | HCl | ¹H-NMR (DMSO-d₆) δ: 12.64-12.34 (m, 1H), 8.83 (s, 1H), 7.44-7.37 (m, 2H), 7.22-7.14 (m, 2H), 464 (dd, 1H, J = 13.4, 1.5 Hz), 4.47 (s, 2H), 4.42 (dd, 1H, J = 13.4, 4.4 Hz), 4.17-4.11 (m, 1H), 3.86 (dq, 1H, J = 14.0, 7.0 Hz), 3.54 (dd, 1H, J = 10.4, 4.9 Hz), 3.50 (dd, 1H, J = 10.4, 6.3 Hz), 3.27 (dq, 1H, J = 14.0, 7.0 Hz), 3.22 (s, 3H), 1.20 (t, 3H, J = 7.0 Hz). |

TABLE 1-31

| No. | structural formula | salt | ¹H-NMR |
|---|---|---|---|
| 114 | | HCl | ¹H-NMR (DMSO-d$_6$) δ: 12.50 (br s, 1H), 8.83 (s, 1H), 7.57-7.50 (m, 1H), 7.33-7.25 (m, 1H), 7.15-7.08 (m, 1H), 4.64 (dd, 1H, J = 13.7, 1.6 Hz), 4.49 (s, 2H), 4.43 (dd, 1H, J = 13.7, 4.1 Hz), 4.17-4.12 (m, 1H), 3.86 (dq, 1H, J = 13.4, 7.0 Hz), 3.54 (dd, 1H, J = 10.2, 5.1 Hz), 3.50 (dd, 1H, J = 10.2, 6.3 Hz), 3.27 (dq, 1H, J = 13.4, 7.0 Hz), 3.21 (s, 3H), 1.18 (t, 3H, J = 7.0 Hz) |
| 115 | | HCl | ¹H-NMR (DMSO-d$_6$) δ: 12.72 (br s, 1H), 8.79 (s, 1H), 7.44-7.37 (m, 2H), 7.22-7.15 (m, 2H), 4.61 (dd, 1H, J = 13.6, 1.6 Hz), 4.47 (s, 2H), 4.35 (dd, 1H, J = 13.6, 4.2 Hz), 3.86-3.80 (m, 1H), 3.62 (dd, 1H, J = 11.5, 3.8 Hz), 3.52 (dd, 1H, J = 11.5, 7.1 Hz), 2.95-2.88 (m, 1H), 1.03-0.94 (m, 1H), 0.90-0.83 (m, 1H), 0.83-0.72 (m, 2H). |
| 116 | | HCl | ¹H-NMR (DMSO-d$_6$) δ: 12.75 (s, 1H), 8.79 (s, 1H), 7.46-7.38 (m, 2H), 7.24-7.15 (m, 2H), 5.02-4.90 (m, 1H), 4.47 (s, 2H), 4.12 (dd, 1H, J = 13.7, 3.9 Hz), 3.87-3.79 (m, 1H), 3.73-3.58 (m, 2H), 3.45 (dd, 1H, J = 14.0, 7.3 Hz), 3.31 (dd, 1H, J = 14.0, 6.8 Hz), 3.26 (s, 3H), 1.15-1.03 (m, 1H), 0.58-0.46 (m, 2H), 0.39-0.26 (m, 2H). |

TABLE 1-32

| No. | structural formula | salt | ¹H-NMR |
|---|---|---|---|
| 117 | | HCl | ¹H-NMR (DMSO-d$_6$) δ: 12.75 (br s, 1H), 8.79 (s, 1H), 7.59-7.50 (m, 1H), 7.33-7.26 (m, 1H), 7.15-7.08 (m, 1H), 4.99-4.92 (m, 1H), 4.49 (s, 2H), 4.12 (dd, 1H, J = 13.8, 4.3 Hz), 3.87-3.80 (m, 1H), 3.69 (dd, 1H, J = 10.4, 5.6 Hz), 3.62 (dd, 1H, J = 10.4, 7.9 Hz), 3.45 (dd, 1H, J = 13.8, 7.3 Hz), 3.31 (dd, 1H, J = 13.9, 7.0 Hz), 3.26 (s, 3H), 1.14-1.03 (m, 1H), 0.57-0.46 (m, 2H), 0.39-0.27 (m, 2H). |
| 118 | | HCl | ¹H-NMR (DMSO-d$_6$) δ: 12.76 (s, 1H), 8.80 (s, 1H), 7.45-7.38 (m, 2H), 7.23-7.15 (m, 2H), 4.96-4.89 (m, 1H), 4.47 (s, 2H), 4.11 (dd, 1H, J = 13.7, 4.2 Hz), 3.84 (dd, 1H, J = 13.7, 1.2 Hz), 3.78 (dd, 1H, J = 10.5, 5.6 Hz), 3.70 (dd, 1H, J = 10.5, 7.7 Hz), 3.59-3.39 (m, 3H), 3.37-3.29 (m, 3H), 3.10 (s, 3H), 1.13-1.04 (m, 1H), 0.58-0.46 (m, 2H), 0.38-0.27 (m, 2H). |

TABLE 1-32-continued

| No. | structural formula | salt | ¹H-NMR |
|---|---|---|---|
| 119 | | HCl | ¹H-NMR (DMSO-$d_6$) δ: 12.75 (br s, 1H), 8.80 (s, 1H), 7.58-7.50 (m, 1H), 7.33-7.25 (m, 1H), 7.16-7.08 (m, 1H), 4.97-4.89 (m, 1H), 4.49 (s, 2H), 4.12 (dd, 1H, J = 13.7, 4.4 Hz), 3.84 (dd, 1H, J = 13.7, 1.2 Hz), 3.78 (dd, 1H, J = 10.5, 5.6 Hz), 3.70 (dd, 1H, J = 10.5, 7.7 Hz), 3.59-3.40 (m, 3H), 3.37-3.29 (m, 3H), 3.10 (s, 3H), 1.14-1.04 (m, 1H), 0.58-0.47 (m, 2H), 0.38-0.27 (m, 2H). |

TABLE 1-33

| No. | structural formula | salt | ¹H-NMR |
|---|---|---|---|
| 120 | | HCl | ¹H-NMR (DMSO-$d_6$) δ: 12.42 (br s, 1H), 8.82 (s, 1H), 7.44-7.37 (m, 2H), 7.22-7.14 (m, 2H), 4.65 (d, 1H, J = 12.5 Hz). 4.55-4.42 (m, 1H), 4.47 (s, 2H), 4.36 (dd, 1H, J = 13.1, 3.6 Hz), 4.23-4.13 (m, 1H), 3.52-3.39 (m, 4H), 3.32-3.25 (m, 2H), 3.09 (s, 3H), 1.29 (d, 3H, J = 6.7 Hz), 1.28 (d, 3H, J = 6.7 Hz). |
| 121 | | HCl | ¹H-NMR (DMSO-$d_6$) δ: 13.10 (br s, 1H), 8.58 (s, 1H), 7.66 (s, 1H), 7.44 (td, 1H, J = 8.7, 6.7 Hz), 7.23 (ddd, 1H, J = 10.4, 9.5, 2.6 Hz), 7.06 (tdd, 1H, J = 8.7, 2.6, 0.9 Hz), 4.78 (sep, 1H, J = 6.7 Hz), 4.20 (s, 2H), 3.73 (d, 1H, J = 13.9 Hz), 3.63 (d, 1H, J = 13.9 Hz), 3.63 (d, 1H, J = 10.2 Hz), 3.56 (d, 1 H, J = 10.2 Hz), 3.22 (s, 3H), 1.61 (s, 3H), 1.16 (d, 3H, J = 6.7 Hz), 1.16 (d, 3H, J = 6.7 Hz). |
| 122 | | HCl | ¹H-NMR (DMSO-$d_6$) δ: 13.12 (br s, 1H), 8.62 (s, 1H), 7.67 (s, 1H), 7.45 (td, 1H, J = 8.8, 7.0 Hz), 7.25 (ddd, 1H, J = 10.4, 9.3, 2.6 Hz), 7.07 (tdd, 1H, J = 8.8, 2.6, 1.0 Hz), 4.79 (sep, 1H, J = 6.7 Hz), 4.21 (s, 2H), 3.78-3.70 (m, 2H), 3.66 (d, 1H, J = 10.2 Hz), 3.65 (d, 1H, J = 13.9 Hz), 3.54-3.42 (m, 2H), 3.37-3.29 (m, 2H), 3.11 (s, 3H), 1.63 (s, 3H), 1.18 (d, 3H, J = 6.7 Hz), 1.17 (d, 3H, J = 6.7 Hz). |

TABLE 1-34

| No. | structural formula | salt | ¹H-NMR |
|---|---|---|---|
| 123 | | HCl | ¹H-NMR (DMSO-d$_6$) δ: 12.78 (s, 1H), 8.82 (s, 1H), 7.45-7.38 (m, 2H), 7.22-7.15 (m, 2H), 4.93-4.86 (m, 1H), 4.47 (s, 2H), 4.19 (dd, 1H, J = 13.7, 4.2 Hz), 3.82 (dd, 1H, J = 10.4, 5.6 Hz), 3.78-3.70 (m, 2H), 3.58-3.47 (m, 2H), 3.42 (d, 1H, J = 13.4 Hz), 3,35-3.31 (m, 2H), 3.23 (d, 1H, J = 13.4 Hz), 3.11 (s, 3H), 0.98 (s, 9H). |
| 124 | | HCl | ¹H-NMR (DMSO-d$_6$) δ: 12.78 (br s, 1H), 8.80 (s, 1H), 7.57-7.50 (m, 1H), 7.32-7.24 (m, 1H), 7.14-7.07 (m, 1H), 4.92-4.85 (m, 1H), 4.48 (s, 2H), 4.18 (dd, 1H, J = 13.7, 4.2 Hz), 3.81 (dd, 1H, J = 10.6, 5.7 Hz), 3.76-3.69 (m, 2H), 3.56-3.46 (m, 2H), 3.41 (d, 1H, J = 13.4 Hz), 3.34-3.30 (m, 2H), 3.22 (d, 1H, J = 13.4 Hz), 3.09 (s, 3H), 0.97 (s, 9H). |
| 125 | | HCl | ¹H-NMR (DMSO-d$_6$) δ: 12.78 (br s, 1H), 8.79 (s, 1H), 7.58-7.50 (m, 1H), 7.33-7.25 (m, 1H), 7.15-7.08 (m, 1H), 4.96-4.88 (m, 1H), 4.49 (s, 2H), 4.07 (dd, 1H, J = 13.6, 4.3 Hz), 3.79-3.59 (m, 4H), 3.57-3.45 (m, 2H), 3.45-3.36 (m, 1H), 3.33 (t, 2H, J = 4.6 Hz), 3.10 (s, 3H), 1.15 (t, 3H, J = 7.2 Hz). |

TABLE 1-35

| No. | structural formula | salt | ¹H-NMR |
|---|---|---|---|
| 126 | | HCl | ¹H-NMR (DMSO-d$_6$) δ: 12.47 (br s, 1H), 8.83 (s, 1H), 7.56-7.49 (m, 1H), 7.32-7.24 (m, 1H), 7.14-7.07 (m, 1H), 4.66 (dd, 1H, J = 13.4, 1.6 Hz), 4.48 (s, 2H), 4.44 (dd, 1H, J = 13.4, 4.2 Hz), 4.25-4.20 (m, 1H), 3.68 (dd, 1H, J = 14.0, 7.0 Hz), 3.57 (dd, 1 H, J = 10.2, 4.6 Hz), 3.50 (dd, 1H, J = 10.2. 6.5 Hz), 3.20 (dd, 1H, J = 14.0, 7.0 Hz), 3.20 (s, 3H), 1.20-1.09 (m, 1H), 0.58-0.46 (m, 2H), 0.43-0.35 (m, 1H), 0.35-0.27 (m, 1H). |
| 127 | | HCl | ¹H-NMR (DMSO-d$_6$) δ: 12.78 (br s, 1H), 8.79 (s, 1H), 7.58-7.50 (m, 1H), 7.33-7.25 (m, 1H), 7.15-7.08 (m, 1H). 4.96-4.88 (m, 1H), 4.49 (s, 2H), 4.07 (dd, 1H, J = 13.6, 4.3 Hz), 3.79-3.59 (m, 4H), 3.57-3.45 (m, 2H), 3.45-3.36 (m, 1H), 3.33 (t, 2H, J = 4.6 Hz), 3.10 (s, 3H), 1.15 (t, 3H, J = 7.2 Hz). |

TABLE 1-35-continued

| No. | structural formula | salt | ¹H-NMR |
|---|---|---|---|
| 128 | | HCl | ¹H-NMR (DMSO-d$_6$) δ: 12.77 (br s, 1H), 8.80 (s, 1H), 7.44-7.39 (m, 2H), 7.22-7.15 (m, 2H), 4.95-4.88 (m, 1H), 4.47 (s, 2H), 4.07 (dd, 1H, J = 13.6, 4.3 Hz), 3.78-3.60 (m, 4H), 3.57-3.46 (m, 2H), 3.43-3.37 (m, 1H), 3.33 (t, 2H, J = 4.6 Hz), 3.10 (s, 3H), 1.15 (t, 3H, J = 7.2 Hz). |

TABLE 1-36

| No. | structural formula | salt | ¹H-NMR |
|---|---|---|---|
| 129 | | HCl | ¹H-NMR (DMSO-d$_6$) δ: 12.67 (s, 1H), 8.83 (s, 1H), 7.59-7.49 (m, 1H), 7.34-7.25 (m, 1H), 7.16-7.07 (m, 1H), 4.70-4.55 (m, 2H), 4.49 (s, 2H), 4.03-3.97 (br m, 1H). 3.95 (d, 1H, J = 13.4 Hz), 3.66-3.59 (m, 2H), 3.47-3.41 (m, 2H), 3.27-3.22 (m, 2H), 3.07 (s, 3H), 2.85 (d, 1H, J = 13.4 Hz), 0.98 (s, 9H). |
| 130 | | HCl | ¹H-NMR (DMSO-d$_6$) δ: 12.50 (s, 1H), 8.80 (s, 1H), 7.59-7.49 (m, 1H), 7.34-7.25 (m, 1H), 7.15-7.07 (m, 1H), 4.68-4.59 (m, 1H), 4.48 (s, 2H), 4.43 (dd, 1H, J = 13.4, 4.2 Hz), 4.17-4.09 (m, 1H), 3.86 (td, 1H, J = 13.9, 7.0 Hz), 3.67-3.56 (m, 2H), 3.52-3.41 (m, 2H), 3.34-3.22 (m, 3H), 3.09 (s, 3H), 1.20 (t, 3H, J = 7.0 Hz). |
| 131 | | HCl | ¹H-NMR (DMSO-d$_6$) δ: 12.97-12.84 (br m, 1H), 8.76 (s, 1H), 7.58-7.50 (m, 1H), 7.33-7.25 (m, 1H), 7.15-7.08 (m, 1H), 4.92-4.85 (br m, 1H), 4.48 (s, 2H), 3.98-3.84 (m, 2H), 3.67 (dd, 1H, J = 10.1, 5.6 Hz), 3.59 (dd, 1H, J = 10.1, 7.7 Hz), 3.28 (s, 3H), 1.48 (s, 9H). |

TABLE 1-37

| No. | structural formula | salt | ¹H-NMR |
|---|---|---|---|
| 132 | | HCl | ¹H-NMR (DMSO-d$_6$) δ: 12.79 (br s, 1H), 8.90 (s, 1H), 7.58-7.50 (m, 1H), 7.33-7.25 (m, 1H), 7.15-7.08 (m, 1H), 4.97-4.88 (m, 1H), 4.84-4.74 (m, 1H), 4.49 (s, 2H), 3.81 (dd, 1H, J = 13.5, 3.7 Hz), 3.63 (dd, 1H, J = 13.5, 2.2 Hz), 1.39 (d, 3H, J = 6.6 Hz), 1.19 (d, 3H, J = 6.8 Hz), 1.16 (d, 3H, J = 6.8 Hz). |
| 133 | | HCl | ¹H-NMR (DMSO-d$_6$) δ: 12.48 (s, 1H), 8.80 (s, 1H), 7.57-7.50 (m, 1H), 7.32-7.25 (m, 1H), 7.15-7.08 (m, 1H), 4.67 (d, 1H, J = 13.1 Hz), 4.51 (sep, 1H, J = 6.8 Hz), 4.49 (s, 2H), 4.34 (dd, 1H, J = 13.1, 3.7 Hz), 4.00-3.93 (m, 1H), 3.57 (dd, 1H, J = 11.4, 3.7 Hz), 3.37 (dd, 1H, J = 11.4, 8.3 Hz), 1.29 (d, 3H, J = 6.7 Hz), 1.28 (d, 3H, J = 6.7 Hz). |
| 134 | | HCl | ¹H-NMR (DMSO-d$_6$) δ: 12.88 (br s, 1H), 8.83-8.80 (m, 1H), 7.59-7.50 (m, 1H), 7.33-7.24 (m, 1H), 7.16-7.08 (m, 1H), 5.01-4.90 (br m, 1H), 4.60-4.50 (m, 1H), 4.49 (s, 2H), 3.87-3.63 (m, 4H), 3.57-3.46 (m, 2H), 3.35-3.30 (m, 2H), 3.12-3.10 (m, 3H), 1.59-1.48 (m, 2H), 1.15 (d, 3H, J = 6.7 Hz), 0.91-0.78 (m, 3H). |

TABLE 1-38

| No. | structural formula | salt | ¹H-NMR |
|---|---|---|---|
| 135 | | HCl | ¹H-NMR (DMSO-d$_6$) δ: 12.89 (br s, 1H), 8.81 (s, 1H), 7.59-7.50 (m, 1H), 7.34-7.25 (m, 1H), 7.16-7.06 (m, 1H), 5.03-4.92 (br m, 1H), 4.59-4.50 (m, 1H), 4.49 (s, 2H), 3.73-3.54 (m, 4H), 3.26-3.23 (m, 3H), 1.61-1.45 (m, 2H), 1.15 (d, 3H, J = 6.7 Hz), 0.91-0.80 (m, 3H), |
| 136 | | HCl | ¹H-NMR (DMSO-d$_6$) δ: 12.96 (br s, 1H), 8.82 (s, 1H), 7.59-7.49 (m, 1H), 7.35-7.24 (m, 1H), 7.17-7.06 (m, 1H), 5.04-4.91 (m, 1H), 4.49 (s, 2H), 4.30-3.57 (m, 5H), 3.27-3.22 (m, 3H), 1.87-1.69 (m, 1H), 1.17 (d, 3H, J = 6.8 Hz), 0.97-0.79 (m, 6H). |

TABLE 1-38-continued

| No. | structural formula | salt | 1H-NMR |
|---|---|---|---|
| 137 | | HCl | 1H-NMR (DMSO-d$_6$) δ: 12.42 (br s, 1H), 8.71 (s, 1H), 8.23-8.17 (m, 1H), 7.58-7.50 (m, 1H), 7.33-7.26 (m, 1H), 7.15-7.08 (m, 1H), 4.58 (sep, 1H, J = 6.7 Hz), 4.49 (s, 2H), 4.43 (dd, 1H, J = 13.0, 1.3 Hz), 4.31 (dd, 1H, J = 13.0, 3.0 Hz), 3.97-3.91 (m, 1H), 3.45-3.36 (m, 1H), 2.97-2.86 (m, 1H), 1.80 (s, 3H), 1.34 (d, 3H, J = 6.7 Hz), 1.27 (d, 3H, J = 6.7 Hz). |
| 138 | | HCl | 1H-NMR (DMSO-d$_6$) δ: 12.49 (br s, 1H), 8.72 (s, 1H), 7.88-7.83 (m, 1H), 7.57-7.50 (m, 1H), 7.32-7.25 (m, 1H), 7.15-7.08 (m, 1H), 4.57 (sep, 1H, J = 6.7 Hz), 4.49 (s, 2H), 4.38-4.28 (m, 2H), 3.99-3.92 (m, 1H), 3.38-3.29 (m, 1H), 3.04-2.95 (m, 1H), 1.38 (d, 3H, J = 6.7 Hz), 1.29 (d, 3H, J = 6.7 Hz), 1.08 (s, 9H). |

TABLE 1-39

| No. | structural formula | salt | 1H-NMR |
|---|---|---|---|
| 139 | | HCl | 1H-NMR (DMSO-d$_6$) δ: 13.18 (br s, 1H), 8.47 (s, 1H), 7.67 (s, 1H), 7.46 (td, 1H, J = 8.8, 6.6 Hz), 7.25 (ddd, 1H, J = 10.4, 9.3, 2.6 Hz), 7.08 (tdd, 1H, J = 8.8, 2.6, 0.9 Hz), 4.79 (sep, 1H, J = 6.7 Hz), 4.21 (s, 2H), 3.79 (d, 1H, J = 13.9 Hz), 3.74 (d, 1H, J = 14.6 Hz), 3.68 (d, 1H, J = 13.9 Hz), 3.57 (d, 1H, J = 14.6 Hz), 2.75 (s, 3H), 1.81 (s, 3H), 1.67 (s, 3H), 1.22 (d, 3H, J = 6.7 Hz), 1.17 (d, 3H, J = 6.7 Hz). |
| 140 | | HCl | 1H-NMR (DMSO-d$_6$) δ: 12.42 (br s, 1H), 8.71 (s, 1H), 8.22-8.17 (m, 1H), 7.57-7.50 (m, 1H), 7.33-7.26 (m, 1H), 7.15-7.08 (m, 1H), 4.58 (sep, 1H, J = 6.8 Hz), 4.49 (s, 2H), 4.43 (d, 1H, J = 13.0 Hz), 4.30 (dd, 1H, J = 13.0, 3.0 Hz), 3.98-3.91 (m, 1H), 2.96-2.86 (m, 1H), 2.56-2.50 (m, 1H), 1.80 (s, 3H), 1.34 (d, 3H, J = 6.8 Hz), 1.27 (d, 3H, J = 6.8 Hz). |

TABLE 1-39-continued

| No. | structural formula | salt | ¹H-NMR |
|---|---|---|---|
| 141 | | HCl | ¹H-NMR (DMSO-d₆) δ: 12.84 (s, 1H), 8.82 (s, 1H), 7.45-7.38 (m, 2H), 7.23-7.15 (m, 2H), 4.99-4.91 (m, 1H), 4.77 (sep, 1H, J = 6.8 Hz), 4.47 (s, 2H), 3.84 (dd, 1H, J = 13.8, 4.1 Hz), 3.75 (dd, 1H, J = 13.8, 1.7 Hz), 3.66 (dd, 1H, J = 10.4, 6.0 Hz), 3.59 (dd, 1H, J = 10.4, 7.5 Hz), 3.50-3.34 (m, 2H), 1.17 (d, 3H, J = 6.8 Hz), 1.16 (d, 3H, J = 6.8 Hz), 1.02 (t, 3H, J = 7.1 Hz). |

TABLE 1-40

| No. | structural formula | salt | ¹H-NMR |
|---|---|---|---|
| 142 | | HCl | ¹H-NMR (DMSO-d₆) δ: 12.83 (br s, 1H), 8.81 (s, 1H), 7.58-7.51 (m, 1H), 7.33-7.25 (m, 1H) 7.15-7.07 (m, 1H), 4.98-4.91 (m, 1H), 4.77 (sep, 1H, J = 6.8 Hz), 4.49 (s, 2H), 3.84 (dd, 1 H, J = 13.7, 4.0 Hz), 3.78-3.73 (m, 1H), 3.69-3.56 (m, 2H), 3.50-3.34 (m, 2H), 1.17 (d, 3H, J = 6.8 Hz), 1.16 (d, 3H, J = 6.8 Hz), 1.02 (t, 3H, J = 7.1 Hz). |
| 143 | | HCl | ¹H-NMR (DMSO-d₆) δ: 12.85 (br s, 1H), 8.80 (s, 1H), 7.58-7.50 (m, 1H), 7.33-7.25 (m, 1H), 7.15-7.08 (m, 1H), 4.99-4.92 (m, 1H), 4.77 (sep, 1H, J = 6.7 Hz), 4.48 (s, 2H), 3.84 (dd, 1H, J = 13.8, 4.1 Hz), 3.79-3.68 (m, 2H), 3.65 (dd, 1H, J = 10.4, 7.9 Hz), 3.56-3.44 (m, 2H), 3.38-3.34 (m, 2H), 3.30-3.22 (m, 2H), 1.17 (d, 3H, J = 6.7 Hz), 1.16 (d, 3H, J = 6.7 Hz), 0.91 (t, 3H, J = 7.0 Hz). |
| 144 | | HCl | ¹H-NMR (DMSO-d₆) δ: 12.82 (br s, 1H), 8.81 (s, 1H), 7.52-7.38 (m, 2H), 7.26-7.21 (m, 1H), 5.00-4.94 (m, 1H), 4.77 (sep, 1H, J = 6.9 Hz), 4.49 (s, 2H), 3.84 (dd, 1H, J = 13.7, 4.0 Hz), 3.75 (dd, 1H, J = 13.7, 1.2 Hz), 3.66-3.54 (m, 2H), 3.25 (s, 3H), 1.16 (d, 3H, J = 6.9 Hz), 1.16 (d, 3H, J = 6.9 Hz). |

TABLE 1-41

| No. | structural formula | salt | $^1$H-NMR |
|---|---|---|---|
| 145 | | HCl | $^1$H-NMR (DMSO-d$_6$) δ: 12.45 (br s, 1H), 8.85 (s, 1H), 7.58-7.50 (m, 1H), 7.33-7.25 (m, 1H), 7.15-7.08 (m, 1H), 4.71-4.65 (m, 1H), 4.49 (s, 2H), 4.38-4.27 (m, 2H), 4.17-4.11 (m, 1H), 3.50 (dd, 1H, J = 10.5, 4.1 Hz), 3.39 (dd, 1H, J = 10.5, 7.7 Hz), 3.20 (s, 3H), 1.78-1.59 (m, 2H), 1.25 (d, 3H, J = 6.8 Hz), 0.86 (t, 3H, J = 7.4 Hz). |
| 146 | | HCl | $^1$H-NMR (DMSO-d$_6$) δ: 12.48 (br s, 1H), 8.83 (s, 1H), 7.57-7.50 (m, 1H), 7.33-7.25 (m, 1H), 7.15-7.08 (m, 1H), 4.65 (dd, 1H, J = 13.5, 1.1 Hz), 4.49 (s, 2H), 4.38 (dd, 1H, J = 13.5, 4.1 Hz), 4.15-4.03 (m, 2H), 3.50 (dd, 1H, J = 10.1, 4.2 Hz), 3.42 (dd, 1H, J = 10.1, 7.1 Hz), 3.20 (s, 3H), 1.83-1.73 (m, 1H), 1.63-1.53 (m, 1H), 1.33 (d, 3H, J = 6.8 Hz), 0.91 (t, 3H, J = 7.4 Hz). |
| 147 | | HCl | $^1$H-NMR (DMSO-d$_6$) δ: 12.85 (br s, 1H), 8.81 (s, 1H), 7.59-7.49 (m, 1H), 7.33-7.25 (m, 1H), 7.16-7.08 (br m, 1H), 5.05-4.86 (br m, 1H), 4.60-4.50 (m, 1H), 4.49 (s, 2H), 3.87-3.56 (m, 4H), 3.25-3.25 (m, 3H), 1.54-1.50 (m, 2H), 1.15 (d, 3H, J = 6.5 Hz), 0.91-0.80 (m, 3H). |

TABLE 1-42

| No. | structural formula | salt | $^1$H-NMR |
|---|---|---|---|
| 148 | | HCl | $^1$H-NMR (DMSO-d$_6$) δ: 12.87 (br s, 1H), 8.81 (s, 1H), 7.58-7.52 (m, 1H), 7.32-7.27 (m, 1H), 7.16-7.07 (m, 1H), 5.05-4.90 (m, 1H), 4.49 (s, 2H), 4.32-4.20 (m, 1H), 3.90-3.57 (m, 4H), 3.26-3.24 (m, 3H), 1.87-1.69 (m, 1H), 1.19-1.10 (m, 3H), 0.97-0.79 (m, 6H). |
| 149 | | HCl | $^1$H-NMR (DMSO-d$_6$) δ: 12.79 (br s, 1H), 8.90 (s, 1H), 7.58-7.50 (m, 1H), 7.33-7.25 (m, 1H), 7.15-7.08 (m, 1H), 4.97-4.88 (m, 1H), 4.84-4.74 (m, 1H), 4.49 (s, 2H), 3.81 (dd, 1H, J = 13.5, 3.7 Hz), 3.63 (dd, 1H, J = 13.5, 2.2 Hz), 1.39 (d, 3H, J = 6.6 Hz), 1.19 (d, 3H, J = 6.8 Hz), 1.16 (d, 3H, J = 6.8 Hz). |

TABLE 1-42-continued

| No. | structural formula | salt | ¹H-NMR |
|---|---|---|---|
| 150 | | HCl | ¹H-NMR (DMSO-$d_6$) δ: 12.44 (br s, 1H), 8.85 (s, 1H), 7.53-7.37 (m, 2H), 7.26-7.19 (m, 1H), 4.66 (dd, 1H, J = 13.5, 1.5 Hz), 4.51-4.43 (m, 1H), 4.49 (s, 2H), 4.38-4.32 (m, 1H), 4.23-4.17 (m, 1H), 3.49 (dd, 1H, J = 10.4, 4.4 Hz), 3.39 (dd, 1H, J = 10.4, 7.5 Hz), 3.22 (s, 3H), 1.30 (d, 3H, J = 6.6 Hz), 1.29 (d, 3H, J = 6.8 Hz). |

TABLE 1-43

| No | structural formula | salt | ¹H-NMR |
|---|---|---|---|
| 151 | | HCl | ¹H-NMR (DMSO-$d_6$) δ: 12.86-12.34 (m, 1H), 8.68 (s, 1H), 7.66 (s, 1H), 7.49-7.39 (m, 1H), 7.29-7.20 (m, 1H), 7.11-7.02 (m, 1H), 5.12-5.03 (m, 1H), 4.84-4.70 (m, 1H), 4.21 (s, 2H), 3.82-3.55 (m, 2H), 3.15-2.96 (m, 2H), 2.08 (s, 3H), 1.17-1.09 (m, 6H). |
| 152 | | HCl | ¹H-NMR (DMSO-$d_6$) δ: 12.77 (br s, 1H), 8.43 (s, 1H), 7.68 (s, 1H), 7.50-7.41 (m, 1H), 7.29-7.20 (m, 1H), 7.11-7.03 (m, 1H), 4.24-4.16 (m, 1H), 4.22 (s, 2H), 3.91 (d, 1H, J = 13.9 Hz), 3.07 (s, 3H), 2.89 (s, 6H), 1.92 (s, 3H). |
| 153 | | HCl | ¹H-NMR (DMSO-$d_6$) δ: 12.64 (br s, 1H), 8.53 (s, 1H), 8.34-8.23 (m, 1H), 7.68 (s, 1H), 7.50-7.40 (m, 1H), 7.30-7.20 (m, 1H), 7.13-7.02 (m, 1H), 4.23 (s, 2H), 4.12 (d, 1H, J = 14.1 Hz), 4.01 (d, 1H, J = 14.1 Hz), 3.17-2.97 (m, 2H), 3.03 (s, 3H), 1.87 (s, 3H), 0.99 (t, 3H, J = 7.4 Hz). |

TABLE 1-43-continued

| No | structural formula | salt | ¹H-NMR |
|---|---|---|---|
| 154 | | HCl | ¹H-NMR (DMSO-$d_6$) δ: 12.32 (s, 1H), 8.79 (s, 1H), 7.58-7.50 (m, 1H), 7.32-7.25 (m, 1H), 7.15-7.08 (m, 1H), 4.60 (d, 1H, J = 13.0 Hz), 4.55 (sep, 1H, J = 6.8 Hz), 4.48 (s, 2H), 4.35 (dd, 1H, J = 13.0, 3.0 Hz), 4.27-4.20 (m, 1H), 3.26 (dd, 1H, J = 13.7, 10.5 Hz), 2.99 (dd, 1H, J = 13.7, 3.0 Hz), 2.87 (s, 3H), 2.84 (s, 3H), 1.30 (d, 6H, J = 6.8 Hz). |

TABLE 1-44

| No. | structural formula | salt | ¹H-NMR |
|---|---|---|---|
| 155 | | HCl | ¹H-NMR (DMSO-$d_6$) δ: 12.83 (br s, 1H), 8.82 (s, 1H), 7.52-7.37 (m, 2H), 7.27-7.20 (m, 1H), 4.99-4.91 (m, 1H), 4.77 (sep, 1H, J = 6.9 Hz), 4.49 (s, 2H), 3.84 (dd, 1H, J = 13.7, 4.0 Hz), 3.79-3.69 (m, 2H), 3.64 (dd, 1H, J = 10.5, 7.7 Hz), 3.58-3.45 (m, 2H), 3.34 (t, 2H, J = 4.6 Hz), 3.11 (s, 3H), 1.17 (d, 3H, J = 6.9 Hz), 1.16 (d, 3H, J = 6.9 Hz). |
| 156 | | HCl | ¹H-NMR (DMSO-$d_6$) δ: 8.84 (s, 1H), 7.58-7.50 (m, 1H), 7.33-7.25 (m, 1H), 7.15-7.08 (m, 1H), 4.62-4.53 (m, 1H), 4.51-4.45 (m, 3H), 4.32 (dd, 1H, J = 13.1, 3.4 Hz), 4.26-4.18 (m, 1H), 1.27 (d, 3H, J = 6.9 Hz), 1.26 (d, 3H, J = 6.9 Hz), 1.21 (d, 3H, J = 6.4 Hz). |
| 157 | | HCl | ¹H-NMR (DMSO-$d_6$) δ: 12.96 (s, 1H), 8.56 (s, 1H), 7.53-7.19 (m, 3H), 4.80-4.66 (m, 1H), 4.50 (s, 2H), 4.15 (d, 1H, J = 14.3 Hz), 3.82 (d, 1H, J = 14.3 Hz), 3.09-2.83 (m, 6H), 2.04 (s, 3H), 1.18 (d, 3H, J = 7.1 Hz), 1.11 (d, 3H, J = 7.1 Hz). |
| 158 | | HCl | ¹H-NMR (DMSO-$d_6$) δ: 12.35 (s, 1H), 8.75 (s, 1H), 7.57-7.49 (m, 2H), 7.32-7.25 (m, 1H), 7.15-7.08 (m, 1H), 4.61-4.53 (m, 2H), 4.49 (s, 2H), 4.40-4.33 (m, 1H), 4.00-3.93 (m, 1H), 3.21-3.12 (m, 1H), 3.02-2.92 (m, 1H), 2.90 (s, 3H), 1.30 (d, 3H, J = 6.7 Hz), 1.28 (d, 3H, J = 6.7 Hz). |

TABLE 1-45

| No. | structural formula | salt | ¹H-NMR |
|---|---|---|---|
| 159 | | HCl | ¹H-NMR (DMSO-d₆) δ: 12.39 (br s, 1H), 8.83 (s, 1H), 7.58-7.49 (m, 1H), 7.32-7.25 (m, 1H), 7.15-7.08 (m, 1H), 4.56 (sep, 1H, J = 6.7 Hz), 4.49 (s, 2H), 4.42-4.28 (m, 2H), 4.26-4.18 (m, 1H), 3.41-3.36 (m, 2H), 3.04 (s, 3H), 2.83 (t, 1H, J = 6.7 Hz), 1.34 (d, 3H, J = 6.7 Hz), 1.29 (d, 3H, J = 6.7 Hz), 1.00 (d, 3H, J = 6.7 Hz), 0.99 (d, 3H, J = 6.7 Hz). |
| 160 | | HCl | ¹H-NMR (DMSO-d₆) δ: 12.67 (br s, 1H), 8.53 (s, 1H), 8.12-8.02 (m, 1H), 7.67 (s, 1H), 7.49-7.40 (m, 1H), 7.29-7.20 (m, 1H), 7.12-7.02 (m, 1H), 4.22 (s, 2H), 4.07 (d, 1H, J = 14.1 Hz), 3.99 (d, 1H, J = 14.1 Hz), 3.03 (s, 3H), 2.60 (d, 3H, J = 4.6 Hz), 1.86 (s, 3H). |
| 161 | | HCl | ¹H-NMR (DMSO-d₆) δ: 12.76 (br s, 1H), 8.41 (s, 1H), 7.66 (s, 1H), 7.50-7.40 (m, 1H), 7.29-7.20 (m, 1H), 7.12-7.03 (m, 1H), 4.22 (s, 2H), 4.17 (d, 1H, J = 13.9 Hz), 3.91 (d, 1H, J = 13.9 Hz), 3.46-3.17 (m, 2H), 3.06 (s, 3H), 2.84 (s, 3H), 1.90 (s, 3H), 0.99 (t, 3H, J = 7.4 Hz). |
| 162 | | HCl | ¹H-NMR (DMSO-d₆) δ: 12.71 (br s, 1H), 8.52 (s, 1H), 8.31-8.22 (m, 1H), 7.67 (s, 1H), 7.50-7.39 (m, 1H), 7.31-7.19 (m, 1H), 7.13-7.03 (m, 1H), 4.22 (s, 2H), 4.14 (d, 1H, J = 13.7 Hz), 3.99 (d, 1H, J = 13.7 Hz), 3.66-3.28 (m, 2H), 3.15-3.00 (m, 2H), 1.89 (s, 3H), 1.11 (t, 3H, J = 7.4 Hz), 0.99 (t, 3H, J = 7.4 Hz). |

TABLE 1-46

| No. | structural formula | salt | ¹H-NMR |
|---|---|---|---|
| 163 | | HCl | ¹H-NMR (DMSO-d₆) δ: 12.34 (br s, 1H), 8.78 (s, 1H), 7.44-7.38 (m, 2H), 7.22-7.15 (m, 2H), 4.55 (sep, 1H, J = 6.7 Hz), 4.47 (s, 2H), 4.43 (d, 1H, J = 12.4 Hz), 4.38-4.27 (m, 1H), 4.25-4.17 (m, 1H), 3.44 (dd, 1H, J = 13.3, 10.0 Hz), 3.34-3.28 (m, 1H), 3.00 (s, 3H), 1.99 (s, 3H), 1.33 (d, 3H, J = 6.7 Hz), 1.29 (d, 3H, J = 6.7 Hz). |

TABLE 1-46-continued

| No. | structural formula | salt | ¹H-NMR |
|---|---|---|---|
| 164 | | HCl | ¹H-NMR (DMSO-d$_6$) δ: 8.71 (s, 1H), 7.66 (s, 1H), 7.49-7.40 (m, 1H), 7.29-7.20 (m, 1H), 7.12-7.03 (m, 1H), 5.06-4.95 (m, 1H), 4.21 (s, 2H), 4.04 (dd, 1H, J = 13.4, 3.5 Hz), 3.68-3.60 (m, 1H), 2.97-2.88 (m, 1H), 2.88-2.82 (m, 2H), 2.87 (s, 3H), 2.79 (s, 3H), 0.96-0.83 (m, 2H), 0.83-0.72 (m, 1H), 0.67-0.55 (m, 1H). |
| 165 | | HCl | ¹H-NMR (DMSO-d$_6$) δ: 8.52 (s, 1H), 7.99 (t, 1H, J= 4.9 Hz), 7.65 (s, 1H), 7.49-7.40 (m, 1H), 7.29-7.20 (m, 1H), 7.12-7.03 (m, 1H), 5.00-4.89 (m, 1H), 4.21 (s, 2H), 4.03 (dd, 1H, J = 13.9, 3.9 Hz), 3.58-3.50 (m, 1H), 3.03-2.83 (m, 3H), 2.56 (d, 2H, J = 7.4 Hz), 1.01-0.71 (m, 4H), 0.80 (t, 3H, J = 7.2 Hz). |
| 166 | | HCl | ¹H-NMR (DMSO-d$_6$) δ: 8.81 (s, 1H), 7.47-7.36 (m, 2H), 7.23-7.12 (m, 2H), 5.04-4.91 (m, 1H), 4.60-4.49 (m, 1H), 4.47 (s, 2H), 3.88-3.54 (m, 4H), 3.27-3.23 (m, 3H), 1.61-1.46 (m, 2H), 1.15 (d, 3H, J = 6.4 Hz), 0.91-0.80 (m, 3H). |

TABLE 1-47

| No. | structural formula | salt | ¹H-NMR |
|---|---|---|---|
| 167 | | HCl | ¹H-NMR (DMSO-d$_6$) δ: 8.81 (s, 1H), 7.46-7.38 (m, 2H), 7.23-7.14 (m, 2H), 5.02-4.92 (m, 1H), 4.60-4.49 (m, 1H), 4.47 (s, 2H), 3.89-3.54 (m, 4H), 3.27-3.23 (m, 3H), 1.59-1.47 (m, 2H), 1.15 (d, 3H, J = 6.4 Hz), 0.91-0.80 (m, 3H). |
| 168 | | HCl | ¹H-NMR (DMSO-d$_6$) δ: 8.66 (s, 1H), 7.65 (s, 1H), 7.49-7.40 (m, 1H), 7.30-7.20 (m, 1H), 7.12-7.02 (m, 1H), 4.64-4.56 (m, 1H), 4.47 (sep, 1H, J = 6.7 Hz), 4.33 (dd, 1H, J = 13.3, 3.6 Hz), 4.24-4.14 (m, 3H), 3.48 (dd, 1H, J = 10.2, 4.2 Hz), 3.36 (dd, 1H, J = 10.2, 7.7 Hz), 3.21 (s, 3H), 1.29 (d, 3H, J = 6.7 Hz), 1.28 (d, 3H, J = 6.7 Hz). |

TABLE 1-47-continued

| No. | structural formula | salt | ¹H-NMR |
|---|---|---|---|
| 169 | | HCl | ¹H-NMR (DMSO-d₆) δ: 12.96 (br s, 1H), 8.55 (s, 1H), 7.54 (td, 1H, J = 8.6, 6.6 Hz), 7.29 (ddd, 1H, J = 10.2, 9.3, 2.6 Hz), 7.11 (tdd, 1H, J = 8.6, 2.6, 0.9 Hz), 4.73 (sep, 1H, J = 6.7 Hz), 4.49 (s, 2H), 4.15 (d, 1H, J = 14.4 Hz), 3.82 (d, 1H, J = 14.4 Hz), 2.95 (br s, 6H), 2.03 (s, 3H), 1.18 (d, 3H, J = 6.7 Hz), 1.11 (d, 3H, J = 6.7 Hz). |
| 170 | | HCl | ¹H-NMR (DMSO-d₆) δ: 12.91 (br s, 1H), 8.64 (s, 1H), 7.54 (td, 1H, J = 8.8, 6.6 Hz), 7.29 (ddd, 1H, J = 10.4, 9.5, 2.8 Hz), 7.12 (tdd, 1H, J = 8.8, 2.8, 1.2 Hz), 4.70 (sep, 1H, J = 6.7 Hz), 4.49 (s, 2H), 4.14 (d, 1H, J = 14.1 Hz), 3.77 (d, 1H, J = 14.1 Hz), 3.71-3.50 (br m, 2H), 3.36-3.24 (br m, 1H), 3.21-3.08 (br m, 1H), 2.06 (s, 3H), 1.97-1.86 (br m, 1H), 1.83-1.59 (br m, 3H), 1.17 (d, 3H, J = 6.7 Hz), 1.08 (d, 3H, J = 6.7 Hz). |

TABLE 1-48

| No. | structural formula | salt | ¹H-NMR |
|---|---|---|---|
| 171 | | HCl | ¹H-NMR (DMSO-d₆) δ: 12.96 (br s, 1H), 8.55 (s, 1H), 7.54 (td, 1H, J = 8.6, 6.6 Hz), 7.29 (ddd, 1H, J = 10.2, 9.3, 2.6 Hz), 7.11 (tdd, 1H, J = 8.6, 2.6, 0.9 Hz), 4.73 (sep, 1H, J = 6.7 Hz), 4.49 (s, 2H), 4.15 (d, 1H, J = 14.4 Hz), 3.82 (d, 1H, J = 14.4 Hz), 2.95 (br s, 6H), 2.03 (s, 3H), 1.18 (d, 3H, J = 6.7 Hz), 1.11 (d, 3H, J = 6.7 Hz). |
| 172 | | HCl | ¹H-NMR (DMSO-d₆) δ: 12.91 (br s, 1H), 8.64 (s, 1H), 7.54 (td, 1H, J = 8.8, 6.6 Hz), 7.29 (ddd, 1H, J = 10.4, 9.5, 2.8 Hz), 7.12 (tdd, 1H, J = 8.8, 2.8, 1.2 Hz), 4.70 (sep, 1H, J = 6.7 Hz), 4.49 (s, 2H), 4.14 (d, 1H, J = 14.1 Hz), 3.77 (d, 1H, J = 14.1 Hz), 3.71-3.50 (br m, 2H), 3.36-3.24 (br m, 1H), 3.21-3.08 (br m, 1H), 2.06 (s, 3H), 1.97-1.86 (br m, 1H), 1.83-1.59 (br m, 3H), 1.17 (d, 3H, J = 6.7 Hz), 1.08 (d, 3H, J = 6.7 Hz). |
| 173 | | HCl | ¹H-NMR (DMSO-d₆) δ: 12.93 (br s, 1H), 8.62 (s, 1H), 8.19 (t, 1H, J = 5.2 Hz), 7.54 (td, 1H, J = 8.7, 6.6 Hz), 7.29 (ddd, 1H, J = 10.4, 9.3, 2.6 Hz), 7.12 (tdd, 1H, J = 8.7, 2.6, 0.9 Hz), 4.71 (sep, 1H, J = 6.7 Hz), 4.50 (s, 2H), 4.11 (d, 1H, J = 13.9 Hz), 3.80 (d, 1H, J = 13.9 Hz), 3.18-2.98 (m, 2H), 1.96 (s, 3H), 1.15 (d, 3H, J = 6.7 Hz), 1.12 (d, 3H, J = 6.7 Hz), 1.00 (t, 3H, J = 7.2 Hz). |

TABLE 1-49

| No. | structural formula | salt | $^1$H-NMR |
|---|---|---|---|
| 174 | | HCl | $^1$H-NMR (DMSO-d$_6$) δ: 12.93 (br s, 1H), 8.62 (s, 1H), 8.19 (t, 1H, J = 5.2 Hz), 7.54 (td, 1H, J = 8.7, 6.6 Hz), 7.29 (ddd, 1H, J = 10.4, 9.3, 2.6 Hz), 7.12 (tdd, 1H, J = 8.7, 2.6, 0.9 Hz), 4.71 (sep, 1H, J = 6.7 Hz), 4.50 (s, 2H), 4.11 (d, 1H, J = 13.9 Hz), 3.80 (d, 1H, J = 13.9 Hz), 3.18-2.98 (m, 2H), 1.96 (s, 3H), 1.15 (d, 3H, J = 6.7 Hz), 1.12 (d, 3H, J = 6.7 Hz), 1.00 (t, 3H, J = 7.2 Hz). |
| 175 | | HCl | $^1$H-NMR (DMSO-d$_6$) δ: 8.43 (s, 1H), 7.42-7.37 (m, 2H), 7.21-7.15 (m, 2H), 4.76 (sep, 1H, J = 6.9 Hz), 4.46 (s, 2H), 3.66 (s, 2H), 1.66-1.61 (m, 2H), 1.13-1.18 (m, 2H), 1.16 (d, 6H, J = 6.9 Hz). |
| 176 | | HCl | $^1$H-NMR (DMSO-d$_6$) δ: 8.67 (s, 1H), 7.43-7.38 (m, 2H), 7.21-7.16 (m, 2H), 4.47 (s, 2H), 4.31 (s, 2H), 4.15 (sep, 1H, J = 6.9 Hz), 1.35-1.29 (m, 2H), 1.32 (d, 6H, J = 6.9 Hz), 1.07-1.02 (m, 2H). |
| 177 | | HCl | $^1$H-NMR (DMSO-d$_6$) δ: 12.95 (s, 1H), 8.55 (s, 1H), 7.44-7.36 (m, 2H), 7.21-7.15 (m, 2H), 4.73 (sep, 1H, J = 6.7 Hz), 4.48 (s, 2H), 4.15 (d, 1H, J = 14.1 Hz), 3.82 (d, 1H, J = 14.1 Hz), 3.07-2.81 (br m, 6H), 2.04 (s, 3H), 1.18 (d, 3H, J = 6.7 Hz), 1.11 (d, 3H, J = 6.7 Hz). |

TABLE 1-50

| No. | structural formula | salt | $^1$H-NMR |
|---|---|---|---|
| 178 | | HCl | $^1$H-NMR (DMSO-d$_6$) δ: 12.87 (s, 1H), 8.55 (s, 1H), 7.44-7.37 (m, 2H), 7.22-7.14 (m, 2H), 4.48 (s, 2H), 4.15 (d, 1H, J = 13.9 Hz), 3.85 (d, 1H, J = 13.9 Hz), 2.95-2.83 (m, 1H), 2.89 (s, 6H), 1.97 (s, 3H), 0.95-0.80 (m, 2H), 0.76-0.62 (m, 2H). |

TABLE 1-50-continued

| No. | structural formula | salt | ¹H-NMR |
|---|---|---|---|
| 179 | | HCl | ¹H-NMR (DMSO-d$_6$) δ: 12.90 (s, 1H), 8.65 (s, 1H), 7.45-7.38 (m, 2H), 7.23-7.15 (m, 2H), 4.70 (sep, 1H, J = 6.7 Hz), 4.48 (s, 2H), 4.14 (d, 1H, J = 13.9 Hz), 3.77 (d, 1H, J = 13.9 Hz), 3.72-3.62 (br m, 1H), 3.36-3.23 (br m, 2H), 3.20-3.09 (br m, 1H), 2.06 (s, 3H), 1.98-1.84 (br m, 1H), 1.83-1.59 (br m, 3H), 1.17 (d, 3H, J = 6.7 Hz), 1.08 (d, 3H, J = 6.7 Hz). |
| 180 | | HCl | ¹H-NMR (DMSO-d$_6$) δ: 12.92 (s, 1H), 8.62 (s, 1H), 8.17 (t, 1H, J = 5.2 Hz), 7.44-7.37 (m, 2H), 7.23-7.15 (m, 2H), 4.71 (sep, 1H, J = 6.7 Hz), 4.48 (s, 2H), 4.10 (d, 1H, J = 13.9 Hz), 3.80 (d, 1H, J = 13.9 Hz), 3.18-2.99 (m, 2H), 1.96 (s, 3H), 1.15 (d, 3H, J = 6.7 Hz), 1.12 (d, 3H, J = 6.7 Hz), 1.01 (t, 3H, J = 7.2 Hz). |
| 181 | | HCl | ¹H-NMR (DMSO-d$_6$) δ: 12.98 (br s, 1H), 8.59 (s, 1H), 7.45-7.37 (m, 2H), 7.23-7.15 (m, 2H), 4.47 (s, 2H), 4.32 (d, 1H, J = 14.4 Hz), 3.82 (d, 1H, J = 14.4 Hz), 2.90 (s, 6H), 2.03 (s, 3H), 1.45 (s, 9H). |

TABLE 1-51

| No. | structural formula | salt | ¹H-NMR |
|---|---|---|---|
| 182 | | HCl | ¹H-NMR (DMSO-d$_6$) δ: 8.91 (s, 1H), 7.44-7.38 (m, 2H), 7.22-7.15 (m, 2H), 4.55 (sep, 1H, J = 6.7 Hz), 4.47 (s, 2H), 4.43-4.29 (m, 2H), 4.26-4.19 (m, 1H), 3.47 (dd, 1H, J = 13.3, 4.0 Hz), 3.28 (dd, 1H, J = 13.3, 10.0 Hz), 3.12 (s, 3H), 1.35 (d, 3H, J = 6.7 Hz), 1.30 (d, 3H, J = 6.7 Hz), 1.20 (s, 9H). |

TABLE 1-51-continued

| No. | structural formula | salt | ¹H-NMR |
|---|---|---|---|
| 183 | | HCl | ¹H-NMR (DMSO-d$_6$) δ: 8.92 (s, 1H), 7.44-7.38 (m, 2H), 7.22-7.15 (m, 2H), 4.55 (sep, 1H, J = 6.7 Hz), 4.47 (s, 2H), 4.38-4.33 (m, 2H), 4.22-4.16 (m, 1H), 3.47 (dd, 1H, J = 13.5, 3.5 Hz), 3.28 (dd, 1H, J = 13.5, 10.0 Hz), 3.12 (s, 3H), 1.65-1.57 (m, 2H), 1.35 (d, 3H, J = 6.7 Hz), 1.30 (d, 3H, J = 6.7 Hz), 1.17 (s, 3H), 1.16 (s, 3H), 0.79 (t, 3H, J = 7.5 Hz). |
| 184 | | HCl | ¹H-NMR (DMSO-d$_6$) δ: 12.41 (br s, 1H), 8.90 (s, 1H), 7.58-7.50 (m, 1H), 7.32-7.25 (m, 1H), 7.15-7.08 (m, 1H), 4.56 (sep, 1H, J = 6.6 Hz), 4.49 (s, 2H), 4.41-4.29 (m, 2H), 4.27-4.18 (m, 1H), 3.48-3.44 (m, 1H), 3.29 (dd, 1H, J = 13.5, 10.0 Hz), 3.12 (s, 3H), 1.35 (d, 3H, J = 6.7 Hz), 1.30 (d, 3H, J = 6.7 Hz), 1.20 (s, 9H). |
| 185 | | HCl | ¹H-NMR (DMSO-d$_6$) δ: 12.90 (br s, 1H), 8.63 (s, 1H), 8.12 (q, 1H, J = 4.4 Hz), 7.45-7.37 (m, 2H), 7.23-7.15 (m, 2H), 4.70 (sep, 1H, J = 6.7 Hz), 4.48 (s, 2H), 4.08 (d, 1H, J = 13.9 Hz), 3.80 (d, 1H, J = 13.9 Hz), 2.59 (d, 3H, J = 4.4 Hz), 1.97 (s, 3H), 1.15 (d, 3H, J = 6.7 Hz), 1.09 (d, 3H, J = 6.7 Hz). |

TABLE 1-52

| No. | structural formula | salt | ¹H-NMR |
|---|---|---|---|
| 186 | | HCl | ¹H-NMR (DMSO-d$_6$) δ: 12.93 (br s, 1H), 8.64 (s, 1H), 8.09 (t, 1H, J = 6.0 Hz), 7.43-7.38 (m, 2H), 7.22-7.15 (m, 2H), 4.69 (sep, 1H, J = 6.7 Hz), 4.48 (s, 2H), 4.14 (d, 1H, J = 13.9 Hz), 3.79 (d, 1H, J = 13.9 Hz), 3.10-3.01 (m, 1H), 2.71-2.62 (m, 1H), 1.97 (s, 3H), 1.75-1.61 (m, 1H), 1.15 (d, 3H, J = 6.7 Hz), 1.11 (d, 3H, J = 6.7 Hz), 0.79 (d, 6H, J = 6.7 Hz). |

TABLE 1-52-continued

| No. | structural formula | salt | ¹H-NMR |
|---|---|---|---|
| 187 | | HCl | ¹H-NMR (DMSO-d$_6$) δ: 12.85 (br s, 1H), 8.62 (s, 1H), 8.19 (t, 1H, J = 5.2 Hz), 7.45-7.36 (m, 2H), 7.22-7.15 (m, 2H), 4.48 (s, 2H), 4.00 (d, 1H, J = 13.7 Hz), 3.96 (d, 1H, J = 13.7 Hz), 3.11-3.02 (m, 2H), 2.88 (sep, 1H, J = 3.9 Hz), 1.92 (s, 3H), 0.98 (t, 3H, J = 7.0 Hz), 0.96-0.89 (m, 1H), 0.85-0.69 (m, 2H), 0.65-0.56 (m, 1H). |
| 188 | | HCl | ¹H-NMR (DMSO-d$_6$) δ: 12.93 (br s, 1H), 8.69 (s, 1H), 7.45-7.39 (m, 2H), 7.22-7.15 (m, 2H), 4.48 (s, 2H), 4.32 (s, 1H, J = 13.9 Hz), 3.77 (d, 1H, J =13.9 Hz), 3.44-3.23 (br m, 4H), 2.01 (s, 3H), 1.92-1.54 (br m, 4H), 1.44 (s, 9H). |
| 189 | | HCl | ¹H-NMR (DMSO-d$_6$) δ: 12.98 (br s, 1H), 8.59 (s, 1H), 8.19 (t, 1H, J = 7.0 Hz), 7.44-7.37 (m, 2H), 7.23-7.15 (m, 2H), 4.48 (s, 2H), 4.23 (d, 1H, J = 13.7 Hz), 3.83 (s, 1H, J = 13.7 Hz), 3.10 (dq, 2H, J = 7.0, 7.0 Hz), 1.94 (s, 3H), 1.45 (s, 9H), 1.02 (t, 3H, J = 7.0 Hz). |

TABLE 1-53

| No. | structural formula | salt | ¹H-NMR |
|---|---|---|---|
| 190 | | HCl | ¹H-NMR (DMSO-d$_6$) δ: 12.90 (br s, 1H), 8.62 (s, 1H), 8.10 (q, 1H, J = 4.4 Hz), 7.53 (td, 1H, J = 8.6, 6.5 Hz), 7.28 (ddd, 1H, J = 10.2, 9.5, 2.6 Hz), 7.11 (tdd, 1H, J = 8.6, 2.6, 1.1 Hz), 4.69 (sep, 1H, J = 6.7 Hz), 4.49 (s, 2H), 4.06 (d, 1H, J = 13.9 Hz), 3.78 (d, 1H, J = 13.9 Hz), 2.58 (d, 3H, J = 4.4 Hz), 1.95 (s, 3H), 1.13 (d, 3H, J = 6.7 Hz), 1.08 (d, 3H, J = 6.7 Hz). |

TABLE 1-53-continued

| No. | structural formula | salt | ¹H-NMR |
|---|---|---|---|
| 191 | | HCl | ¹H-NMR (DMSO-d₆) δ: 12.90 (br s, 1H), 8.62 (s, 1H), 8.10 (q, 1H, J = 4.4 Hz), 7.53 (td, 1H, J = 8.6, 6.5 Hz), 7.28 (ddd, 1H, J = 10.2, 9.5, 2.6 Hz), 7.11 (tdd, 1H, J = 8.6, 2.6, 1.1 Hz), 4.69 (sep, 1H, J = 6.7 Hz), 4.49 (s, 2H), 4.06 (d, 1H, J = 13.9 Hz), 3.78 (d, 1H, J = 13.9 Hz), 2.58 (d, 3H, J = 4.4 Hz), 1.95 (s, 3H), 1.13 (d, 3H, J = 6.7 Hz), 1.08 (d, 3H, J = 6.7 Hz). |
| 192 | | HCl | ¹H-NMR (DMSO-d₆) δ: 12.88 (br s, 1H), 8.82 (s, 1H), 7.45-7.39 (m, 2H), 7.22-7.16 (m, 2H), 4.77 (sep, 1H, J = 6.9 Hz), 4.63-4.59 (m, 1H), 4.47 (s, 2H), 3.89-3.82 (m, 2H), 1.27 (d, 3H, J = 6.9 Hz), 1.19 (d, 3H, J = 6.9 Hz), 0.96 (s, 9H). |
| 193 | | HCl | ¹H-NMR (DMSO-d₆) δ: 12.88 (br s, 1H), 8.82 (s, 1H), 7.45-7.39 (m, 2H), 7.22-7.16 (m, 2H), 4.77 (sep, 1H, J = 6.9 Hz), 4.63-4.59 (m, 1H), 4.47 (s, 2H), 3.89-3.83 (m, 2H), 1.28 (d, 3H, J = 6.9 Hz), 1.19 (d, 3H, J = 6.9 Hz), 0.96 (s, 9H). |

TABLE 1-54

| No. | structural formula | salt | ¹H-NMR |
|---|---|---|---|
| 194 | | HCl | ¹H-NMR (DMSO-d₆) δ: 12.76 (br s, 1H), 8.90 (s, 1H), 7.45-7.39 (m, 2H), 7.22-7.16 (m, 2H), 4.79-4.79 (sep, 1H, J = 6.7 Hz), 4.50-4.43 (m, 1H), 4.47 (s, 2H), 3.86-3.78 (m, 2H), 2.03-1.92 (m, 1H), 1.20 (d, 3H, J = 6.7 Hz), 1.18 (d, 3H, J = 6.7 Hz), 1.04 (d, 3H, J = 6.7 Hz), 0.69 (d, 3H, J = 6.7 Hz). |
| 195 | | HCl | ¹H-NMR (DMSO-d₆) δ: 12.49 (br s, 1H), 8.85 (s, 1H), 7.44-7.38 (m, 2H), 7.22-7.15 (m, 2H), 4.68 (dd, 1H, J = 13.5, 1.3 Hz), 4.61-4.49 (m, 1H), 4.47 (s, 2H), 4.41 (dd, 1H, J = 13.5, 4.0 Hz), 4.31-4.25 (m, 1H), 3.43 (dd, 1H, J = 10.6, 5.0 Hz), 3.39 (dd, 1H, J = 10.6, 6.8 Hz), 3.21 (s, 3H), 2.38-2.11 (m, 4H), 1.77-1.64 (m, 2H). |

TABLE 1-54-continued

| No. | structural formula | salt | ¹H-NMR |
|---|---|---|---|
| 196 | | HCl | ¹H-NMR (DMSO-d$_6$) δ: 12.49 (br s, 1H), 8.85 (s, 1H), 7.44-7.37 (m, 2H), 7.22-7.15 (m, 2H), 4.65 (dd, 1H, J = 13.7, 1.5 Hz), 4.47 (s, 2H), 4.44-4.34 (m, 2H), 4.20-4.13 (m, 1H), 3.47 (dd, 1H, J = 10.4, 4.6 Hz), 3.41 (dd, 1H, J = 10.4, 7.3 Hz), 3.21 (s, 3H), 1.95-1.72 (m, 6H), 1.63-1.49 (m, 2H). |
| 197 | | HCl | ¹H-NMR (DMSO-d$_6$) δ: 13.29 (br s, 1H), 8.52 (s, 1H), 7.60-7.50 (m, 1H), 7.36-7.25 (m, 1H), 7.17-7.08 (m, 1H), 4.86-4.73 (m, 1H), 4.49 (s, 2H), 3.91-3.64 (m, 4H), 2.82 (s, 3H), 1.81 (s, 3H), 1.71 (s, 3H), 1.23 (d, 3H, J = 6.7 Hz), 1.17 (d, 3H, J = 7.0 Hz). |

TABLE 1-55

| No. | structural formula | salt | ¹H-NMR |
|---|---|---|---|
| 198 | | HCl | ¹H-NMR (DMSO-d$_6$) δ: 8.88 (s, 1H), 7.45-7.37 (m, 2H), 7.23-7.15 (m, 2H), 4.70 (d, 1H, J = 13.0 Hz), 4.47 (s, 2H), 4.39-4.27 (m, 2H), 3.73-3.61 (m, 2H), 3.49-3.41 (m, 1H), 3.22 (s, 3H), 1.34 (d, 3H, J = 6.7 Hz), 1.26-1.13 (m, 1H), 0.69-0.60 (m, 1H), 0.54-0.45 (m, 1H), 0.42-0.37 (m, 2H). |
| 199 | | HCl | ¹H-NMR (DMSO-d$_6$) δ: 12.87 (s, 1H), 8.56 (s, 1H), 7.45-7.37 (m, 2H), 7.23-7.15 (m, 2H), 4.48 (s, 2H), 4.21 (d, 1H, J = 13.9 Hz), 3.98 (d, 1H, J = 13.9 Hz), 3.53 (q, 2H, J = 7.0 Hz), 2.50 (s, 6H), 2.01 (s, 3H), 1.11 (t, 3H, J = 7.0 Hz). |
| 200 | | HCl | ¹H-NMR (DMSO-d$_6$) δ: 12.81 (br s, 1H), 8.67 (s, 1H), 7.45-7.39 (m, 2H), 7.22-7.15 (m, 2H), 4.48 (s, 2H), 4.19 (d, 1H, J = 13.9 Hz), 3.96 (d, 1H, J = 13.9 Hz), 3.59-3.25 (br m, 3H), 3.53 (dq, 1H, J = 14.0, 7.0 Hz), 3.49 (dq, 1H, J = 14.0, 7.0 Hz), 3.12-2.96 (br m, 1H), 2.01 (s, 3H), 1.96-1.48 (m, 4H), 1.09 (t, 3H, J = 7.0 Hz). |

TABLE 1-55-continued

| No. | structural formula | salt | ¹H-NMR |
|---|---|---|---|
| 201 | (structure) | HCl | ¹H-NMR (DMSO-d$_6$) δ: 12.81 (br s, 1H), 8.62 (s, 1H), 8.26 (t, 1H, J = 5.6 Hz), 7.44-7.38 (m, 2H), 7.22-7.15 (m, 2H), 4.48 (s, 2H), 4.13 (d, 1H, J = 13.9 Hz), 4.01 (d, 1H, J = 13.9 Hz), 3.62 (dq, 1H, J = 14.2, 7.1 Hz), 3.36 (dq, 1H, J = 14.2, 7.1 Hz), 3.14-3.04 (m, 2H), 1.93 (s, 3H), 1.11 (t, 3H, J = 7.1 Hz), 1.00 (t, 3H, J = 7.1 Hz). |

TABLE 1-56

| No. | structural formula | salt | ¹H-NMR |
|---|---|---|---|
| 202 | (structure) | HCl | ¹H-NMR (DMSO-d$_6$) δ: 13.00 (br s, 1H), 8.57 (s, 1H), 7.45-7.37 (m, 2H), 7.22-7.15 (m, 2H), 4.72 (sep, 1H, J = 6.7 Hz), 4.48 (s, 2H), 4.18 (d, 1H, J = 14.4 Hz), 3.81 (d, 1H, J = 14.4 Hz), 3.64 (br s, 3H), 3.42 (t, 2H, J = 5.3 Hz), 3.20 (s, 3H), 3.05-2.92 (br m, 2H), 2.02 (s, 3H), 1.18 (d, 3H, J = 6.7 Hz), 1.13 (d, 3H, J = 6.7 Hz). |
| 203 | (structure) | HCl | ¹H-NMR (DMSO-d$_6$) δ: 13.06 (br s, 1H), 8.52 (s, 1H), 7.46-7.38 (m, 2H), 7.23-7.15 (m, 2H), 4.75 (sep, 1H, J = 6.7 Hz), 4.48 (s, 2H), 4.50 (d, 1H, J = 14.4 Hz), 3.84 (d, 1H, J = 14.4 Hz), 3.62-3.48 (br m, 8H), 1.98 (s, 3H), 1.18 (d, 3H, J = 6.7 Hz), 1.16 (d, 3H, J = 6.7 Hz). |
| 204 | (structure) | HCl | ¹H-NMR (DMSO-d$_6$) δ: 12.95 (br s, 1H), 8.68-8.61 (m, 1H), 7.45-7.38 (m, 2H), 7.22-7.15 (m, 2H), 4.69 (sep, 1H, J = 6.7 Hz), 4.48 (s, 2H), 4.23-4.15 (br m, 1H), 4.11 (d, 1H, J = 13.9 Hz), 3.76 (d, 1H, J = 13.9 Hz), 3.69-3.59 (br m, 1H), 3.46-3.36 (br m, 2H), 3.30-2.88 (br m, 1H), 2.09-2.00 (m, 3H), 2.02-1.55 (br m, 2H), 1.21-1.06 (m, 6H). |

TABLE 1-56-continued

| No. | structural formula | salt | ¹H-NMR |
|---|---|---|---|
| 205 | | HCl | ¹H-NMR (DMSO-d₆) δ: 12.91 (br s, 1H), 8.71-8.61 (m, 1H), 7.46-7.37 (m, 2H), 7.24-7.14 (m, 2H), 4.69 (sep, 1H, J = 6.7 Hz), 4.48 (s, 2H), 4.33-4.13 (br m, 2H), 4.08 (d, 1H, J = 13.9 Hz), 3.77 (d, 1H, J = 13.9 Hz), 3.51-3.15 (br m, 3H), 2.14-2.01 (m, 3H), 1.89-1.61 (br m, 2H), 1.21-1.02 (m, 6H). |

TABLE 1-57

| No. | structural formula | salt | ¹H-NMR |
|---|---|---|---|
| 206 | | HCl | ¹H-NMR (DMSO-d₆) δ: 8.87 (s, 1H), 7.44-7.38 (m, 2H), 7.23-7.15 (m, 2H), 4.72 (d, 1H, J = 12.3 Hz), 4.47 (s, 2H), 4.43-4.33 (m, 2H), 3.67-3.58 (m, 1H), 3.57-3.51 (m, 1H), 3.47-3.40 (m, 1H), 3.22 (s, 3H), 1.34 (d, 3H, J = 6.7 Hz), 1.31-1.21 (m, 1H), 0.68-0.59 (m, 1H), 0.54-0.46 (m, 1H), 0.44-0.36 (m, 1H), 0.32-0.24 (m, 1H). |
| 207 | | HCl | ¹H-NMR (DMSO-d₆) δ: 13.31 (br s, 1H), 8.48 (s, 1H), 7.59-7.49 (m, 1H), 7.38-7.22 (m, 1H), 7.20-7.05 (m, 1H), 4.78-4.73 (m, 1H), 4.48 (s, 2H), 4.02-3.86 (m, 1H), 3.80 (d, 1H, J = 13.7 Hz), 3.71 (d, 1H, J = 13.7 Hz), 3.47-3.32 (m, 1H), 2.85 (s, 3H), 2.17-2.04 (m, 2H), 1.71 (s, 3H), 1.23 (d, 3H, J = 7.0 Hz), 1.17 (d, 3H, J = 7.0 Hz), 0.65 (t, 3H, J = 7.4 Hz). |
| 208 | | HCl | ¹H-NMR (DMSO-d₆) δ: 12.93 (br s, 1H), 8.72 (s, 1H), 7.45-7.38 (m, 2H), 7.23-7.15 (m, 2H), 4.69 (sep, 1H, J = 6.7 Hz), 4.48 (s, 2H), 4.44-4.27 (br m, 2H), 4.11-3.82 (br m, 2H), 4.02 (d, 1H, J = 13.9 Hz), 3.72 (d, 1H, J = 13.9 Hz), 3.64-3.40 (br m, 1H), 1.99 (s, 3H), 1.16 (d, 3H, J = 6.7 Hz), 1.12 (d, 3H, J = 6.7 Hz). |

TABLE 1-58

| No. | structural formula | salt | ¹H-NMR |
|---|---|---|---|
| 209 | | HCl | ¹H-NMR (DMSO-$d_6$) δ: 12.89 (br s, 1H), 8.71 (s, 1H), 7.45-7.38 (m, 2H), 7.22-7.15 (m, 2H), 4.70 (sep, 1H, J = 6.8 Hz), 4.48 (s, 2H), 4.22-3.90 (br m, 4H), 4.00 (d, 1H, J = 13.9 Hz), 3.74-3.57 (br m, 1H), 3.74 (d, 1H, J = 13.9 Hz), 3.14 (s, 3H), 2.00 (s, 3H), 1.19-1.09 (m, 6H). |
| 210 | | HCl | ¹H-NMR (DMSO-$d_6$) δ: 13.30 (s, 1H), 8.60 (s, 1H), 7.56-7.50 (m, 1H), 7.35-7.25 (m, 1H), 7.13-7.08 (m, 1H), 4.80-4.74 (m, 1H), 4.47 (s, 2H), 3.75 (s, 2H), 3.48-3.30 (m, 2H), 2.84 (s, 3H), 2.57 (s, 3H), 1.74 (s, 3H), 1.24 (d, 3H, J = 6.7 Hz), 1.15 (d, 3H, J = 6.7 Hz). |
| 211 | | HCl | ¹H-NMR (DMSO-$d_6$) δ: 12.91 (s, 0.5H), 12.86 (s, 0.5H), 8.68 (s, 0.5H), 8.60 (s, 0.5H), 7.42-7.38 (m, 2H), 7.20-7.15 (m, 2H), 4.72-4.65 (m, 1H), 4.47 (s, 2H), 4.16 (d, 0.5H, J = 13.7 Hz), 4.08 (d, 0.5H, J = 13.7 Hz), 4.00-3.98 (m, 0.5H), 3.86-3.84 (m, 0.5H), 3.81-3.74 (m, 2H), 3.51-3.33 (m, 3H), 3.17 (s, 3H), 2.54-2.49 (m, 2H), 2.07 (s, 3H), 1.15 (d, 3H, J = 6.7 Hz). |

TABLE 1-59

| No. | structural formula | salt | ¹H-NMR |
|---|---|---|---|
| 212 | | HCl | ¹H-NMR (DMSO-$d_6$) δ: 12.94 (s, 1H), 8.66 (s, 0.5H), 8.62 (s, 0.5H), 7.42-7.38 (m, 2H), 7.20-7.15 (m, 2H), 4.70-4.65 (m, 1H), 4.47 (s, 2H), 4.11-4.06 (m, 1H), 3.93-3.90 (m, 1H), 3.87-3.84 (m, 1H), 3.81-3.75 (m, 1H), 3.69-3.65 (m, 1H), 3.62-3.45 (m, 1H), 3.17 (s, 1.5H), 3.15 (s, 1.5H), 3.10-3.06 (m, 1H), 2.07 (s, 1.5H), 2.05 (s, 1.5H), 1.99-1.96 (m, 1H), 1.79-1.76 (m, 1H), 1.16 (d, 3H, J = 6.7 Hz), 1.06 (d, 3H, J = 6.7 Hz). |
| 213 | | HCl | ¹H-NMR (DMSO-$d_6$) δ: 12.77 (br s, 1H), 8.55 (s, 0.5H), 8.48 (s, 0.5H), 7.67 (s, 1H), 7.34-7.29 (m, 2H), 7.17-7.11 (m, 2H), 4.71-4.65 (m, 1H), 4.25-4.04 (m, 1H), 4.20 (s, 2H), 3.98-3.86 (m, 0.5H), 3.85-3.84 (m, 0.5H), 3.78-3.68 (m, 2H), 3.50-3.25 (m, 2H), 3.17 (s, 1.5H), 3.15 (s, 1.5H), 2.54-2.49 (m, 1H), 2.02 (s, 3H), 1.91-1.85 (m, 1H), 1.78-1.71 (m, 1H), 1.15 (d, 3H, J = 6.7 Hz), 1.05 (d, 3H, J = 6.7 Hz). |

TABLE 1-59-continued

| No. | structural formula | salt | ¹H-NMR |
|---|---|---|---|
| 214 | | HCl | ¹H-NMR (DMSO-d₆) δ: 12.84 (br s, 1H), 8.54 (s, 0.5H), 8.50 (s, 0.5H), 7.68 (s, 1H), 7.34-7.31 (m, 2H), 7.17-7.11 (m, 2H), 4.71-4.65 (m, 1H), 4.20 (s, 2H), 4.07 (dd, 1H, J = 13.9, 5.3 Hz), 3.90-3.85 (m, 1H), 3.75 (dd, 1H, J = 13.9, 7.4 Hz), 3.59-3.36 (m, 3H), 3.15 (s, 3H), 2.54-2.49 (m, 1H), 2.02 (s, 1.5H), 1.99 (s, 1.5H), 1.99-1.97 (m, 1H), 1.78-1.71 (m, 1H), 1.16 (d, 3H, J = 6.7 Hz), 1.08 (d, 3H, J = 6.7 Hz). |

TABLE 1-60

| No. | structural formula | salt | ¹H-NMR |
|---|---|---|---|
| 215 | | HCl | ¹H-NMR (DMSO-d₆) δ: 13.20 (br s, 1H), 8.44 (s, 1H), 7.67 (s, 1H), 7.35-7.31 (m, 2H), 7.16-7.11 (m, 2H), 4.81-4.74 (m, 1H), 4.19 (s, 2H), 3.79-3.65 (m, 3H), 3.57 (d, 1H, J = 14.4 Hz), 2.74 (s, 3H), 1.81 (s, 3H), 1.66 (s, 3H), 1.21 (d, 3H, J = 6.7 Hz), 1.15 (d, 3H, J = 6.7 Hz). |
| 216 | | HCl | ¹H-NMR (DMSO-d₆) δ: 12.60 (br s, 1H), 8.63 (s, 1H), 7.66 (s, 1H), 7.35-7.30 (m, 2H), 7.17-7.11 (m, 2H), 4.89-4.85 (m, 1H), 4.19 (s, 2H), 4.08 (dd, 1H, J = 13.7, 4.2 Hz), 3.81 (d, 1H, J = 13.7 Hz), 3.57 (dd, 1H, J = 10.5, 5.7 Hz), 3.66 (dd, 1H, J = 10.5, 7.9 Hz), 3.56-3.39 (m, 3H), 3.33-3.27 (m, 3H), 3.10 (s, 3H), 1.10-1.04 (m, 1H), 0.55-0.46 (m, 2H), 0.36-026 (m, 2H). |
| 217 | | HCl | ¹H-NMR (DMSO-d₆) δ: 12.30 (br s, 1H), 8.65 (s, 1H), 7.66 (s, 1H), 7.34-7.30 (m, 2H), 7.16-7.11 (m, 2H), 4.60 (d, 1H, J = 13.2 Hz), 4.42 (dd, 1H, J = 13.2, 3.9 Hz), 4.24-4.19 (m, 1H), 4.19 (s, 2H), 3.67 (dd, 1H, J = 14.2, 7.0 Hz), 3.55 (dd, 1H, J = 10.3, 4.8 Hz), 3.47 (dd, 1H, J = 10.3, 7.0 Hz), 3.20 (s, 3H), 3.19 (dd, 1H, J = 14.2, 7.4 Hz), 1.18-1.12 (m, 1H), 0.55-0.46 (m, 2H), 0.41-0.37 (m, 1H), 0.31-0.28 (m, 1H). |

TABLE 1-61

| No. | structural formula | salt | ¹H-NMR |
|---|---|---|---|
| 218 | | HCl | ¹H-NMR (DMSO-$d_6$) δ: 12.30 (br s, 1H), 8.65 (s, 1H), 7.66 (s, 1H), 7.34-7.31 (m, 2H), 7.16-7.11 (m, 2H), 4.61 (d, 1H, J = 13.5 Hz), 4.42 (dd, 1H, J = 13.5, 4.2 Hz), 4.24-4.19 (m, 1H), 4.19 (s, 2H), 3.67 (dd, 1H, J = 14.0, 7.1 Hz), 3.60 (dd, 1H, J = 10.3, 4.2 Hz), 3.52 (dd, 1H, J = 10.3, 6.4 Hz), 3.42-3.30 (m, 2H), 3.20 (dd, 1H, J = 14.0, 7.0 Hz), 1.16-1.11 (m, 1H), 0.95 (t, 3H, J = 7.0 Hz), 0.56-0.46 (m, 2H), 0.41-0.37 (m, 1H), 0.31-0.27 (m, 1H). |
| 219 | | HCl | ¹H-NMR (DMSO-$d_6$) δ: 12.79 (br s, 1H), 8.78 (s, 1H), 7.35 (dd, 1H, J = 8.4, 7.0 Hz), 6.93 (dd, 1H, J = 11.4, 2.6 Hz), 6.74 (td, 1H, J = 8.4, 2.6 Hz), 4.97-4.93 (m, 1H), 4.79-4.72, (m, 1H), 4.33 (s, 2H), 4.06 (q, 2H, J = 7.0 Hz), 3.79-3.65 (m, 2H), 3.61 (dd, 1H, J = 10.3, 5.7 Hz), 3.55 (dd, 1H, J = 10.3, 7.7 Hz), 3.23 (s, 3H), 1.31 (t, 3H, J = 7.0 Hz), 1.15 (d, 3H, J = 2.3 Hz), 1.14 (d, 3H, J = 2.3 Hz). |
| 220 | | HCl | ¹H-NMR (DMSO-$d_6$) δ: 12.80 (s, 1H), 8.76 (s, 1H), 6.93-6.87 (m, 2H), 4.97-4.93 (m, 1H), 4.79-4.72 (m, 1H), 4.33 (s, 2H), 3.85 (s, 3H), 3.84-3.72 (m, 2H), 3.61 (dd, 1H, J = 10.3, 5.7 Hz), 3.55 (dd, 1H, J = 10.3, 7.8 Hz), 3.23 (s, 3H), 1.15 (d, 3H, J = 2.3 Hz), 1.14 (d, 3H, J = 2.3 Hz). |

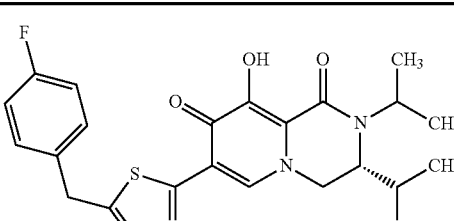

TABLE 1-62

| No. | structural formula | salt | ¹H-NMR |
|---|---|---|---|
| 221 | | HCl | ¹H-NMR (DMSO-$d_6$) δ: 12.50 (br s, 1H), 9.02 (s, 1H), 7.43-7.39 (m, 2H), 7.21-7.16 (m, 2H), 4.76 (d, 1H, J = 13.3 Hz), 4.47 (s, 2H), 4.30 (dd, 1H, J = 13.3, 4.6 Hz), 4.21-4.14 (m, 1H), 3.83 (br t, 1H, J = 4.6 Hz), 2.04-1.99 (m, 1H), 1.39 (d, 3H, J = 6.9 Hz), 1.35 (d, 3H, J = 6.9 Hz), 1.05 (d, 3H, J = 6.9 Hz), 0.64 (d, 3H, J = 6.9 Hz). |
| 222 | | HCl | ¹H-NMR (DMSO-$d_6$) δ: 12.30 (br s, 1H), 8.65 (s, 1H), 7.67 (s, 1H), 7.35-7.31 (m, 2H), 7.18-7.13 (m, 2H), 4.59, (br d, 1H, J = 13.3 Hz), 4.41 (dd, 1H, J = 13.3, 4.1 Hz), 4.20 (s, 2H), 4.12-4.09 (m, 1H), 3.89-3.84 (m, 1H), 3.58-3.50 (m, 2H), 3.41-3.34 (m, 2H), 3.29-3.24 (m, 1H), 1.20 (t, 3H, J = 7.2 Hz), 0.97 (t, 3H, J = 7.0 Hz). |

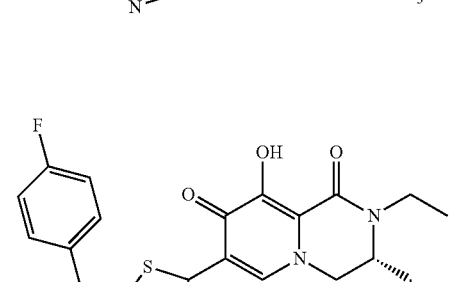

TABLE 1-62-continued

| No. | structural formula | salt | ¹H-NMR |
|---|---|---|---|
| 223 | | HCl | ¹H-NMR (DMS-d₆) δ: 12.80 (m, 1H), 8.59 (s, 1H), 7.69 (s, 1H), 7.34-7.30 (m, 2H), 7.17-7.11 (m, 2H), 4.72-4.65 (m, 1H), 4.20 (s, 2H), 4.20-4.13 (m, 1H), 4.00 (d, 1H, J = 13.5 Hz), 3.86-3.80 (m, 2H), 3.75-3.66 (m, 2H), 2.12-2.03 (m, 2H), 1.93 (s, 3H), 1.14 (d, 3H, J = 6.7 Hz), 1.12 (d, 3H, J = 6.7 Hz). |
| 224 | | HCl | ¹H-NMR (DMSO-d₆) δ: 12.55 (br s, 1H), 9.02 (s, 1H), 7.43-7.39 (m, 2H), 7.21-7.16 (m, 2H), 4.76 (d, 1H, J = 13.3 Hz), 4.47 (s, 2H), 4.30 (dd, 1H, J = 13.3, 4.6 Hz), 4.21-4.14 (m, 1H), 3.83 (br t, 1H, J = 4.6 Hz), 2.04-1.99 (m, 1H), 1.39 (d, 3H, J = 6.9 Hz), 1.35 (d, 3H, J = 6.9 Hz), 1.05 (d, 3H, J = 6.9 Hz), 0.64 (d, 3H, J = 6.9 Hz). |

TABLE 1-63

| No. | structural formula | salt | ¹H-NMR |
|---|---|---|---|
| 225 | | HCl | ¹H-NMR (DMSO-d₆) δ: 12.78 (s, 1H), 8.52 (s, 1H), 7.67 (s, 1H), 7.34-7.30 (m, 2H), 7.16-7.12 (m, 2H), 4.72-4.66 (m, 1H), 4.19 (s, 2H), 4.11 (d, 1H, J = 13.9 Hz), 3.74 (d, 1H, J = 13.9 Hz), 3.41-3.25 (m, 1H), 3.13-3.06 (m, 1H), 3.81-3.74 (m, 2H), 2.00 (s, 3H), 1.92-1.84 (m, 1H), 1.75-1.61 (m, 3H), 1.15 (d, 3H, J = 6.7 Hz), 1.07 (d, 3H, J = 6.7 Hz). |
| 226 | | HCl | ¹H-NMR (DMSO-d₆) δ: 12.81 (br s, 1H), 8.51 (s, 1H), 8.20 (br t, 1H, J = 5.5 Hz), 7.67 (s, 1H), 7.34-7.30 (m, 2H), 7.16-7.11 (m, 2H), 4.73-4.66 (m, 1H), 4.20 (s, 2H), 4.11 (d, 1H, J = 13.7 Hz), 3.77 (d, 1H, J = 13.7 Hz), 3.13-2.99 (m, 2H), 1.92 (s, 3H), 1.14 (d, 3H, J = 6.7 Hz), 1.10 (d, 3H, J = 6.7 Hz), 0.99 (t, 3H, J = 7.2 Hz). |

TABLE 1-63-continued

| No. | structural formula | salt | ¹H-NMR |
|---|---|---|---|
| 227 | | HCl | ¹H-NMR (DMSO-$d_6$) δ: 12.80 (br s, 1H), 8.54 (s, 1H), 8.22 (d, 1H, J = 4.4 Hz), 7.69 (s, 1H), 7.34-7.30 (m, 2H), 7.16-7.12 (m, 2H), 4.73-4.66 (m, 1H), 4.20 (s, 2H), 4.13 (d, 1H, J = 13.7 Hz), 3.78 (d, 1H, J = 13.7 Hz), 2.57 (d, 3H, J = 4.4 Hz), 1.93 (s, 3H), 1.13 (d, 3H, J = 7.0 Hz), 1.08 (d, 3H, J = 7.0 Hz). |

TABLE 1-64

| No. | structural formula | salt | ¹H-NMR |
|---|---|---|---|
| 228 | | HCl | ¹H-NMR (DMSO-$d_6$) δ: 12.85 (br s, 1H), 8.81 (s, 1H), 7.48-7.46 (m, 1H), 7.42-7.33 (m, 3H), 4.98-4.96 (m, 1H), 4.80-4.73 (m, 1H), 4.50 (s, 2H), 3.84 (dd, 1H, J = 13.8, 4.1 Hz), 3.75 (br d, 1H, J = 13.8 Hz), 3.63 (dd, 1H, J = 10.4, 5.7 Hz), 3.57 (dd, 1H, J = 10.4, 7.5 Hz), 3.25 (s, 3H), 1.17 (d, 3H, J = 2.0 Hz), 1.15 (d, 3H, J = 2.0 Hz). |
| 229 | | HCl | ¹H-NMR (DMSO-$d_6$) δ: 12.83 (br s, 1H), 8.80 (s, 1H), 7.51 (t, 1H, J = 8.3 Hz), 7.48 (dd, 1H, J = 8.3, 2.0 Hz), 7.32 (dd, 1H, J = 8.3, 2.0 Hz), 5.00-4.95 (m, 1H), 4.80-4.74 (m, 1H), 4.50 (s, 2H), 3.84 (dd, 1H, J = 13.7, 4.0 Hz), 3.75 (dd, 1H, J = 13.7, 1.6 Hz), 3.62 (dd, 1H, J = 10.3, 5.8 Hz), 3.57 (dd, 1H, J = 10.3, 7.7 Hz), 3.25 (s, 3H), 1.17 (d, 3H, J = 2.0 Hz), 1.15 (d, 3H, J = 2.0 Hz). |
| 230 | | HCl | ¹H-NMR (DMSO-$d_6$) δ: 12.83 (br s, 1H), 8.79 (s, 1H), 7.66 (dd, 1H, J = 8.7, 2.6 Hz), 7.61 (dd, 1H, J = 8.7, 6.0 Hz), 7.32 (td, 1H, J = 8.7, 2.6 Hz), 4.99-4.95 (m, 1H), 4.80-4.74 (m, 1H), 4.57 (s, 2H), 3.84 (dd, 1H, J = 13.7, 4.0 Hz), 3.75 (dd, 1H, J = 13.7, 1.6 Hz), 3.62 (dd, 1H, J = 10.3, 5.8 Hz), 3.57 (dd, 1H, J = 10.3, 7.7 Hz), 3.25 (s, 3H), 1.17 (d, 3H, J = 2.0 Hz), 1.15 (d, 3H, J = 2.0 Hz). |

TABLE 1-65

| No. | structural formula | salt | ¹H-NMR |
|---|---|---|---|
| 231 | | HCl | ¹H-NMR (DMSO-d$_6$) δ: 12.80 (br s, 1H), 8.79 (s, 1H), 7.37 (dd, 1H, J = 8.5, 6.1 Hz), 7.10-7.01 (m, 2H), 4.99-4.95 (m, 1H), 4.80-4.74 (m, 1H), 4.45 (s, 2H), 3.84 (dd, 1H, J = 13.7, 4.1 Hz), 3.75 (br d, 1H, J = 13.7 Hz), 3.62 (dd, 1H, J = 10.4, 5.7 Hz), 3.57 (dd, 1H, J = 10.4, 7.6 Hz), 3.25 (s, 3H), 2.29 (s, 3H), 1.17 (d, 3H, J = 2.0 Hz), 1.15 (d, 3H, J = 2.0 Hz). |
| 232 | | HCl | ¹H-NMR (DMSO-d$_6$) δ: 12.75 (br s, 1H), 8.56 (s, 1H), 7.42-7.38 (m, 2H), 7.20-7.16 (m, 2H), 4.66-4.64 (m, 1H), 4.47 (s, 2H), 4.45-4.40 (m, 1H), 4.08-4.05 (m, 1H), 3.56 (dd, 1H, J = 11.3, 3.2 Hz), 3.50 (dd, 1H, J = 11.3, 4.2 Hz), 3.11 (s, 3H), 1.75 (d, 3H, J = 6.5 Hz), 1.33 (d, 3H, J = 6.0 Hz), 1.32 (d, 3H, J = 6.0 Hz). |
| 233 | | HCl | ¹H-NMR (DMSO-d$_6$) δ: 12.54 (br s, 1H), 8.85 (s, 1H), 7.44-7.38 (m, 2H), 7.22-7.15 (m, 2H), 4.62-4.53 (m, 1H), 4.51-4.44 (m, 3H), 4.32 (dd, 1H, J = 13.1, 3.4 Hz), 4.26-4.18 (m, 1H), 1.27 (d, 3H, J = 6.7 Hz), 1.26 (d, 3H, J = 6.7 Hz), 1.21 (d, 3H, J = 6.5 Hz). |
| 234 | | HCl | ¹H-NMR (DMSO-d$_6$) δ: 12.85 (s, 1H), 8.43 (s, 1H), 7.69 (s, 1H), 7.37-7.29 (m, 2H), 7.19-7.11 (m, 2H), 4.73 (sep, 1H, J = 6.7 Hz), 4.21 (s, 2H), 4.12 (d, 1H, J = 14.1 Hz), 3.79 (d, 1H, J = 14.1 Hz), 2.93 (s, 6H), 1.98 (s, 3H), 1.17 (d, 3H, J = 6.7 Hz), 1.11 (d, 3H, J = 6.7 Hz). |

TABLE 1-66

| No. | structural formula | salt | ¹H-NMR |
|---|---|---|---|
| 235 | | HCl | ¹H-NMR (DMSO-d$_6$) δ: 12.89 (br s, 1H), 8.46 (s, 1H), 7.69 (s, 1H), 7.34-7.31 (m, 2H), 7.16-7.12 (m, 2H), 4.74-4.68 (m, 1H), 4.20 (s, 2H), 4.15 (d, 1H, J = 14.2 Hz), 3.78 (d, 1H, J = 14.2 Hz), 3.60-3.53 (m, 1H), 3.40 (br t, 2H, J = 5.2 Hz), 3.36-3.28 (m, 1H), 3.18 (s, 3H), 2.95 (br s, 3H), 1.97 (s, 3H), 1.17 (d, 3H, J = 6.7 Hz), 1.12 (d, 3H, J = 6.7 Hz). |

TABLE 1-66-continued

| No. | structural formula | salt | ¹H-NMR |
|---|---|---|---|
| 236 | | HCl | ¹H-NMR (DMSO-d$_6$) δ: 12.80 (m, 1H), 8.59 (s, 1H), 7.69 (s, 1H), 7.34-7.30 (m, 2H), 7.17-7.11 (m, 2H), 4.72-4.65 (m, 1H), 4.20 (s, 2H), 4.20-4.13 (m, 1H), 4.00 (d, 1H, J = 13.5 Hz), 3.86-3.80 (m, 2H), 3.75-3.66 (m, 2H), 2.12-2.03 (m, 2H), 1.93 (s, 3H), 1.14 (d, 3H, J = 6.7 Hz), 1.12 (d, 3H, J = 6.7 Hz). |
| 237 | | HCl | ¹H-NMR (DMSO-d$_6$) δ: 12.77 (br s, 1H), 8.55 (s, 1H), 7.69 (s, 1H), 7.34-7.30 (m, 2H), 7.17-7.11 (m, 2H), 4.72-4.66 (m, 1H), 4.20 (s, 2H), 4.17-3.96 (m, 4H), 3.73-3.53 (m, 3H), 3.12 (s, 3H), 2.95 (s, 3H), 1.18-1.07 (m, 6H). |
| 238 | | HCl | ¹H-NMR (DMSO-d$_6$) δ: 12.80 (br s, 1H), 8.58-8.53 (m, 1H), 7.69-7.68 (m, 1H), 7.34-7.30 (m, 2H), 7.16-7.12 (m, 2H), 4.72-4.66 (m, 2H), 4.20 (s, 2H), 3.99-3.84 (m, 2H), 3.78-3.67 (m, 1H), 3.60-3.47 (m, 2H), 3.36-3.33 (m, 2H), 3.27-3.25 (m, 1H), 3.28-3.16 (m, 3H), 1.93 (s, 3H), 1.15-1.10 (m, 6H). |

TABLE 1-67

| No. | structural formula | salt | ¹H-NMR |
|---|---|---|---|
| 239 | | HCl | ¹H-NMR (DMSO-d$_6$) δ: 12.81 (br s, 1H), 8.51 (s, 1H), 8.20 (br t, 1H, J = 5.5 Hz), 7.67 (s, 1H), 7.34-7.30 (m, 2H), 7.18-7.11 (m, 2H), 4.73-4.66 (m, 1H), 4.20 (s, 2H), 4.11 (d, 1H, J = 13.7 Hz), 3.77 (d, 1H, J = 13.7 Hz), 3.13-2.99 (m, 2H), 1.92 (s, 3H), 1.14 (d, 3H, J = 6.7 Hz), 1.10 (d, 3H, J = 6.7 Hz), 0.99 (t, 3H, J = 7.2 Hz). |

TABLE 1-67-continued

| No. | structural formula | salt | ¹H-NMR |
|---|---|---|---|
| 240 | | HCl | ¹H-NMR (DMSO-d₆) δ: 12.80 (br s, 1H), 8.80 (s, 1H), 7.29 (d, 2H, J = 8.9 Hz), 6.92 (d, 2H, J = 8.9 Hz), 4.99-4.94 (m, 1H), 4.80-4.73 (m, 1H), 4.39 (s, 2H), 3.84 (dd, 1H, J = 13.7, 4.0 Hz), 3.75 (d, 1H, J = 13.7 Hz), 3.74 (s, 3H), 3.62 (dd, 1H, J = 10.3, 5.8 Hz), 3.57 (dd, 1H, J = 10.3, 7.7 Hz), 3.25 (s, 3H), 1.17 (d, 3H, J = 2.4 Hz), 1.15 (d, 3H, J = 2.4 Hz). |
| 241 | | HCl | ¹H-NMR (DMSO-d₆) δ: 12.80 (br s, 1H), 8.80 (s, 1H), 7.32 (dd, 2H, J = 8.5, 5.6 Hz), 7.11 (t, 2H, J = 8.5 Hz), 4.98-4.94 (m, 1H), 4.81-4.74 (m, 1H), 3.84 (dd, 1H, J = 13.9. 3.8 Hz), 3.76 (d, 1H, J = 13.9 Hz), 3.63 (dd, 1H, J = 10.3, 5.8 Hz), 3.57 (dd, 1H, J = 10.3, 7.5 Hz), 3.41 (t, 2H, J = 7.7 Hz), 3.26 (s, 3H), 3.09 (t, 2H, J = 7.7 Hz), 1.17 (d, 3H, J = 1.6 Hz), 1.15 (d, 3H, J = 1.6 Hz). |

TABLE 1-68

| No. | structural formula | salt | ¹H-NMR |
|---|---|---|---|
| 242 | | HCl | ¹H-NMR (DMSO-d₆) δ: 12.81 (br s, 1H), 8.81 (s, 1H), 7.28 (dd, 2H, J = 8.5, 5.6 Hz), 7.11 (t, 2H, J = 8.5 Hz), 4.98-4.94 (m, 1H), 4.81-4.74 (m, 1H), 3.85 (dd, 1H, J = 13.9, 4.0 Hz), 3.76 (dd, 1H, J = 13.9, 1.4 Hz), 3.63 (dd, 1H, J = 10.3, 5.8 Hz), 3.58 (dd, 1H, J = 10.3, 7.7 Hz), 3.26 (s, 3H), 3.10 (t, 2H, J = 7.7 Hz), 2.68 (t, 2H, J = 7.7 Hz), 2.09-2.01 (m, 2H), 1.18 (d, 3H, J = 2.0 Hz), 1.16 (d, 3H, J = 2.0 Hz). |
| 243 | | HCl | ¹H-NMR (DMSO-d₆) δ: 12.83 (br s, 1H), 8.81 (s, 1H), 7.65-7.63 (m, 1H), 7.41-7.39 (m, 2H), 5.00-4.95 (m, 1H), 4.80-4.74 (m, 1H), 4.50 (s, 2H), 3.84 (dd, 1H, J = 13.7, 4.0 Hz), 3.76 (dd, 1H, J = 13.7, 1.6 Hz), 3.63 (dd, 1H, J = 10.1, 5.6 Hz), 3.57 (dd, 1H, J = 10.1, 7.7 Hz), 3.25 (s, 3H), 1.17 (d, 3H, J = 2.0 Hz), 1.15 (d, 3H, J = 2.0 Hz). |
| 244 | | HCl | ¹H-NMR (DMSO-d₆) δ: 12.83 (br s, 1H), 8.81 (s, 1H), 7.73 (d, 2H, J = 8.1 Hz), 7.60 (d, 2H, J = 8.1 Hz), 4.99-4.94 (m, 1H), 4.80-4.73 (m, 1H), 4.61 (s, 2H), 3.84 (dd, 1H, J = 13.7, 4.0 Hz), 3.76 (dd, 1H, J = 13.7, 1.6 Hz), 3.63 (dd, 1H, J = 10.1, 5.6 Hz), 3.57 (dd, 1H, J = 10.1, 7.7 Hz), 3.25 (s, 3H), 1.17 (d, 3H, J = 2.0 Hz), 1.15 (d, 3H, J = 2.0 Hz). |

TABLE 1-69

| No. | structural formula | salt | ¹H-NMR |
|---|---|---|---|
| 245 | | HCl | ¹H-NMR (DMSO-$d_6$) δ: 12.79 (br s, 1H), 8.48 (s, 1H), 8.34-8.33 (m, 1H), 7.67 (s, 1H), 7.34-7.30 (m, 2H), 7.16-7.12 (m, 2H), 4.73-4.67 (m, 1H), 4.20 (s, 2H), 4.06 (d, 1H, J = 13.7 Hz), 3.78 (d, 1H, J = 13.7 Hz), 3.61-3.44 (m, 1H), 1.90 (s, 3H), 1.13 (d, 3H, J = 6.7 Hz), 1.09 (d, 3H, J = 6.7 Hz), 0.62 (d, 2H, J = 7.4 Hz), 0.46-0.41 (m, 2H). |
| 246 | | HCl | ¹H-NMR (DMSO-$d_6$) δ: 12.82 (br s, 1H), 8.51 (s, 1H), 8.28 (t, 1H, J = 5.5 Hz), 7.67 (s, 1H), 7.33-7.30 (m, 2H), 7.16-7.11 (m, 2H), 4.73-4.66 (m, 1H), 4.20 (s, 2H), 4.15 (d, 1H, J = 13.9 Hz), 3.78 (d, 1H, J = 13.9 Hz), 2.98-2.84 (m, 2H), 1.93 (s, 3H), 1.14 (d, 3H, J = 7.2 Hz), 1.12 (d, 3H, J = 7.2 Hz), 0.89-0.85 (m, 1H), 0.40-0.37 (m, 2H), 0.14-0.10 (m, 2H). |
| 247 | | HCl | ¹H-NMR (DMSO-$d_6$) δ: 12.70 (br s, 1H), 8.51 (s, 1H), 7.71 (s, 1H), 7.34-7.30 (m, 2H), 7.18-7.12 (m, 2H), 4.64-4.62 (m, 1H), 4.45-4.49 (m, 1H), 4.21 (s, 2H), 4.06-4.02 (m, 1H), 3.53 (dd, 1H, J = 11.1, 3.4 Hz), 3.48 (dd, 1H, J = 11.1, 4.2 Hz), 3.11 (s, 3H), 1.72 (d, 3H, J = 6.5 Hz), 1.33 (d, 3H, J = 5.6 Hz), 1.31 (d, 3H, J = 5.6 Hz). |
| 248 | | HCl | ¹H-NMR (DMSO-$d_6$) δ: 12.77 (br s, 1H), 8.44 (s, 1H), 7.68 (s, 1H), 7.37-7.29 (m, 2H), 7.16-7.11 (m, 2H), 4.20 (s, 2H), 4.19 (d, 1H, J = 14.1 Hz), 3.93 (d, 1H, J = 14.1 Hz), 3.56-3.44 (m, 2H), 2.90 (s, 6H), 1.94 (s, 3H), 1.10 (s, 3H, J = 7.2 Hz). |

TABLE 1-70

| No. | structural formula | salt | ¹H-NMR |
|---|---|---|---|
| 249 | | HCl | ¹H-NMR (DMSO-$d_6$) δ: 12.68 (br s, 1H), 8.50 (s, 1H), 8.20 (br t, 1H, J = 5.1 Hz), 7.67 (s, 1H), 7.33-7.30 (m, 2H), 7.16-7.11 (m, 2H), 4.20 (s, 2H), 4.09 (d, 1H, J = 13.7 Hz), 3.97 (d, 1H, J = 13.7 Hz), 3.64-3.55 (m, 1H), 3.38-3.32 (m, 1H), 3.11-3.04 (m, 2H), 1.88 (s, 3H), 1.10 (s, 3H, J = 7.2 Hz), 0.98 (s, 3H, J = 7.2 Hz). |

TABLE 1-70-continued

| No. | structural formula | salt | ¹H-NMR |
|---|---|---|---|
| 250 | | HCl | ¹H-NMR (DMSO-$d_6$) δ: 12.79 (br s, 1H), 8.81 (s, 1H), 7.23-7.16 (m, 2H), 6.94-6.90 (m, 1H), 4.99-4.95 (m, 1H), 4.80-4.74 (m, 1H), 4.45 (s, 2H), 3.86-3.83 (m, 1H), 3.83 (s, 3H), 3.76 (dd, 1H, J = 13.9, 1.4 Hz), 3.63 (dd, 1H, J = 10.3, 5.8 Hz), 3.57 (dd, 1H, J = 10.3, 7.7 Hz), 3.25 (s, 3H), 1.17 (d, 3H, J = 2.0 Hz), 1.15 (d, 3H, J = 2.0 Hz). |
| 251 | | HCl | ¹H-NMR (DMSO-$d_6$) δ: 12.80 (br s, 1H), 8.79 (s, 1H), 7.38 (dd, 1H, J = 8.5, 6.5 Hz), 7.02 (td, 1H, 8.5, 2.8 Hz), 6.81 (dd, 1H, J = 8.5, 2.8 Hz), 4.98-4.94 (m, 1H), 4.78-4.64 (m, 1H), 4.60 (s, 2H), 3.83 (dd, 1H, J = 13.7, 4.0 Hz), 3.75 (dd, 1H, J = 13.7, 1.4 Hz), 3.62 (dd, 1H, J = 10.3, 5.8 Hz), 3.57 (dd, 1H, J = 10.3, 7.7 Hz), 3.25 (s, 3H), 2.06-1.99 (m, 1H), 1.17 (d, 3H, J = 2.0 Hz), 1.15 (d, 3H, J = 2.0 Hz), 0.90-0.84 (m, 2H), 0.66-0.63 (m, 2H). |

TABLE 1-71

| No. | structural formula | salt | ¹H-NMR |
|---|---|---|---|
| 252 | | HCl | ¹H-NMR (DMSO-$d_6$) δ: 12.40 (br s, 1H), 8.52 (s, 1H), 8.09-8.05 (m, 1H), 7.65 (s, 1H), 7.34-7.29 (m, 2H), 7.16-7.10 (m, 2H), 4.67 (d, 1H, J = 13.5 Hz), 4.37 (d, 1H, J = 13.5 Hz), 4.19 (s, 2H), 3.76-3.68 (m, 1H), 3.38-3.29 (m, 1H), 2.54 (d, 3H, J = 4.4 Hz), 1.65 (s, 3H), 1.51 (t, 3H, J = 7.1 Hz). |
| 253 | | HCl | ¹H-NMR (DMSO-$d_6$) δ: 12.40 (br s, 1H), 8.68 (s, 1H), 7.66 (s, 1H), 7.34-7.30 (m, 2H), 7.16-7.11 (m, 2H), 4.86 (d, 1H, J = 14.1 Hz), 4.46 (d, 1H, J = 14.1 Hz), 4.19 (s, 2H), 3.78-3.69 (m, 1H), 3.18-3.09 (m, 1H), 2.99 (br s, 6H), 1.71 (s, 3H), 1.19 (t, 3H, J = 7.1 Hz). |
| 254 | | HCl | ¹H-NMR (DMSO-$d_6$) δ: 12.42 (br s, 1H), 8.69 (s, 1H), 7.65 (s, 1H), 7.34-7.29 (m, 2H), 7.16-7.11 (m, 2H), 4.86 (d, 1H, J = 13.9 Hz), 4.46 (d, 1H, J = 13.9 Hz), 4.30-4.03 (m, 1H), 4.19 (s, 2H), 3.78-3.68 (m, 2H), 3.46-3.17 (m, 3H), 1.98-1.78 (m, 4H), 1.73 (s, 3H), 1.17 (t, 3H, J = 7.1 Hz). |

TABLE 1-71-continued

| No. | structural formula | salt | ¹H-NMR |
|---|---|---|---|
| 255 | | HCl | ¹H-NMR (DMSO-d$_6$) δ: 12.70 (br s, 1H), 8.61 (s, 1H), 7.70 (s, 1H), 7.35-7.32 (m, 2H), 7.17-7.13 (m, 2H), 4.21 (s, 2H), 4.21-4.17 (m, 1H), 4.11 (d, 1H, J = 13.7 Hz), 3.96 (d, 1H, J = 13.7 Hz), 3.89-3.82 (m, 2H), 3.78-3.73 (m, 1H), 3.46 (dd, 1H, J = 13.9, 6.9 Hz), 3.25 (dd, 1H, J = 13.9, 7.5 Hz), 2.14-2.06 (m, 2H), 1.94 (s, 3H), 1.09-1.03 (m, 1H), 0.52-0.49 (m, 2H), 0.34-0.31 (m, 2H). |

TABLE 1-72

| No. | structural formula | salt | ¹H-NMR |
|---|---|---|---|
| 256 | | HCl | ¹H-NMR (DMSO-d$_6$) δ: 12.77 (br s, 1H), 8.78 (s, 1H), 7.42-7.39 (m, 2H), 7.20-7.16 (m, 2H), 4.72-4.70 (m, 1H), 4.60-4.53 (m, 1H), 4.47 (s, 2H), 4.18-4.10 (m, 2H), 3.94 (dd, 1H, J = 11.9, 2.2 Hz), 3.46 (s, 3H), 1.29 (d, 3H, J = 6.9 Hz), 1.27 (d, 3H, J = 6.9 Hz), 1.05 (d, 3H, J = 6.5 Hz). |
| 257 | | HCl | ¹H-NMR (DMSO-d$_6$) δ: 12.76 (br s, 1H), 8.62 (s, 1H), 7.42-7.38 (m, 2H), 7.20-7.16 (m, 2H), 4.77-4.74 (m, 1H), 4.47 (s, 2H), 4.19 (q, 1H, J = 4.0 Hz), 3.71 (dd, 1H, J = 14.1, 7.3 Hz), 3.62 (d, 2H, J = 4.4 Hz), 3.23 (dd, 1H, J = 14.1, 6.9 Hz), 3.16 (s, 3H), 1.69 (d, 3H, J = 6.9 Hz), 1.22-1.16 (m, 1H), 0.58-0.48 (m, 2H), 0.44-0.39 (m, 1H), 0.34-0.29 (m, 1H). |
| 258 | | HCl | ¹H-NMR (DMSO-d$_6$) δ: 12.82 (br s, 1H), 8.72 (s, 1H), 7.43-7.39 (m, 2H), 7.21-7.16 (m, 2H), 4.84-4.79 (m, 1H), 4.47 (s, 2H), 4.26-4.21 (m, 1H), 3.89-3.76 (m, 3H), 3.33 (s, 3H), 3.33-3.26 (m, 1H), 1.24 (d, 3H, J = 6.9 Hz), 1.17 (t, 3H, J = 7.3 Hz). |
| 259 | | HCl | ¹H-NMR (DMSO-d$_6$) δ: 12.78 (br s, 1H), 8.74 (s, 1H), 7.43-7.38 (m, 2H), 7.21-7.16 (m, 2H), 4.85-4.81 (m, 1H), 4.47 (s, 2H), 4.30-4.24 (m, 1H), 3.93 (dd, 1H, J = 11.5, 8.5 Hz), 3.85 (dd, 1H, J = 11.5, 3.0 Hz), 3.56 (dd, 1H, J = 14.1, 7.5 Hz), 3.37 (s, 3H), 3.30 (dd, 1H, J = 14.1, 6.9 Hz), 1.24 (d, 3H, J = 6.9 Hz), 1.15-1.09 (m, 1H), 0.58-0.48 (m, 2H), 0.41-0.30 (m, 2H). |

TABLE 1-73

| No. | structural formula | salt | ¹H-NMR |
|---|---|---|---|
| 260 | | HCl | ¹H-NMR (DMSO-$d_6$) δ: 12.67 (br s, 1H), 8.53 (s, 1H), 7.69 (s, 1H), 7.33-7.29 (m, 2H), 7.17-7.11 (m, 2H), 4.73-4.67 (m, 1H), 4.19 (s, 2H), 4.10 (q, 1H, J = 4.1 Hz), 3.90-3.83 (m, 1H), 3.56 (d, 2H, J = 4.6 Hz), 3.33-3.32 (m, 1H), 3.16 (s, 3H), 1.61 (d, 3H, J = 6.5 Hz), 1.20 (t, 3H, J = 7.1 Hz). |
| 261 | | HCl | ¹H-NMR (DMSO-$d_6$) δ: 12.69 (br s, 1H), 8.59 (s, 1H), 7.67 (s, 1H), 7.34-7.30 (m, 2H), 7.16-7.11 (m, 2H), 4.79-4.75 (m, 1H), 4.22-4.19 (m, 1H), 4.19 (s, 2H), 3.85-3.73 (m, 3H), 3.31 (s, 3H), 3.31-3.24 (m, 1H), 1.22 (d, 3H, J = 6.7 Hz), 1.15 (t, 3H, J = 7.1 Hz). |
| 262 | | HCl | ¹H-NMR (DMSO-$d_6$) δ: 12.71 (br s, 1H), 8.60 (s, 1H), 7.70 (s, 1H), 7.35-7.31 (m, 2H), 7.16-7.12 (m, 2H), 4.41-4.38 (m, 1H), 4.20 (s, 2H), 4.10-4.02 (m, 4H), 3.98 (d, 1H, J = 13.7 Hz), 3.68-3.59 (m, 1H), 3.43-3.35 (m, 1H), 3.32-3.26 (m, 1H), 3.13 (s, 3H), 1.94 (s, 3H), 1.07-1.00 (m, 1H), 0.53-0.45 (m, 2H), 0.34-0.28 (m, 2H). |
| 263 | | HCl | ¹H-NMR (DMSO-$d_6$) δ: 12.69 (br s, 1H), 8.60 (s, 1H), 7.69 (s, 1H), 7.34-7.31 (m, 2H), 7.14 (br t, 2H, J = 8.8 Hz), 4.39-4.36 (m, 1H), 4.20 (s, 2H), 4.11-3.90 (m, 5H), 3.69-3.65 (m, 1H), 3.57-3.40 (m, 2H), 3.12 (s, 3H), 1.92 (s, 3H), 1.09 (t, 3H, J = 6.6 Hz). |

TABLE 1-74

| No. | structural formula | salt | ¹H-NMR |
|---|---|---|---|
| 264 | | HCl | ¹H-NMR (DMSO-$d_6$) δ: 12.75 (s, 1H), 8.41 (s, 1H), 7.68 (s, 1H), 7.32 (dd, 2H, J = 8.2, 5.9 Hz), 7.16-7.13 (m, 2H), 4.19 (s, 2H), 4.18 (d, 1H, J = 13.9 Hz), 3.90 (d, 1H, J = 13.9 Hz), 3.05 (s, 3H), 2.88 (s, 6H), 1.91 (s, 3H). |

TABLE 1-74-continued

| No. | structural formula | salt | ¹H-NMR |
|---|---|---|---|
| 265 | | HCl | ¹H-NMR (DMSO-d₆) δ: 12.75 (s, 1H), 8.40 (s, 1H), 7.67 (s, 1H), 7.35-7.29 (m, 2H), 7.16-7.11 (m, 2H), 4.19 (s, 2H), 4.17 (d, 1H, J = 13.9 Hz), 3.89 (d, 1H, J = 13.9 Hz), 3.43-3.35 (m, 1H), 3.28-3.19 (m, 1H), 3.05 (s, 3H), 2.83 (s, 3H), 1.89 (s, 3H), 0.98 (t, 3H, J = 7.1 Hz). |
| 266 | | HCl | ¹H-NMR (DMSO-d₆) δ: 12.66 (br s, 1H), 8.62 (s, 1H), 7.70 (s, 1H), 7.34-7.31 (m, 2H), 7.16-7.12 (m, 2H), 4.20 (s, 2H), 4.18-4.11 (m, 1H), 4.04-3.97 (m, 1H), 3.91-3.82 (m, 2H), 3.28-3.19 (m, 1H), 3.64-3.57 (m, 1H), 3.03 (s, 3H), 2.09-2.03 (m, 2H), 1.90 (s, 3H). |
| 267 | | HCl | ¹H-NMR (DMSO-d₆) δ: 12.73 (br s, 1H), 8.50 (s, 1H), 8.18 (br t, 1H, J = 5.6 Hz), 7.67 (s, 1H), 7.34-7.29 (m, 2H), 7.17-7.11 (m, 2H), 4.20 (s, 2H), 3.99 (d, 1H, J = 13.7 Hz), 3.93 (d, 1H, J = 13.7 Hz), 3.08-3.01 (m, 2H), 2.87-2.84 (m, 1H), 1.87 (s, 3H), 0.96 (t, 3H, J = 7.2 Hz), 0.94-0.89 (m, 1H), 0.81-0.69 (m, 2H), 0.62-0.56 (m, 1H). |

TABLE 1-75

| No. | structural formula | salt | ¹H-NMR |
|---|---|---|---|
| 268 | | HCl | ¹H-NMR (DMSO-d₆) δ: 12.70 (br s, 1H), 8.61 (s, 1H), 7.69 (s, 1H), 7.34-7.30 (m, 2H), 7.16-7.11 (m, 2H), 4.20 (s, 2H), 4.07-4.01 (m, 1H), 3.92 (d, 1H, J = 13.2 Hz), 3.87-3.82 (m, 2H), 3.80 (d, 1H, J = 13.2 Hz), 3.50-3.42 (m, 1H), 2.89-2.84 (m, 1H), 208-2.00 (m, 2H), 1.89 (s, 3H), 0.91-0.85 (m, 1H), 0.82-0.73 (m, 2H), 0.67-0.61 (m, 1H). |
| 269 | | HCl | ¹H-NMR (DMSO-d₆) δ: 13.18 (br s, 1H), 8.67 (s, 1H), 7.42-7.38 (m, 2H), 7.20-7.14 (m, 2H), 4.46 (s, 2H), 3.83 (d, 1H, J = 13.7 Hz), 3.74 (d, 1H, J = 13.7 Hz), 3.64 (d, 1H, J = 11.8 Hz), 3.62 (d, 1H, J = 11.8 Hz). 3.60-3.44 (m, 3H), 1.59 (s, 3H), 1.15 (t, 3H, J = 7.2 Hz). |

TABLE 1-75-continued

| No. | structural formula | salt | ¹H-NMR |
|---|---|---|---|
| 270 | (structure) | HCl | ¹H-NMR (DMSO-d₆) δ: 12.69 (br s, 1H), 8.75 (s, 1H), 7.41-7.38 (m, 2H), 7.20-7.15 (m, 2H), 4.53 (d, 1H, J = 13.7 Hz), 4.46 (s, 2H), 4.30 (d, 1H, J = 13.7 Hz), 3.68-3.59 (m, 1H), 3.51 (d, 1H, J = 10.4 Hz), 3.48-3.43 (m, 2H), 3.20 (s, 3H), 1.35 (s, 3H), 1.19 (t, 3H, J = 7.1 Hz). |
| 271 | (structure) | HCl | ¹H-NMR (DMSO-d₆) δ: 12.69 (br s, 1H), 8.61 (s, 1H), 7.69 (s, 1H), 7.34-7.31 (m, 2H), 7.16-7.12 (m, 2H), 4.20 (s, 2H), 4.17-4.15 (m, 1H), 4.02 (d, 1H, J = 13.5 Hz), 4.00-3.87 (m, 2H), 3.89 (d, 1H, J = 13.5 Hz), 3.65-3.63 (m, 1H), 3.54-3.44 (m, 2H), 2.10-2.06 (m, 2H), 1.91 (s, 3H), 1.10 (t, 3H, J = 7.1 Hz). |

TABLE 1-76

| No. | structural formula | salt | ¹H-NMR |
|---|---|---|---|
| 272 | (structure) | HCl | ¹H-NMR (DMSO-d₆) δ: 12.65 (br s, 1H), 8.66 (s, 1H), 7.64 (s, 1H), 7.47-7.41 (m, 1H), 7.24 (dt, 1H, J = 14.0, 5.0 Hz), 7.06 (td, 1H, J = 8.5, 2.3 Hz), 5.10-5.03 (m, 1H), 4.80-4.73 (m, 1H), 4.20 (s, 2H), 4.18-4.04 (m, 2H), 3.98-3.85 (m, 1H), 3.87-3.71 (m, 3H), 3.61-3.53 (m, 1H), 3.15 (s, 1.5H), 3.08 (s, 1.5H), 2.66-2.58 (m, 2H), 1.15-1.11 (m, 6H). |
| 273 | (structure) | HCl | ¹H-NMR (DMSO-d₆) δ: 12.83 (br s, 1H), 8.59 (s, 1H), 7.70 (s, 1H), 7.35-7.32 (m, 2H), 7.17-7.13 (m, 2H), 4.21 (s, 2H), 4.21-4.17 (m, 1H), 4.14 (d, 1H, J = 13.7 Hz), 3.93-3.76 (m, 5H), 2.16-2.08 (m, 2H), 1.97 (s, 3H), 1.24 (d, 3H, J = 6.8 Hz), 1.13-1.10 (m, 1H), 0.64-0.58 (m, 1H), 0.43-0.38 (m, 2H), 0.20-0.15 (m, 1H). |
| 274 | (structure) | HCl | ¹H-NMR (DMSO-d₆) δ: 12.81 (br s, 1H), 8.58 (s, 1H), 7.70 (s, 1H), 7.35-7.32 (m, 2H), 7.17-7.13 (m, 2H), 4.21 (s, 2H), 4.21-4.14 (m, 3H), 4.06-4.00 (m, 1H), 3.87-3.64 (m, 4H), 3.15 (s, 3H), 1.98 (s, 3H), 1.24 (d, 3H, J = 6.6 Hz), 1.13-1.09 (m, 1H), 0.61-0.57 (m, 1H), 0.49-0.36 (m, 2H), 0.15-0.07 (m, 1H). |

TABLE 1-77

| No. | structural formula | salt | ¹H-NMR |
|---|---|---|---|
| 275 | (structure) | HCl | ¹H-NMR (DMSO-d$_6$) δ: 12.84 (br s, 1H), 8.48 (s, 1H), 7.69 (s, 1H), 7.35-7.32 (m, 2H), 7.17-7.13 (m, 2H), 4.31 (d, 1H, J = 14.3 Hz), 4.21 (s, 2H), 3.93 (d, 1H, J = 14.3 Hz), 3.83-3.75 (m, 1H), 2.98 (br s, 6H), 2.05 (s, 3H), 1.25 (d, 3H, J = 6.8 Hz), 1.10-1.03 (m, 1H), 0.64-0.58 (m, 1H), 0.42-0.33 (m, 2H), 0.12-0.08 (m, 1H). |
| 276 | (structure) | HCl | ¹H-NMR (DMSO-d$_6$) δ: 12.86 (br s, 1H), 8.52 (s, 1H), 8.21 (t, 1H, J = 5.4 Hz), 7.69 (s, 1H), 7.36-7.31 (m, 2H), 7.18-7.13 (m, 2H), 4.29 (d, 1H, J = 13.7 Hz), 4.21 (s, 2H), 3.87 (d, 1H, J = 13.7 Hz), 3.81-3.73 (m, 1H), 3.20-3.14 (m, 1H), 3.02-2.96 (m, 1H), 1.94 (s, 3H), 1.24 (d, 3H, J = 6.8 Hz), 1.13-1.07 (m, 1H), 1.01 (t, 3H, J = 7.2 Hz), 0.62-0.57 (m, 1H), 0.37-0.31 (m, 2H), 0.18-0.12 (m, 1H). |
| 277 | (structure) | HCl | ¹H-NMR (DMSO-d$_6$) δ: 12.82 (br s, 1H), 8.80 (s, 1H), 7.38-7.32 (m, 2H), 4.99-4.97 (m, 1H), 4.80-4.74 (m, 1H), 4.46 (s, 2H), 3.84 (dd, 1H, J = 13.5, 4.2 Hz), 3.83 (s, 3H), 3.75 (dd, 1H, J = 13.5, 1.2 Hz), 3.63 (dd, 1H, J = 10.3, 5.8 Hz), 3.57 (dd, 1H, J = 10.3, 7.7 Hz), 3.25 (s, 3H), 1.17 (d, 3H, J = 2.0 Hz), 1.15 (d, 3H, J = 2.0 Hz). |

TABLE 1-78

| No. | structural formula | salt | ¹H-NMR |
|---|---|---|---|
| 278 | (structure) | HCl | ¹H-NMR (DMSO-d$_6$) δ: 12.45 (br s, 1H), 8.98 (s, 1H), 7.43-7.38 (m, 2H), 7.21-7.16 (m, 2H), 4.71-4.67 (m, 1H), 4.56-4.49 (m, 1H), 4.47 (s, 2H), 4.30-4.25 (m, 1H), 3.93-3.90 (m, 1H), 1.65-1.61 (m, 1H), 1.46-1.38 (m, 1H), 1.29 (d, 3H, J = 2.4 Hz), 1.27 (d, 3H, J = 2.0 Hz), 0.92 (t, 3H, J = 7.5 Hz). |
| 279 | (structure) | HCl | ¹H-NMR (DMSO-d$_6$) δ: 12.60 (br s, 1H), 8.84 (s, 1H), 7.43-7.38 (m, 2H), 7.20-7.15 (m, 2H), 4.50-4.46 (m, 1H), 4.46 (s, 2H), 4.41 (dd, 1H, J = 13.1, 3.6 Hz), 420-4.17 (m, 1H), 3.57 (dd, 1H, J = 14.0, 7.1 Hz), 3.22 (dd, 1H, J = 14.0, 7.0 Hz), 1.24 (d, 3H, J = 6.5 Hz), 1.14-1.10 (m, 1H), 0.56-0.47 (m, 2H), 0.39-0.36 (m, 1H), 0.33-0.29 (m, 1H). |

TABLE 1-78-continued

| No. | structural formula | salt | ¹H-NMR |
|---|---|---|---|
| 280 | (structure) | HCl | ¹H-NMR (DMSO-$d_6$) δ: 12.75 (br s, 1H), 8.61 (s, 1H), 7.70 (s, 1H), 7.35-7.32 (m, 2H), 7.18-7.13 (m, 2H), 4.21 (s, 2H), 4.21-4.13 (m, 2H), 3.86-3.73 (m, 5H), 2.14-2.06 (m, 2H), 1.96 (s, 3H), 1.20 (d, 3H, J = 6.6 Hz), 1.15-1.07 (m, 1H), 0.64-0.58 (m, 1H), 0.45-0.38 (m, 2H), 0.23-0.20 (m, 1H). |
| 281 | (structure) | HCl | ¹H-NMR (DMSO-$d_6$) δ: 12.74 (br s, 1H), 8.60 (s, 1H), 7.70 (s, 1H), 7.36-7.32 (m, 2H), 7.17-7.13 (m, 2H), 4.21 (s, 2H), 4.15-4.04 (m, 4H), 3.89-3.78 (m, 2H), 3.68-3.58 (m, 2H), 3.15 (s, 1.5H), 3.14 (s, 1.5H), 1.98 (s, 3H), 1.19-1.11 (m, 4H), 0.61-0.57 (m, 1H), 0.49-0.38 (m, 2H), 0.22-0.19 (m, 1H). |

TABLE 1-79

| No. | structural formula | salt | ¹H-NMR |
|---|---|---|---|
| 282 | (structure) | HCl | ¹H-NMR (DMSO-$d_6$) δ: 12.84 (br s, 1H), 8.42 (s, 1H), 7.69 (s, 1H), 7.35-7.32 (m, 2H), 7.18-7.12 (m, 2H), 4.24 (d, 1H, J = 14.3 Hz), 4.21 (s, 2H), 3.93 (d, 1H, J = 14.3 Hz), 3.89-3.81 (m, 1H), 2.94 (br s, 6H), 1.99 (s, 3H), 1.19 (d, 3H, J = 6.6 Hz), 1.15-1.09 (m, 1H), 0.63-0.58 (m, 1H), 0.48-0.39 (m, 2H), 0.26-0.22 (m, 1H). |
| 283 | (structure) | HCl | ¹H-NMR (DMSO-$d_6$) δ: 12.77 (br s, 1H), 8.53 (s, 1H), 8.25 (t, 1H, J = 5.4 Hz), 7.69 (s, 1H), 7.35-7.32 (m, 2H), 7.17-7.13 (m, 2H), 4.29 (d, 1H, J = 13.9 Hz), 4.21 (s, 2H), 3.92 (d, 1H, J = 13.9 Hz), 3.89-3.83 (m, 1H), 3.16-3.02 (m, 2H), 1.95 (s, 3H), 1.18 (d, 3H, J = 6.8 Hz), 1.03-1.01 (m, 1H), 1.01 (t, 3H, J = 7.2 Hz), 0.62-0.58 (m, 1H), 0.47-0.39 (m, 2H), 0.24-0.19 (m, 1H). |
| 284 | (structure) | HCl | ¹H-NMR (DMSO-$d_6$) δ: 12.66 (br s, 1H), 8.82 (s, 1H), 7.43-7.39 (m, 2H), 7.21-7.16 (m, 2H), 4.83 (br t, 1H, J = 6.6 Hz), 4.48 (s, 2H), 4.04 (q, 1H, J = 6.2 Hz), 3.95-3.86 (m, 1H), 3.64 (dd, 1H, J = 10.4, 5.3 Hz), 3.53 (dd, 1H, J = 10.4, 7.9 Hz), 3.24 (s, 3H), 3.16-3.07 (m, 1H), 1.26 (d, 3H, J = 6.6 Hz), 1.16 (t, 3H, J = 7.1 Hz). |

TABLE 1-80

| No. | structural formula | salt | ¹H-NMR |
|---|---|---|---|
| 285 | 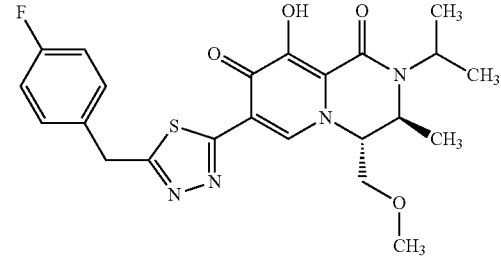 [SMILES: COC[C@H]1[C@H](C)N(C(C)C)C(=O)c2c(O)c(=O)c(-c3nnc(Cc4ccc(F)cc4)s3)cn21] | HCl | ¹H-NMR (DMSO-$d_6$) δ: 12.67 (br s, 1H), 8.82 (s, 1H), 7.43-7.39 (m, 2H), 7.22-7.15 (m, 2H), 4.82 (br t, 1H, J = 6.0 Hz), 4.65-4.58 (m, 1H), 4.48 (s, 2H), 4.16 (q, 1H, J = 6.5 Hz), 3.60 (dd, 1H, J = 10.3, 5.4 Hz), 3.49 (dd, 1H, J = 10.3, 7.9 Hz), 3.24 (s, 3H), 1.27 (d, 3H, J = 2.0 Hz), 1.26 (d, 3H, J = 2.0 Hz), 1.21 (t, 3H, J = 6.8 Hz). |
| 286 | 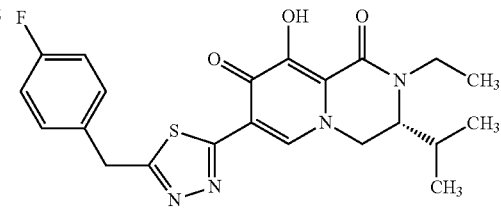 | HCl | ¹H-NMR (DMSO-$d_6$) δ: 12.53 (br s, 1H), 9.01 (s, 1H), 7.43-7.38 (m, 2H), 7.21-7.15 (m, 2H), 4.75 (d, 1H, J = 13.8 Hz), 4.47 (s, 2H), 4.34 (dd, 1H, J = 13.8, 4.3 Hz), 4.01 (td, 1H, J = 13.8, 6.9 Hz), 3.74 (br t, 1H, J = 5.0 Hz), 3.74 (td, 1H, J = 13.8, 6.9 Hz), 1.92 (td, 1H, J = 13.8, 6.9 Hz), 1.20 (t, 3H, J = 6.9 Hz), 0.99 (d, 3H, J = 6.9 Hz), 0.79 (d, 3H, J = 6.9 Hz). |
| 287 | 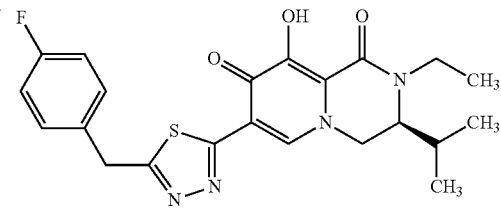 [SMILES: CCN1C(=O)c2c(O)c(=O)c(-c3nnc(Cc4ccc(F)cc4)s3)cn2C[C@@H]1C(C)C] | HCl | ¹H-NMR (DMSO-$d_6$) δ: 12.53 (br s, 1H), 9.01 (s, 1H), 7.43-7.38 (m, 2H), 7.21-7.15 (m, 2H), 4.75 (d, 1H, J = 13.8 Hz), 4.47 (s, 2H), 4.34 (dd, 1H, J = 13.8, 4.3 Hz), 4.01 (td, 1H, J = 13.8, 6.9 Hz), 3.74 (br t, 1H, J = 5.0 Hz), 3.74 (td, 1H, J = 13.8, 6.9 Hz), 1.92 (td, 1H, J = 13.8, 6.9 Hz), 1.20 (t, 3H, J = 6.9 Hz), 0.99 (d, 3H, J = 6.9 Hz), 0.79 (d, 3H, J = 6.9 Hz). |

TABLE 1-81

| No. | structural formula | salt | ¹H-NMR |
|---|---|---|---|
| 288 | 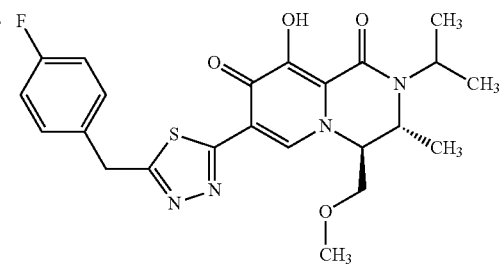 | HCl | ¹H-NMR (DMSO-$d_6$) δ: 12.67 (br s, 1H), 8.82 (s, 1H), 7.43-7.39 (m, 2H), 722-7.15 (m, 2H), 4.82 (br t, 1H, J = 6.0 Hz), 4.65-4.58 (m, 1H), 4.48 (s, 2H), 4.16 (q, 1H, J = 6.5 Hz), 3.60 (dd, 1H, J = 10.3, 5.4 Hz), 3.49 (dd, 1H, J = 10.3, 7.9 Hz), 3.24 (s, 3H), 1.27 (d, 3H, J = 2.0 Hz), 1.26 (d, 3H, J = 2.0 Hz), 1.21 (t, 3H, J = 6.8 Hz). |
| 289 | 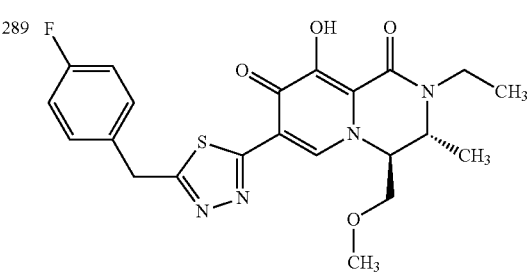 | HCl | ¹H-NMR (DMSO-$d_6$) δ: 12.66 (br s, 1H), 8.82 (s, 1H), 7.43-7.39 (m, 2H), 721-7.16 (m, 2H), 4.83 (br t, 1H, J = 6.6 Hz), 4.48 (s, 2H), 4.04 (q, 1H, J = 6.2 Hz), 3.95-3.86 (m, 1H), 3.64 (dd, 1H, J = 10.4, 5.3 Hz), 3.53 (dd, 1H, J = 10.4, 7.9 Hz), 3.24 (s, 3H), 3.16-3.07 (m, 1H), 1.26 (d, 3H, J = 6.6 Hz), 1.16 (t, 3H, J = 7.1 Hz). |

TABLE 1-81-continued

| No. | structural formula | salt | ¹H-NMR |
|---|---|---|---|
| 290 | (structure) | HCl | ¹H-NMR (DMSO-d₆) δ: 1286 (br s, 1H), 8.56 (s, 1H), 7.70 (s, 1H), 7.37-7.31 (m, 2H), 7.19-7.12 (m, 2H), 4.73-4.66 (m, 1H), 4.21 (s, 2H), 4.19-4.07 (m, 2H), 3.86-3.70 (m, 6H), 2.03 (s, 3H), 1.17 (d, 3H, J = 6.5 Hz), 1.10 (d, 3H, J = 6.5 Hz). |
| 291 | (structure) | HCl | ¹H-NMR (DMSO-d₆) δ: 12.53 (br s, 1H), 8.96 (s, 1H), 7.43-7.38 (m, 2H), 7.21-7.16 (m, 2H), 4.65 (d, 1H, J = 13.5 Hz), 4.47 (s, 2H), 4.35 (dd, 1H, J = 13.5, 3.8 Hz), 3.92-3.84 (m, 2H), 3.24-3.16 (m, 1H), 1.72-1.66 (m, 1H), 1.51-1.41 (m, 1H), 1.20 (t, 3H, J = 7.3 Hz), 0.92 (t, 3H, J = 7.5 Hz). |

TABLE 1-82

| No. | structural formula | salt | ¹H-NMR |
|---|---|---|---|
| 292 | (structure) | HCl | ¹H-NMR (DMSO-d₆) δ: 12.40 (br s, 1H), 8.52 (s, 1H), 8.09-8.05 (m, 1H), 7.65 (s, 1H), 7.34-7.29 (m, 2H), 7.16-7.10 (m, 2H), 4.67 (d, 1H, J = 13.5 Hz). 4.37 (d, 1H, J = 13.5 Hz), 4.19 (s, 2H), 3.76-3.68 (m, 1H), 3.38-3.29 (m, 1H), 2.54 (d, 3H, J = 4.4 Hz), 1.65 (s, 3H), 1.51 (t, 3H, J = 7.1 Hz). |
| 293 | (structure) | HCl | ¹H-NMR (DMSO-d₆) δ: 12.40 (br s, 1H), 8.68 (s, 1H), 7.66 (s, 1H), 7.34-7.30 (m, 2H), 7.16-7.11 (m, 2H), 4.86 (d, 1H, J = 14.1 Hz), 4.46 (d, 1H, J = 14.1 Hz), 4.19 (s, 2H), 3.78-3.69 (m, 1H), 3.18-3.09 (m, 1H), 2.99 (br s, 6H), 1.71 (s, 3H), 1.19 (t, 3H, J = 7.1 Hz). |
| 294 | (structure) | HCl | ¹H-NMR (DMSO-d₆) δ: 12.42 (br s, 1H), 8.69 (s, 1H), 7.65 (s, 1H), 7.34-7.29 (m, 2H), 7.16-7.11 (m, 2H), 4.86 (d, 1H, J = 13.9 Hz), 4.46 (d, 1H, J = 13.9 Hz), 4.30-4.03 (m, 1H), 4.19 (s, 2H), 3.78-3.68 (m, 2H), 3.46-3.17 (m, 3H), 1.98-1.78 (m, 4H), 1.73 (s, 3H), 1.17 (t, 3H, J = 7.1 Hz). |
| 295 | (structure) | HCl | ¹H-NMR (DMSO-d₆) δ: 12.46 (br s, 1H), 8.84 (s, 1H), 7.43-7.39 (m, 2H), 7.20-7.15 (m, 2H), 4.68 (d, 1H, J = 13.5 Hz), 4.46 (s, 2H), 4.36 (dd, 1H, J = 13.5, 3.7 Hz), 4.08-4.00 (m, 2H), 3.49 (dd, 1H, J = 10.2, 3.9 Hz), 3.41 (dd, 1H, J = 10.2, 7.0 Hz), 3.17 (s, 3H), 1.77-1.59 (m, 4H), 0.90 (t, 3H, J = 7.3 Hz), 0.85 (t, 3H, J = 7.3 Hz). |

TABLE 1-83

| No. | structural formula | salt | ¹H-NMR |
|---|---|---|---|
| 296 | (structure) | HCl | ¹H-NMR (DMSO-d$_6$) δ: 13.19 (br s, 1H), 8.71 (s, 1H), 7.43-7.38 (m, 2H), 7.21-7.16 (m, 2H), 4.47 (s, 2H), 3.86-3.76 (m, 3H), 3.70 (d, 1H, J = 10.4 Hz), 3.63-3.45 (m, 4H), 3.35-3.33 (m, 2H), 3.11 (s, 3H), 1.64 (s, 3H), 1.17 (t, 3H, J = 7.2 Hz). |
| 297 | (structure) | HCl | ¹H-NMR (DMSO-d$_6$) δ: 13.21 (br s, 1H), 8.71 (s, 1H), 7.42-7.38 (m, 2H), 7.21-7.16 (m, 2H), 4.47 (s, 2H), 3.80-3.63 (m, 4H), 3.51-3.44 (m, 2H), 3.35-3.33 (m, 2H), 3.12 (s, 3H), 2.95-2.90 (m, 1H), 1.62 (s, 3H), 0.93-0.76 (m, 4H). |
| 298 | (structure) | HCl | ¹H-NMR (DMSO-d$_6$) δ: 12.51 (br s, 1H), 8.93 (s, 1H), 7.42-7.38 (m, 2H), 7.21-7.16 (m, 2H), 4.91 (q, 1H, J = 6.8 Hz), 4.48 (s, 2H), 4.04-3.95 (m, 2H), 3.52 (dd, 1H, J = 10.3, 5.2 Hz), 3.46 (dd, 1H, J = 10.3, 6.5 Hz), 3.22 (s, 3H), 3.20-3.13 (m, 1H), 1.42 (d, 3H, J = 6.6 Hz), 1.19 (t, 3H, J = 7.1 Hz). |
| 299 | (structure) | HCl | ¹H-NMR (DMSO-d$_6$) δ: 12.48 (br s, 1H), 8.95 (s, 1H), 7.42-7.38 (m, 2H), 7.21-7.16 (m, 2H), 4.95 (q, 1H, J = 6.5 Hz), 4.58-4.51 (m, 1H), 4.48 (s, 2H), 4.07-4.04 (m, 1H), 3.50 (dd, 1H, J = 10.5, 4.1 Hz), 3.36 (dd, 1H, J = 10.5, 7.9 Hz), 3.22 (s, 3H), 1.39 (d, 3H, J = 6.8 Hz), 1.29 (d, 3H, J = 5.0 Hz), 1.27 (d, 3H, J = 5.0 Hz). |

TABLE 1-84

| No. | structural formula | salt | ¹H-NMR |
|---|---|---|---|
| 300 | (structure) | HCl | ¹H-NMR (DMSO-d$_6$) δ: 12.50 (br s, 1H), 8.82 (s, 1H), 7.39 (dd, 1H, J = 15.3, 8.7 Hz), 7.22-7.16 (m, 1H), 7.02 (td, 1H, J = 8.7, 2.4 Hz), 4.63 (d, 1H, J = 13.3 Hz), 4.42 (dd, 1H, J = 13.3, 4.3 Hz), 4.17-4.13 (m, 1H), 3.87 (td, 1H, J = 14.0, 7.1 Hz), 3.56-3.49 (m, 2H), 3.40 (t, 2H, J = 7.5 Hz), 3.32-3.25 (m, 1H), 3.22 (s, 3H), 3.09 (t, 2H, J = 7.5 Hz), 1.21 (t, 3H, J = 7.1 Hz). |

TABLE 1-84-continued

| No. | structural formula | salt | ¹H-NMR |
|---|---|---|---|
| 301 | (structure) | HCl | ¹H-NMR (DMSO-d$_6$) δ: 12.61 (br s, 1H), 8.78 (s, 1H), 7.42-7.39 (m, 2H), 7.20-7.16 (m, 2H), 4.51 (s, 2H), 4.47 (s, 2H), 3.65-3.53 (m, 6H), 3.26 (s, 6H), 1.19 (t, 3H, J = 7.1 Hz). |
| 302 | (structure) | HCl | ¹H-NMR (DMSO-d$_6$) δ: 12.75 (br s, 1H), 8.80 (s, 1H), 7.43-7.38 (m, 2H), 7.21-7.15 (m, 2H), 4.99-4.95 (m, 1H), 4.46 (s, 2H), 3.99-3.84 (m, 3H), 3.63 (dd, 1H, J = 10.3, 5.7 Hz), 3.57 (dd, 1H, J = 10.3, 7.7 Hz), 3.24 (s, 3H), 1.22 (d, 3H, J = 7.0 Hz), 1.08-1.00 (m, 1H), 0.61-0.55 (m, 1H), 0.47-0.36 (m, 2H), 0.23-0.18 (m, 1H). |
| 303 | (structure) | HCl | ¹H-NMR (DMSO-d$_6$) δ: 12.50 (br s, 1H), 8.97 (s, 1H), 7.43-7.39 (m, 2H), 7.21-7.16 (m, 2H), 4.69 (d, 1H, J = 13.3 Hz), 4.48 (s, 2H), 4.38 (dd, 1H, J = 13.3, 3.4 Hz), 3.95-3.93 (m, 1H), 3.69 (dd, 1H, J = 13.9, 7.1 Hz), 3.16 (dd, 1H, J = 13.9 7.2 Hz), 1.79-1.72 (m, 1H), 1.48-1.40 (m, 1H), 1.19-1.12 (m, 1H), 0.93 (t, 3H, J = 7.4 Hz), 0.55-0.48 (m, 2H), 0.42-0.37 (m, 1H), 0.34-0.30 (m, 1H). |

TABLE 1-85

| No. | structural formula | salt | ¹H-NMR |
|---|---|---|---|
| 304 | (structure) | HCl | ¹H-NMR (DMSO-d$_6$) δ: 12.48 (br s, 1H), 8.95 (s, 1H), 7.42-7.38 (m, 2H), 7.21-7.16 (m, 2H), 4.95 (q, 1H, J = 6.5 Hz), 4.58-4.51 (m, 1H), 4.48 (s, 2H), 4.07-4.04 (m, 1H), 3.50 (dd, 1H, J = 10.5, 4.1 Hz), 3.36 (dd, 1H, J = 10.5, 7.9 Hz), 3.22 (s, 3H), 1.39 (d, 3H, J = 6.8 Hz), 1.29 (d, 3H, J = 5.0 Hz), 1.27 (d, 3H, J = 5.0 Hz). |
| 305 | (structure) | HCl | ¹H-NMR (DMSO-d$_6$) δ: 12.51 (br s, 1H), 8.93 (s, 1H), 7.42-7.38 (m, 2H), 7.21-7.16 (m, 2H), 4.91 (q, 1H, J = 6.8 Hz), 4.48 (s, 2H), 4.04-3.95 (m, 2H), 3.52 (dd, 1H, J = 10.3, 5.2 Hz), 3.46 (dd, 1H, J = 10.3, 6.5 Hz), 3.22 (s, 3H), 3.20-3.13 (m, 1H), 1.42 (d, 3H, J = 6.6 Hz), 1.19 (t, 3H, J = 7.1 Hz). |
| 306 | (structure) | HCl | ¹H-NMR (DMSO-d$_6$) δ: 12.70 (br s, 1H), 8.86 (s, 1H), 7.44-7.38 (m, 2H), 7.22-7.15 (m, 2H), 4.80 (d, 1H, J = 14.0 Hz), 4.49 (d, 1H, J = 14.0 Hz), 4.47 (s, 2H), 4.11-3.06 (m, 4H), 3.60 (sep, 1H, J = 6.6 Hz), 2.06-1.63 (m, 4H), 1.73 (s, 3H), 1.46 (d, 3H, J = 6.6 Hz), 1.43 (d, 3H, J = 6.6 Hz). |

TABLE 1-85-continued

| No. | structural formula | salt | ¹H-NMR |
|---|---|---|---|
| 307 |  | HCl | ¹H-NMR (DMSO-d₆) δ: 12.65 (br s, 1H), 8.74 (s, 1H), 8.31 (t, 1H, J = 5.5 Hz), 7.44-7.38 (m, 2H), 7.22-7.15 (m, 2H), 4.58 (d, 1H, J = 13.5 Hz), 4.48 (d, 1H, J = 13.5 Hz), 4.47 (s, 2H), 3.53 (sep, 1H, J = 6.6 Hz), 3.20-3.09 (m, 2H), 1.58 (s, 3H), 1.48 (d, 3H, J = 6.6 Hz), 1.41 (d, 3H, J = 6.6 Hz), 1.01 (t, 3H, J = 7.2 Hz). |

TABLE 1-86

| No. | structural formula | salt | ¹H-NMR |
|---|---|---|---|
| 308 | | HCl | ¹H-NMR (DMSO-d₆) δ: 12.68 (br s, 1H), 8.74 (s, 1H), 8.11 (d, 1H, J = 7.7 Hz), 7.45-7.38 (m, 2H), 7.22-7.15 (m, 2H), 4.61 (d, 1H, J = 14.0 Hz), 4.49 (d, 1H, J = 14.0 Hz), 4.47 (s, 2H), 3.91 (sep, 1H, J = 6.6 Hz), 3.48 (sep, 1H, J = 6.6 Hz), 1.55 (s, 3H), 1.51 (d, 3H, J = 6.6 Hz), 1.41 (d, 3H, J = 6.6 Hz), 1.09 (d, 3H, J = 6.6 Hz), 1.06 (d, 3H, J = 6.6 Hz). |
| 309 | | HCl | ¹H-NMR (DMSO-d₆) δ: 12.75 (br s, 1H), 8.75 (s, 1H), 7.77 (s, 1H), 7.44-7.37 (m, 2H), 7.22-7.15 (m, 2H), 4.67 (d, 1H, J = 13.5 Hz), 4.49 (d, 1H, J = 13.5 Hz), 4.47 (s, 2H), 3.40 (sep, 1H, J = 6.7 Hz), 1.54 (d, 3H, J = 6.7 Hz), 1.50 (s, 3H), 1.41 (d, 3H, J = 6.7 Hz), 1.29 (s, 9H). |
| 310 | | HCl | ¹H-NMR (DMSO-d₆) δ: 12.66 (br s, 1H), 8.85 (s, 1H), 7.44-7.38 (m, 2H), 7.22-7.15 (m, 2H), 4.68-3.76 (m, 4H), 4.64 (d, 1H, J = 13.9 Hz), 4.47 (s, 2H), 4.46 (d, 1H, J = 13.9 Hz), 3.69 (sep, 1H, J = 6.7 Hz), 2.28-2.15 (m, 2H), 1.66 (s, 3H), 1.44 (d, 3H, J = 6.7 Hz), 1.43 (d, 3H, J = 6.7 Hz). |
| 311 | | HCl | ¹H-NMR (DMSO-d₆) δ: 12.67 (br s, 1H), 8.81 (s, 1H), 7.45-7.38 (m, 2H), 7.22-7.15 (m, 2H), 4.71 (d, 1H, J = 14.0 Hz), 4.58 (d, 1H, J = 14.0 Hz), 4.47 (s, 2H), 3.75-3.40 (m, 9H), 1.66 (s, 3H), 1.53 (d, 3H, J = 6.6 Hz), 1.42 (d, 3H, J = 6.6 Hz). |

TABLE 1-87

| No. | structural formula | salt | $^1$H-NMR |
|---|---|---|---|
| 312 | (structure) | HCl | $^1$H-NMR (DMSO-$d_6$) δ: 13.99 (br s, 1H), 12.50 (br s, 1H), 8.83 (s, 1H), 7.45-7.37 (m, 2H), 7.23-7.13 (m, 2H), 4.78 (d, 1H, J = 14.0 Hz), 4.49 (d, 1H, J = 14.0 Hz), 4.47 (s, 2H), 3.85 (sep, 1H, J = 6.8 Hz), 1.66 (s, 3H), 1.49 (d, 3H, J = 6.8 Hz), 1.45 (d, 3H, J = 6.8 Hz). |
| 313 | (structure) | HCl | $^1$H-NMR (DMSO-$d_6$) δ: 12.88 (br s, 1H), 8.55 (s, 1H), 7.45-7.38 (m, 2H), 7.22-7.15 (m, 2H), 4.48 (s, 2H), 4.21 (d, 1H, J = 14.0 Hz), 3.96 (d, 1H, J = 14.0 Hz), 3.07 (s, 3H), 2.91 (s, 6H), 1.98 (s, 3H). |
| 314 | (structure) | HCl | $^1$H-NMR (DMSO-$d_6$) δ: 12.75 (br s, 1H), 8.42 (s, 1H), 7.69 (s, 1H), 7.36-7.30 (m, 2H), 7.18-7.11 (m, 2H), 4.21 (s, 2H), 4.20 (d, 1H, J = 13.9 Hz), 3.91 (d, 1H, J = 13.9 Hz), 3.07 (s, 3H), 2.89 (s, 6H), 1.92 (s, 3H). |
| 315 | (structure) | HCl | $^1$H-NMR (DMSO-$d_6$) δ: 12.70 (br s, 1H), 8.84 (s, 1H), 7.44-7.38 (m, 2H), 7.22-7.16 (m, 2H), 4.80 (d, 1H, J = 13.9 Hz), 4.53 (d, 1H, J = 13.9 Hz), 4.47 (s, 2H), 3.45 (sep, 1H, J = 6.6 Hz), 3.08 (s, 6H), 1.65 (s, 3H), 1.49 (d, 3H, J = 6.6 Hz), 1.42 (d, 3H, J = 6.6 Hz). |

TABLE 1-88

| No. | structural formula | salt | $^1$H-NMR |
|---|---|---|---|
| 316 | (structure) | HCl | $^1$H-NMR (DMSO-$d_6$) δ: 12.79 (br s, 1H), 8.80 (s, 1H), 7.45-7.39 (m, 2H), 7.23-7.15 (m, 2H), 5.06-4.97 (m, 1H), 4.48 (s, 2H), 3.94-3.91 (m, 2H), 3.90-3.80 (m, 1H), 3.72-3.58 (m, 2H), 3.26 (s, 3H), 1.23 (d, 3H, J = 6.8 Hz), 1.18-1.07 (m, 1H), 0.66-0.57 (m, 1H), 0.50-0.37 (m, 2H), 0.31-0.20 (m, 1H). |

TABLE 1-88-continued

| No. | structural formula | salt | ¹H-NMR |
|-----|---|---|---|
| 317 | | HCl | ¹H-NMR (DMSO-d₆) δ: 12.48 (br s, 1H), 8.84 (s, 1H), 7.44-7.36 (m, 1H), 7.23-7.15 (m, 1H), 7.06-6.98 (m, 1H), 4.66 (dd, 1H, J = 13.6, 1.4 Hz), 4.48 (sep, 1H, J = 6.8 Hz), 4.35 (dd, 1H, J = 13.6, 3.6 Hz), 4.24-4.17 (m, 1H), 3.50 (dd, 1H, J = 10.4, 4.2 Hz), 3.44-3.37 (m, 3H), 3.22 (s, 3H), 3.09 (t, 2H, J = 7.5 Hz), 1.30 (d, 3H, J = 6.8 Hz), 1.29 (d, 3H, J = 6.8 Hz). |
| 318 | | HCl | ¹H-NMR (DMSO-d₆) δ: 12.71 (br s, 1H), 8.76 (s, 1H), 7.44-7.37 (m, 2H), 7.22-7.15 (m, 2H), 4.55 (d, 1H, J = 13.5 Hz), 4.47 (s, 2H), 4.31 (d, 1H, J = 13.5 Hz), 3.71-3.59 (m, 1H), 3.56-3.42 (m, 3H), 3.21 (s, 3H), 1.37 (s, 3H), 1.20 (t, 3H, J = 7.1 Hz). |
| 319 | | HCl | ¹H-NMR (DMSO-d₆) δ: 12.63 (br s, 1H), 8.77 (s, 1H), 7.58-7.48 (m, 1H), 7.33-7.25 (m, 1H), 7.16-7.08 (m, 1H), 4.52 (s, 2H), 4.49 (s, 2H), 3.63 (d, 2H, J = 10.6 Hz), 3.58 (q, 2H, J = 7.1 Hz), 3.54 (d, 2H, J = 10.6 Hz), 3.26 (s, 6H), 1.19 (t, 3H, J = 7.1 Hz). |

TABLE 1-89

| No. | structural formula | salt | ¹H-NMR |
|-----|---|---|---|
| 320 | | HCl | ¹H-NMR (DMSO-d₆) δ: 12.74 (br s, 1H), 8.74 (s, 1H), 7.44-7.37 (m, 2H), 7.22-7.14 (m, 2H), 4.50 (s, 2H), 4.47 (s, 2H), 3.94 (sep, 1H, J = 6.6 Hz), 3.66 (d, 2H, J = 10.6 Hz), 3.51 (d, 2H, J = 10.6 Hz), 3.27 (s, 6H), 1.45 (d, 6H, J = 6.6 Hz). |
| 321 | | HCl | ¹H-NMR (DMSO-d₆) δ: 12.71 (br s, 1H), 8.83 (s, 1H), 7.58-7.50 (m, 1H), 7.33-7.26 (m, 1H), 7.15-7.08 (m, 1H), 4.80 (d, 1H, J = 14.0 Hz), 4.54 (d, 1H, J = 14.0 Hz), 4.49 (s, 2H), 3.45 (sep, 1H, J = 6.7 Hz), 3.07 (s, 3H), 1.65 (s, 3H), 1.49 (d, 3H, J = 6.7 Hz). 1.42 (d, 3H, J = 6.7 Hz). |
| 322 | | HCl | ¹H-NMR (DMSO-d₆) δ: 13.25 (br s, 1H), 8.71 (s, 1H), 7.44-7.38 (m, 2H), 7.22-7.15 (m, 2H), 4.79 (sep, 1H, J = 6.8 Hz), 4.47 (s, 2H), 3.80-3.73 (m, 2H), 3.71-3.64 (m, 2H), 3.55-3.43 (m, 2H), 3.37-3.31 (m, 2H), 3.11 (s, 3H), 1.65 (s, 3H), 1.18 (d, 3H, J = 6.8 Hz), 1.18 (d, 3H, J = 6.8 Hz). |

TABLE 1-89-continued

| No. | structural formula | salt | ¹H-NMR |
|---|---|---|---|
| 323 | | HCl | ¹H-NMR (DMSO-$d_6$) δ: 12.69 (br s, 1H), 8.73 (s, 1H), 7.44-7.38 (m, 2H), 7.23-7.15 (m, 2H), 4.55 (d, 1H, J = 13.5 Hz), 4.47 (s, 2H), 4.31 (d, 1H, J = 13.5 Hz), 3.71-3.46 (m, 4H), 3.46-3.42 (m, 2H), 3.29-3.24 (m, 2H), 3.07 (s, 3H), 1.37 (s, 3H), 1.20 (t, 3H, J = 7.1 Hz). |

TABLE 1-90

| No. | structural formula | salt | ¹H-NMR |
|---|---|---|---|
| 324 | | HCl | ¹H-NMR (DMSO-$d_6$) δ: 12.52 (br s, 1H), 8.91 (s, 1H), 7.44-7.36 (m, 2H), 7.22-7.14 (m, 2H), 4.82 (d, 1H, J = 13.5 Hz), 4.47 (s, 2H), 4.35 (sep, 1H, J = 6.8 Hz), 4.30 (dd, 1H, J = 13.5, 4.5 Hz), 4.01-3.96 (m, 1H), 3.64-3.55 (m, 1H), 3.05 (s, 3H), 1.35 (d, 3H, J = 6.8 Hz), 1.33 (d, 3H, J = 6.8 Hz), 1.19 (d, 3H, J = 6.2 Hz). |
| 325 | | HCl | ¹H-NMR (DMSO-$d_6$) δ: 12.64 (br s, 1H), 8.83 (s, 1H), 7.44-7.35 (m, 1H), 7.23-7.15 (m, 1H), 7.05-6.98 (m, 1H), 4.50-4.37 (m, 2H), 4.16-4.07 (m, 1H), 3.88-3.76 (m, 1H), 3.40 (t, 2H, J = 7.5 Hz), 3.30-3.19 (m, 1H), 3.10 (t, 2H, J = 7.5 Hz), 1.24 (d, 3H, J = 6.6 Hz), 1.20 (t, 3H, J = 7.2 Hz). |
| 326 | | HCl | ¹H-NMR (DMSO-$d_6$) δ: 12.50 (br s, 1H), 8.91 (s, 1H), 7.44-7.37 (m, 2H), 7.22-7.15 (m, 2H), 4.80 (d, 1H, J = 13.5 Hz), 4.47 (s, 2H), 4.36 (dd, 1H, J = 13.5, 4.6 Hz), 4.00-3.87 (m, 2H), 3.66-3.58 (m, 1H), 3.31-3.18 (m, 1H), 3.08 (s, 3H), 1.21 (t, 3H, J = 7.1 Hz), 1.16 (d, 3H, J = 6.4 Hz). |
| 327 | | HCl | ¹H-NMR (DMSO-$d_6$) δ: 12.42 (br s, 1H), 8.76 (s, 1H), 7.67 (s, 1H), 7.36-7.30 (m, 2H), 7.19-7.11 (m, 2H), 4.61 (d, 1H, J = 13.2 Hz), 4.33 (dd, 1H, J = 13.2, 3.7 Hz), 4.20 (s, 2H), 3.95-3.83 (m, 1H), 3.88-3.80 (m, 1H), 3.22-3.11 (m, 1H), 1.74-1.62 (m, 1H), 1.50-1.36 (m, 1H), 1.20 (t, 3H, J = 7.2 Hz), 0.91 (t, 3H, J = 7.4 Hz). |

TABLE 1-91

| No. | structural formula | salt | ¹H-NMR |
|---|---|---|---|
| 328 | 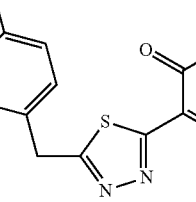 | HCl | ¹H-NMR (DMSO-d$_6$) δ: 12.62 (br s, 1H), 8.84 (s, 1H), 7.45-7.37 (m, 2H), 7.23-7.14 (m, 2H), 4.49-4.35 (m, 2H), 4.47 (s, 2H), 4.15-4.07 (m, 1H), 3.87-3.75 (m, 1H), 3.31-3.18 (m, 1H), 1.26-1.14 (m, 6H). |
| 329 | | HCl | ¹H-NMR (DMSO-d$_6$) δ: 12.33 (br s, 1H), 8.82 (s, 1H), 7.67 (s, 1H), 7.37-7.30 (m, 2H), 7.18-7.11 (m, 2H), 4.71 (d, 1H, J = 13.9 Hz), 4.32 (dd, 1H, J = 13.9, 4.4 Hz), 4.20 (s, 2H), 4.07-3.94 (m, 1H), 3.75-3.69 (m, 1H), 3.16-3.04 (m, 1H), 1.97-1.85 (m, 1H), 1.20 (t, 3H, J = 7.1 Hz), 0.98 (d, 3H, J = 6.8 Hz), 0.78 (d, 3H, J = 6.8 Hz). |
| 330 | | HCl | ¹H-NMR (DMSO-d$_6$) δ: 12.52 (br s, 1H), 8.66 (s, 1H), 7.67 (s, 1H), 7.37-7.30 (m, 2H), 7.19-7.11 (m, 2H), 4.46-4.33 (m, 2H), 4.20 (s, 2H), 4.14-4.04 (m, 1H), 3.86-3.75 (m, 1H), 3.29-3.18 (m, 1H), 1.22 (d, 3H, J = 6.6 Hz), 1.19 (t, 3H, J = 7.2 Hz). |
| 331 | 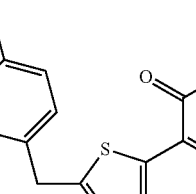 | HCl | ¹H-NMR (DMSO-d$_6$) δ: 12.68 (br s, 1H), 8.83 (s, 1H), 7.44-7.38 (m, 2H), 7.22-7.15 (m, 2H), 4.77 (d, 1H, J = 13.7 Hz), 4.55 (d, 1H, J = 13.7 Hz), 4.47 (s, 2H), 4.16-3.03 (m, 5H), 3.44 (sep, 1H, J = 6.6 Hz), 1.63 (s, 3H), 1.49 (d, 3H, J = 6.6 Hz), 1.42 (d, 3H, J = 6.6 Hz), 1.09-1.00 (m, 3H). |

TABLE 1-92

| No. | structural formula | salt | ¹H-NMR |
|---|---|---|---|
| 332 | 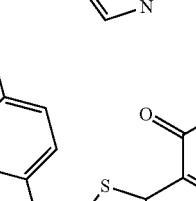 | HCl | ¹H-NMR (DMSO-d$_6$) δ: 12.50 (br s, 1H), 8.95 (s, 1H), 7.44-7.36 (m, 2H), 7.22-7.15 (m, 2H), 4.69 (dd, 1H, J = 14.0, 1.5 Hz), 4.47 (s, 2H), 4.39 (dd, 1H, J = 14.0, 4.2 Hz), 4.04-3.98 (m, 1H), 3.97-3.92 (m, 1H), 3.51-3.43 (m, 1H), 3.26-3.18 (m, 1H), 3.18 (s, 3H), 1.19 (t, 3H, J = 7.2 Hz), 1.10 (d, 3H, J = 6.2 Hz). |
| 333 | 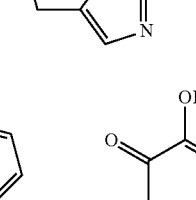 | HCl | ¹H-NMR (DMSO-d$_6$) δ: 8.76 (s, 1H), 7.67 (s, 1H), 7.36-7.30 (m, 2H), 7.18-7.11 (m, 2H), 4.64 (dd, 1H, J = 13.6, 1.5 Hz), 4.37 (dd, 1H, J = 13.6, 4.0 Hz), 4.20 (s, 2H), 4.06-3.97 (m, 1H), 3.95-3.90 (m, 1H), 3.51-3.40 (m, 1H), 3.27-3.19 (m, 1H), 3.19 (s, 3H), 1.19 (t, 3H, J = 6.8 Hz), 1.08 (d, 3H, J = 6.4 Hz). |

TABLE 1-92-continued
| No. | structural formula | salt | ¹H-NMR |
|---|---|---|---|
| 334 | 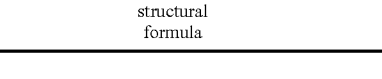 | HCl | ¹H-NMR (DMSO-$d_6$) δ: 12.47 (br s, 1H), 8.96 (s, 1H), 7.44-7.38 (m, 2H), 7.22-7.15 (m, 2H), 4.68 (dd, 1H, J = 13.9, 1.3 Hz), 4.47 (s, 2H), 4.35 (dd, 1H, J = 13.9, 3.5 Hz), 4.14-4.06 (m, 1H), 3.98-3.93 (m, 1H), 3.41 (sep, 1H, J = 6.7 Hz), 3.24 (s, 3H), 1.39 (d, 3H, J = 6.7 Hz), 1.34 (d, 3H, J = 6.7 Hz), 1.02 (d, 3H, J = 6.3 Hz). |
| 335 | 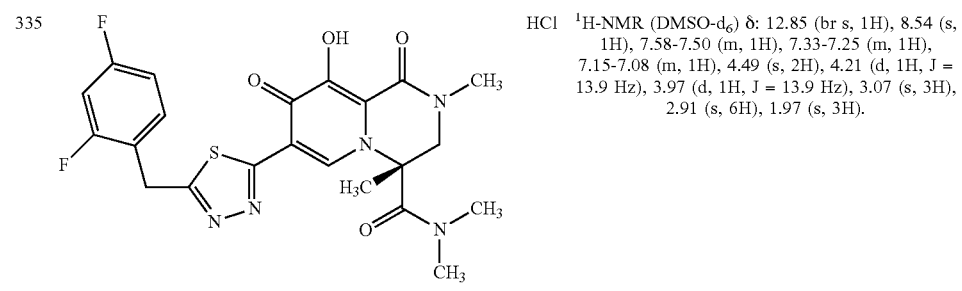 | HCl | ¹H-NMR (DMSO-$d_6$) δ: 12.85 (br s, 1H), 8.54 (s, 1H), 7.58-7.50 (m, 1H), 7.33-7.25 (m, 1H), 7.15-7.08 (m, 1H), 4.49 (s, 2H), 4.21 (d, 1H, J = 13.9 Hz), 3.97 (d, 1H, J = 13.9 Hz), 3.07 (s, 3H), 2.91 (s, 6H), 1.97 (s, 3H). |
TABLE 1-93
| No. | structural formula | salt | ¹H-NMR |
|---|---|---|---|
| 336 | 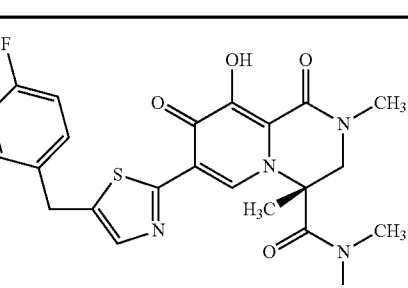 | HCl | ¹H-NMR (DMSO-$d_6$) δ: 12.75 (br s, 1H), 8.46 (s, 1H), 7.69 (s, 1H), 7.50-7.42 (m, 1H), 7.29-7.21 (m, 1H), 7.11-7.05 (m, 1H), 4.22 (s, 2H), 4.21 (d, 1H, J = 14.0 Hz), 3.93 (d, 1H, J = 14.0 Hz). 3.07 (s, 3H), 2.89 (s, 6H), 1.93 (s, 3H). |
| 337 | 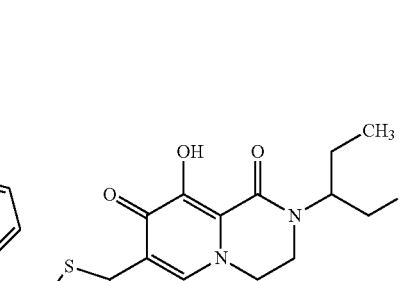 | HCl | ¹H-NMR (DMSO-$d_6$) δ: 12,86 (br s, 1H), 8.83 (s, 1H), 7.45-7.39 (m, 2H), 7.23-7.16 (m, 2H), 5.02-4.94 (m, 1H), 4.47 (s, 2H), 4.40-4.29 (m, 1H), 3.83-3.56 (m, 4H), 3.26 (s, 3H), 1.64-1.43 (m, 4H), 0.92-0.78 (m, 6H). |

TABLE 1-94

| No. | structural formula | salt | ¹H-NMR |
|---|---|---|---|
| 338 | | HCl | ¹H-NMR (DMSO-d$_6$) δ: 12.83 (br s, 1H), 8.92 (s, 1H), 7.44-7.39 (m, 2H), 7.21-7.16 (m, 2H), 4.78 (quint, 1H, J = 6.9 Hz), 4.71 (ddd, 1H, J = 6.4, 4.0, 1.6 Hz), 4.47 (s, 2H), 3.87 (dd, 1H, J = 13.7, 1.6 Hz), 3.78 (dd, 1H, J = 13.7, 4.0 Hz), 3.58 (dq, 1H, J = 6.4, 6.0 Hz), 3.22 (s, 3H), 1.19 (d, 3H, J = 6.9 Hz), 1.17 (d, 3H, J = 6.9 Hz), 1.03 (d, 3H, J = 6.0 Hz). |
| 339 | | | ¹H-NMR (DMSO-d$_6$) δ: 8.21 (s, 1H), 7.42-7.39 (m, 2H), 7.20-7.16 (m, 2H), 4.85 (quint, 1H, J = 6.6 Hz), 4.71-4.65 (m, 1H), 4.41 (s, 2H), 3.58-3.53 (m, 3H), 3.48-3.44 (m, 1H), 3.24 (s, 3H), 1.09 (d, 6H, J = 6.6 Hz). |
| 340 | | HCl | ¹H-NMR (DMSO-d$_6$) δ: 12.82 (br s, 1H), 8.72 (s, 1H), 7.44-7.41 (m, 2H), 7.21-7.17 (m, 2H), 4.77 (sep, 1H, J = 6.6 Hz), 4.65 (ddd, 1H, J = 8.2, 4.1, 0.9 Hz), 4.47 (s, 2H), 3.88 (dd, 1H, J = 14.0, 4.1 Hz), 3.76 (dd, 1H, J = 14.0, 0.9 Hz), 3.52 (dq, 1H, J = 8.2, 6.2 Hz), 3.03 (s, 3H), 1.21 (d, 3H, J = 6.2 Hz), 1.20 (d, 3H, J = 6.6 Hz), 1.17 (d, 3H, J = 6.6 Hz). |
| 341 | | HCl | ¹H-NMR (DMSO-d$_6$) δ: 8.95 (s, 1H), 7.43-7.38 (m, 2H), 7.21-7.16 (m, 2H), 4.68 (dd, 1H, J = 13.8, 1.5 Hz), 4.47 (s, 2H), 4.35 (dd, 1H, J = 13.8, 3.9 Hz), 4.10 (quint, 1H, J = 6.6 Hz), 3.96 (ddd, 1H, J = 6.6, 3.9, 1.5 Hz), 3.41 (dq, 1H, J = 6.6, 6.4 Hz), 3.24 (s, 3H), 1.39 (d, 3H, J = 6.6 Hz), 1.34 (d, 3H, J = 6.6 Hz), 1.02 (d, 3H, J = 6.4 Hz). |
| 342 | | HCl | ¹H-NMR (DMSO-d$_6$) δ: 12.83 (br s, 1H), 8.72 (s, 1H), 7.45-7.41 (m, 3H), 7.22-7.17 (m, 2H), 4.77 (quint, 1H, J = 6.8 Hz), 4.60 (ddd, 1H, J = 8.4, 4.2, 0.9 Hz), 4.47 (s, 2H), 3.88 (dd, 1H, J = 14.3, 4.2 Hz), 3.74 (dd, 1H, J = 14.3, 0.9 Hz), 3.56 (dq, 1H, J = 8.4, 6.2 Hz), 3.41 (dq, 1H, J = 9.5, 7.1 Hz), 2.91 (dq, 1H, J = 9.5, 7.1 Hz), 1.22 (d, 3H, J = 6.2 Hz), 1.20 (d, 3H, J = 6.8 Hz), 1.17 (d, 3H, J = 6.8 Hz), 0.75 (t, 3H, J = 7.1 Hz). |

TABLE 1-95

| No. | structural formula | salt | ¹H-NMR |
|---|---|---|---|
| 343 | (structure) | HCl | ¹H-NMR (DMSO-d$_6$) δ: 8.85 (s, 1H), 7.43-7.39 (m, 2H), 7.21-7.15 (m, 2H), 4.66 (dd, 1H, J = 12.4, 1.5 Hz), 4.48 (sep, 1H, J = 6.6 Hz), 4.47 (s, 2H), 4.35 (dd, 1H, J = 13.2, 3.7 Hz), 4.20-4.16 (m, 1H), 3.54 (dd, 1H, J = 10.5, 4.1 Hz), 3.45-3.30 (m, 3H), 1.30 (d, 3H, J = 6.6 Hz), 1.28 (d, 3H, J = 6.6 Hz), 0.96 (t, 3H, J = 6.9 Hz). |
| 344 | (structure) | | ¹H-NMR (DMSO-d$_6$) δ: 12.81 (s, 1H), 8.80 (s, 1H), 7.44-7.39 (m, 2H), 7.22-7.16 (m, 2H), 4.99-4.95 (m, 1H), 4.77 (sep, 1H, J = 6.7 Hz), 4.47 (s, 2H), 3.84 (dd, 1H, J = 13.7, 3.9 Hz), 3.75 (dd, 1H, J = 13.9, 1.6 Hz), 3.63 (dd, 1H, J = 10.2, 6.0 Hz), 3.57 (dd, 1H, J = 10.2, 7.7 Hz), 3.25 (s, 3H), 1.16 (d, 3H, J = 6.7 Hz), 1.16 (d, 3H, J = 6.7 Hz). |
| 345 | (structure) | | ¹H-NMR (DMSO-d$_6$) δ: 8.10 (s, 1H), 7.41-7.36 (m, 2H), 7.20-7.14 (m, 2H), 4.83 (quint, 1H, J = 6.7 Hz), 4.62-4.57 (m, 1H), 4.38 (s, 2H), 3.57-3.44 (m, 4H), 3.25 (s, 3H), 1.05 (d, 6H, J = 6.7 Hz). |
| 346 | (structure) | | ¹H-NMR (DMSO-d$_6$) δ: 12.44 (br s, 1H), 8.85 (s, 1H), 7.44-7.37 (m, 2H), 7.23-7.14 (m, 2H), 4.70-4.61 (m, 1H), 4.54-4.41 (m, 1H), 4.47 (s, 2H), 4.39-4.30 (m, 1H), 4.25-4.14 (m, 1H), 3.53-3.34 (m, 2H), 3.21 (s, 3H), 1.30 (d, 3H, J = 6.3 Hz), 1.28 (d, 3H, J = 6.3 Hz). |
| 347 | (structure) | | ¹H-NMR (DMSO-d$_6$) δ: 8.02 (br s, 1H), 7.42-7.33 (m, 2H), 7.21-7.13 (m, 2H), 4.73-4.59 (m, 1H), 4.38 (s, 2H), 4.34-4.22 (m, 1H), 4.07-3.96 (m, 1H), 3.89-3.78 (m, 1H), 3.30-3.05 (m, 2H), 3.24 (s, 3H), 1.13 (d, 3H, J = 7.0 Hz), 1.06 (d, 3H, J = 7.0 Hz). |

TABLE 1-96

| No. | structural formula | salt | ¹H-NMR |
|---|---|---|---|
| 348 | | HCl | ¹H-NMR (DMSO-$d_6$) δ: 12.81 (br s, 1H), 8.72 (s, 1H), 7.47-7.37 (m, 2H), 7.23-7.14 (m, 2H), 4.83-4.71 (m, 1H), 4.69-4.60 (m, 1H), 4.47 (s, 2H), 3.88 (dd, 1H, J = 14.1, 3.7 Hz), 3.81-3.71 (m, 1H), 3.56-3.47 (m, 1H), 3.03 (s, 3H), 1.24-1.13 (m, 9H). |
| 349 | | HCl | ¹H-NMR (DMSO-$d_6$) δ: 12.52 (s, 1H), 8.90 (s, 1H), 7.40 (dd, 2H, J = 8.3, 5.6 Hz), 7.17 (dd, 2H, J = 8.3, 8.4 Hz), 4.81 (d, 1H, J = 14.1 Hz), 4.46 (s, 2H), 4.38-4.27 (m, 2H), 3.98 (s, 1H), 3.62-3.56 (m, 1H), 3.04 (s, 3H), 1.33 (t, 6H, J = 6.0 Hz), 1.18 (d, 3H, J = 7.0 Hz). |
| 350 | | HCl | ¹H-NMR (DMSO-$d_6$) δ: 12.80 (s, 1H), 8.91 (s, 1H), 7.43-7.39 (m, 2H), 7.21-7.15 (m, 2H), 4.78 (quint, 1H, J = 6.9 Hz), 4.70 (dd, 1H, J = 6.4, 4.2 Hz), 4.47 (s, 2H), 3.86 (d, 1H, J = 13.7 Hz), 3.77 (dd, 1H, J = 13.7, 4.2 Hz), 3.58 (dq, 1H, J = 6.4, 6.0 Hz), 3.21 (s, 3H), 1.19 (d, 3H, J = 6.9 Hz), 1.17 (d, 3H, J = 6.9 Hz), 1.02 (d, 3H, J = 6.0 Hz). |
| 351 | | HCl | ¹H-NMR (DMSO-$d_6$) δ: 12.71 (br s, 1H), 8.56 (s, 1H), 7.44-7.36 (m, 2H), 7.23-7.14 (m, 2H), 4.70-4.60 (m, 1H), 4.50-4.38 (m, 1H), 4.47 (s, 2H), 4.08-4.02 (m, 1H), 3.61 (dd, 1H, J = 11.1, 3.7 Hz), 3.53 (dd, 1H, J = 11.1, 3.9 Hz), 3.27 (q, 2H, J = 7.4 Hz), 1.75 (d, 3H, J = 6.5 Hz), 1.32 (t, 6H, J = 7.0 Hz), 0.82 (t, 3H, J = 7.0 Hz). |
| 352 | | | ¹H-NMR (DMSO-$d_6$) δ: 12.79 (br s, 1H), 8.74 (s, 1H), 7.45-7.38 (m, 2H), 7.23-7.15 (m, 2H), 5.32-5.23 (m, 1H), 4.81-4.65 (m, 2H), 4.47 (s, 2H), 3.86-3.64 (m, 3H), 3.60-3.51 (m, 1H), 1.16 (d, 3H, J = 6.7 Hz), 1.15 (d, 3H, J = 6.7 Hz). |

TABLE 1-97

| No. | structural formula | salt | ¹H-NMR |
|---|---|---|---|
| 353 | (structure) | HCl | ¹H-NMR (DMSO-d₆) δ: 12.77 (br s, 1H), 8.56 (s, 1H), 7.44-7.36 (m, 2H), 7.23-7.14 (m, 2H), 4.70-4.59 (m, 1H), 4.49-4.37 (m, 1H), 4.47 (s, 2H), 4.11-4.03 (m, 1H), 3.59-3.46 (m, 2H), 3.11 (s, 3H), 1.75 (d, 3H, J = 6.5 Hz), 1.32 (t, 6H, J = 6.5 Hz). |
| 354 | (structure) | HBr | ¹H-NMR (DMSO-D₆) δ: 8.80 (s, 1H), 7.43-7.37 (m, 2H), 7.21-7.14 (m, 2H), 4.70-4.64 (m, 1H), 4.55-4.44 (m, 3H), 4.33 (dd, 1H, J = 13.3, 3.6 Hz), 3.99-3.93 (m, 1H), 3.56 (dd, 1H, J = 11.4, 3.7 Hz), 3.35 (dd, 1H, J = 11.4, 8.1 Hz), 1.28 (d, 3H, J = 6.7 Hz), 1.27 (d, 3H, J = 6.7 Hz). |
| 355 | (structure) | HCl | ¹H-NMR (DMSO-d₆) δ: 12.78 (br s, 1H), 8.76 (s, 1H), 7.44-7.37 (m, 2H), 7.22-7.14 (m, 2H), 4.47 (s, 2H), 4.34 (s, 2H), 3.55 (q, 2H, J = 7.1 Hz), 1.36 (s, 6H), 1.19 (t, 3H, J = 7.1 Hz). |
| 356 | (structure) | HCl | ¹H-NMR (DMSO-d₆) δ: 12.76 (s, 1H), 8.77 (s, 1H), 7.42-7.36 (m, 2H), 7.21-7.14 (m, 2H), 4.71 (ddd, 1H, J = 8.0, 2.2, 2.0 Hz), 4.56 (quint, 1H, J = 6.9 Hz), 4.46 (s, 2H), 4.19-4.09 (m, 2H), 3.93 (dd, 1H, J = 11.7, 2.2 Hz), 3.45 (s, 3H), 1.29 (d, 3H, J = 6.9 Hz), 1.27 (d, 3H, J = 6.9 Hz), 1.04 (d, 3H, J = 6.5 Hz). |
| 357 | (structure) | HCl | ¹H-NMR (DMSO-d₆) δ: 12.76 (s, 1H), 8.80 (s, 1H), 7.41 (tt, 2H, J = 8.7, 3.1 Hz), 7.18 (tt, 2H, J = 8.9, 2.5 Hz), 4.94-4.88 (m, 1H), 4.46 (s, 2H), 4.06 (dd, 1H, J = 13.8, 4.3 Hz), 3.73-3.67 (m, 2H), 3.64-3.52 (m, 2H), 3.49-3.27 (m, 3H), 1.63-1.53 (m, 2H), 1.01 (t, 3H, J = 7.0 Hz), 0.89 (t, 3H, J = 8.2 Hz). |

TABLE 1-98

| No. | structural formula | salt | ¹H-NMR |
|---|---|---|---|
| 358 | | HCl | ¹H-NMR (DMSO-d$_6$) δ: 12.90 (br s, 1H), 8.37 (s, 1H), 8.07 (s, 1H), 8.00 (s, 1H), 7.45-7.37 (m, 2H), 7.23-7.13 (m, 2H), 5.28-5.18 (m, 1H), 4.89-4.60 (m, 3H), 4.44 (s, 2H), 3.98-3.83 (m, 2H), 1.25 (d, 3H, J = 6.7 Hz), 1.18 (d, 3H, J = 6.7 Hz). |
| 359 | | HCl | ¹H-NMR (DMSO-d$_6$) δ: 12.88 (br s, 1H), 8.99 (s, 1H), 8.20 (s, 1H), 7.46-7.37 (m, 2H), 7.24-7.14 (m, 2H), 5.48-5.38 (m, 1H), 5.37-5.19 (m, 2H), 4.84-4.72 (m, 1H), 4.45 (s, 2H), 3.96 (d, 2H, J = 3.0 Hz), 1.25 (d, 3H, J = 6.7 Hz), 1.17 (d, 3H, J = 6.7 Hz). |
| 360 | | HCl | ¹H-NMR (DMSO-d$_6$) δ: 12.85 (br s, 1H), 8.75 (s, 1H), 7.45-7.37 (m, 2H), 7.22-7.14 (m, 2H), 5.52-5.41 (m, 1H), 4.81-4.71 (m, 1H), 4.47 (s, 2H), 3.98-3.81 (m, 2H), 3.66 (d, 2H, J = 7.0 Hz), 1.29 (s, 9H), 1.21 (d, 3H, J = 6.5 Hz), 1.15 (d, 3H, J = 6.5 Hz). |
| 361 | | HCl | ¹H-NMR (DMSO-d$_6$) δ: 12.94 (s, 1H), 8.80 (s, 1H), 7.43-7.39 (m, 2H), 7.21-7.15 (m, 2H), 4.89-4.85 (m, 1H), 4.47 (s, 2H), 3.96 (dd, 1H, J = 14.0, 1.5 Hz), 3.87 (dd, 1H, J = 14.0, 3.0 Hz), 3.70 (dd, 1H, J = 10.2, 6.7 Hz), 3.62 (dd, 1H, J = 10.2, 7.5 Hz), 3.50-3.41 (m, 2H), 1.49 (s, 9H), 1.05 (t, 3H, J = 6.9 Hz). |
| 362 | | HCl | ¹H-NMR (DMSO-d$_6$) δ: 8.80 (s, 1H), 7.44-7.39 (m, 2H), 7.21-7.16 (m, 2H), 4.94-4.89 (m, 1H), 4.47 (s, 2H), 4.06 (dd, 1H, J = 13.6, 4.3 Hz), 3.77-3.72 (m, 2H), 3.70-3.46 (m, 5H), 3.38-3.31 (m, 3H), 3.11 (s, 3H), 1.60-1.52 (m, 2H), 1.37-1.27 (m, 2H), 0.92 (t, 3H, J = 7.4 Hz). |

TABLE 1-99

| No. | structural formula | salt | ¹H-NMR |
|---|---|---|---|
| 363 | | HCl | ¹H-NMR (DMSO-d$_6$) δ: 12.83 (br s, 1H), 8.82 (s, 1H), 7.46-7.38 (m, 2H), 7.24-7.14 (m, 2H), 5.01-4.91 (br m, 1H), 4.77 (sep, 1H, J = 6.7 Hz), 4.47 (s, 2H), 3.88-3.54 (m, 4H), 3.41-3.24 (m, 2H), 1.41 (td, 2H, J = 13.9, 7.2 Hz), 1.17 (d, 3H, J = 6.7 Hz), 1.16 (d, 3H, J = 6.7 Hz), 0.74 (t, 3H, J = 7.2 Hz). |
| 364 | | HCl | ¹H-NMR (DMSO-d$_6$) δ: 12.83 (br s, 1H), 8.80 (s, 1H), 7.44-7.37 (m, 2H), 7.22-7.13 (m, 2H), 4.99-4.89 (m, 1H), 4.76 (sep, 1H, J = 7.0), 4.46 (s, 2H), 3.88-3.52 (m, 4H), 3.43-3.24 (m, 2H), 1.40-1.29 (m, 2H), 1.22-1.09 (m, 8H), 0.69 (t, 3H, J = 7.3 Hz). |
| 365 | | HCl | ¹H-NMR (DMSO-d$_6$) δ: 12.84 (br s, 1H), 8.83 (s, 1H), 7.46-7.38 (m, 2H), 7.23-7.15 (m, 2H), 4.94-4.71 (m, 2H), 4.47 (s, 2H), 3.85-3.45 (m, 5H), 1.21-1.12 (m, 6H), 1.02 (d, 3H, J = 6.0 Hz), 0.96 (d, 3H, J = 6.3 Hz). |
| 366 | | | ¹H-NMR (DMSO-d$_6$) δ: 12.77 (s, 1H), 8.80 (s, 1H), 7.45-7.38 (m, 2H), 7.23-7.14 (m, 2H), 4.91-4.83 (m, 1H), 4.83-4.73 (m, 2H), 4.47 (s, 2H), 3.86 (dd, 1H, J = 14.1, 3.5 Hz), 3.76-3.67 (m, 1H), 3.54-3.43 (m, 1H), 1.96-1.71 (m, 2H), 1.19 (d, 3H, J = 7.0 Hz), 1.16 (d, 3H, J = 6.7 Hz). |
| 367 | | HCl | ¹H-NMR (DMSO-d$_6$) δ: 12.42 (br s, 1H), 8.84 (s, 1H), 7.45-7.37 (m, 2H), 7.23-7.14 (m, 2H), 4.69-4.63 (m, 1H), 4.53-4.44 (m, 3H), 4.35 (dd, 1H, J = 13.3, 4.0 Hz), 4.18-4.11 (m, 1H), 3.55 (dd, 1H, J = 10.5, 3.6 Hz), 3.48-3.39 (m, 2H), 1.30 (d, 3H, J = 6.9 Hz), 1.28 (d, 3H, J = 6.9 Hz), 0.95-0.90 (m, 6H). |

TABLE 1-100

| No. | structural formula | salt | ¹H-NMR |
|---|---|---|---|
| 368 | | HCl | ¹H-NMR (DMSO-d₆) δ: 8.78 (s, 1H), 7.44-7.40 (m, 2H), 7.22-7.16 (m, 2H), 4.74-4.70 (m, 1H), 4.74 (quint, 1H, J = 7.1 Hz), 4.47 (s, 2H), 3.91-3.82 (m, 2H), 3.05 (s, 3H), 1.20 (d, 3H, J = 7.1 Hz), 1.19 (s, 3H), 1.18 (d, 3H, J = 7.1 Hz), 1.10 (s, 3H). |
| 369 | | HCl | ¹H-NMR (DMSO-d₆) δ: 12.80 (s, 1H), 8.81 (s, 1H), 7.44-7.38 (m, 2H), 7.21-7.16 (m, 2H), 4.95 (s, 1H), 4.80-4.73 (m, 1H), 4.47 (s, 2H), 3.85 (dd, 1H, J = 13.7, 4.0 Hz), 3.75 (d, 1H, J = 13.7 Hz), 3.67 (dd, 1H, J = 10.3, 5.4 Hz), 3.58 (dd, 1H, J = 10.3, 7.7 Hz), 3.45 (dt, 1H, J = 11.4, 4.6 Hz), 3.34 (dt, 1H, J = 11.4, 4.8 Hz), 3.20-3.13 (m, 2H), 3.00 (s, 3H), 1.64-1.58 (m, 2H), 1.16 (dd, 6H, J = 6.9, 2.4 Hz). |
| 370 | | HCl | ¹H-NMR (DMSO-d₆) δ: 12.78 (br s, 1H), 8.72 (s, 1H), 7.46-7.38 (m, 2H), 7.24-7.15 (m, 2H), 4.91-4.81 (m, 1H), 4.84-4.72 (m, 1H), 4.47 (s, 2H), 3.89-3.65 (m, 2H), 3.45-3.35 (m, 1H), 3.20-3.07 (m, 1H), 3.18 (s, 3H), 2.07-1.93 (m, 1H), 1.93-1.80 (m, 1H), 1.18 (d, 3H, J = 6.7 Hz), 1.16 (d, 3H, J = 6.7 Hz). |
| 371 | | HCl | ¹H-NMR (DMSO-d₆) δ: 12.77 (br s, 1H), 8.75 (s, 1H), 7.47-7.37 (m, 2H), 7.24-7.15 (m, 2H), 4.91-4.73 (m, 2H), 4.47 (s, 2H), 3.90-3.63 (m, 2H), 3.58-3.01 (m, 4H), 2.11-1.79 (m, 2H), 1.19 (d, 3H, J = 7.2 Hz), 1.16 (d, 3H, J = 7.2 Hz), 1.03 (t, 3H, J = 7.2 Hz). |
| 372 | | HCl | ¹H-NMR (DMSO-d₆) δ: 12.81 (br s, 1H), 8.80 (s, 1H), 7.44-7.36 (m, 2H), 7.23-7.14 (m, 2H), 4.93-4.84 (m, 1H), 4.47 (s, 2H), 4.04 (dd, 1H, J = 13.7, 4.0 Hz), 3.69 (dd, 1H, J = 10.5, 5.6 Hz), 3.66-3.59 (m, 2H), 3.53-3.32 (m, 5H), 2.93-2.85 (m, 1H), 0.96-0.69 (m, 4H), 0.93 (d, 3H, J = 6.0 Hz), 0.90 (d, 3H, J = 6.0 Hz). |

TABLE 1-101

| No. | structural formula | salt | ¹H-NMR |
|---|---|---|---|
| 373 | | HCl | ¹H-NMR (DMSO-d$_6$) δ: 12.83 (br s, 1H), 8.80 (s, 1H), 7.44-7.38 (m, 2H), 7.22-7.15 (m, 2H), 5.00-4.91 (m, 1H), 4.77 (sep, 1H, J = 6.9 Hz), 4.47 (s, 2H), 3.84 (dd, 1H, J = 13.7, 4.0 Hz), 3.80-3.74 (m, 1H), 3.71 (dd, 1H, J = 10.3, 5.8 Hz), 3.65 (dd, 1H, J = 10.3, 7.9 Hz), 3.54-3.32 (m, 5H), 1.17 (d, 3H, J = 6.9 Hz), 1.16 (d, 3H, J = 6.9 Hz), 0.92 (d, 3H, J = 6.0 Hz), 0.89 (d, 3H, J = 6.0 Hz). |
| 374 | | HCl | ¹H-NMR (DMSO-d$_6$) δ: 8.89 (s, 1H), 7.70 (d, 1H, J = 2.2 Hz), 7.45 (d, 1H, J = 1.8 Hz), 7.44-7.39 (m, 2H), 7.22-7.16 (m, 2H), 6.20 (dd, 1H, J = 2.2, 1.8 Hz), 4.86-4.82 (m, 1H), 4.78 (quint, 1H, J = 7.1 Hz), 4.47 (s, 2H), 4.26-4.14 (m, 2H), 3.84 (dd, 1H, J = 13.6, 3.6 Hz), 3.68 (dd, 1H, J = 13.6, 0.9 Hz), 2.27-2.20 (m, 2H), 1.18 (d, 3H, J = 7.1 Hz), 1.14 (d, 3H, J = 7.1 Hz). |
| 375 | | HCl | ¹H-NMR (DMSO-d$_6$) δ: 13.19 (br s, 1H), 8.41 (s, 1H), 7.46-7.38 (m, 2H), 7.23-7.14 (m, 2H), 4.80-4.68 (m, 1H), 4.47 (s, 2H), 4.08 (d, 1H, J = 14.1 Hz), 3.81 (d, 1H, J = 14.1 Hz), 2.93 (s, 6H), 2.61-2.11 (m, 2H), 1.19 (d, 3H, J = 7.0 Hz), 1.16 (d, 3H, J = 7.0 Hz), 0.91 (t, 3H, J = 7.2 Hz). |
| 376 | | HCl | ¹H-NMR (DMSO-d$_6$) δ: 13.09 (br s, 1H), 8.30 (s, 1H), 7.70 (s, 1H), 7.38-7.28 (m, 2H), 7.19-7.10 (m, 2H), 4.80-4.69 (m, 1H), 4.20 (s, 2H), 4.06 (d, 1H, J = 14.1 Hz), 3.78 (d, 1H, J = 14.1 Hz), 2.91 (s, 6H), 2.47-2.07 (m, 2H), 1.22-1.12 (m, 6H), 0.87 (t, 3H, J = 7.2 Hz). |
| 377 | | HCl | ¹H-NMR(DMSO-d$_6$) δ: 12.78 (br s, 1H), 8.96 (s, 1H), 7.43-7.40 (m, 2H), 7.21-7.16 (m, 2H), 4.87-4.80 (m, 1H), 4.80 (quint, 1H, J = 6.6 Hz), 4.47 (s, 2H), 4.23 (t, 2H, J = 7.9 Hz), 3.87-3.82 (m, 1H), 3.76-3.73 (m, 1H), 3.57-3.46 (m, 2H), 3.33-3.25 (m, 1H), 3.19-3.11 (m, 1H), 1.95 (dt, 2H, J = 7.1, 7.9 Hz), 1.22 (d, 3H, J = 6.6 Hz), 1.16 (d, 3H, J = 6.6 Hz). |

TABLE 1-102

| No. | structural formula | salt | ¹H-NMR |
|---|---|---|---|
| 378 | | HCl | ¹H-NMR (DMSO-d₆) δ: 12.75 (br s, 1H), 8.75 (s, 1H), 7.44-7.40 (m, 2H), 7.21-7.16 (m, 2H), 4.88-4.83 (m, 1H), 4.78 (sep, 1H, J = 6.7 Hz), 4.47 (s, 2H), 3.85 (dd, 1H, J = 13.6, 3.6 Hz), 3.73 (dd, 1H, J = 13.6, 0.9 Hz), 3.53-3.48 (m, 1H), 3.45-3.31 (m, 4H), 3.29-3.18 (m, 1H), 3.15 (s, 3H), 2.04-1.96 (m, 1H), 1.91-1.83 (m, 1H), 1.19 (d, 3H, J = 6.7 Hz), 1.16 (d, 3H, J = 6.7 Hz). |
| 379 | | HCl | ¹H-NMR (DMSO-d₆) δ: 12.78 (br s, 1H), 8.91 (s, 1H), 7.44-7.39 (m, 2H), 7.22-7.16 (m, 2H), 4.83-4.81 (m, 1H), 4.79 (sep, 1H, J = 6.7 Hz), 4.47 (s, 2H), 3.83 (dd, 1H, J = 13.8, 3.6 Hz), 3.72 (dd, 1H, J = 13.8, 1.5 Hz), 3.35-3.22 (m, 2H), 3.18 (s, 3H), 1.81-1.71 (m, 1H), 1.70-1.58 (m, 2H), 1.37-1.33 (m, 1H), 1.18 (d, 3H, J = 6.7 Hz), 1.16 (d, 3H, J = 6.7 Hz). |
| 380 | | HCl | ¹H-NMR (DMSO-d₆) δ: 12.85 (br s, 1H), 8.83 (s, 1H), 7.46-7.39 (m, 2H), 7.23-7.15 (m, 2H), 4.92-4.83 (br m, 1H), 4.81-4.70 (m, 1H), 4.47 (s, 2H), 3.85-3.62 (m, 4H), 3.59-3.48 (m, 1H), 3.26-3.18 (m, 2H), 3.17 (s, 3H), 1.21-1.12 (m, 6H), 0.91 (d, 3H, J = 6.5 Hz). |
| 381 | | HCl | ¹H-NMR (DMSO-d₆) δ: 12.85 (br s, 1H), 8.83 (s, 1H), 7.45-7.37 (m, 2H), 7.23-7.15 (m, 2H), 4.86-4.76 (br m, 1H), 4.47 (s, 2H), 4.02 (dd, 1H, J = 13.4, 4.2 Hz), 3.77-3.58 (m, 3H), 3.57-3.48 (m, 1H), 3.26-3.19 (m, 2H), 3.18 (s, 3H), 2.93-2.84 (m, 1H), 0.92 (d, 3H, J = 6.3 Hz), 0.91-0.70 (m, 4H). |
| 382 | | HCl | ¹H-NMR (DMSO-d₆) δ: 12.80 (s, 1H), 8.71 (s, 1H), 7.44-7.42 (m, 2H), 7.21-7.17 (m, 2H), 4.78 (quint, 1H, J = 6.9 Hz), 4.70 (dd, 1H, J = 9.0, 3.7 Hz), 4.47 (s, 2H), 3.87 (dd, 1H, J = 14.5, 3.7 Hz), 3.74 (d, 1H, J = 14.5 Hz), 3.32 (ddd, 1H, J = 9.0, 3.6, 6.0 Hz), 2.96 (s, 3H), 1.79-1.70 (m, 1H), 1.54-1.43 (m, 1H), 1.19 (dd, 6H, J = 10.9, 6.9 Hz), 0.94 (t, 3H, J = 7.5 Hz). |

TABLE 1-103

| No. | structural formula | salt | ¹H-NMR |
|---|---|---|---|
| 383 | 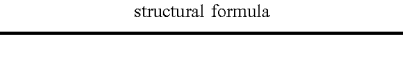 | HCl | ¹H-NMR (DMSO-d₆) δ: 12.88 (s, 1H), 7.44-7.40 (m, 2H), 7.21-7.16 (m, 2H), 4.86-4.82 (m, 1H), 4.77 (quint, 1H, J = 6.9 Hz), 4.47 (s, 2H), 3.83-3.78 (m, 2H), 3.47-3.42 (m, 1H), 3.18 (s, 3H), 1.53-1.47 (m, 1H), 1.33-1.25 (m, 1H), 1.19 (d, 3H, J = 6.9 Hz), 1.17 (d, 3H, J = 6.9 Hz), 0.87 (t, 3H, J = 7.5 Hz). |

TABLE 1-103-continued

| No. | structural formula | salt | ¹H-NMR |
|---|---|---|---|
| 384 | | HCl | ¹H-NMR (DMSO-d₆) δ: 12.82 (br s, 1H), 8.81 (s, 1H), 7.46-7.36 (m, 2H), 7.23-7.15 (m, 2H), 4.93-4.86 (m, 1H), 4.47 (s, 2H), 4.04 (dd, 1H, J = 13.2, 4.2 Hz), 3.75-3.57 (m, 3H), 3.39-3.25 (m, 3H), 3.10 (s, 3H), 2.92-2.87 (m, 1H), 0.93 (d, 3H, J = 5.8 Hz), 0.91-0.67 (m, 4H). |
| 385 | | HCl | ¹H-NMR (DMSO-d₆) δ: 12.84 (br s, 1H), 8.82 (s, 1H), 7.45-7.38 (m, 2H), 7.23-7.15 (m, 2H), 5.00-4.92 (br m, 1H), 4.83-4.72 (m, 1H), 4.47 (s, 2H), 3.89-3.59 (m, 4H), 3.41-3.24 (m, 3H), 3.09 (s, 3H), 1.17 (d, 3H, J = 6.7 Hz), 1.15 (d, 3H, J = 6.7 Hz), 0.93 (d, 3H, J = 6.3 Hz). |
| 386 | | HCl | ¹H-NMR (DMSO-d₆) δ: 12.69 (br s, 1H), 8.56 (s, 1H), 7.66 (s, 1H), 7.39-7.30 (m, 2H), 7.19-7.11 (m, 2H), 4.83-4.71 (m, 1H), 4.63-4.54 (m, 1H), 4.20 (s, 2H), 3.86 (dd, 1H, J = 14.1, 4.2 Hz), 3.78-3.70 (m, 1H), 3.55-3.45 (m, 1H), 3.02 (s, 3H), 1.23-1.14 (m, 9H). |
| 387 | | HCl | ¹H-NMR (DMSO-d₆) δ: 12.68 (br s, 1H), 8.74 (s, 1H), 7.68 (s, 1H), 7.37-7.30 (m, 2H), 7.19-7.11 (m, 2H), 4.84-4.73 (m, 1H), 4.69-4.63 (m, 1H), 4.20 (s, 2H), 3.89-3.81 (m, 1H), 3.76 (dd, 1H, J = 13.7, 4.0 Hz), 3.60-3.52 (m, 1H), 3.22 (s, 3H), 1.21-1.15 (m, 6H), 1.00 (d, 3H, J = 6.0 Hz). |

TABLE 1-104

| No. | structural formula | salt | ¹H-NMR |
|---|---|---|---|
| 388 | | HCl | ¹H-NMR (DMSO-d₆) δ: 8.74 (s, 1H), 7.68 (s, 1H), 7.37-7.31 (m, 2H), 7.18-7.11 (m, 2H), 4.84-4.73 (m, 1H), 4.69-4.63 (m, 1H), 4.20 (s, 2H), 3.89-3.81 (m, 1H), 3.76 (dd, 1H, J = 13.7, 4.0 Hz), 3.60-3.51 (m, 1H), 3.22 (s, 3H), 1.21-1.14 (m, 6H), 1.00 (d, 3H, J = 6.0 Hz). |

TABLE 1-104-continued

| No. | structural formula | salt | ¹H-NMR |
|---|---|---|---|
| 389 | | HCl | ¹H-NMR (DMSO-d₆) δ: 12.81 (s, 1H), 8.73 (s, 1H), 7.45-7.42 (m, 2H), 7.21-7.18 (m, 2H), 4.82-4.75 (m, 1H), 4.65 (dd, 1H, J = 9.1, 2.6 Hz), 4.47 (s, 3H), 3.87 (dd, 1H, J = 13.3, 3.8 Hz), 3.74 (d, 1H, J = 13.3 Hz), 3.39-3.27 (m, 2H), 2.77-2.73 (m, 1H), 1.79-1.70 (m, 1H), 1.51-1.43 (m, 1H), 1.20 (d, 3H, J = 6.9 Hz), 1.17 (d, 3H, J = 6.9 Hz), 0.96 (t, 3H, J = 7.5 Hz), 0.74 (t, 3H, J = 6.9 Hz). |
| 390 | | HCl | ¹H-NMR (DMSO-d₆) δ: 12.72 (s, 1H), 7.44-7.42 (m, 2H), 7.21-7.17 (m, 2H), 4.62 (d, 1H, J = 5.6 Hz), 4.47 (s, 2H), 4.05 (dd, 1H, J = 13.9, 3.8 Hz), 3.57 (d, 1H, J = 13.3 Hz), 3.47-3.45 (m, 1H), 3.34 (dd, 1H, J = 9.3, 6.9 Hz), 2.94 (dd, 1H, J = 7.7, 3.6 Hz), 2.86 (dd, 1H, J = 9.3, 7.3 Hz), 1.55-1.38 (m, 2H), 0.94 (t, 3H, J = 7.0 Hz), 0.78 (t, 3H, J = 6.5 Hz), 0.42-0.36 (m, 1H), 0.34-0.27 (m, 2H), 0.24-0.20 (m, 1H). |
| 391 | | HCl | ¹H-NMR (DMSO-d₆) δ: 12.90 (s, 1H), 8.86 (s, 1H), 7.47-7.37 (m, 2H), 7.23-7.15 (m, 2H), 4.81-4.65 (m, 1H), 4.47 (s, 2H), 4.41 (d, 1H, J = 12.1 Hz), 4.25 (d, 1H, J = 12.1 Hz), 4.06 (d, 1H, J = 14.1 Hz), 3.81 (d, 1H, J = 14.1 Hz), 3.75-3.63 (m, 2H), 3.62-3.36 (m, 2H), 3.21 (s, 3H), 3.11-2.73 (m, 6H), 1.16 (d, 3H, J = 6.8 Hz), 1.10 (d, 3H, J = 6.8 Hz). |
| 392 | | HCl | ¹H-NMR (DMSO-d₆) δ: 13.04 (s, 1H), 8.69 (s, 1H), 7.46-7.38 (m, 2H), 7.23-7.14 (m, 2H), 4.76-4.62 (m, 1H), 4.48 (s, 2H), 4.18-4.04 (m, 1H), 3.98 (d, 1H, J = 13.5 Hz), 3.94-3.82 (m, 2H), 3.78 (d, 1H, J = 13.5 Hz), 3.70-3.57 (m, 1H), 2.50-2.22 (m, 2H), 2.15-2.00 (m, 2H), 1.16 (t, 6H, J = 6.8 Hz), 1.03 (t, 3H, J = 7.5 Hz). |

TABLE 1-105

| No. | structural formula | salt | ¹H-NMR |
|---|---|---|---|
| 393 | | HCl | ¹H-NMR (DMSO-d₆) δ: 8.80 (s, 1H), 8.16 (t, 1H, J = 5.5 Hz), 7.67 (s, 1 H), 7.38-7.28 (m, 2H), 7.19-7.10 (m, 2H), 4.76-4.63 (m, 1H), 4.20 (s, 2H), 4.17 (d, 1H, J = 11.9 Hz), 4.12 (d, 1H, J = 11.9 Hz), 4.03 (d, 1H, J = 13.9 Hz), 3.76 (d, 1H, J = 13.9 Hz), 3.40 (s, 3H), 3.21-2.92 (m, 2H), 1.13 (d, 3H, J = 6.8 Hz), 1.10 (d, 3H, J = 6.8 Hz), 0.99 (t, 3H, J = 7.5 Hz). |

TABLE 1-105-continued

| No. | structural formula | salt | ¹H-NMR |
|---|---|---|---|
| 394 | | HCl | ¹H-NMR (DMSO-$d_6$) δ: 8.88 (s, 1 H), 8.17 (t, 1H, J = 5.1 Hz), 7.66 (s, 1H), 7.37-7.29 (m, 2H), 7.19-7.10 (m, 2H), 4.76-4.64 (m, 1H), 4.33-4.16 (m, 2H), 4.20 (s, 2H), 4.04 (d, 1H, J = 13.9 Hz), 3.78 (d, 1H, J = 13.9 Hz), 3.72-3.66 (m, 2H), 3.57-3.50 (m, 2H), 3.25 (s, 3H), 3.20-2.96 (m, 2H), 1.14 (d, 3H, J = 6.8 Hz), 1.10 (d, 3H, J = 6.8 Hz), 1.04 (t, 3H, J = 7.3 Hz). |
| 395 | | HCl | ¹H-NMR (DMSO-$d_6$) δ: 12.50 (br s, 1H), 8.95 (s, 1H), 7.44-7.36 (m, 2H), 7.22-7.15 (m, 2H), 4.69 (dd, 1H, J = 14.0, 1.5 Hz), 4.47 (s, 2H), 4.39 (dd, 1H, J = 14.0, 4.2 Hz), 4.04-3.98 (m, 1H), 3.97-3.92 (m, 1H), 3.51-3.43 (m, 1H), 3.26-3.18 (m, 1H), 3.18 (s, 3H), 1.19 (t, 3H, J = 7.2 Hz), 1.10 (d, 3H, J = 6.2 Hz). |
| 396 | | HCl | ¹H-NMR (DMSO-$d_6$) δ: 12.92 (s, 1H), 8.77 (s, 1H), 7.47-7.37 (m, 2H), 7.23-7.14 (m, 2H), 4.79-4.66 (m, 1H), 4.47 (s, 2H), 4.28 (d, 1H, J = 11.9 Hz), 4.12 (d, 1H, J = 11.9 Hz), 4.06 (d, 1H, J = 14.3 Hz), 3.82 (d, 1H, J = 14.3 Hz), 3.47-3.29 (m, 5H), 3.05-2.78 (m, 3H), 1.16 (d, 3H, J = 7.1 Hz), 1.12 (d, 3H, J = 7.1 Hz), 1.08-0.97 (m, 3H). |
| 397 | | HCl | ¹H-NMR (DMSO-$d_6$) δ: 12.93 (s, 1H), 8.85 (s, 1H), 7.48-7.34 (m, 2H), 7.24-7.13 (m, 2H), 4.77-4.65 (m, 1H), 4.47 (s, 2H), 4.38 (d, 1H, J = 11.9 Hz), 4.23 (d, 1H, J = 11.9 Hz), 4.06 (d, 1H, J = 14.3 Hz), 3.82 (d, 1H, J = 14.3 Hz), 3.73-3.24 (m, 6H), 3.19 (s, 3H), 3.06-2.84 (m, 3H), 1.16 (d, 3H, J = 6.6 Hz), 1.12 (d, 3H, J = 6.6 Hz), 1.07-0.94 (m, 3H). |

TABLE 1-106

| No. | structural formula | salt | ¹H-NMR |
|---|---|---|---|
| 398 | | HCl | ¹H-NMR (DMSO-$d_6$) δ: 12.69 (br s, 1H), 8.78 (s, 1H), 7.44-7.36 (m, 2H), 7.22-7.14 (m, 2H), 4.84-4.79 (m, 1H), 4.47 (s, 2H), 4.46-4.37 (m, 1H), 4.22-4.13 (m, 2H), 4.01 (dd, 1H, J = 11.9, 2.2 Hz), 3.49-3.39 (m, 2H), 3.46 (s, 3H), 3.14 (s, 3H), 1.33 (d, 3H, J = 6.9 Hz), 1.30 (d, 3H, J = 6.9 Hz). |

TABLE 1-106-continued

| No. | structural formula | salt | ¹H-NMR |
|---|---|---|---|
| 399 | | HCl | ¹H-NMR (DMSO-$d_6$) δ: 12.75 (s, 1H), 8.73 (s, 1H), 7.47-7.39 (m, 2H), 7.23-7.15 (m, 2H), 4.60-4.52 (m, 1H), 4.47 (s, 2H), 4.06 (dd, 1H, J = 14.1, 4.0 Hz), 3.65-3.55 (m, 2H), 3.47-3.36 (m, 1H), 3.02-2.88 (m, 2H), 1.16 (d, 3H, J = 6.2 Hz), 0.94-0.82 (m, 3H), 0.79 (t, 3H, J = 7.3 Hz), 0.75-0.64 (m, 1H). |
| 400 | | HCl | ¹H-NMR (DMSO-$d_6$) δ: 12.83 (s, 1H), 8.72 (s, 1H), 7.47-7.39 (m, 2H), 7.24-7.15 (m, 2H), 4.84-4.71 (m, 1H), 4.60 (dd, 1H, J = 8.6, 2.6 Hz), 4.47 (s, 2H), 3.88 (dd, 1H, J = 14.3, 4.0 Hz), 3.75 (d, 1H, J = 13.9 Hz), 3.58-3.53 (m, 1H), 3.46-3.34 (m, 1H), 2.97-2.85 (m, 1H), 1.26-1.14 (m, 9H), 0.75 (t, 3H, J = 6.9 Hz). |
| 401 | | HCl | ¹H-NMR (DMSO-$d_6$) δ: 8.72 (s, 1H), 7.47-7.39 (m, 2H), 7.24-7.15 (m, 2H), 4.60-4.53 (m, 1H), 4.47 (s, 2H), 4.11 (dd, 1H, J = 14.1, 4.2 Hz), 3.75 (d, 1H, J = 13.5 Hz), 3.65-3.37 (m, 4H), 3.00-2.90 (m, 1H), 1.22 (d, 3H, J = 6.2 Hz), 1.16 (t, 3H, J = 7.1 Hz), 0.77 (t, 3H, J = 6.9 Hz). |
| 402 | | HCl | ¹H-NMR (DMSO-$d_6$) δ: 12.90 (s, 1H), 8.32 (s, 1H), 7.44-7.40 (m, 2H), 7.22-7.17 (m, 2H), 4.81-4.74 (m, 1H), 4.71 (t, 1H, J = 4.8 Hz), 4.47 (s, 2H), 3.87 (d, 1H, J = 12.5 Hz), 3.78 (dd, 1H, J = 13.9, 4.2 Hz), 3.71-3.65 (m, 1H), 3.57-3.50 (m, 1H), 3.17-3.10 (m, 1H), 1.19 (t, 6H, J = 7.0 Hz), 1.06 (d, 3H, J = 6.0 Hz), 1.02 (t, 3H, J = 6.9 Hz). |

TABLE 1-107

| No. | structural formula | salt | ¹H-NMR |
|---|---|---|---|
| 403 | 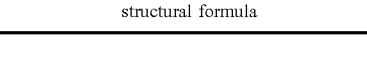 | HCl | ¹H-NMR (DMSO-$d_6$) δ: 12.80 (s, 1H), 8.91 (s, 1H), 7.43-7.39 (m, 2H), 7.21-7.16 (m, 2H), 4.69 (t, 1H, J = 4.6 Hz), 4.47 (s, 2H), 4.02 (dd, 1H, J = 14.1, 4.4 Hz), 3.84 (d, 1H, J = 13.7 Hz), 3.73-3.67 (m, 1H), 3.65-3.58 (m, 1H), 3.56-3.39 (m, 2H), 3.21-3.15 (m, 1H), 1.16 (t, 3H, J = 7.1 Hz), 1.07 (d, 3H, J = 6.0 Hz), 1.01 (t, 3H, J = 6.9 Hz). |

TABLE 1-107-continued

| No. | structural formula | salt | ¹H-NMR |
|---|---|---|---|
| 404 | | HCl | ¹H-NMR (DMSO-d₆) δ: 1.280 (s, 1H), 8.90 (s, 1H), 7.43-7.39 (m, 2H), 7.22-7.16 (m, 2H), 4.66 (t, 1H, J = 4.4 Hz), 4.47 (s, 2H), 3.98 (dd, 1H, J = 13.9, 4.2 Hz), 3.74-3.65 (m, 2H), 3.56-3.48 (m, 1H), 3.20-3.14 (m, 1H), 2.92-2.87 (m, 1H), 1.04 (d, 3H, J = 7.0 Hz), 1.02 (t, 3H, J = 7.2 Hz), 0.94-0.89 (m, 1H), 0.87-0.80 (m, 2H), 0.75-0.70 (m, 1H). |
| 405 | | HCl | ¹H-NMR (DMSO-d₆) δ: 12.77 (br s, 1H), 8.62 (s, 1H), 7.42-7.38 (m, 2H), 7.20-7.16 (m, 2H), 4.77-4.71 (m, 1H), 4.47 (s, 2H), 4.14 (q, 1H, J = 4.0 Hz), 3.92-3.84 (m, 1H), 3.59 (d, 2H, J = 4.4 Hz), 3.33-3.26 (m, 1H), 3.18 (s, 3H), 1.64 (d, 3H, J = 6.5 Hz), 1.21 (t, 3H, J = 7.1 Hz). |
| 406 | | HCl | ¹H-NMR (DMSO-d₆) δ: 12.44 (br s, 1H), 8.89 (s, 1H), 7.44-7.38 (m, 2H), 7.22-7.15 (m, 2H), 4.66-4.60 (m, 1H), 4.56-4.45 (m, 3H), 4.34-4.27 (m, 1H), 4.10-4.04 (m, 1H), 3.50-3.36 (m, 2H), 3.24 (s, 3H), 1.89-1.79 (m, 1H), 1.73-1.62 (m, 1H), 1.28 (d, 6H, J = 6.9 Hz). |
| 407 | | HCl | ¹H-NMR (DMSO-d₆) δ: 12.77 (br s, 1H), 8.88 (s, 1H), 7.44-7.37 (m, 2H), 7.22-7.15 (m, 2H), 4.71-4.66 (m, 1H), 4.62-4.52 (m, 1H), 4.47 (s, 2H), 4.21-4.07 (m, 2H), 3.99 (dd, 1H, J = 11.7, 2.0 Hz), 3.71-3.62 (m, 2H), 1.32-1.22 (m, 9H), 1.05(d, 3H, J = 6.4 Hz). |

TABLE 1-108

| No. | structural formula | salt | ¹H-NMR |
|---|---|---|---|
| 408 | 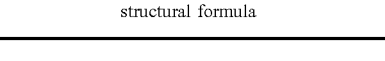 | HCl | ¹H-NMR (DMSO-d₆) δ: 12.73 (s, 1H), 8.72 (s, 1H), 7.44-7.40 (m, 2H), 7.22-7.16 (m, 2H), 4.64-4.55 (m, 1H), 4.47 (s, 2H), 4.06 (dd, 1H, J = 14.1, 4.2 Hz), 3.66-3.49 (m, 2H), 3.06 (s, 3H), 2.96-2.88 (m, 1H), 1.15 (d, 3H, J = 6.0 Hz), 0.96-0.78 (m, 3H), 0.75-0.63 (m, 1H). |

TABLE 1-108-continued

| No. | structural formula | salt | ¹H-NMR |
|---|---|---|---|
| 409 | | HCl | ¹H-NMR (DMSO-D₆) δ: 12.73 (br s, 1H), 8.71 (s, 1H), 7.47-7.39 (m, 2H), 7.24-7.15 (m, 2H), 4.66-4.56 (m, 1H), 4.47 (s, 2H), 4.11 (dd, 1H, J = 14.1, 4.2 Hz), 3.76 (d, 1H, J = 13.7 Hz), 3.66-3.42 (m, 3H), 3.06 (s, 3H), 1.21 (d, 3H, J = 5.7 Hz), 1.16 (t, 3H, J = 7.3 Hz). |
| 410 | | HCl | ¹H-NMR (DMSO-d₆) δ: 12.71 (br s, 1H), 8.71 (s, 1H), 7.47-7.39 (m, 2H), 7.24-7.15 (m, 2H), 4.65-4.57 (m, 1H), 4.47 (s, 2H), 4.10 (dd, 1H, J = 14.1, 4.0 Hz), 3.77 (d, 1H, J = 14.8 Hz), 3.59-3.38 (m, 3H), 3.05 (s, 3H), 1.60 (dt, 2H, J = 7.4, 7.4 Hz), 1.21 (d, 3H, J = 6.2 Hz), 0.90 (t, 3H, J = 7.4 Hz). |
| 411 | | HCl | ¹H-NMR (DMSO-d₆) δ: 12.67 (s, 1H), 8.83 (s, 1H), 7.45-7.37 (m, 2H), 7.23-7.14 (m, 2H), 4.81 (t, 1H, J = 6.3 Hz), 4.48 (s, 2H), 4.09-3.99 (m, 1H), 3.97-3.85 (m, 1H), 3.68 (dd, 1H, J = 10.6, 5.7 Hz), 3.55 (dd, 1H, J = 10.6, 7.6 Hz), 3.51-3.30 (m, 2H), 3.19-3.06 (m, 1H), 1.27 (d, 3H, J = 6.6 Hz), 1.17 (t, 3H, J = 6.8 Hz), 1.01 (t, 3H, J = 7.3 Hz). |
| 412 | | HCl | ¹H-NMR (DMSO-d₆) δ: 12.68 (br s, 1H), 8.83 (s, 1H), 7.46-7.37 (m, 2H), 7.23-7.15 (m, 2H), 4.85-4.76 (m, 1H), 4.67-4.57 (m, 1H), 4.48 (s, 2H), 4.20-4.10 (m, 1H), 3.64 (dd, 1H, J = 10.5, 5.8 Hz), 3.56-3.32 (m, 3H), 1.31-1.18 (m, 9H), 1.02 (t, 3H, J = 7.1 Hz). |

TABLE 1-109

| No. | structural formula | salt | ¹H-NMR |
|---|---|---|---|
| 413 | | HCl | ¹H-NMR (DMSO-d₆) δ: 12.70 (s, 1H), 8.87 (s, 1H), 7.43-7.40 (m, 2H), 7.21-7.16 (m, 2H), 4.69 (t, 1H, J = 4.4 Hz), 4.47 (s, 2H), 4.09-4.04 (m, 1H), 3.76 (d, 1H, J = 12.9 Hz), 3.66-3.60 (m, 1H), 3.23 (s, 3H), 3.07 (s, 3H), 1.04 (d, 3H, J = 6.4 Hz). |

TABLE 1-109-continued

| No. | structural formula | salt | ¹H-NMR |
|---|---|---|---|
| 414 | | HCl | ¹H-NMR (DMSO-d$_6$) δ: 12.76 (s, 1H), 8.90 (s, 1H), 7.44-7.39 (m, 2H), 7.21-7.17 (m, 2H), 4.69 (t, 1H, J = 4.4 Hz), 4.47 (s, 2H), 4.05-4.00 (m, 1H), 3.83 (d, 1H, J = 13.3 Hz), 3.67-3.59 (m, 2H), 3.45-3.39 (m, 1H), 3.23 (s, 3H), 1.16 (t, 3H, J = 7.1 Hz), 1.04 (d, 3H, J = 6.0 Hz). |
| 415 | | HCl | ¹H-NMR (DMSO-d$_6$) δ: 12.75 (s, 1H), 8.89 (s, 1H), 7.43-7.40 (m, 2H), 7.21-7.16 (m, 2H), 4.66 (t, 1H, J = 4.6 Hz), 4.47 (s, 2H), 3.98 (dd, 1H, J = 13.7, 4.0 Hz), 3.71 (d, 1H, J = 12.5 Hz), 3.59-3.53 (m, 1H), 3.22 (s, 3H), 2.94-2.88 (m, 1H), 1.02 (d, 3H, J = 6.0 Hz), 0.95-0.89 (m, 1H), 0.85-0.80 (m, 2H), 0.75-0.69 (m, 1H). |
| 416 | | HCl | ¹H-NMR (DMSO-d$_6$) δ: 12.75 (s, 1H), 8.90 (s, 1H), 7.43-7.40 (m, 2H), 7.21-7.16 (m, 2H), 4.69 (t, 1H, J = 4.8 Hz), 4.47 (s, 2H), 4.01 (dd, 1H, J = 13.9, 4.2 Hz), 3.83 (d, 1H, J = 12.9 Hz), 3.64-3.58 (m, 1H), 3.55-3.48 (m, 1H), 3.41-3.34 (m, 1H), 3.21 (s, 3H), 1.63-1.58 (m, 2H), 1.05 (d, 3H, J = 6.0 Hz), 0.91 (t, 3H, J = 7.3 Hz). |
| 417 | | HCl | ¹H-NMR (DMSO-d$_6$) δ: 8.86 (s, 1H), 7.44-7.35 (m, 2H), 7.19-7.09 (m, 2H), 4.86-4.68 (m, 2H), 4.45 (s, 2H), 3.90-3.80 (m, 1H), 3.76-3.67 (m, 1H), 3.46-2.59 (m, 3H), 2.14-1.65 (m, 5H), 1.24 (d, 3H, J = 7.1 Hz), 1.19 (d, 3H, J = 7.1 Hz), 1.14-0.98 (m, 6H). |

TABLE 1-110

| No. | structural formula | salt | ¹H-NMR |
|---|---|---|---|
| 418 | | HCl | ¹H-NMR (DMSO-d$_6$) δ: 8.84 (s, 1H), 7.46-7.36 (m, 2H), 7.23-7.14 (m, 2H), 5.21-5.10 (m, 1H), 4.86-4.73 (m, 1H), 4.47 (s, 2H), 3.84 (d, 2H, J = 2.2 Hz), 3.37-3.11 (m, 4H), 2.87 (d, 2H, J = 7.1 Hz), 1.13 (t, 6H, J = 7.3 Hz), 0.99 (t, 3H, J = 7.1 Hz), 0.96 (t, 3H, J = 7.1 Hz). |

TABLE 1-110-continued

| No. | structural formula | salt | ¹H-NMR |
|---|---|---|---|
| 419 | | HCl | ¹H-NMR (DMSO-d₆) δ: 8.73 (s, 1H), 7.47-7.38 (m, 2H), 7.23-7.15 (m, 2H), 4.89-4.76 (m, 1H), 4.47 (s, 2H), 4.20-3.99 (m, 2H), 3.72-3.57 (m, 2H), 3.51-3.32 (m, 2H), 3.18 (s, 3H), 2.14-1.83 (m, 2H), 1.16 (t, 3H, J = 7.3 Hz). |
| 420 | | HCl | ¹H-NMR (DMSO-d₆) δ: 12.75 (br s, 1H), 8.64 (s, 1H), 7.46-7.39 (m, 2H), 7.22-7.15 (m, 2H), 4.77-4.71 (m, 1H), 4.47 (s, 2H), 4.11 (dd, 1H, J = 13.7, 4.0 Hz), 3.77-3.71 (m, 1H), 3.64-3.44 (m, 5H), 3.33 (s, 3H), 3.10 (s, 3H), 1.20-1.13 (m, 3H). |
| 421 | | HCl | ¹H-NMR (DMSO-d₆) δ: 12.77 (br s, 1H), 8.61 (s, 1H), 7.46-7.34 (m, 2H), 7.24-7.14 (m, 2H), 4.81-4.69 (m, 1H), 4.47 (s, 2H), 4.15-4.08 (m, 1H), 3.90 (td, 1H, J = 13.9, 7.0 Hz), 3.64 (d, 2H, J = 4.2 Hz), 3.38-3.21 (m, 3H), 1.65 (d, 3H, J = 7.0 Hz), 1.22 (t, 3H, J = 7.3 Hz), 0.89 (t, 3H, J = 6.8 Hz). |
| 422 | | HCl | ¹H-NMR (DMSO-d₆) δ: 12.72 (br s, 1H), 8.55 (s, 1H), 7.45-7.36 (m, 2H), 7.23-7.14 (m, 2H), 4.72-4.61 (m, 1H), 4.49-4.38 (m, 1H), 4.47 (s, 2H), 4.09-4.02 (m, 1H), 3.61 (dd, 1H, J = 11.1, 3.0 Hz), 3.54 (dd, 1H, J = 11.1, 3.9 Hz), 3.27 (q, 2H, J = 7.0 Hz), 1.75 (d, 3H, J = 6.6 Hz), 1.32 (t, 6H, J = 6.8 Hz), 0.82 (t, 3H, J = 7.0 Hz). |

TABLE 1-111

| No. | structural formula | salt | ¹H-NMR |
|---|---|---|---|
| 423 | | HCl | ¹H-NMR (DMSO-d₆) δ: 8.83 (s, 1H), 7.44-7.35 (m, 2H), 7.18-7.09 (m, 2H), 4.84-4.66 (m, 2H), 4.45 (s, 2H), 3.90-3.79 (m, 1H), 3.77-3.64 (m, 1H), 3.48-2.60 (m, 4H), 2.33-2.17 (m, 2H), 2.08-1.77 (m, 2H), 1.24 (d, 3H, J = 6.4 Hz), 1.19 (d, 3H, J = 6.6 Hz), 1.12-1.00 (m, 3H), 0.97 (t, 3H, J = 7.7 Hz). |

TABLE 1-111-continued

| No. | structural formula | salt | ¹H-NMR |
|---|---|---|---|
| 424 | | HCl | ¹H-NMR (DMSO-d$_6$) δ: 9.02 (s, 0.25H), 8.94 (s, 0.75H), 7.46-7.36 (m, 2H), 7.23-7.14 (m, 2H), 4.95-4.66 (br m, 2H), 4.47 (s, 2H), 3.92-3.67 (m, 2H), 3.53-2.98 (br m, 4H), 2.87-2.53 (br m, 1H), 2.14-1.63 (br m, 2H), 1.29-0.86 (br m, 15H). |
| 425 | | HCl | ¹H-NMR (DMSO-d$_6$) δ: 8.86 (s, 1H), 7.44-7.35 (m, 2H), 7.19-7.08 (m, 2H), 4.85-4.69 (m, 2H), 4.45 (s, 2H), 4.22-3.98 (m, 2H), 3.90-3.80 (m, 1H), 3.78-3.68 (m, 1H), 3.13-3.00 (m, 1H), 2.35-2.15 (m, 2H), 2.09-1.93 (m, 1H), 1.87-1.71 (m, 1H), 1.24 (d, 3H, J = 6.6 Hz), 1.19 (d, 3H, J = 6.8 Hz), 1.07 (t, 6H, J = 6.4 Hz), 0.96 (t, 3H, J = 7.3 Hz). |
| 426 | | HCl | ¹H-NMR (DMSO-d$_6$) δ: 12.49 (s, 1H), 8.91 (s, 1H), 7.42-7.39 (m, 2H), 7.20-7.16 (m, 2H), 4.80 (d, 1H, J = 13.3 Hz), 4.47 (s, 2H), 4.36 (dd, 1H, J = 13.7, 4.8 Hz), 3.96-3.89 (m, 2H), 3.65-3.60 (m, 1H), 3.28-3.20 (m, 1H), 3.08 (s, 3H), 1.21 (t, 3H, J = 7.1 Hz), 1.16 (d, 3H, J = 6.4 Hz). |
| 427 | | HCl | ¹H-NMR (DMSO-d$_6$) δ: 8.65 (s, 1H), 7.44-7.39 (m, 2H), 7.22-7.16 (m, 2H), 4.88-4.84 (m, 1H), 4.46 (s, 2H), 4.08 (dd, 1H, J = 13.5, 3.8 Hz), 3.65-3.62 (m, 1H), 3.62 (dq, 1H, J = 13.7, 7.3 Hz), 3.45 (dq, 1H, J = 13.7, 7.3 Hz), 3.21 (s, 3H), 3.02-2.97 (m, 1H), 1.93-1.78 (m, 2H), 1.16 (t, 3H, J = 7.3 Hz), 1.04 (d, 3H, J = 6.0 Hz). |

TABLE 1-112

| No. | structural formula | salt | ¹H-NMR |
|---|---|---|---|
| 428 | 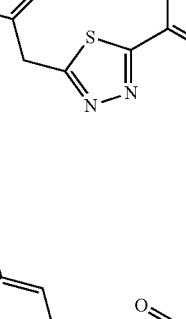 | HCl | ¹H-NMR (DMSO-d$_6$) δ: 12.80 (s, 1H), 8.64 (s, 1H), 7.44-7.40 (m, 2H), 7.21-7.17 (m, 2H), 4.91-4.87 (m, 1H), 4.78 (sep, 1H, J = 6.8 Hz), 4.46 (s, 2H), 3.84 (dd, 1H, J = 13.5, 3.6 Hz), 3.68 (dd, 1H, J = 13.5, 1.3 Hz), 3.22 (s, 3H), 2.99-2.95 (m, 1H), 1.86 (ddd, 1H, J = 14.6, 9.9, 3.1 Hz), 1.77 (ddd, 1H, J = 14.6, 10.4, 4.9 Hz), 1.18 (d, 3H, J = 6.8 Hz), 1.15 (d, 3H, J = 6.8 Hz), 1.04 (d, 3H, J = 6.0 Hz). |
| 429 | 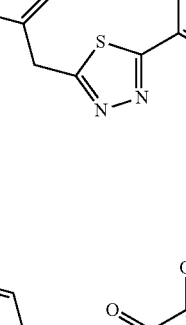 | HCl | ¹H-NMR (DMSO-d$_6$) δ: 12.77 (br s, 1H), 8.65 (s, 1H), 7.44-7.40 (m, 2H), 7.21-7.16 (m, 2H), 4.85-4.80 (m, 1H), 4.46 (s, 2H), 4.02 (dd, 1H, J = 13.2, 3.7 Hz), 3.54 (dd, 1H, J = 13.2, 0.9 Hz), 3.21 (s, 3H), 3.03-2.96 (m, 1H), 2.97-2.91 (m, 1H), 1.85-1.75 (m, 2H), 1.03 (d, 3H, J = 6.0 Hz), 0.95-0.72 (m, 4H). |
| 430 | 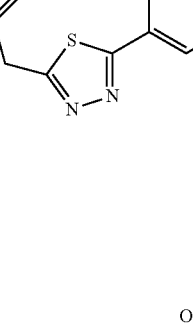 | HCl | ¹H-NMR (DMSO-d$_6$) δ: 12.48 (br s, 1H), 8.95 (s, 1H), 7.45-7.37 (m, 2H), 7.23-7.14 (m, 2H), 5.01-4.90 (m, 1H), 4.56 (sep, 1H, J = 6.8 Hz), 4.48 (s, 2H), 4.08-4.01 (m, 1H), 3.55 (dd, 1H, J = 10.5, 3.9 Hz), 3.45-3.31 (m, 3H), 1.40 (d, 3H, J = 6.6 Hz), 1.29 (d, 3H, J = 6.8 Hz), 1.28 (d, 3H, J = 6.8 Hz), 0.98 (t, 3H, J = 6.9 Hz). |
| 431 | 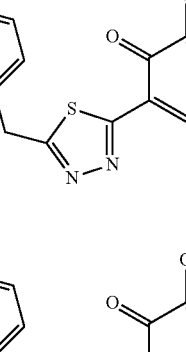 | HCl | ¹H-NMR (DMSO-d$_6$) δ: 12.50 (br s, 1H), 8.93 (s, 1H), 7.45-7.36 (m, 2H), 7.23-7.14 (m, 2H), 4.92 (q, 1H, J = 6.7 Hz), 4.48 (s, 2H), 4.04-3.96 (m, 2H), 3.59-3.47 (m, 2H), 3.44-3.31 (m, 2H), 3.22-3.09 (m, 1H), 1.42 (d, 3H, J = 6.7 Hz), 1.20 (t, 3H, J = 7.1 Hz), 0.97 (t, 3H, J = 6.9 Hz). |
| 432 | 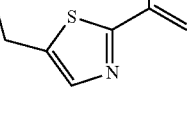 | HCl | ¹H-NMR (DMSO-d$_6$) δ: 8.80-8.74 (m, 1H), 7.68 (s, 1H), 7.38-7.29 (m, 2H), 7.20-7.10 (m, 2H), 4.97-4.55 (m, 2H), 4.20 (s, 2H), 3.92-3.60 (m, 2H), 2.93 (s, 2H), 2.72 (s, 1H), 2.08-1.59 (m, 5H), 1.22 (d, 3H, J = 7.1 Hz), 1.16 (d, 3H, J = 6.4 Hz). |

TABLE 1-113

| No. | structural formula | salt | ¹H-NMR |
|---|---|---|---|
| 433 | | HCl | ¹H-NMR (DMSO-d₆) δ: 8.66 (s, 1H), 7.61 (s, 1H), 7.36-7.27 (m, 2H), 7.16-7.04 (m, 2H), 4.84-4.56 (m, 2H), 4.19 (s, 2H), 3.88-3.76 (m, 1H), 3.75-3.63 (m, 1H), 3.52-3.14 (m, 2H), 3.03-2.70 (m, 3H), 2.33-2.17 (m, 2H), 2.06-1.76 (m, 2H), 1.24 (d, 3H, J = 6.6 Hz), 1.19 (d, 3H, J = 6.6 Hz), 0.96 (t, 3H, J = 7.5 Hz). |
| 434 | | HCl | ¹H-NMR (DMSO-d₆) δ: 12.63 (br s, 1H), 8.73 (s, 1H), 7.44-7.41 (m, 2H), 7.21-7.17 (m, 2H), 4.60-4.55 (m, 1H), 4.47 (s, 2H), 4.05 (dd, 1H, J = 13.9, 3.4 Hz), 3.78 (dd, 1H, J = 13.9, 1.1 Hz), 3.63 (dq, 1H, J = 13.5, 7.1 Hz), 3.48 (dq, 1H, J = 13.5, 7.1 Hz), 3.18 (dd, 1H, J = 9.9, 4.2 Hz), 3.02 (s, 3H), 2.88 (dd, 1H, J = 9.9, 3.4 Hz), 2.11-2.04 (m, 1H), 1.16 (t, 3H, J = 7.1 Hz), 1.07 (d, 3H, J = 6.8 Hz). |
| 435 | | HCl | ¹H-NMR (DMSO-d₆) δ: 12.71 (br s, 1H), 8.75 (s, 1H), 7.44-7.41 (m, 2H), 7.22-7.17 (m, 2H), 4.79 (sep, 1H, J = 6.8 Hz), 4.60-4.57 (m, 1H), 4.46 (s, 2H), 3.82 (dd, 1H, J = 14.3, 3.5 Hz), 3.77 (dd, 1H, J = 14.3, 1.3 Hz), 3.16 (dd, 1H, J = 9.9, 4.1 Hz), 2.99 (s, 3H), 2.83 (dd, 1H, J = 9.9, 3.3 Hz), 2.06-2.02 (m, 1H), 1.20 (d, 3H, J = 6.8 Hz), 1.19 (d, 3H, J = 6.8 Hz), 1.08 (d, 3H, J = 6.8 Hz). |
| 436 | | HCl | ¹H-NMR (DMSO-d₆) δ: 12.64 (br s, 1H), 8.73 (s, 1H), 7.44-7.40 (m, 2H), 7.21-7.17 (m, 2H), 4.57-4.54 (m, 1H), 4.46 (s, 2H), 4.01 (dd, 1H, J = 13.7, 3.6 Hz), 3.61 (dd, 1H, J = 13.7, 1.2 Hz), 3.17 (dd, 1H, J = 9.9, 4.4 Hz), 3.02 (s, 3H), 2.98-2.92 (m, 1H), 2.88 (dd, 1H, J = 9.9, 3.4 Hz), 2.07-1.99 (m, 1H), 1.03 (d, 3H, J = 6.9 Hz), 0.93-0.81 (m, 3H), 0.72-0.65 (m, 1H). |
| 437 | | HCl | ¹H-NMR (DMSO-d₆) δ: 12.83 (br s, 1H), 8.65 (s, 1H), 7.46-7.40 (m, 2H), 7.22-7.16 (m, 2H), 4.83-4.71 (m, 2H), 4.47 (s, 2H), 3.93-3.86 (m, 1H), 3.79-3.73 (m, 1H), 3.60-3.47 (m, 3H), 3.33 (s, 3H), 3.08 (s, 3H), 1.22 (d, 3H, J = 6.9 Hz), 1.18 (d, 3H, J = 6.9 Hz). |

TABLE 1-114

| No. | structural formula | salt | ¹H-NMR |
|---|---|---|---|
| 438 | (structure) | HCl | ¹H-NMR (DMSO-d₆) δ: 12.74 (br s, 1H), 8.64 (s, 1H), 7.46-7.39 (m, 2H), 7.22-7.15 (m, 2H), 4.76-4.70 (m, 1H), 4.47 (s, 2H), 4.10-4.02 (m, 1H), 3.67-3.60 (m, 1H), 3.60-3.53 (m, 1H), 3.48 (dd, 1H, J = 10.9, 4.0 Hz), 3.43 (dd, 1H, J = 10.9, 5.2 Hz), 3.32 (s, 3H), 3.10 (s, 3H), 2.96-2.88 (m, 1H), 0.95-0.73 (m, 4H). |
| 439 | (structure) | HCl | ¹H-NMR (DMSO-d₆) δ: 12.46 (br s, 1H), 8.87 (s, 1H), 7.45-7.36 (m, 2H), 7.23-7.14 (m, 2H), 4.65-4.56 (m, 1H), 4.47 (s, 2H), 4.38 (dd, 1H, J = 13.7, 3.6 Hz), 4.07-3.98 (m, 1H), 3.91 (td, 1H, J = 13.9, 7.1 Hz), 3.48-3.33 (m, 2H), 3.23 (s, 3H), 3.11 (td, 1H, J = 13.9, 7.1 Hz), 1.91-1.79 (m, 1H), 1.79-1.67 (m, 1H), 1.20 (t, 3H, J = 7.1 Hz). |
| 440 | (structure) racemate, containing two kinds of diatereomers of Example No. 441 | HCl | ¹H-NMR (DMSO-d₆) δ: 12.63 (s, 1H), 8.76 (s, 1H), 7.44-7.40 (m, 2H), 7.21-7.16 (m, 2H), 4.66 (dd, 1H, J = 9.7, 4.4 Hz), 4.47 (s, 2H), 3.97 (dd, 1H, J = 13.9, 6.2 Hz), 3.92-3.86 (m, 1H), 3.41-3.36 (m, 1H), 3.17-3.10 (m, 5H), 2.08-2.01 (m, 1H), 1.87-1.80 (m, 1H), 1.24 (d, 3H, J = 6.4 Hz), 1.19 (t, 3H, J = 7.1 Hz). |
| 441 | (structure) racemate, containing two kinds of diatereomers of Example No. 440 | HCl | ¹H-NMR (DMSO-d₆) δ: 12.77 (s, 1H), 8.64 (s, 1H), 7.44-7.40 (m, 2H), 7.22-7.17 (m, 2H), 4.71-4.67 (m, 1H), 4.47 (s, 2H), 4.33-4.27 (m, 1H), 3.76 (td, 1H, J = 14.1, 7.1 Hz), 3.43-3.36 (m, 2H), 3.15 (s, 3H), 3.12-3.05 (m, 1H), 2.09-2.02 (m, 1H), 1.94-1.84 (m, 1H), 1.33 (d, 3H, J = 5.2 Hz), 1.14 (t, 3H, J = 7.1 Hz). |

TABLE 1-114-continued

| No. | structural formula | salt | ¹H-NMR |
|---|---|---|---|
| 442 | 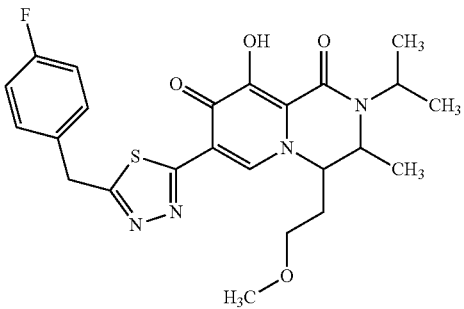 racemate, containing two kinds of diatereomers of Example No. 443 | HCl | ¹H-NMR (DMSO-$d_6$) δ: 12.65 (s, 1H), 8.75 (s, 1H), 7.43-7.40 (m, 2H), 7.21-7.17 (m, 2H), 4.67-4.58 (m, 2H), 4.47 (s, 2H), 4.10-4.04 (m, 1H), 3.42-3.37 (m, 1H), 3.17 (s, 3H), 3.15-3.09 (m, 1H), 2.05-1.97 (m, 1H), 1.82-1.75 (m, 1H), 1.28-1.23 (m, 9H). |

TABLE 1-115

| No. | structural formula | salt | ¹H-NMR |
|---|---|---|---|
| 443 | 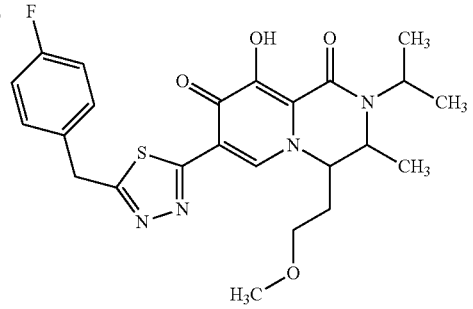 racemate, containing two kinds of diatereomers of Example No. 442 | HCl | ¹H-NMR (DMSO-$d_6$) δ: 12.76 (s, 1H), 8.65 (s, 1H), 7.42-7.39 (m, 2H), 7.20-7.16 (m, 2H), 4.56-4.51 (m, 2H), 4.47 (s, 2H), 4.09-.403 (m, 1H), 3.63-3.54 (m, 2H), 3.31 (s, 3H), 2.50-2.48 (m, 1H), 2.12-2.06 (m, 1H), 1.30 (d, 3H, J = 7.0 Hz), 1.28 (d, 3H, J = 7.0 Hz), 1.09 (d, 3H, J = 6.0 Hz). |
| 444 | 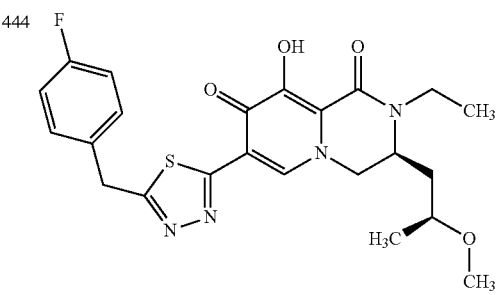 | HCl | ¹H-NMR (DMSO-$d_6$) δ: 12.48 (br s, 1H), 8.80 (s, 1H), 7.43-7.38 (m, 2H), 7.21-7.16 (m, 2H), 4.55 (dd, 1H, J = 13.2, 1.5 Hz), 4.47 (s, 2H), 4.38 (dd, 1H, J = 13.2, 3.5 Hz), 4.08-4.04 (m, 1H), 3.98 (dq, 1H, J = 13.5, 7.1 Hz), 3.42-3.37 (m, 1H), 3.20 (s, 3H), 3.06 (dq, 1H, J = 13.5, 7.1 Hz), 1.71-1.59 (m, 2H), 1.20 (t, 3H, J = 7.1 Hz), 1.06 (d, 3H, J = 6.2 Hz). |
| 445 | 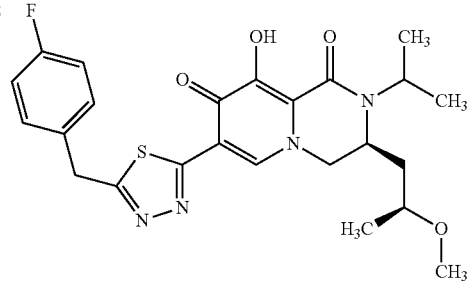 [SMILES: CO[C@@H](C)C[C@H]1Cn2cc(-c3nnc(Cc4ccc(F)cc4)s3)c(=O)c(O)c2C(=O)N1C(C)C] | HCl | ¹H-NMR (DMSO-$d_6$) δ: 8.81 (s, 1H), 7.44-7.39 (m, 2H), 7.21-7.16 (m, 2H), 4.57 (dd, 1H, J = 13.2, 1.3 Hz), 4.47 (s, 2H), 4.45 (sep, 1H, J = 6.8 Hz), 4.31 (dd, 1H, J = 13.2, 3.3 Hz), 4.11-4.06 (m, 1H), 3.50-3.45 (m, 1H), 3.19 (s, 3H), 1.68-1.57 (m, 2H), 1.31 (d, 3H, J = 6.8 Hz), 1.28 (d, 3H, J = 6.8 Hz), 1.08 (d, 3H, J = 6.2 Hz). |

TABLE 1-115-continued

| No. | structural formula | salt | ¹H-NMR |
|---|---|---|---|
| 446 | 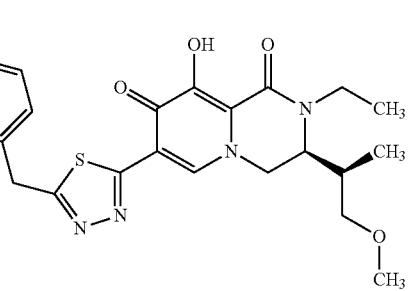 | HCl | ¹H-NMR (DMSO-d₆) δ: 12.80 (br s, 1H), 8.75 (s, 1H), 7.45-7.39 (m, 2H), 7.22-7.16 (m, 2H), 4.86-4.75 (m, 2H), 4.47 (s, 2H), 3.86-3.80 (m, 1H), 3.76 (dd, 1H, J = 13.3, 3.6 Hz), 3.61 (dd, 1H, J = 11.7, 2.8 Hz), 3.58-3.51 (m, 1H), 3.30 (s, 3H), 3.18 (s, 3H), 2.97 (dd, 1H, J = 11.7, 2.8 Hz), 1.20 (d, 3H, J = 6.9 Hz), 1.17 (d, 3H, J = 6.9 Hz). |
| 447 | | HCl | ¹H-NMR (DMSO-d₆) δ: 12.47 (br s, 1H), 8.99 (s, 1H), 7.44-73.8 (m, 2H), 7.22-7.15 (m, 2H), 4.73 (d, 1H, J = 13.7 Hz), 4.47 (s, 2H), 4.34 (dd, 1H, J = 13.7, 4.4 Hz), 4.23-4.14 (m, 1H), 4.05-4.00 (m, 1H), 3.46 (dd, 1H, J = 9.7, 8.1 Hz), 3.37 (dd, 1H, J = 9.7, 5.2 Hz), 3.30 (s, 3H), 2.22-2.11 (m, 1H), 1.38 (d, 3H, J = 6.9 Hz), 1.34 (d, 3H, J = 6.9 Hz), 0.60 (d, 3H, J = 7.3 Hz). |

TABLE 1-116

| No. | structural formula | salt | ¹H-NMR |
|---|---|---|---|
| 448 | | HCl | ¹H-NMR (DMSO-d₆) δ: 12.42 (br s, 1H), 9.00 (s, 1H), 7.44-7.37 (m, 2H), 7.22-7.14 (m, 2H), 4.76-4.68 (m, 1H), 4.47 (s, 2H), 4.37 (dd, 1H, J = 14.1, 4.0 Hz), 4.07-3.96 (m, 1H), 3.93-3.86 (m, 1H), 3.38-3.28 (m, 2H), 3.26 (s, 3H), 3.11-2.99 (m, 1H), 2.05-1.95 (m, 1H), 1.19 (t, 3H, J = 7.1 Hz), 0.81 (d, 3H, J = 6.9 Hz). |
| 449 | 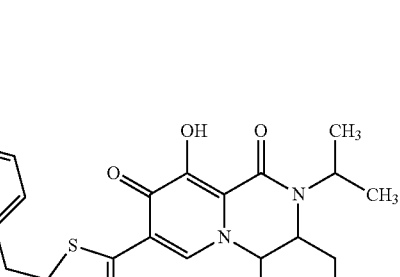 | HCl | ¹H-NMR (DMSO-d₆) δ: 12.50 (s, 1H), 8.57 (s, 1H), 7.43-7.38 (m, 2H), 7.21-7.16 (m, 2H), 4.66-4.59 (m, 1H), 4.47 (s, 2H), 4.30-4.24 (m, 1H), 4.01-3.96 (m, 1H), 3.33-3.24 (m, 2H), 3.11 (s, 3H), 1.92-1.86 (m, 1H), 1.70 (d, 3H, J = 6.4 Hz), 1.66-1.59 (m, 1H), 1.38 (d, 3H, J = 6.9 Hz), 1.33 (d, 3H, J = 6.9 Hz). | racemate, containing two kinds of diatereomers of Example No. 451

TABLE 1-116-continued

| No. | structural formula | salt | ¹H-NMR |
|---|---|---|---|
| 450 | [structure: 4-fluorobenzyl-thiadiazolyl pyrido-pyrazinone with N-ethyl and methyl, methoxyethyl substituents] racemate, containing two kinds of diatereomers of Example No. 452 | HCl | ¹H-NMR (DMSO-$d_6$) δ: 12.52 (s, 1H), 8.93 (s, 1H), 7.43-7.38 (m, 2H), 7.21-7.16 (m, 2H), 4.88-4.84 (m, 1H), 4.48 (s, 2H), 4.08-4.02 (m, 1H), 3.83 (t, 1H, J = 7.1 Hz), 3.44-3.37 (m, 2H), 3.23 (s, 3H), 3.04-2.96 (m, 1H), 1.85-1.73 (m, 2H), 1.41 (d, 3H, J = 6.9 Hz), 1.19 (t, 3H, J = 7.0 Hz). |
| 451 | [structure: 4-fluorobenzyl-thiadiazolyl pyrido-pyrazinone with N-isopropyl and methyl, methoxyethyl substituents] racemate, containing two kinds of diatereomers of Example No. 449 | HCl | ¹H-NMR (DMSO-$d_6$) δ: 12.50 (s, 1H), 8.95 (s, 1H), 7.42-7.38 (m, 2H), 7.21-7.16 (m, 2H), 4.91 (dd, 1H, J = 12.7, 5.8 Hz), 4.61-4.54 (m, 1H), 4.48 (s, 2H), 3.88 (d, 1H, J = 8.9 Hz), 3.50-3.39 (m, 2H), 3.24 (s, 3H), 1.91-1.85 (m, 1H), 1.69-1.61 (m, 1H), 1.39 (d, 3H, J = 6.9 Hz), 1.28 (d, 3H, J = 6.4 Hz), 1.26 (d, 3H, J = 6.4 Hz). |
| 452 | [structure: 4-fluorobenzyl-thiadiazolyl pyrido-pyrazinone with N-ethyl and methyl, methoxyethyl substituents] racemate, containing two kinds of diatereomers of Example No. 450 | HCl | ¹H-NMR (DMSO-$d_6$) δ: 12.70 (s, 1H), 8.65 (s, 1H), 7.42-7.38 (m, 2H), 7.22-7.15 (m, 2H), 4.75-4.70 (m, 1H), 4.47 (s, 2H), 4.08-3.96 (m, 2H), 3.37-3.31 (m, 2H), 3.20 (s, 3H), 3.15-3.07 (m, 1H), 1.94-1.87 (m, 1H), 1.68-1.58 (m, 4H), 1.20 (t, 3H, J = 7.1 Hz). |

TABLE 1-117

| No. | structural formula | salt | ¹H-NMR |
|---|---|---|---|
| 453 | [structure: 4-fluorobenzyl-thiadiazolyl pyrido-pyrazinone with N-isopropyl and (S)-methoxypropyl substituent] | HCl | ¹H-NMR (DMSO-$d_6$) δ: 12.72 (br s, 1H), 8.81 (s, 1H), 7.45-7.39 (m, 2H), 7.23-7.15 (m, 2H), 4.95-4.88 (m, 1H), 4.78 (sep, 1H, J = 6.9 Hz), 4.47 (s, 2H), 3.81 (dd, 1H, J = 13.5, 3.4 Hz), 3.74-3.65 (m, 1H), 3.58-3.48 (m, 1H), 3.03 (s, 3H), 1.88-1.80 (m, 1H), 1.78-1.68 (m, 1H), 1.19 (d, 3H, J = 6.9 Hz), 1.16 (d, 3H, J = 6.9 Hz), 1.07 (d, 3H, J = 6.0 Hz). |

TABLE 1-117-continued

| No. | structural formula | salt | ¹H-NMR |
|---|---|---|---|
| 454 | | HCl | ¹H-NMR (DMSO-d₆) δ: 12.67 (br s, 1H), 8.82 (s, 1H), 7.45-7.38 (m, 2H), 7.23-7.14 (m, 2H), 4.93-4.83 (m, 1H), 4.47 (s, 2H), 4.05 (dd, 1H, J = 13.5, 3.8 Hz), 3.71-3.42 (m, 4H), 3.05 (s, 3H), 1.95-1.86 (m, 1H), 1.82-1.71 (m, 1H), 1.16 (t, 3H, J = 7.1 Hz), 1.09 (d, 3H, J = 6.0 Hz). |
| 455 | | HCl | ¹H-NMR (DMSO-d₆) δ: 8.62 (s, 1H), 7.43-7.40 (m, 2H), 7.21-7.16 (m, 2H), 4.88-4.83 (m, 1H), 4.46 (s, 2H), 3.98 (dd, 1H, J = 13.3, 3.6 Hz), 3.53 (dd, 1H, J = 13.3, 1.8 Hz), 3.52-3.46 (m, 1H), 3.02 (s, 3H), 2.98-2.93 (m, 1H), 1.86 (ddd, 1H, J = 14.3, 6.2, 2.6 Hz), 1.71 (ddd, 1H, J = 14.3, 8.8, 7.9 Hz), 1.08 (d, 3H, J = 6.0 Hz), 0.94-0.79 (m, 3H), 0.75-0.70 (m, 1H). |
| 456 diatereomer of Example No. 463 | | HCl | ¹H-NMR (DMSO-d₆) δ: 8.66 (s, 0.7H), 8.50 (s, 0.3H), 7.70-7.64 (m, 1.0H), 7.37-7.30 (m, 2.0H), 7.19-7.11 (m, 2.0H), 4.70-4.62 (m, 0.3H), 4.59-4.51 (m, 0.7H), 4.44-4.34 (m, 0.7H), 4.20 (s, 2.0H), 4.08-3.99 (m, 1.0H), 3.80-3.70 (m, 0.3H), 3.69-3.47 (m, 3.0H), 2.80 (s, 2.1H), 2.69 (s, 0.9H), 2.12-1.86 (m, 4.3H), 1.83-1.73 (m, 0.7H), 1.22-1.12 (m, 3.0H), 1.05(d, 0.9H, J = 6.4 Hz), 1.00 (d, 2.1H, J = 6.4 Hz). |
| 457 | | HCl | ¹H-NMR (DMSO-d₆) δ: 12.80 (br s, 1H), 8.82 (s, 1H), 7.44-7.39 (m, 2H), 7.21-7.16 (m, 2H), 4.77 (sep, 1H, J = 6.9 Hz), 4.69-4.65 (m, 1H), 4.47 (s, 2H), 3.86 (d, 2H, J = 2.8 Hz), 3.37 (d, 2H, J = 5.2 Hz), 3.28 (s, 3H), 2.22-2.15 (m, 1H), 1.21 (d, 3H, J = 6.9 Hz), 1.18 (d, 3H, J = 6.9 Hz), 0.66 (d, 3H, J = 6.9 Hz). |

TABLE 1-118

| No. | structural formula | salt | ¹H-NMR |
|---|---|---|---|
| 458 | (structure shown) | HCl | ¹H-NMR (DMSO-d$_6$) δ: 8.63 (s, 0.67H), 8.46 (s, 0.33H), 7.71-7.61 (m, 1H), 7.39-7.28 (m, 2H), 7.21-7.10 (m, 2H), 4.67-4.31 (m, 2H), 4.26-4.16 (m, 2H), 4.07-3.42 (br m, 2H), 3.03-2.56 (br m, 4H), 2.14-1.59 (m, 5H), 1.28-0.60 (m, 7H). |
| 459 | (structure shown) diatereomer of Example No. 460 | HCl | ¹H-NMR (DMSO-d$_6$) δ: 9.18-8.08 (m, 1H), 7.49-7.10 (m, 4H), 5.28-3.81 (m, 6H), 3.07-2.45 (m, 4H), 2.36-1.64 (m, 5H), 1.38-0.32 (m, 7H). |
| 460 | (structure shown) diatereomer of Example No. 459 | HCl | ¹H-NMR (DMSO-d$_6$) δ: 12.72 (br s, 1H), 8.92-8.63 (m, 1H), 7.47-7.37 (m, 2H), 7.24-7.13 (m, 2H), 4.80-4.19 (m, 4H), 4.10-3.39 (m, 2H), 3.04-2.48 (m, 4H), 2.15-1.61 (m, 5H), 1.18-0.59 (m, 7H). |
| 461 | (structure shown) diatereomer of Example No. 462 | HCl | ¹H-NMR (DMSO-d$_6$) δ: 8.63 (s, 1H), 7.68 (s, 1H), 7.37-7.29 (m, 2H), 7.19-7.10 (m, 2H), 4.90-4.65 (m, 2H), 4.61-4.45 (m, 1H), 4.20 (s, 2H), 3.89-3.55 (m, 2H), 2.81 (s, 3H), 2.00 (s, 3H), 1.95-1.76 (m, 2H), 1.29-1.11 (br, 6H), 1.02 (d, 3H, J = 7.1 Hz). |

TABLE 1-119

| No. | structural formula | salt | ¹H-NMR |
|---|---|---|---|
| 462 | diatereomer of Example No. 461 | HCl | ¹H-NMR (DMSO-$d_6$) δ: 8.63 (s, 0.75H), 8.44 (s, 0.25H), 7.69-7.63 (m, 1H), 7.39-7.29 (m, 2H), 7.19-7.10 (m, 2H), 4.85-3.97 (m, 3H), 4.20 (s, 2H), 3.85-3.54 (m, 2H), 2.81 (s, 2.25H), 2.72 (s, 0.75H), 2.06-1.61 (m, 5H), 1.33-1.08 (m, 6H), 1.08-0.93 (m, 3H). |
| 463 | diatereomer of Example No. 456 | HCl | ¹H-NMR (DMSO-$d_6$) δ: 12.58 (br s, 1.0H), 8.62 (s, 0.9H), 8.58 (s, 0.1H), 7.68 (s, 0.9H), 7.67 (s, 0.1H), 7.36-7.30 (m, 2.0H), 7.18-7.11 (m, 2.0H), 4.76-4.65 (m, 1.0H), 4.57-4.49 (m, 1.0H), 4.20 (s, 2.0H), 3.99-3.93 (m, 1.0H), 3.75-3.59 (m, 1.9H), 3.59-3.38 (m, 1.1H), 2.80 (s, 2.7H), 2.58 (s, 0.3H), 1.98 (s, 2.7H), 1.92-1.83 (m, 2.3H), 1.22-1.13 (m, 3.3H), 1.03 (d, 2.7H, J = 6.9 Hz). |
| 464 | | HCl | ¹H-NMR (DMSO-$d_6$) δ: 12.72 (br s, 1H), 8.81 (s, 1H), 7.44-7.39 (m, 2H), 7.21-7.16 (m, 2H), 4.65-4.62 (m, 1H), 4.47 (s, 2H), 4.09 (dd, 1H, J = 13.7, 4.0 Hz), 3.82 (dd, 1H, J = 13.7, 0.8 Hz), 3.58 (dq, 1H, J = 13.3, 7.3 Hz), 3.53 (dq, 1H, J = 13.3, 7.3 Hz), 3.37 (dd, 1H, J = 9.7, 4.8 Hz), 3.32 (dd, 1H, J = 9.7, 6.4 Hz), 3.26 (s, 3H), 2.24-2.17 (m, 1H), 1.17 (t, 3H, J = 7.3 Hz), 0.72 (d, 3H, J = 6.9 Hz). |
| 465 | | HCl | ¹H-NMR (DMSO-$d_6$) δ: 12.71 (br s, 1H), 8.81 (s, 1H), 7.43-7.39 (m, 2H), 7.21-7.16 (m, 2H), 4.64-4.61 (m, 1H), 4.47 (s, 2H), 4.01 (dd, 1H, J = 13.7, 4.0 Hz), 3.72 (dd, 1H, J = 13.7, 1.2 Hz), 3.34-3.29 (m, 2H), 3.27 (s, 3H), 2.98-2.92 (m, 1H), 2.20-2.14 (m, 1H), 0.90-0.79 (m, 4H), 0.67 (d, 3H, J = 6.9 Hz). |

Experimental Example 1

The following explains evaluation methods of the HIV integrase inhibitory activity of the compound of the present invention.

(i) Construction of Recombinant Integrase Gene Expression System

A full-length gene sequence (Accession No.: M19921) of HIV-1 pNL4-3 integrase was inserted into restriction enzyme Nde I and Xho I sites of plasmid pET21a(+) (manufactured by Novagen) to construct an integrase expression vector pET21a-IN-Wild type.

(ii) Production and Purification of Integrase Protein

*Escherichia coli* recombinant BL21(DE3) transformed with plasmid pET21a-IN-Wild type obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 5 hr to promote accumulation of the integrase protein. The recombinant *E. coli* was collected in pellets by centrifugal separation and preserved at −80° C.

This *Escherichia coli* was suspended in Lysis buffer (50 mM Tris-HCl (pH 7.6), 10 mM $MgCl_2$, 5 mM DTT), and disrupted by repeating treatments of pressurization and depressurization, and insoluble fraction was collected by centrifugation at 4° C., 18,000 rpm for 60 min. This was suspended in Lysis buffer containing a protease inhibitor, 1.25 mM sodium chloride and 10 mM CHAPS were added, and the mixture was stirred at 4° C. for 30 min. Water-soluble fraction was collected by centrifugation at 4° C., 9,000 rpm for 30 min. The obtained fraction was diluted with a column buffer (50 mM Tris-HCl (pH 7.6), 1 mM DTT, 10% Glycerol, 10 mM CHAPS) to 5-fold, and the mixture was applied to heparin column (HiPrep 16/10 Heparin FF column: manufactured by GE Healthcare Bio-Sciences). Using a column buffer containing 1M NaCl, a protein was eluted with 0-1M NaCl concentration gradient, and an eluted fraction containing an integrase protein was collected. The obtained fraction was diluted 5-fold with a column buffer (50 mM Tris-HCl (pH 7.6), 1 mM DTT, 10% Glycerol, 10 mM CHAPS), and the mixture was applied to cation exchange column (Mono-S column: manufactured by GE Healthcare Bio-Sciences). Using a column buffer containing 1M NaCl, a protein was eluted with 0-1M NaCl concentration gradient, and an eluted fraction containing an integrase protein was collected. The obtained fractions of the integrase protein were collected, and preserved at −80° C.

(iii) Preparation of DNA Solution

The following DNA synthesized by FASMAC was dissolved in TE buffer (10 mM Tris-hydrochloric acid (pH 8.0), 1 mM EDTA) and mixed with donor DNA, target DNA, and each complementary strand (+ and − strands) to 1 µM. The mixture was heated at 95° C. for 5 min, 80° C. for 10 min, 70° C. for 10 min, 60° C. for 10 min, 50° C. for 10 min and 40° C. for 10 min and kept at 25° C. to give a double stranded DNA, which was used for the test.

Donor DNA (+strand having biotin attached to the 5' terminal)

```
                                    (SEQ ID NO: 1)
Donor + strand: 5'-Biotin-ACC CTT TTA GTC AGT GTG
GAA AAT CTC TAG CA-3'
```

```
                                    (SEQ ID NO: 2)
Donor - strand: 5'-ACT GCT AGA GAT TTT CCA CAC TGA
CTA AAA G-3'
```

Target DNA (+, − strands both having digoxigenin attached to the 3' terminal)

```
Target + strand:
                                    (SEQ ID NO: 3)
5'-TGA CCA AGG GCT AAT TCA CT-Dig-3'

Target - strand:
                                    (SEQ ID NO: 4)
5'-AGT GAA TTA GCC CTT GGT CA-Dig-3'
```

(iv) Determination of Enzyme (HIV Integrase) Inhibitory Activity

The donor DNA was diluted with TE buffer to 20 nM, of which 50 µL was added to each well of streptavidin-coated black plate (manufactured by PIAS Corporation) and allowed to adsorb at 37° C. for 20 min. The plate was washed with phosphate buffer (Dulbecco's PBS, Sanko Junyaku Co., Ltd.) containing 0.1% Tween 20 and phosphate buffer. Then, an enzyme reaction mixture (70 µL), a test substance (10 µL) diluted with the enzyme reaction mixture and 0.75 µM integrase protein (10 µL) were added to each well and the mixture was reacted at 37° C. for 60 min. composition of enzyme reaction mixture: 30 mM MOPS (3-morpholinopropanesulfonic acid), 5 mM magnesium chloride, 3 mM DTT (dithiothreitol), 0.1 mg/mL BSA (bovine serum albumin), 5% glycerol, 10% DMSO (dimethyl sulfoxide), 0.01% Tween 20.

Then, 25 nM target DNA (10 µL) was added, and the mixture was reacted at 37° C. for 20 min and washed with phosphate buffer containing 0.1% Tween 20 to stop the reaction. Then, 100 mU/mL peroxidase labeled anti-digoxigenin antibody solution (Roche, 100 µL) was added, and the mixture was reacted at 37° C. for 60 min, followed by washing with phosphate buffer containing 0.1% Tween 20.

Then, peroxidase fluorescence substrate solution (manufactured by PIAS Corporation, 100 µL) was added, and the mixture was reacted at room temperature for 20 min to 30 min. A reaction quenching liquid (manufactured by PIAS Corporation, 100 µL) was added to discontinue the reaction, and fluorescence intensity at excitation wavelength 325 nm/fluorescence wavelength 420 nm was measured.

The HIV integrase inhibitory activity ($IC_{50}$) of the compound of the present invention was calculated from the inhibition rate according to the following formula:

inhibition rate (%)=[1−(Object−Blank)/(Control−Blank)]×100

Object: fluorescence intensity of well in the presence of test compound

Control: fluorescence intensity of well in the absence of test compound

Blank: fluorescence intensity of well in the absence of test compound and integrase protein The results are shown in the following Tables.

TABLE 2-1

| Example No. | inhibitory activity $IC_{50}$ (µM) |
|---|---|
| 2 | 0.013 |
| 3 | 0.0085 |

TABLE 2-1-continued

| Example No. | inhibitory activity IC$_{50}$ (μM) |
|---|---|
| 4 | 0.01 |
| 5 | 0.0074 |
| 6 | 0.0056 |
| 7 | 0.013 |
| 8 | 0.0089 |
| 9 | 0.0091 |
| 10 | 0.0088 |
| 11 | 0.0064 |
| 12 | 0.0073 |
| 13 | 0.0064 |
| 14 | 0.01 |
| 15 | 0.013 |
| 16 | 0.02 |
| 17 | 0.0079 |
| 18 | 0.0082 |
| 19 | 0.0081 |
| 20 | 0.017 |

TABLE 2-2

| Example No. | inhibitory activity IC$_{50}$ (μM) |
|---|---|
| 21 | 0.0094 |
| 22 | 0.007 |
| 23 | 0.012 |
| 24 | 0.023 |
| 25 | 0.011 |
| 26 | 0.0076 |
| 27 | 0.01 |
| 28 | 0.015 |
| 29 | 0.01 |
| 30 | 0.009 |
| 31 | 0.0083 |
| 32 | 0.0077 |
| 33 | 0.0062 |
| 34 | 0.0082 |
| 35 | 0.0067 |
| 36 | 0.013 |
| 37 | 0.0063 |
| 38 | 0.012 |
| 39 | 0.01 |
| 40 | 0.013 |

TABLE 2-3

| Example No. | inhibitory activity IC$_{50}$ (μM) |
|---|---|
| 41 | 0.0072 |
| 42 | 0.0034 |
| 43 | 0.0046 |
| 44 | 0.0081 |
| 45 | 0.011 |
| 46 | 0.011 |
| 47 | 0.012 |
| 48 | 0.0069 |
| 49 | 0.0051 |
| 50 | 0.0064 |
| 51 | 0.0057 |
| 52 | 0.013 |
| 53 | 0.01 |
| 54 | 0.0075 |
| 55 | 0.021 |
| 56 | 0.01 |
| 57 | 0.011 |
| 58 | 0.017 |

TABLE 2-3-continued

| Example No. | inhibitory activity IC$_{50}$ (μM) |
|---|---|
| 59 | 0.012 |
| 60 | 0.017 |

TABLE 2-4

| Example No. | inhibitory activity IC$_{50}$ (μM) |
|---|---|
| 61 | 0.0066 |
| 62 | 0.0092 |
| 63 | 0.0083 |
| 64 | 0.0061 |
| 65 | 0.013 |
| 66 | 0.0064 |
| 67 | 0.0076 |
| 68 | 0.0098 |
| 69 | 0.013 |
| 70 | 0.0089 |
| 71 | 0.011 |
| 72 | 0.011 |
| 73 | 0.0077 |
| 74 | 0.0057 |
| 75 | 0.0091 |
| 76 | 0.0083 |
| 77 | 0.011 |
| 78 | 0.0089 |
| 79 | 0.0064 |
| 80 | 0.0098 |

TABLE 2-5

| Example No. | inhibitory activity IC$_{50}$ (μM) |
|---|---|
| 81 | 0.0075 |
| 82 | 0.0049 |
| 83 | 0.0071 |
| 84 | 0.011 |
| 85 | 0.0075 |
| 86 | 0.0095 |
| 87 | 0.0077 |
| 88 | 0.0087 |
| 89 | 0.008 |
| 90 | 0.0067 |
| 92 | 0.0087 |
| 93 | 0.0078 |
| 94 | 0.0088 |
| 95 | 0.0095 |
| 96 | 0.0067 |
| 97 | 0.0066 |
| 98 | 0.0075 |
| 99 | 0.0061 |
| 100 | 0.0081 |
| 101 | 0.0064 |

TABLE 2-6

| Example No. | inhibitory activity IC$_{50}$ (μM) |
|---|---|
| 102 | 0.0071 |
| 103 | 0.018 |
| 104 | 0.015 |
| 105 | 0.017 |
| 106 | 0.02 |
| 107 | 0.019 |
| 108 | 0.018 |
| 109 | 0.021 |

TABLE 2-6-continued

| Example No. | inhibitory activity IC$_{50}$ (μM) |
|---|---|
| 110 | 0.023 |
| 111 | 0.02 |
| 112 | 0.019 |
| 113 | 0.013 |
| 114 | 0.0081 |
| 115 | 0.012 |
| 116 | 0.0096 |
| 117 | 0.0094 |
| 118 | 0.013 |
| 119 | 0.011 |
| 120 | 0.015 |
| 121 | 0.016 |

TABLE 2-7

| Example No. | inhibitory activity IC$_{50}$ (μM) |
|---|---|
| 122 | 0.019 |
| 123 | 0.027 |
| 124 | 0.015 |
| 125 | 0.011 |
| 126 | 0.0073 |
| 127 | 0.014 |
| 128 | 0.019 |
| 129 | 0.012 |
| 130 | 0.013 |
| 131 | 0.013 |
| 132 | 0.0091 |
| 133 | 0.0074 |
| 134 | 0.016 |
| 135 | 0.012 |
| 136 | 0.011 |
| 137 | 0.0086 |
| 138 | 0.011 |
| 139 | 0.012 |
| 140 | 0.0058 |
| 141 | 0.008 |

TABLE 2-8

| Example No. | inhibitory activity IC$_{50}$ (μM) |
|---|---|
| 142 | 0.0064 |
| 143 | 0.0069 |
| 144 | 0.0077 |
| 145 | 0.0056 |
| 146 | 0.0059 |
| 147 | 0.0083 |
| 148 | 0.0098 |
| 149 | 0.0059 |
| 150 | 0.0061 |
| 151 | 0.0054 |
| 152 | 0.0059 |
| 153 | 0.0058 |
| 154 | 0.0073 |
| 155 | 0.01 |
| 156 | 0.0046 |
| 157 | 0.029 |
| 158 | 0.0054 |
| 159 | 0.0066 |
| 160 | 0.0061 |
| 161 | 0.0078 |

TABLE 2-9

| Example No. | inhibitory activity IC$_{50}$ (μM) |
|---|---|
| 162 | 0.0071 |
| 163 | 0.0077 |
| 164 | 0.0065 |
| 165 | 0.0074 |
| 166 | 0.012 |
| 167 | 0.01 |
| 168 | 0.0058 |
| 169 | 0.012 |
| 170 | 0.012 |
| 171 | 0.016 |
| 172 | 0.014 |
| 173 | 0.016 |
| 174 | 0.014 |
| 175 | 0.0095 |
| 176 | 0.0085 |
| 177 | 0.017 |
| 178 | 0.02 |
| 179 | 0.019 |
| 180 | 0.01 |
| 181 | 0.014 |

TABLE 2-10

| Example No. | inhibitory activity IC$_{50}$ (μM) |
|---|---|
| 182 | 0.0097 |
| 183 | 0.01 |
| 184 | 0.006 |
| 185 | 0.015 |
| 186 | 0.018 |
| 187 | 0.019 |
| 188 | 0.018 |
| 189 | 0.02 |
| 190 | 0.011 |
| 191 | 0.012 |
| 192 | 0.015 |
| 193 | 0.011 |
| 194 | 0.0082 |
| 195 | 0.0059 |
| 196 | 0.0067 |
| 197 | 0.014 |
| 198 | 0.0057 |
| 199 | 0.0084 |
| 200 | 0.0096 |
| 201 | 0.0095 |

TABLE 2-11

| Example No. | inhibitory activity IC$_{50}$ (μM) |
|---|---|
| 202 | 0.013 |
| 203 | 0.013 |
| 204 | 0.013 |
| 205 | 0.013 |
| 206 | 0.0059 |
| 207 | 0.024 |
| 208 | 0.012 |
| 209 | 0.012 |
| 210 | 0.023 |
| 211 | 0.016 |
| 212 | 0.014 |
| 213 | 0.015 |
| 214 | 0.016 |
| 217 | 0.0053 |
| 218 | 0.0065 |
| 219 | 0.015 |
| 220 | 0.0068 |

TABLE 2-11-continued

| Example No. | inhibitory activity IC$_{50}$ (μM) |
|---|---|
| 221 | 0.0084 |
| 222 | 0.0065 |
| 223 | 0.012 |

TABLE 2-12

| Example No. | inhibitory activity IC$_{50}$ (μM) |
|---|---|
| 224 | 0.0073 |
| 225 | 0.018 |
| 226 | 0.013 |
| 227 | 0.013 |
| 228 | 0.011 |
| 229 | 0.012 |
| 230 | 0.069 |
| 231 | 0.011 |
| 232 | 0.015 |
| 233 | 0.0064 |
| 234 | 0.018 |
| 235 | 0.016 |
| 236 | 0.013 |
| 237 | 0.013 |
| 238 | 0.018 |
| 239 | 0.016 |
| 240 | 0.052 |
| 241 | 0.014 |
| 242 | 0.013 |
| 243 | 0.0076 |

TABLE 2-13

| Example No. | inhibitory activity IC$_{50}$ (μM) |
|---|---|
| 244 | 0.074 |
| 245 | 0.0081 |
| 246 | 0.0084 |
| 247 | 0.01 |
| 248 | 0.014 |
| 249 | 0.012 |
| 250 | 0.017 |
| 251 | 0.011 |
| 252 | 0.0092 |
| 253 | 0.0077 |
| 254 | 0.0076 |
| 255 | 0.009 |
| 256 | 0.0082 |
| 257 | 0.0091 |
| 258 | 0.0093 |
| 259 | 0.009 |
| 260 | 0.012 |
| 261 | 0.011 |
| 262 | 0.01 |
| 263 | 0.009 |

TABLE 2-14

| Example No. | inhibitory activity IC$_{50}$ (μM) |
|---|---|
| 264 | 0.0085 |
| 265 | 0.0093 |
| 266 | 0.011 |
| 267 | 0.011 |
| 268 | 0.015 |

TABLE 2-14-continued

| Example No. | inhibitory activity IC$_{50}$ (μM) |
|---|---|
| 269 | 0.0094 |
| 270 | 0.0095 |
| 271 | 0.011 |
| 272 | 0.0089 |
| 273 | 0.014 |
| 274 | 0.012 |
| 275 | 0.014 |
| 276 | 0.016 |
| 277 | 0.012 |
| 278 | 0.0099 |
| 279 | 0.0063 |
| 280 | 0.016 |
| 281 | 0.016 |
| 282 | 0.015 |
| 283 | 0.018 |

TABLE 2-15

| Example No. | inhibitory activity IC$_{50}$ (μM) |
|---|---|
| 284 | 0.011 |
| 285 | 0.011 |
| 286 | 0.0078 |
| 287 | 0.008 |
| 288 | 0.0088 |
| 289 | 0.01 |
| 290 | 0.014 |
| 291 | 0.0087 |
| 292 | 0.0073 |
| 293 | 0.0096 |
| 294 | 0.011 |
| 295 | 0.012 |
| 296 | 0.019 |

TABLE 2-16

| Example No. | inhibitory activity IC$_{50}$ (μM) |
|---|---|
| 297 | 0.02 |
| 298 | 0.009 |
| 299 | 0.0098 |
| 300 | 0.009 |
| 301 | 0.008 |
| 302 | 0.0099 |
| 303 | 0.0058 |
| 304 | 0.0091 |
| 305 | 0.0095 |
| 306 | 0.01 |
| 307 | 0.011 |
| 308 | 0.013 |
| 309 | 0.0088 |
| 310 | 0.0099 |
| 311 | 0.0097 |
| 312 | 0.012 |
| 313 | 0.0097 |
| 314 | 0.0079 |
| 315 | 0.0088 |

TABLE 2-17

| Example No. | inhibitory activity IC$_{50}$ (μM) |
|---|---|
| 316 | 0.012 |
| 317 | 0.0098 |
| 318 | 0.0065 |

TABLE 2-17-continued

| Example No. | inhibitory activity IC$_{50}$ (μM) |
|---|---|
| 319 | 0.0058 |
| 320 | 0.0094 |
| 321 | 0.007 |
| 323 | 0.014 |

TABLE 2-18

| Example No. | inhibitory activity IC$_{50}$ (μM) |
|---|---|
| 327 | 0.0059 |
| 328 | 0.0071 |
| 329 | 0.0061 |
| 330 | 0.0064 |
| 331 | 0.0093 |
| 332 | 0.012 |
| 333 | 0.0075 |
| 334 | 0.0091 |
| 335 | 0.0098 |
| 336 | 0.0072 |
| 337 | 0.017 |
| 338 | 0.0071 |
| 353 | 0.013 |
| 354 | 0.0080 |
| 355 | 0.0066 |
| 356 | 0.0089 |
| 357 | 0.0073 |
| 358 | 0.012 |
| 359 | 0.0048 |
| 360 | 0.011 |

TABLE 2-19

| Example No. | inhibitory activity IC$_{50}$ (μM) |
|---|---|
| 361 | 0.015 |
| 362 | 0.010 |
| 363 | 0.0087 |
| 364 | 0.010 |
| 365 | 0.012 |
| 382 | 0.0087 |
| 383 | 0.0079 |
| 384 | 0.012 |
| 385 | 0.0082 |
| 386 | 0.015 |
| 387 | 0.011 |
| 388 | 0.0086 |
| 389 | 0.014 |
| 391 | 0.024 |
| 392 | 0.011 |
| 393 | 0.015 |
| 394 | 0.014 |
| 395 | 0.010 |
| 396 | 0.015 |
| 397 | 0.019 |

Experimental Example 2 Evaluation of Antiviral Activity

The effect of combined use of the compound of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and test substance A and the like are evaluated using CEM-SS cells infected with HIV-1 IIIB by XTT method.

In addition, the effect of combined use of three agents of test substance A, zidovudine and lamivudine, or test substance A, tenofovir and lamivudine, and the like is is evaluated.

Prior to the combined use test, IC$_{50}$ and CC$_{50}$ of each medicament alone are measured. 5 concentrates of medicament A and 9 concentrates of medicament B, determined based on these results, are combined to evaluate the effect of combined use of two agents. For combined use of three agents, a high concentrated medicament B and a medicament C are mixed and medicament A and concentration thereof are combined for evaluation.

The test results of the test substance and concomitant drug alone or in combination thereof are analyzed based on the programs of Prichard and Shipman MacSynergy II version 2.01 and Deltagraph version 1.5d. A three-dimensional plot is drawn from % inhibition at the concentrations of each combined medicament, the obtained from 3 times of tests, with 95% (or 68%, 99%) confidence limits, and the effect of the combined use is evaluated based on the numerical values of μM$^2$% calculated therefrom. The criteria of evaluation are shown in the following.

| Definition of interaction | μM$^2$ % |
|---|---|
| Strong synergistic action | >100 |
| Slight synergistic action | +51-+100 |
| Additive action | +50--50 |
| Slight antagonistic action | -51--100 |
| Strong antagonistic action | <-100 |

Experimental Example 3 Metabolism Stability Test

Metabolism Stability Test in Liver Microsome

Liver microsome of human or animal species (rat or monkey) (manufactured by Xenotech LLC (Lenexa, Kans., USA), 20 mg protein/mL) (2.5 μL) and NADPH-generating system coenzyme solution ((3-nicotinamide adenine dinucleotide phosphate: 5.2 mM, D-glucose-6-phosphate: 13.2 mM, magnesium chloride: 13.2 mM, glucose-6-phosphate dehydrogenase: 1.8 U/mL) (50 μL) are suspended in 100 mM potassium phosphate buffer (pH 7.4, 147.5 μL), and mixed with a test substance (2 μL) dissolved in acetonitrile containing 0.5% DMSO. After incubation at 37° C. for 0, 10 and 60 min, acetonitrile containing formic acid (final concentrated 0.1%) is added and the mixture is centrifuged. The test substance (unchanged form) in the supernatant is measured by high performance liquid chromatography/Mass Spectrometry (LC/MS). The residual ratio (%) is calculated from the obtained measurement values according to the following formula.

residual ratio (%)=amount of test substance after incubation (0, 10 or 60 min)/amount of test substance at incubation 0 min×100

Preferred as the compound of the present invention is a compound with a residual ratio at 60 min later of not less than 40%, more preferably not less than 60%, further preferably not less than 80%.

Formulation Example is given below. This example is merely for the exemplification purpose and does not limit the invention.

Formulation Example

| | | |
|---|---|---|
| (a) compound of Example 1 | 10 g | |
| (b) lactose | 50 g | |
| (c) corn starch | 15 g | |
| (d) sodium carboxymethylcellulose | 44 g | |
| (e) magnesium stearate | 1 g | |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

INDUSTRIAL APPLICABILITY

The compounds of the present invention show a high inhibitory activity against HIV integrase.

Therefore, these compounds can be medicaments effective for, for example, the prophylaxis or treatment of AIDS, as integrase inhibitors, antiviral agents, anti-HIV agents and the like, having an HIV integrase inhibitory activity. In addition, by a combined use with other anti-HIV agent(s) such as protease inhibitor, reverse transcriptase inhibitor and the like, they can be more effective anti-HIV agents. Furthermore, having high inhibitory activity specific for integrase, they can be medicaments safe for human body with a fewer side effects.

Sequence Listing Free Text

SEQ ID NO: 1: Donor+ chain for HIV integrase activity measurement
SEQ ID NO: 2: Donor− chain for HIV integrase activity measurement
SEQ ID NO: 3: Target+ chain for HIV integrase activity measurement
SEQ ID NO: 4: Target− chain for HIV integrase activity measurement

The invention claimed is:

1. A compound represented by the following formula [I] or a pharmaceutically acceptable salt thereof:
wherein

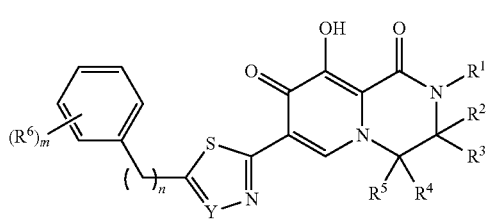

[I]

$R^1$ is
(1) a $C_{1-6}$ alkyl group optionally substituted by the same or different 1 to 5 substituents selected from
  (i) a $C_{3-8}$ cycloalkyl group, and
  (ii) a $C_{1-6}$ alkoxy group,
(2) a $C_{3-8}$ cycloalkyl group, or
(3) a saturated monocyclic heterocyclic group containing, besides carbon atom, 1 to 3 hetero atoms selected from a nitrogen atom, an oxygen atom and a sulfur atom,
$R^2$, $R^3$, $R^4$ and $R^5$ are the same or different and each is
(1) a hydrogen atom,
(2) a carboxyl group,
(3) —CO—$NR^aR^b$ wherein $R^a$ and $R^b$ are the same or different and each is
  (i) a hydrogen atom,
  (ii) a $C_{1-6}$ alkyl group optionally substituted by the same or different 1 to 5 substituents selected from the following group B, or
  (iii) a $C_{3-8}$ cycloalkyl group, or
  $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from the following group B,
(4) a $C_{1-6}$ alkyl group optionally substituted by the same or different 1 to 5 substituents selected from the following group A, or
(5) a cyano group,
or
$R^2$ and $R^3$, or $R^4$ and $R^5$ optionally form, together with the carbon atom bonded thereto,
  i) $C_{3-8}$ cycloalkane, or
  ii) a saturated monocyclic hetero ring containing, besides carbon atom, 1 to 6 hetero atoms selected from a nitrogen atom, an oxygen atom and a sulfur atom, wherein $R^2$, $R^3$, $R^4$ and $R^5$ are not hydrogen atoms at the same time, $R^6$ is
(1) a $C_{1-6}$ alkyl group optionally substituted by the same or different 1 to 5 halogen atoms,
(2) a $C_{1-6}$ alkoxy group,
(3) a halogen atom, or
(4) a $C_{3-8}$ cycloalkyl group,
Y is CH,
m is an integer of 1 to 5, and when m is an integer of 2 to 5, then each $R^6$ may be the same or different, and
n is an integer of 1 to 3,
and wherein group A is selected from
(a) —CO—$NR^{41}R^{42}$
  wherein $R^{41}$ and $R^{42}$ are the same or different and each is
  (i) a hydrogen atom,
  (ii) a $C_{1-6}$ alkyl group optionally substituted by the same or different 1 to 5 substituents selected from the following group B, or
  (iii) a $C_{3-8}$ cycloalkyl group, or
  $R^{41}$ and $R^{42}$ optionally form, together with the nitrogen atom bonded thereto, a saturated monocyclic hetero ring optionally containing, besides carbon atom and one nitrogen atom, 1 to 3 hetero atoms selected from a nitrogen atom, an oxygen atom and a sulfur atom, and optionally substituted by the same or different 1 to 5 substituents selected from the following group B,
(b) a hydroxyl group,
(c) a $C_{1-6}$ alkoxy group,
(d) a $C_{1-6}$ alkoxy-$C_{1-6}$ alkoxy group,
(e) a cyano group,
(f) —$NR^{43}R^{44}$
  wherein $R^{43}$ and $R^{44}$ are the same or different and each is
  (i) a hydrogen atom,
  (ii) a $C_{1-6}$ alkyl group,
  (iii) a $C_{1-6}$ alkyl-carbonyl group, or
  (iv) a $C_{1-6}$ alkyl-sulfonyl group, or
  $R^{43}$ and $R^{44}$ optionally form, together with the nitrogen atom bonded thereto, a hetero ring optionally containing, besides carbon atom and one nitrogen atom, 1 to 5 hetero atoms selected from a nitrogen atom, an oxygen atom and a sulfur atom, and optionally substituted by 1 or 2 oxo groups,
(g) a carboxyl group,
(h) a $C_{1-6}$ alkyl-sulfonyl group, and
(i) a $C_{1-6}$ alkyl-carbonyl group;
and group B is selected from
(a) a hydroxyl group,
(b) a $C_{1-6}$ alkoxy group,
(c) a $C_{1-6}$ alkoxy-$C_{1-6}$ alkyl group
(d) a $C_{3-8}$ cycloalkyl group, and
(e) an oxo group.

2. The compound according to claim 1, wherein m is 1 or 2, or a pharmaceutically acceptable salt thereof, or a solvate thereof.

3. The compound according to claim 1, wherein n is 1, or a pharmaceutically acceptable salt thereof, or a solvate thereof.

4. The compound according to claim 1, wherein $R^1$ is a $C_{1-6}$ alkyl group optionally substituted by the same or different 1 to 5 substituents selected from
(i) a $C_{3-8}$ cycloalkyl group, and
(ii) a $C_{1-6}$ alkoxy group,
or a pharmaceutically acceptable salt thereof, or a solvate thereof.

5. The compound according to claim 4, wherein $R^1$ is a $C_{1-6}$ alkyl group, or a pharmaceutically acceptable salt thereof.

6. The compound according to claim 4, wherein $R^1$ is a $C_{1-6}$ alkyl group substituted by a $C_{3-8}$ cycloalkyl group, or a pharmaceutically acceptable salt thereof.

7. The compound according to claim 1, wherein $R^1$ is a $C_{3-8}$ cycloalkyl group, or a pharmaceutically acceptable salt thereof.

8. The compound according to claim 1, wherein one of $R^2$, $R^3$, $R^4$ and $R^5$ is —CO—$NR^aR^b$
wherein $R^a$ and $R^b$ are the same or different and each is
(i) a hydrogen atom,
(ii) a $C_{1-6}$ alkyl group optionally substituted by the same or different 1 to 5 substituents selected from group B, or
(iii) a $C_{3-8}$ cycloalkyl group, or
$R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B,
or a pharmaceutically acceptable salt thereof, or a solvate thereof.

9. The compound according to claim 1, wherein one of $R^2$, $R^3$, $R^4$ and $R^5$ is a $C_{1-6}$ alkyl group optionally substituted by the same or different 1 to 5 substituents selected from group A,
or a pharmaceutically acceptable salt thereof, or a solvate thereof.

10. The compound according to claim 1, wherein $R^6$ is a halogen atom, or a pharmaceutically acceptable salt thereof.

11. The compound according to claim 1, which is represented by the following formula [I-2], or a pharmaceutically acceptable salt thereof:
wherein

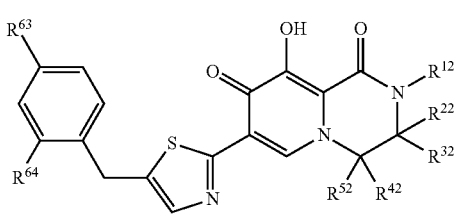

[I-2]

$R^{12}$ is a $C_{1-6}$ alkyl group optionally substituted by the same or different 1 to 5 substituents selected from
(i) a $C_{3-8}$ cycloalkyl group, and
(ii) a $C_{1-6}$ alkoxy group, $R^{22}$, $R^{32}$, $R^{42}$ and $R^{52}$ are the same or different and each is
(1) a hydrogen atom,
(2) —CO—$NR^aR^b$ wherein $R^a$ and $R^b$ are the same or different and each is
  (i) a hydrogen atom,
  (ii) a $C_{1-6}$ alkyl group optionally substituted by the same or different 1 to 5 substituents selected from group B, or
  (iii) a $C_{3-8}$ cycloalkyl group, or
  $R^a$ and $R^b$ optionally form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B, or
(3) a $C_{1-6}$ alkyl group optionally substituted by the same or different 1 to 5 substituents selected from group A,
wherein $R^{22}$, $R^{32}$, $R^{42}$ and $R^{52}$ are not hydrogen atoms at the same time,
$R^{63}$ is a halogen atom, and
$R^{64}$ is a hydrogen atom or a halogen atom.

12. The compound according to claim 11, wherein $R^{42}$ is —CO—$NR^aR^b$ wherein $R^a$ and $R^b$ form, together with the nitrogen atom bonded thereto, a saturated monocyclic hetero ring optionally containing, besides carbon atom and one nitrogen atom, 1 to 5 hetero atoms selected from a nitrogen atom, an oxygen atom and a sulfur atom, and optionally substituted by the same or different 1 to 5 substituents selected from group B,
$R^{52}$ is a $C_{1-6}$ alkyl group, and
$R^{22}$ and $R^{32}$ is a hydrogen atom,
or a pharmaceutically acceptable salt thereof, or a solvate thereof.

13. A pharmaceutical composition comprising the compound according to claim 1 or a pharmaceutically acceptable salt thereof, and a pharmaceutically acceptable carrier.

14. The pharmaceutical composition according to claim 13, which further comprises one or more other anti-HIV active substances.

15. A commercial package comprising the pharmaceutical composition according to claim 13 and a written matter associated therewith, which states that the pharmaceutical composition can or should be used for treating HIV.

16. A kit comprising the pharmaceutical composition according to claim 13 and a written matter associated therewith, which states that the pharmaceutical composition can or should be used for treating HIV.

17. An anti-HIV agent comprising the compound according to claim 1 or a pharmaceutically acceptable salt thereof, in combination with one or more other kinds of anti-HIV active substances.

18. A method for the prophylaxis or treatment of an HIV infectious disease in a mammal, which comprises administering an effective amount of the compound according to claim 1 or a pharmaceutically acceptable salt thereof, to said mammal.

19. The method according to claim 18, which further comprises administering an effective amount of one or more other kinds of anti-HIV active substances to the mammal.

20. A method for inhibiting HIV integrase in a mammal, which comprises administering an effective amount of the compound according to claim 1 or a pharmaceutically acceptable salt thereof, to said mammal.

* * * * *